(12) United States Patent
Picataggio et al.

(10) Patent No.: US 8,778,658 B2
(45) Date of Patent: *Jul. 15, 2014

(54) BIOLOGICAL METHODS FOR PREPARING ADIPIC ACID

(75) Inventors: Stephen Picataggio, Carlsbad, CA (US); Tom Beardslee, Carlsbad, CA (US)

(73) Assignee: Verdezyne, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/549,076

(22) Filed: Jul. 13, 2012

(65) Prior Publication Data

US 2013/0157343 A1    Jun. 20, 2013

Related U.S. Application Data

(63) Continuation of application No. 13/245,777, filed on Sep. 26, 2011, now Pat. No. 8,241,879, which is a continuation of application No. PCT/US2010/040837, filed on Jul. 1, 2010.

(60) Provisional application No. 61/222,902, filed on Jul. 2, 2009.

(51) Int. Cl.
| | | |
|---|---|---|
| C12N 1/14 | (2006.01) | |
| C12P 7/46 | (2006.01) | |
| C12Q 1/68 | (2006.01) | |
| C12N 15/00 | (2006.01) | |
| C12N 9/02 | (2006.01) | |
| C12N 9/00 | (2006.01) | |
| C07H 21/04 | (2006.01) | |

(52) U.S. Cl.
USPC .............. 435/254.22; 435/440; 435/320.1; 435/6.1; 435/189; 435/183; 435/145; 536/23.2

(58) Field of Classification Search
None
See application file for complete search history.

(56) References Cited

U.S. PATENT DOCUMENTS

| | | |
|---|---|---|
| 3,843,466 A | 10/1974 | Akabori et al. |
| 3,912,586 A | 10/1975 | Kaneyuki et al. |
| 4,400,468 A | 8/1983 | Faber |
| 4,683,195 A | 7/1987 | Mullis et al. |
| 4,683,202 A | 7/1987 | Mullis |
| 4,725,542 A | 2/1988 | Barer et al. |
| 4,965,188 A | 10/1990 | Mullis et al. |
| 4,965,201 A | 10/1990 | Casey et al. |
| 5,104,492 A | 4/1992 | King et al. |
| 5,204,252 A | 4/1993 | Cregg et al. |
| 5,232,841 A | 8/1993 | Hashimoto et al. |
| 5,254,466 A | 10/1993 | Picataggio et al. |
| 5,268,273 A | 12/1993 | Buckholz |
| 5,296,639 A | 3/1994 | Klug et al. |
| 5,349,084 A | 9/1994 | Shishikura et al. |
| 5,389,529 A | 2/1995 | Panayotatos et al. |
| 5,412,126 A | 5/1995 | King et al. |
| 5,470,719 A | 11/1995 | Meng et al. |
| 5,487,987 A | 1/1996 | Frost et al. |
| 5,595,899 A | 1/1997 | Sato et al. |
| 5,620,878 A | 4/1997 | Picataggio et al. |
| 5,635,369 A | 6/1997 | Pompon et al. |
| 5,648,247 A | 7/1997 | Picataggio et al. |
| 5,656,493 A | 8/1997 | Mullis et al. |
| 5,712,114 A | 1/1998 | Mankovich et al. |
| 5,766,891 A | 6/1998 | Shuman |
| 5,846,818 A | 12/1998 | Robinson |
| 5,888,732 A | 3/1999 | Hartley et al. |
| 5,932,474 A | 8/1999 | Tsien et al. |
| 5,962,285 A | 10/1999 | Anderson et al. |
| 6,008,378 A | 12/1999 | Tsien et al. |
| 6,054,271 A | 4/2000 | Tsien et al. |
| 6,066,480 A | 5/2000 | Mobley et al. |
| 6,087,527 A | 7/2000 | Niwa et al. |
| 6,143,532 A | 11/2000 | Wenzel et al. |
| 6,143,557 A | 11/2000 | Hartley et al. |
| 6,171,861 B1 | 1/2001 | Hartley et al. |
| 6,245,538 B1 | 6/2001 | Wenzel et al. |
| 6,270,969 B1 | 8/2001 | Hartley et al. |
| 6,277,608 B1 | 8/2001 | Hartley et al. |
| 6,288,275 B1 | 9/2001 | Turner |
| 6,288,302 B1 | 9/2001 | Yu et al. |
| 6,331,420 B1 | 12/2001 | Wilson et al. |
| 6,365,376 B1 | 4/2002 | Brzostowicz et al. |
| 6,376,223 B1 | 4/2002 | Staley |
| 6,440,688 B1 | 8/2002 | Bruce et al. |
| 6,451,569 B1 | 9/2002 | Tsien et al. |
| 6,465,224 B2 | 10/2002 | Brzostowicz et al. |
| 6,498,242 B1 | 12/2002 | Cheng et al. |
| 6,503,734 B1 | 1/2003 | Craft et al. |
| 6,569,670 B2 | 5/2003 | Anderson et al. |
| 6,632,650 B1 | 10/2003 | Chen et al. |

(Continued)

FOREIGN PATENT DOCUMENTS

| | | |
|---|---|---|
| EP | 1273663 | 1/2003 |
| RU | 2296743 | 4/2007 |

(Continued)

OTHER PUBLICATIONS

Office action mailed: Sep. 6, 2012 in U.S. Appl. No. 13/245,780, filed Sep. 26, 2011 and published as: 2012/077252 on Mar. 29, 2012.
International Search Report and Written Opinion dated: Aug. 30, 2012 in International Patent Application No. PCT/US2012/020230 filed, Jan. 4, 2012 and published as: WO/2012/094425 on: Jul. 20, 2012.
Genbank Accession No. AAA34362, Acyl-coenzyme A Oxidase II precursor [*Candida tropicalis*], Apr. 27, 1993.(http://www.ncbi.nlm.nih.gov/protein/AAA34362).
Extended European Search Report dated Nov. 7, 2012 in European Patent Application No. EP10794794 filed on: Jul. 1, 2010.

(Continued)

*Primary Examiner* — Yong Pak
(74) *Attorney, Agent, or Firm* — Wilson Sonsini Goodrich & Rosati, P.C.

(57) ABSTRACT

The technology relates in part to biological methods for producing adipic acid and engineered microorganisms capable of such production.

9 Claims, 37 Drawing Sheets

(56) References Cited

U.S. PATENT DOCUMENTS

| | | |
|---|---|---|
| 6,660,505 B2 | 12/2003 | Staley |
| 6,673,613 B2 | 1/2004 | Craft et al. |
| 6,720,140 B1 | 4/2004 | Hartley et al. |
| 6,777,213 B2 | 8/2004 | Staley |
| 6,787,669 B1 | 9/2004 | Costantini et al. |
| 6,790,640 B2 | 9/2004 | Craft et al. |
| 6,790,645 B2 | 9/2004 | Brzostowicz et al. |
| 6,794,165 B2 | 9/2004 | Cheng et al. |
| 6,797,500 B2 | 9/2004 | Chen et al. |
| 7,018,829 B1 | 3/2006 | Nielsen et al. |
| 7,043,681 B2 | 5/2006 | Kroger |
| 7,049,112 B2 | 5/2006 | Wilson et al. |
| 7,063,972 B2 | 6/2006 | Wilson et al. |
| 7,083,960 B2 | 8/2006 | Donnelly |
| 7,109,009 B2 | 9/2006 | Wilson et al. |
| 7,157,237 B2 | 1/2007 | Zhang et al. |
| 7,160,708 B2 | 1/2007 | Eirich et al. |
| 7,226,768 B2 | 6/2007 | Farinas et al. |
| 7,232,664 B2 | 6/2007 | Van Hoek et al. |
| 7,270,947 B2 | 9/2007 | Anderson et al. |
| 7,320,884 B2 | 1/2008 | Anderson et al. |
| 7,326,829 B1 | 2/2008 | Knerr |
| 7,388,084 B2 | 6/2008 | Wilson et al. |
| 7,405,063 B2 | 7/2008 | Eirich et al. |
| 7,670,823 B1 | 3/2010 | Hartley et al. |
| 7,799,545 B2 | 9/2010 | Burgard et al. |
| 8,133,704 B2 | 3/2012 | Baynes et al. |
| 8,158,391 B2 | 4/2012 | Gross |
| 8,241,879 B2 | 8/2012 | Picataggio et al. |
| 8,343,752 B2 | 1/2013 | Picataggio et al. |
| 2002/0007051 A1 | 1/2002 | Cheo et al. |
| 2002/0061566 A1 | 5/2002 | Eirich et al. |
| 2002/0127666 A1 | 9/2002 | Brzostowicz et al. |
| 2003/0049822 A1 | 3/2003 | Wilson et al. |
| 2003/0083373 A1 | 5/2003 | Tsien et al. |
| 2003/0087403 A1 | 5/2003 | Cheng et al. |
| 2003/0113886 A1 | 6/2003 | Brzostowicz et al. |
| 2003/0212946 A1 | 11/2003 | Kroger |
| 2003/0215930 A1 | 11/2003 | Chen et al. |
| 2004/0014198 A1 | 1/2004 | Craft |
| 2004/0053412 A1 | 3/2004 | Hartley et al. |
| 2004/0146999 A1 | 7/2004 | Fallon et al. |
| 2004/0265980 A1 | 12/2004 | Zhang et al. |
| 2005/0112590 A1 | 5/2005 | Van Den Boom et al. |
| 2005/0287592 A1 | 12/2005 | Kless |
| 2009/0098626 A1 | 4/2009 | Chang et al. |
| 2009/0305364 A1 | 12/2009 | Burgard et al. |
| 2010/0167361 A1 | 7/2010 | Craft et al. |
| 2010/0285545 A1 | 11/2010 | Gross et al. |
| 2010/0291653 A1 | 11/2010 | Ness et al. |
| 2011/0229945 A1 | 9/2011 | Jansen et al. |
| 2012/0021474 A1 | 1/2012 | Picataggio et al. |
| 2012/0077237 A1 | 3/2012 | Picataggio et al. |
| 2012/0077252 A1 | 3/2012 | Picataggio et al. |

FOREIGN PATENT DOCUMENTS

| | | |
|---|---|---|
| WO | WO 91/14781 | 10/1991 |
| WO | WO 96/19497 | 6/1996 |
| WO | WO 97/04083 | 2/1997 |
| WO | WO 97/42307 | 11/1997 |
| WO | WO 99/04014 | 1/1999 |
| WO | WO 99/21013 | 4/1999 |
| WO | WO 00/20620 | 4/2000 |
| WO | WO 01/04337 | 1/2001 |
| WO | WO 01/21572 | 3/2001 |
| WO | WO 02/08412 | 1/2002 |
| WO | WO 03/057896 | 7/2003 |
| WO | WO 2004/013336 | 2/2004 |
| WO | WO 2007/044688 | 4/2007 |
| WO | WO 2007/107256 | 9/2007 |
| WO | WO 2009/113853 | 9/2009 |
| WO | WO 2010/003728 | 1/2010 |
| WO | WO 2010/085712 | 7/2010 |
| WO | WO 2011/003034 | 1/2011 |
| WO | WO 2012/094425 | 7/2012 |
| WO | WO 2013/006730 | 1/2013 |
| WO | WO 2013/006733 | 1/2013 |
| WO | WO 2013/048898 | 4/2013 |

OTHER PUBLICATIONS

Thomas et al., "Biocatalysis applications and potentials for the chemical industry," Trends in Biotechnology, vol. 20, No. 6, Jun. 1, 2002, pp. 238-242.
Hitchman, "Hexanote Synthase, a Specialized Type I fatty Acid Synthase in Aflatoxin B1 Biosynthesis," Bioorganic Chemistry, vol. 20, No. 5, Oct. 1, 2001, pp. 293-307.
Coleman et al., "Biosynthesis of carbonic anhydrase in *Chlamydomonas reinharditii* during adaptation to low CO(2)" PNAS vol. 81, No. 19, Oct. 1, 1984 pp. 6049-6053.
Partial International Search Report dated: Nov. 6, 2012 in International Application No. PCT/US2012/045622 filed: Jul. 5, 2012.
Hara et al., "Repression of fatty-acyl-CoA oxidase-endoding gene expression is not necessarily a determinant of high-level production of dicarboxylic acids in industrial dicarboxylic-acid-producing *Candida tropicalis*," Applied Microbiology and Biotechnology, vol. 56, No. 3-4, Aug. 1, 2001 pp. 478-485.
Nandy et al, "Medium-Long-Chain Chimeric Human Acyl-CoA Dehydrogenase Medium-Chain Enzyme with the Active Center Base Arrangement of Long-Chain Acyl-CoA Dehydrogenase," Biochemistry, vol. 35, No. 38, Jan. 1, 1996, pp. 12402-12411.
Zeng et al., "Mutation of Tyr357 to Lys375 allows medium-chain acyl-CoA dehydrogenase to acquire acyl-CoA oxidase activity." Biochemica et Biophysica Acta (BBA) Proteins & Proteomics, Elsevier Netherlands, vol. 1774, No. 12, Dec. 1, 2007, pp. 1628-1634.
Arie et al., "Phylogenic identification of n-alkane assimilating *Candida* yeasts based on nucleotide divergence in the 59 end of LSU rDNA gene," The Journal of General and Applied Microbiology, vol. 46, No. 5, Oct. 1, 2000, pp. 257-262.
Kim et al., "Acyl-CoA dehrdrogenase and acyl-CoA oxidases. Structural basis for mechanistic similarities and differences," European Journal of Biochemistry, vol. 271, No. 3, Feb. 1, 2004, pp. 483-493.
International Search Report and Written Opinion dated: Jan. 30, 2013 in International Patent Application No. PCT/US2012/045615 filed, Jul. 5, 2012 and published as: WO/2013/006730 on: Jan. 10, 2013.
International Search Report and Written Opinion dated: Feb. 8, 2013 in International Patent Application No. PCT/US2012/045622 filed, Jul. 5, 2012 and published as: WO/2013/006733 on: Jan. 10, 2013.
International Search Report and Written Opinion dated: Mar. 23, 2013 in International Patent Application No. PCT/US2012/056562 filed, Sep. 21, 2012 and published as: WO/2013/048898 on: Apr. 4, 2013.
U.S. Appl. No. 60/587,583, filed Jul. 14, 2004, Wieslaw.
"Biosynthesis: Yeast yields plastic ingredient," Nature, Research Highlights, vol. 467, Iss. 7318, 887, Oct. 20, 2010.
"From field to plastic to biodiesel," Biodiesel Magazine, May 25, 2007.
"Latest Genomica Patents Enable Sustainable Nylon, Low-cost Chemicals," PR Newswire, Oct. 19, 2010.
Akbergenov et al., "ARC-1, a sequence element complementary to an internal 18S rRNA segment, enhances translation efficiency in plants when present in the leader or intercistronic region of mRNAs," Nucleic Acids Res. Jan. 12, 2004;32(1):239-47.
Alani et al., "A method for gene disruption that allows repeated use of URA3 selection in the construction of multiply disrupted yeast strains", Genetics 116(4):541-545 Aug. 1987.
Beretta et al., "Optimization of *Candida tropicalis* cytochrom P450alk gene expression in *Saccharomyces cerevisiae* with continuous cultures.," Appl Microbiol Biotechnol. Oct. 1991; 36(1):48-60.
Bertrand et al., "NADPH-Cytochrome c Reductase of *Candida tropicalis* Grown on Alkane," Eur. J. Biochem. 93, 237-243 (1979).
Capone et al., "Amber, ochre and opal suppressor tRNA genes derived from a human serine tRNA gene," EMBO J. Jan. 1985;4(1):213-221.

(56) References Cited

OTHER PUBLICATIONS

Cheng et al., "*Candida* yeast long chain fatty alcohol oxidase is a c-type haemoprotein and plays and important role in long chain fatty acid metabolism," Biochim Biophys Acta, Aug. 15, 2005, 1735(3):192-203.
Choi et al., "The *Saccharomyces cerevisiae* FAT Gene Encodes an Acey-CoA Synthetase That is Required for Maintenance of Very Long Chain Fatty Acid Levels," JBC (1999), 274: 4671-4683.
Craft et al., "Identification and characterization of the CYP450 Family of *Candida tropicalis* ATCC 20336, Important for the Conversion of Fatty Acids and Alkanes to α, ω-dicarboxylic acids," Applied and Environmental Microbiology, 2003, 69(10):5983-5991.
Current Protocols in Molecular Biology, John Wiley & Sons, N.Y., 6.3.1-6.3.6 (1989).
Duppel et al., "Properties of a Yeast Cytochrome P-450-Containing Enzyme System which Catalyzes the Hydroxilation of Fatty Acids, Alkanes and Drugs," Eur J. Biochem, 36, 583-592 (1973).
Durrett, Russell, "NYU—Poly researcher makes bioplastics from yeast," A Yeast Grown in Brooklyn, http://russellDurrett.com, Dec. 18, 2010.
Eggertsson, et al., (1988) Microbiological Review 52(3):354-374.
Eirich et al., "Cloning and characterization of three fatty alcohol oxidase genes from *Candida tropicalis* strain ATCC 20336," Appl Environ Microbiol. Aug. 2004;70(8):4872-4879.
Eschenfeldt et al., "Transformation of Fatty Acids Catalyzed by Cytochrome P450 Monooxygenase Enzymes of *Candida tropicalis*," Applied and Environmental Microbiology, Oct. 2003, 5992-5999.
Gallie, "The 5'-leader of tobacco mosaic virus promotes translation through enhanced recruitment of eIF4F," Nucleic Acids Research 30: 3401-3411 (2002).
Gallie, et al., "The 5'-leader sequence of tobacco mosaic virus RNA enhances the expression of foreign gene transcripts in vitro and in vivo," Nucleic Acids Res. Apr. 24, 1987;15(8):3257-3273.
Gilewicz et al., "Hyroxylase requlation in *Candida tropicalis* grown on alkanes," Can J Microbiol. Feb. 1979; 25(2):201-206.
Hill et al. "Studies on the formation of long-chain dicarboxylic acids from pure n-alkanes by mutant of *Candida tropicalis*," App Microbiol Biotechnol, 24:168-174 (1986).
Hill, Craig, "Automating nucleic acid amplification tests" IVD Technology Magazine, published Nov./Dec. 2000, downloaded from: http://www.devicelink.com/ivdt/archive/00/11/007.
Innis et al., "PCR Protocols: A Guide to Methods and Applications," eds, 1990.
Landy, A., "Mechanistic and structural complexity in the site-specific recombination pathways of Int and FLP," Curr Opin Genet Dev. Oct. 1993;3(5):699-707.
Lu et al., "Biosynthesis of Monomers for Plastics from Renewable Oils," JACS, 132, pp. 15451-15455, Oct. 11, 2010.
Masters, B.S.S., Williams, C.H., Kamin, H. (1967) Methods in Enzymology, X, 565-573).
Meyers & Miller, "Optimal alignments in linear space," CABIOS 4:11-17 (1989).
Mignone et al., "UTRdb and UTRsite: a collection of sequences and regulatory motifs of the untranslated regions of eukaryotic mRNAs," Nucleic Acids Research 33: D141-D146 (2005).
Mignone et al., Genome Biology 3(3): reviews 0004.1-0001.10 (2002).
Murakami et al., "Expression of Cloned Yeast NADPH-Cytochrome P450 Reductase Gene in *Saccharomyces cerevisiae*," J Biochem (1990) 108(5):859-865.
Nebert et al., "The P450 Superfamily: Recommended Nomenclature," DNA, vol. 6, No. 1, 1987, Mary Ann Liebert Inc Publishing, pp. 1-11.
Nebert et al., "The P450 Superfamily: Update on New Sequences, gene Mapping, and Recommended Nomenclature," DNA and Cell Biology, vol. 10, No. 1, 1991, Mary Ann Liebert, Inc. Publishers, pp. 1-14.
Nebert et al., "The P450 Superfamily: Updated Listing of All Genes and Reccomended Nomenclature for the Chromosomal Loci," DNA, vol. 8, No. 1, 1989, Mary Ann Liebert, Inc. Publishers, pp. 1-13.

Needleman & Wunsch, "A general method applicable to the search for similarities in the Amino Acid Sequence of two proteins." J. Mol. Biol. 48: 443-453 (1970).
Nelson et al., "Simultaneous detection of multiple nucleic acid targets in a homogeneous format," Biochemistry Jun. 25, 1996;35(25):8429-8438.
Ohkuma et al., "CYP52 (cytochrom P450alk) multigene family in *Candida maltosa*: molecular cloning and nucleotide sequence of the two tandemly arranged genes," DNA Cell Biol, May 1991; 10(4):271-282.
Osmundson et al., "Metabolic aspects of peroxisomal beta-oxidation," Biochim Biophis Acta, Sep. 11, 1991, 1085(2):141-158.
Papanikolaou, et al., "Lipid production by *Yarrowia lipolytica* growing on industrial glycerol in a single-stage continuous culture," Bioresour. Technol. 82(1):43-49 (2002).
Paulous et al., "Comparison of the capacity of different viral internal ribosome entry segments to direct translation initiation in poly(A)-dependent reticulocyte lysates," Nucleic Acids Research 31: 722-733 (2003).
Picataggio et al., "Determination of *Candida tropicalis* Acyl Coenzyme A Oxidase Isoenzyme Function by Sequential Gene Disruption," Molecular and Cellular Biology, vol. 11, No. 9, Sep. 1991, pp. 4333-4339.
Picataggio et al., "Metabolic engineering of *Candida tropicals* for the production of long-chain dicarboxylic acids," Biotechnology (NY), Aug. 1992; 10(8):894-898.
Sanglard et al., "Characterization of the alkane-inducable cytochrome P450 (P450alk) gene from the yeast *Candida Tropicalis*: identification of a new P450 gene family," Gene Mar. 15, 1989;76(1):121-136.
Sanglard et al., "Heterogenity within the alkane-inducible cytochrome P450 gene of the yeast *Candida tropicalis*," FEB Letters, Oct. 1989, vol. 256, No. 1,2, 128-134.
Sanglard et al., "Isolation of the Alkane Inducible Cytochrome P450(P450alk) Gene From the Yeast *Candida Tropicalis*," vol. 144, No. 1, Apr. 14, 1987, pp. 251-257.
Sanglard et al., "Metabolic Conditions Determining the Composition and Catalytic Activity of Cytochrom P-450 Monooxygenases in *Candida tropicalis*," Journal of Bacteriology, Jan. 1984, vol. 157, No. 1, p. 297-302.
Sanglard et al., "The distinction of different types of cytochromes P-450 from yeasts *Candida tropicalis* and *Saccharomyces uvarum*," Arch Biochem Biophys, Nov. 15, 1986, 251(1):276-286.
Sauer, B., "Site-specific recombination: developments and applications," Curr. Opin. Biotech. 5:521-527 (1994).
Seghezzi et al., "Characterization of a second alkane-inducible cytochrome P450-encoding gene, CYP52A2 from *Candida tropicalis*," Gene, Sep. 30, 1991;106(1):51-60.
Seghezzi et al., "Identification and characterization of additional members of the cytochrom p450 multigene family CYP52 of *Candida tropicalis*," DNA Cell Biol, Dec. 1992; 11(10):767-780.
Sekiguchi et al., "Requirements for noncovalent binding of vaccinia topoisomerase I to duplex DNA," Nucleic Acids Res. Dec. 11, 1994;22(24):5360-5365.
Shaloiko et al., "Effective non-viral leader for cap-independent translation in a eukaryotic cell-free system," Biotechnology and Bioengeneering, vol. 88, Iss. 6, pp. 730-739, Dec. 20, 2004.
Shimizu et al, "Enzymatic microdetermination of serum free fatty acids," Anal Biochem. Oct. 1, 1979;98(2):341-345.
Shuman, S., "Site-specific interaction of vaccinia virus topoisomerase I with duplex DNA. Minimal DNA substrate for strand cleavage in vitro," J Biol Chem. Jun. 15, 1991;266(17):11372-9.
Stahley et al., "Mechanism and specificity of DNA strand exchange catalyzed by vaccinia DNA topoisomerase type I." Biochemistry. Apr. 6, 2010;49(13):2786-95.
Stieglitz et al., "Novel microbial screen for detection of 1,4-butanediol, ethylene glycol, and adipic acid," Appl Environ Microbiol. Mar. 1985;49(3):593-8.
Sutter et al., "Isolation and Characterization of the Alkane-inducible NADPH-Cytochrome P-450 Oxidoreductase Gene from *Candida tropicalis*," The Journal of Biological Chemistry, vol. 265, No. 27, Sep. 27, 1990, pp. 16428-16436.

(56) References Cited

OTHER PUBLICATIONS

Tjalsma, et al., "Signal peptide-dependent protein transport in *Bacillus subtilis*: a genome-based survey of the secretome," Microbiol Mol Biol Rev. Sep. 2000;64(3):515-547.

Ueda et al., "Long-chain alcohol dehydrogenase of *Candida* yeast.," Methods Enzymol. 1990;188:171-175.

Ueda et al., "Long-chain aldehyde dehydrogenase of *Candida* yeast.," Methods Enzymol. 1990;188:176-178.

Vincent et al., "Helicase-dependent isothermal DNA amplification". EMBO reports 5 (8): 795-800 (2004).

Wang, L., "Expanding the Genetic Code of *Escherichia coli*," Honorable Mention Essay from IUPAC Prize for Young Chemists, 2003.

Watanabe et al., "Initial characterization of a type I fatty acid synthase and polyketide synthase multienzyme complex NorS in the biosynthesis of aflatoxin B(1)," Chem Biol. Sep. 2002;9(9):981-8.

Yamada et al., "Assay of fatty acid omega-hydroxylation using high-performance liquid chromatography with fluorescence labeling reagent, 3-bromomethy1-7-methoxy-1,4-benzoxazin-2-one (BrMB)," 1991, AnalBiochem 199: 132-136.

Zimmer et al., "Mutual conversion of fatty-acid substrate specificity by a single amino-acid exchange at position 527 in P-450Cm2 and P-450Alk3A," Eur J. Biochem, 256, 398-403 (1998).

Zimmer et al., "Relationship between evolutionary distance and enzymatic distance and enzymatic properties among the members of the CYP52A subfamily of *Candida maltosa*," BiochemBiophys Res Commun, Oct. 9, 1989;251(1):244-247.

Zimmer et al., "The CYP450 multigene family of *Candida maltosa* encodes functionally diverse n-alkane-inducable cytochrome P450," Biochem Biophys Res Comm. Jul. 25, 1996; 224(3)784-789.

Office action mailed: Mar. 14, 2012 in U.S. Appl. No. 13/245,780, filed Sep. 26, 2011 and published as: 2012/077252 on Mar. 29, 2012.

Office action mailed: Mar. 13, 2012 in U.S. Appl. No. 13/245,782, filed Sep. 26, 2011 and published as: 2012/0077237 on Mar. 29, 2012.

Office action mailed: Jun. 4, 2012 in U.S. Appl. No. 13/245,777, filed Sep. 26, 2011 and published as: 2012/0021474 on Jan. 26, 2012.

Office action mailed: Nov. 23, 2011 in U.S. Appl. No. 13/245,777, filed Sep. 26, 2011 and published as: 2012/0021474 on Jan. 26, 2012.

Plasmid diagram for inserting Aspergillus hexanoate synthase gene into C. tropicalis or Y. lipolytica.

Plasmid diagram for inserting heterologous cytochrome p450 gene into C. tropicalis or Y. lipolytica.

Plasmid diagram for inserting heterologous cytochrome p450 gene into
A. parasiticus or A. nidulans ble=bleomycin.

SEQUENCE LISTING

```
<160> NUMBER OF SEQ ID NOS: 328

<210> SEQ ID NO 1
<211> LENGTH: 2115
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atggctccat ttttgcccga ccaggtcgac tacaaacacg tcgacaccct tatgttatta      60
tgtgacggga tcatccacga aaccaccgtc gaccaaatca aagacgttat tgctcctgac     120
ttccctgctg acaagtacga agagtacgtc aggacattca ccaaaccctc cgaaacccca     180
gggttcaggg aaaccgtcta caacacagtc aacgcaaaca ccacggacgc aatccaccag     240
ttcattatct tgaccaatgt tttggcatcc agggtcttgg ctccagcttt gaccaactcg     300
```

-continued

```
ttgacgccta tcaaggacat gagcttggaa gaccgtgaaa aattgttggc ctcgtggcgc      360
gactccccaa tcgctgccaa aaggaagttg ttcaggttgg tttctacgct taccttggtc      420
acgttcacga gattggccaa tgagttgcat ttgaaagcca ttcattatcc aggaagagaa      480
gaccgtgaaa aggcttatga aacccaggag attgacccct ttaagtacca gttttggaa       540 aaaccgaagt tttacggcgc tgagttgtac ttgccagata ttgatgtgat cattattgga      600
tctggtgccg gtgctggtgt tgtggcccac actttggcca acgatggctt caagagtttg      660
gttttggaaa agggcaaata ctttagcaac tccgagttga actttgatga caaggacggc      720
gttcaagaat tataccaaag tggaggtact ttgactacag tcaaccaaca gttgtttgtt      780
cttgctggtt ccacttttgg tggcggtacc actgtcaatt ggtcagcctg tcttaagacg      840
ccattcaagg tgcgtaagga atggtatgat gagtttggtg ttgactttgc tgctgatgaa      900
gcatacgata aagcgcagga ttatgtttgg cagcaaatgg gagcttctac cgaaggcatc      960
acccactctt tggctaacga gattattatt gaaggtggta agaaattagg ttacaaggcc     1020
aaggtattag accaaaacag cggtggtcat cctcagcaca gatgcggttt ctgttatttg     1080
ggctgtaagc acggtatcaa gcagggttct gttaataact ggtttagaga cgcagctgcc     1140
cacggttccc agttcatgca acaggttaga gttttgcaaa tacttaacaa gaaggggatc     1200
gcttacggta tcttgtgtga ggatgttgta accggcgcca agttcaccat tactggcccc     1260
aaaaagtttg ttgttgctgc cggtgctttg aacactccat ctgtgttggt caactccggc     1320
ttcaagaaca agaacatcgg taagaactta actttgcacc cagtttctgt cgtgtttggt     1380
gattttggca aagacgttca agcagaccac ttccacaact ccatcatgac tgcccttgt     1440 tcagaagccg ctgatttaga cggcaagggc catggatgca gaattgaaac catcttgaac     1500
gctccattca tccaggcttc attcttacca tggagaggta gtaacgaggc tagacgagac     1560
ttgttgcgtt acaacaacat ggtggcgatg ttgctcctta gtcgtgacac caccagtggt     1620
tccgtttctg ctcatccaac caaacctgaa gctttggttg tcgagtacga cgtgaacaag     1680
tttgacagaa actcgatctt gcaggcattg ttggtcactg ctgacttgtt gtatatccaa     1740
ggtgccaaga gaatccttag tccacaggca tgggtgccaa ttttgaatc cgacaagcca      1800 aaggataaga gatcaatcaa ggacgaggac tatgtcgaat ggagagccaa ggttgccaag     1860 attccttttcg acacctacgg ctcaccttat ggttcggcac atcaaatgtc ttcttgccgt     1920
atgtcaggta agggtcctaa atacggtgct gttgacaccg atggtagatt gtttgaatgt     1980
tcgaatgttt atgttgccga tgcaagtctt ttgccaactg caagcggtgc caaccctatg     2040
gtcaccacca tgactcttgc cagacatgtt gcgttaggtt tggcagactc cttgaagacc     2100
aaagccaagt tgtag                                                      2115
```

<210> SEQ ID NO 2
<211> LENGTH: 2115
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2

```
atggctccat ttttgcccga ccaggtcgac tacaaacacg tcgacaccct tatgttatta       60
tgtgacggga tcatccacga aaccaccgtg gacgaaatca aagacgtcat tgcccctgac      120
ttccccgccg acaaatacga ggagtacgtc aggacattca ccaaaccctc cgaaaccca       180
```

```
gggttcaggg aaaccgtcta caacaccgtc aacgcaaaca ccatggatgc aatccaccag    240
ttcattatct tgaccaatgt tttgggatca agggtcttgg caccagcttt gaccaactcg    300
ttgactccta tcaaggacat gagcttggaa gaccgtgaaa agttgttagc ctcgtggcgt    360 gactcccta ttgctgctaa aaggaagttg ttcaggttgg tttctacgct taccttggtc    420
acgttcacga gattggccaa tgagttgcat ttgaaagcca ttcattatcc aggaagagaa    480
gaccgtgaaa aggcttatga aacccaggag attgacccctt ttaagtacca gttttggaa    540 aaaccgaagt tttacggcgc tgagttgtac ttgccagata ttgatgtgat cattattgga    600
tctggtgccg gtgctggtgt tgtggcccac actttggcca acgatggctt caagagtttg    660
gttttggaaa agggcaaata ctttagcaac tccgagttga actttgatga caaggacggc    720
gttcaagaat ataccaaagt tggaggtact ttgactacag tcaaccaaca gttgtttgtt    780
cttgctggtt ccactttttgg tggcggtacc actgtcaatt ggtcagcctg tcttaagacg    840
ccattcaagg tgcgtaagga atggtatgat gagtttggtg ttgactttgc tgctgatgaa    900
gcatacgata aagcgcagga ttatgtttgg cagcaaatgg gagcttctac cgaaggcatc    960
acccactctt tggctaacga gattattatt gaaggtggta agaaattagg ttacaaggcc    1020
aaggtattag accaaaacag cggtggtcat cctcagcaca gatgcggttt ctgttatttg    1080
ggttgtaagc acggtatcaa gcagggctct gttaataact ggtttagaga cgcagctgcc    1140
cacggttctc agttcatgca acaggttaga gttttgcaaa tccttaacaa gaagggcatc    1200
gcttatggta tcttgtgtga ggatgttgta accggtgcca agttcaccat tactggcccc    1260
aaaaagtttg ttgttgccgc cggcgcctta aacactccat ctgtgttggt caactccgga    1320
ttcaagaaca gaacatcgg taagaactta actttgcatc cagtttctgt cgtgtttggt    1380
gattttggca aagacgttca agcagaccac ttccacaact ccatcatgac tgcccttttgt    1440 tcagaagccg ctgatttaga cggcaagggc catggatgca gaattgaaac catcttgaac    1500
gctccattca tccaggcttc attcttacca tggagaggta gtaacgaggc tagacgagac    1560
ttgttgcgtt acaacaacat ggtggcgatg ttgctcctta gtcgtgacac caccagtggt    1620
tccgtttctg ctcatccaac caaacctgaa gctttggttg tcgagtacga cgtgaacaag    1680
tttgacagaa actcgatctt gcaggcattg ttggtcactg ctgacttgtt gtatatccaa    1740
ggtgccaaga gaatccttag tccacaggca tgggtgccaa ttttttgaatc cgacaagcca    1800 aaggataaga gatcaatcaa ggacgaggac tatgtcgaat ggagagccaa ggttgccaag    1860
attcctttcg acacctacgg ctcacctat tggttcggcac atcaaatgtc ttcttgccgt    1920
atgtcaggta agggtcctaa atacggtgct gttgacaccg atggtagatt gtttgaatgt    1980
tcgaatgttt atgttgccga tgcaagtctt ttgccaactg caagcggtgc caaccctatg    2040
gtcaccacca tgactcttgc aagacatgtt gcgttaggtt tggcagactc cttgaagacc    2100
aaggccaagt tgtag                                                   2115
```

<210> SEQ ID NO 3
<211> LENGTH: 2115
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
atggctccat ttttgcccga ccaggtcgac tacaaacacg tcgacaccct tatgttatta    60
```

```
tgtgacggga tcatccacga aaccaccgtc gaccaaatca aagacgttat tgctcctgac      120
ttccctgctg acaagtacga agagtacgtc aggacattca ccaaaccctc cgaaacccca      180
gggttcaggg aaaccgtcta caacacagtc aacgcaaaca ccacggacgc aatccaccag      240
ttcattatct tgaccaatgt tttggcatcc agggtcttgg ctccagcttt gaccaactcg      300
ttgacgccta tcaaggacat gagcttggaa gaccgtgaaa aattgttggc ctcgtggcgc      360
gactccccaa tcgctgccaa aaggaaattg ttcaggttgg tttccacgct taccttggtt      420
actttcacga gattggccaa tgagttgcat ttgaaagcca ttcactatcc aggaagagaa      480
gaccgtgaaa aggcttatga aacccaggag attgaccctt tcaagtacca gtttatggaa      540
aagccaaagt ttgacggcgc tgagttgtac ttgccagata ttgatgttat cattattgga      600
tctggtgccg gtgctggtgt tgtggcccac actttggcca acgatggctt caagagtttg      660
gttttggaaa agggcaaata ctttagcaac tccgagttga actttgatga caaggacggc      720
gttcaagaat ataccaaagt ggaggtact ttgactacag tcaaccaaca gttgtttgtt      780
cttgctggtt ccactttttgg tggcggtacc actgtcaatt ggtcagcctg tcttaagacg      840
ccattcaagg tgcgtaagga atggtatgat gagtttggtg ttgactttgc tgctgatgaa      900
gcatacgata aagcgcagga ttatgtttgg cagcaaatgg gagcttctac cgaaggcatc      960
acccactctt tggctaacga gattattatt gaaggtggta agaaattagg ttacaaggcc     1020
aaggtattag accaaaacag cggtggtcat cctcagcaca gatgcggttt ctgttatttg     1080
ggctgtaagc acggtatcaa gcagggttct gttaataact ggtttagaga cgcagctgcc     1140
cacggttccc agttcatgca acaggttaga gttttgcaaa tacttaacaa gaaggggatc     1200
gcttacggta tcttgtgtga ggatgttgta accggcgcca gttcaccat tactggcccc      1260 aaaaagtttg ttgttgctgc cggtgctttg aacactccat ctgtgttggt caactccggc     1320
ttcaagaaca agaacatcgg taagaactta actttgcacc cagtttctgt cgtgtttggt     1380
gattttggca aagacgttca agcagaccac ttccacaact ccatcatgac tgcccttttgt    1440 tcagaagccg ctgatttaga cggcaagggc catggatgca gaattgaaac catcttgaac     1500
gctccattca tccaggcttc attcttacca tggagaggta gtaacgaggc tagacgagac     1560
ttgttgcgtt acaacaacat ggtggcgatg ttgctcctta gtcgtgacac caccagtggt     1620
tccgtttctg ctcatccaac caaacctgaa gctttggttg tcgagtacga cgtgaacaag     1680
tttgacagaa actcgatctt gcaggcattg ttggtcactg ctgacttgtt gtatatccaa     1740
ggtgccaaga gaatccttag tccacaggca tgggtgccaa ttttttgaatc cgacaagcca    1800 aaggataaga gatcaatcaa ggacgaggac tatgtcgaat ggagagccaa ggttgccaag     1860
attcctttcg acacctacgg ctcacctat ggttcggcac atcaaatgtc ttcttgccgt      1920
atgtcaggta agggtcctaa atacggtgct gttgacaccg atggtagatt gtttgaatgt     1980
tcgaatgttt atgttgccga tgcaagtctt ttgccaactg caagcggtgc caaccctatg     2040
gtcaccacca tgactcttgc cagacatgtt gcgttaggtt tggcagactc cttgaagacc     2100
aaagccaagt tgtag                                                      2115
```

<210> SEQ ID NO 4
<211> LENGTH: 2115
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

```
atgaataccT tcttgccaga cgtgctcgaa tacaaacacg tcgacaccct tttgttattg      60
tgtgacggga tcatccacga aaccacagtc gatcagatca aggacgccat tgctcccgac     120
ttccctgagg accagtacga ggagtatctc aagaccttca ccaagccatc tgagacccct     180
gggttcagag aagccgtcta cgacacgatc aacgccaccc caaccgatgc cgtgcacatg     240
tgtattgtct tgaccaccgc attggactcc agaatcttgg cccccacgtt gaccaactcg     300
ttgacgccta tcaaggatat gaccttgaag gagcgtgaac aattgttggc ctcttggcgt     360
gattccccga ttgcggcaaa gagaagattg ttcagattga tttcctcgct taccttgacg     420
acgtttacga gattggccag cgaattgcac ttgaaagcca tccactaccc tggcagagac     480
ttgcgtgaaa aggcgtatga aacccaggtg gttgacccTT tcaggtacct gtttatggag     540
aaaccaaagt tgacggcgc cgaattgtac ttgccagata tcgacgtcat catcattgga     600
tcaggcgccg gtgctggtgt catggcccac actctcgcca acgacgggtt caagaccttg     660
gttttggaaa agggaaagta tttcagcaac tccgagttga actttaatga cgctgatggc     720
gtgaaagagt gtaccaagg taaaggtgct ttggccacca ccaatcagca gatgtttatt     780
cttgccggtt ccactttggg cggtggtacc actgtcaact ggtctgcttg ccttaaaaca     840
ccatttaaag tgcgtaagga gtggtacgac gagtttggtc ttgaatttgc tgccgatgaa     900
gcctacgaca aagcgcagga ttatgtttgg aaacaaatgg gtgcttcaac agatggaatc     960
actcactcct tggccaacga agttgtggtt gaaggaggta agaagttggg ctacaagagc    1020
aaggaaattg agcagaacaa cggtggccac cctgaccacc catgtggttt ctgttacttg    1080
ggctgtaagt acggtattaa acagggttct gtgaataact ggtttagaga cgcagctgcc    1140
cacgggtcca agttcatgca acaagtcaga gttgtgcaaa tcctcaacaa gaatggcgtc    1200
gcttatggta tcttgtgtga ggatgtcgaa accggagtca ggttcactat tagtggcccc    1260
aaaaagtttg ttgtttctgc tggttctttg aacacgccaa ctgtgttgac caactccgga    1320
ttcaagaaca agcacattgg taagaacttg acgttgcacc cagtttccac cgtgtttggt    1380
gactttggca gagacgtgca agccgaccat ttccacaaat ctattatgac ttcgctttgt    1440
tacgaggttg ctgacttgga cggcaagggc cacggatgca gaatcgaaac catcttgaac    1500
gctccattca tccaagcttc tttgttgcca tggagaggaa gtgacgaggt cagaagagac    1560
ttgttgcgtt acaacaacat ggtggccatg ttgcttatca cgcgtgatac caccagtggt    1620
tcagtttctg ctgacccaaa gaagcccgac gctttgattg tcgactatga gattaacaag    1680
tttgacaaga atgccatctt gcaagctttc ttgatcactt ccgacatgtt gtacattgaa    1740
ggtgccaaga gaatcctcag tccacagcca tgggtgccaa tctttgagtc gaacaagcca    1800
aaggagcaaa gaacgatcaa ggacaaggac tatgttgagt ggagagccaa ggctgctaag    1860
atacctttcg acacctacgg ttctgcatat ggtccgcac atcaaatgtc cacctgtcgt    1920
atgtccggaa agggtcctaa atacggtgct gttgatactg atggtagatt gtttgaatgt    1980
tcgaatgtct atgttgctga tgctagtgtt ttgcctactg ccagcggtgc caacccaatg    2040
atatccacca tgacctttgc tagacagatt gcgttaggtt ggctgactc cttgaagacc    2100
aaacccaagt tgtag                                                    2115
```

<210> SEQ ID NO 5
<211> LENGTH: 2115
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 5

```
atgaataect tcttgccaga cgtgctcgaa tacaaacacg tcgatacct tttgttatta      60
tgtgacggga tcatccacga aaccacagtc gaccagatca gggacgccat tgctcccgac    120
ttccctgaag accagtacga ggagtatctc aagaccttca ccaagccatc tgagacccct    180
gggttcagag aagccgtcta cgacacgatc aacagcaccc caaccgaggc tgtgcacatg    240
tgtattgtat tgaccaccgc attggactcg agaatcttgg cccccacgtt gaccaactcg    300
ttgacgccta tcaaggatat gaccttgaaa gagcgtgaac aattgttggc tgcctggcgt    360
gattccccga tcgcggccaa gagaagattg ttcagattga tttcctcact taccttgacg    420
acctttacga gattggccag cgacttgcac ttgagagcca tccactaccc tggcagagac    480
ttgcgtgaaa aggcatatga aacccaggtg gttgacccctt tcaggtacct gtttatggaa    540
aaaccaaagt ttgacggcac cgagttgtac ttgccagata tcgacgtcat catcattgga    600
tccggtgccg gtgctggtgt catggcccac actttagcca acgacgggta caagaccttg    660
gttttggaaa agggaaagta tttcagcaac tccgagttga actttaatga tgccgatggt    720
atgaaagagt gtaccaagg taaatgtgcg ttgaccacca cgaaccagca gatgtttatt    780
cttgccggtt ccactttggg cggtggtacc actgttaact ggtctgcttg tcttaaaaca    840
ccatttaaag tgcgtaagga gtggtacgac gagtttggtc ttgaatttgc tgccgacgaa    900
gcctacgaca aagcacaaga ctatgtttgg aaacaaatgg gcgcttctac cgaaggaatc    960
actcactctt tggcgaacgc ggttgtggtt gaaggaggta agaagttggg ttacaagagc   1020
aaggaaatcg agcagaacaa tggtggccat cctgaccacc cctgtggttt ctgttacttg   1080
ggctgtaagt acggtattaa gcagggttct gtgaataact ggtttagaga cgcagctgcc   1140
cacgggtcca agttcatgca acaagtcaga gttgtgcaaa tcctccacaa taaaggcgtc   1200
gcttatggca tcttgtgtga ggatgtcgag accggagtca aattcactat cagtggcccc   1260
aaaaagtttg ttgtttctgc aggttctttg aacacgccaa cggtgttgac caactccgga   1320
ttcaagaaca aacacatcgg taagaacttg acgttgcacc cagtttcgac cgtgtttggt   1380
gactttggca gagacgtgca agccgaccat ttccacaaat ctattatgac ttcgctctgt   1440
tacgaagtcg ctgacttgga cggcaagggc cacggatgca gaatcgagac catcttgaac   1500
gctccattca tccaagcttc tttgttgcca tggagaggaa gcgacgaggt cagaagagac   1560
ttgttgcgtt acaacaacat ggtggccatg ttgcttatca cccgtgacac caccagtggt   1620
tcagtttctg ctgacccaaa gaagcccgac gctttgattg tcgactatga catcaacaag   1680
tttgacaaga atgccatctt gcaagctttc ttgatcacct ccgacatgtt gtacatcgaa   1740
ggtgccaaga gaatcctcag tccacaggca tgggtgccaa tctttgagtc gaacaagcca   1800
aaggagcaaa gaacaatcaa ggacaaggac tatgtcgaat ggagagccaa ggctgccaag   1860
atacctttcg acacctacgg ttctgcctat gggtccgcac atcaaatgtc cacctgtcgt   1920
atgtccggaa agggtcctaa atacggcgcc gttgataccg atggtagatt gtttgaatgt   1980
tcgaatgtct atgttgctga tgctagtgtt ttgcctactg ccagcggtgc caacccaatg   2040
atctccacca tgcgtttgc tagacagatt gcgttaggtt tggctgactc tttgaagacc   2100
aaacccaagt tgtag                                                    2115
```

<210> SEQ ID NO 6
<211> LENGTH: 2115
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

```
atggctccat ttttgcccga ccaggtcgac tacaaacacg tcgacaccct tatgttatta        60
tgtgacggga tcatccacga aaccaccgtg gacgaaatca agacgtcat tgcccctgac       120
ttccccgccg acaaatacga ggagtacgtc aggacattcc ccaaaccctc cgaaacccca       180
gggttcaggg aaaccgtcta caacaccgtc aacgcaaaca ccatggatgc aatccaccag       240
ttcattatct tgaccaatgt tttgggatca agggtcttgg caccagcttt gaccaactcg       300
ttgactccta tcaaggacat gagcttggaa gaccgtgaaa agttgttagc ctcgtggcgt       360
gactcccta ttgctgctaa aaggaagttg ttcaggttgg tttctacgct taccttggtc       420
acgttcacga gattggccaa tgagttgcat ttgaaagcca ttcattatcc aggaagagaa       480
gaccgtgaaa aggcttatga aacccaggag attgacccct ttaagtacca gttttttggaa      540
aaaccgaagt tttacggcgc tgagttgtac ttgccagata ttgatgtgat cattattgga       600
tctggggccg gtgctggtgt cgtggcccac actttgacca acgacggctt caagagtttg       660
gttttggaaa agggcagata cttagcaac tccgagttga cttttgatga caaggacggg        720
gttcaagaat tataccaaag tggaggtact ttgaccaccg tcaaccagca gttgtttgtt       780
cttgctggtt ccactttggg tggtggtacc actgtcaatt ggtcggcctg tcttaaaacg       840
ccattcaagg tgcgtaagga atggtatgat gagtttggcg ttgactttgc tgccgatgaa       900
gcctacgaca aagcacagga ttatgtttgg cagcaaatgg gagcttctac cgaaggcatc       960
acccactctt tggctaacga gattattatt gaaggtggca agaaattagg ttacaaggcc      1020
aaggtattag accaaaacag cggtggtcat cctcatcaca gatgcggttt ctgttatttg      1080
ggttgtaagc acggtatcaa gcagggctct gttaataact ggtttagaga cgcagctgcc      1140
cacggttctc agttcatgca acaggttaga gttttgcaaa tccttaacaa gaagggcatc      1200
gcttatggta tcttgtgtga ggatgttgta accggtgcca agttcaccat tactggcccc      1260
aaaaagtttg ttgttgccgc cggcgcctta aacactccat ctgtgttggt caactccgga      1320
ttcaagaaca gaacatcgg taagaactta actttgcatc cagtttctgt cgtgtttggt      1380
gattttggca agacgttca gcagatcac ttccacaact ccatcatgac tgctctttgt       1440
tcagaagccg ctgatttaga cggcaagggt catggatgca gaattgaaac catcttgaac      1500
gctccattca tccaggcttc attcttacca tggagaggta gtaacgaggc tagacgagac      1560
ttgttgcgtt acaacaacat ggtggccatg ttacttctta gtcgtgatac caccagtggt      1620
tccgtttcgt cccatccaac taaacctgaa gcattagttg tcgagtacga cgtgaacaag      1680
tttgacagaa actccatctt gcaggcattg ttggtcactg ctgacttgtt gtacattcaa      1740
ggtgccaaga gaatccttag tccccaacca tgggtgccaa ttttgaatc cgacaagcca       1800
aaggataaga gatcaatcaa ggacgaggac tatgtcgaat ggagagccaa ggttgccaag      1860
attccttttg acacctacgg ctcgccttat ggttcggcgc atcaaatgtc ttcttgtcgt      1920
atgtcaggta agggtcctaa atacggtgct gttgataccg atggtagatt gttttgaatgt      1980
tcgaatgttt atgttgctga cgctagtctt ttgccaactg ctagcggtgc taatcctatg      2040
```

```
gtcaccacca tgactcttgc aagacatgtt gcgttaggtt tggcagactc cttgaagacc    2100
aaggccaagt tgtag                                                    2115
```

<210> SEQ ID NO 7
<211> LENGTH: 704
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Ala Pro Phe Leu Pro Asp Gln Val Asp Tyr Lys His Val Asp Thr
1               5                   10                  15

Leu Met Leu Leu Cys Asp Gly Ile Ile His Glu Thr Thr Val Asp Glu
                20                  25                  30

Ile Lys Asp Val Ile Ala Pro Asp Phe Pro Ala Asp Lys Tyr Glu Glu
            35                  40                  45

Tyr Val Arg Thr Phe Thr Lys Pro Ser Glu Thr Pro Gly Phe Arg Glu
50                  55                  60

Thr Val Tyr Asn Thr Val Asn Ala Asn Thr Met Asp Ala Ile His Gln
65                  70                  75                  80

Phe Ile Ile Leu Thr Asn Val Leu Gly Ser Arg Val Leu Ala Pro Ala
                85                  90                  95

Leu Thr Asn Ser Leu Thr Pro Ile Lys Asp Met Ser Leu Glu Asp Arg
                100                 105                 110

Glu Lys Leu Leu Ala Ser Trp Arg Asp Ser Pro Ile Ala Ala Lys Arg
            115                 120                 125

Lys Leu Phe Arg Leu Val Ser Thr Leu Thr Leu Val Thr Phe Thr Arg
130                 135                 140

Leu Ala Asn Glu Leu His Leu Lys Ala Ile His Tyr Pro Gly Arg Glu
145                 150                 155                 160

Asp Arg Glu Lys Ala Tyr Glu Thr Gln Glu Ile Asp Pro Phe Lys Tyr
                165                 170                 175

Gln Phe Leu Glu Lys Pro Lys Phe Tyr Gly Ala Glu Leu Tyr Leu Pro
            180                 185                 190

Asp Ile Asp Val Ile Ile Gly Ser Gly Ala Gly Ala Gly Val Val
            195                 200                 205

Ala His Thr Leu Thr Asn Asp Gly Phe Lys Ser Leu Val Leu Glu Lys
210                 215                 220

Gly Arg Tyr Phe Ser Asn Ser Glu Leu Asn Phe Asp Asp Lys Asp Gly
225                 230                 235                 240

Val Gln Glu Leu Tyr Gln Ser Gly Gly Thr Leu Thr Thr Val Asn Gln
                245                 250                 255

Gln Leu Phe Val Leu Ala Gly Ser Thr Phe Gly Gly Gly Thr Thr Val
            260                 265                 270

Asn Trp Ser Ala Cys Leu Lys Thr Pro Phe Lys Val Arg Lys Glu Trp
            275                 280                 285

Tyr Asp Glu Phe Gly Val Asp Phe Ala Ala Asp Glu Ala Tyr Asp Lys
290                 295                 300

Ala Gln Asp Tyr Val Trp Gln Gln Met Gly Ala Ser Thr Glu Gly Ile
305                 310                 315                 320

Thr His Ser Leu Ala Asn Glu Ile Ile Ile Glu Gly Gly Lys Lys Leu
                325                 330                 335

Gly Tyr Lys Ala Lys Val Leu Asp Gln Asn Ser Gly Gly His Pro His

```
                340                 345                 350
His Arg Cys Gly Phe Cys Tyr Leu Gly Cys Lys His Gly Ile Lys Gln
            355                 360                 365

Gly Ser Val Asn Asn Trp Phe Arg Asp Ala Ala His Gly Ser Gln
    370                 375                 380

Phe Met Gln Gln Val Arg Val Leu Gln Ile Leu Asn Lys Lys Gly Ile
385                 390                 395                 400

Ala Tyr Gly Ile Leu Cys Glu Asp Val Val Thr Gly Ala Lys Phe Thr
            405                 410                 415

Ile Thr Gly Pro Lys Lys Phe Val Ala Ala Gly Ala Leu Asn Thr
            420                 425                 430

Pro Ser Val Leu Val Asn Ser Gly Phe Lys Asn Lys Asn Ile Gly Lys
            435                 440                 445

Asn Leu Thr Leu His Pro Val Ser Val Val Phe Gly Asp Phe Gly Lys
    450                 455                 460

Asp Val Gln Ala Asp His Phe His Asn Ser Ile Met Thr Ala Leu Cys
465                 470                 475                 480

Ser Glu Ala Ala Asp Leu Asp Gly Lys Gly His Gly Cys Arg Ile Glu
            485                 490                 495

Thr Ile Leu Asn Ala Pro Phe Ile Gln Ala Ser Phe Leu Pro Trp Arg
            500                 505                 510

Gly Ser Asn Glu Ala Arg Arg Asp Leu Leu Arg Tyr Asn Asn Met Val
            515                 520                 525

Ala Met Leu Leu Leu Ser Arg Asp Thr Thr Ser Gly Ser Val Ser Ser
            530                 535                 540

His Pro Thr Lys Pro Glu Ala Leu Val Val Glu Tyr Asp Val Asn Lys
545                 550                 555                 560

Phe Asp Arg Asn Ser Ile Leu Gln Ala Leu Leu Val Thr Ala Asp Leu
            565                 570                 575

Leu Tyr Ile Gln Gly Ala Lys Arg Ile Leu Ser Pro Gln Pro Trp Val
            580                 585                 590

Pro Ile Phe Glu Ser Asp Lys Pro Lys Asp Lys Arg Ser Ile Lys Asp
            595                 600                 605

Glu Asp Tyr Val Glu Trp Arg Ala Lys Val Ala Lys Ile Pro Phe Asp
            610                 615                 620

Thr Tyr Gly Ser Pro Tyr Gly Ser Ala His Gln Met Ser Ser Cys Arg
625                 630                 635                 640

Met Ser Gly Lys Gly Pro Lys Tyr Gly Ala Val Asp Thr Asp Gly Arg
            645                 650                 655

Leu Phe Glu Cys Ser Asn Val Tyr Val Ala Asp Ala Ser Leu Leu Pro
            660                 665                 670

Thr Ala Ser Gly Ala Asn Pro Met Val Thr Thr Met Thr Leu Ala Arg
            675                 680                 685

His Val Ala Leu Gly Leu Ala Asp Ser Leu Lys Thr Lys Ala Lys Leu
            690                 695                 700

<210> SEQ ID NO 8
<211> LENGTH: 704
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8
```

```
Met Ala Pro Phe Leu Pro Asp Gln Val Asp Tyr Lys His Val Asp Thr
1               5                   10                  15

Leu Met Leu Leu Cys Asp Gly Ile Ile His Glu Thr Thr Val Asp Gln
            20                  25                  30

Ile Lys Asp Val Ile Ala Pro Asp Phe Pro Ala Asp Lys Tyr Glu Glu
        35                  40                  45

Tyr Val Arg Thr Phe Thr Lys Pro Ser Glu Thr Pro Gly Phe Arg Glu
    50                  55                  60

Thr Val Tyr Asn Thr Val Asn Ala Asn Thr Thr Asp Ala Ile His Gln
65                  70                  75                  80

Phe Ile Ile Leu Thr Asn Val Leu Ala Ser Arg Val Leu Ala Pro Ala
                85                  90                  95

Leu Thr Asn Ser Leu Thr Pro Ile Lys Asp Met Ser Leu Glu Asp Arg
            100                 105                 110

Glu Lys Leu Leu Ala Ser Trp Arg Asp Ser Pro Ile Ala Ala Lys Arg
        115                 120                 125

Lys Leu Phe Arg Leu Val Ser Thr Leu Thr Leu Val Thr Phe Thr Arg
    130                 135                 140

Leu Ala Asn Glu Leu His Leu Lys Ala Ile His Tyr Pro Gly Arg Glu
145                 150                 155                 160

Asp Arg Glu Lys Ala Tyr Glu Thr Gln Glu Ile Asp Pro Phe Lys Tyr
                165                 170                 175

Gln Phe Leu Glu Lys Pro Lys Phe Tyr Gly Ala Glu Leu Tyr Leu Pro
            180                 185                 190

Asp Ile Asp Val Ile Ile Gly Ser Gly Ala Gly Ala Gly Val Val
                195                 200                 205

Ala His Thr Leu Ala Asn Asp Gly Phe Lys Ser Leu Val Leu Glu Lys
210                 215                 220

Gly Lys Tyr Phe Ser Asn Ser Glu Leu Asn Phe Asp Asp Lys Asp Gly
225                 230                 235                 240

Val Gln Glu Leu Tyr Gln Ser Gly Gly Thr Leu Thr Thr Val Asn Gln
            245                 250                 255

Gln Leu Phe Val Leu Ala Gly Ser Thr Phe Gly Gly Gly Thr Thr Val
            260                 265                 270

Asn Trp Ser Ala Cys Leu Lys Thr Pro Phe Lys Val Arg Lys Glu Trp
        275                 280                 285

Tyr Asp Glu Phe Gly Val Asp Phe Ala Ala Asp Glu Ala Tyr Asp Lys
    290                 295                 300

Ala Gln Asp Tyr Val Trp Gln Gln Met Gly Ala Ser Thr Glu Gly Ile
305                 310                 315                 320

Thr His Ser Leu Ala Asn Glu Ile Ile Ile Glu Gly Gly Lys Lys Leu
                325                 330                 335

Gly Tyr Lys Ala Lys Val Leu Asp Gln Asn Ser Gly Gly His Pro Gln
            340                 345                 350

His Arg Cys Gly Phe Cys Tyr Leu Gly Cys Lys His Gly Ile Lys Gln
        355                 360                 365

Gly Ser Val Asn Asn Trp Phe Arg Asp Ala Ala His Gly Ser Gln
    370                 375                 380

Phe Met Gln Gln Val Arg Val Leu Gln Ile Leu Asn Lys Lys Gly Ile
385                 390                 395                 400

Ala Tyr Gly Ile Leu Cys Glu Asp Val Val Thr Gly Ala Lys Phe Thr
                405                 410                 415

Ile Thr Gly Pro Lys Lys Phe Val Val Ala Ala Gly Ala Leu Asn Thr
```

```
            420                 425                 430
Pro Ser Val Leu Val Asn Ser Gly Phe Lys Asn Lys Asn Ile Gly Lys
            435                 440                 445

Asn Leu Thr Leu His Pro Val Ser Val Phe Gly Asp Phe Gly Lys
        450                 455                 460

Asp Val Gln Ala Asp His Phe His Asn Ser Ile Met Thr Ala Leu Cys
465                 470                 475                 480

Ser Glu Ala Ala Asp Leu Asp Gly Lys Gly His Gly Cys Arg Ile Glu
                485                 490                 495

Thr Ile Leu Asn Ala Pro Phe Ile Gln Ala Ser Phe Leu Pro Trp Arg
            500                 505                 510

Gly Ser Asn Glu Ala Arg Arg Asp Leu Leu Arg Tyr Asn Asn Met Val
        515                 520                 525

Ala Met Leu Leu Leu Ser Arg Asp Thr Thr Ser Gly Ser Val Ser Ala
        530                 535                 540

His Pro Thr Lys Pro Glu Ala Leu Val Val Glu Tyr Asp Val Asn Lys
545                 550                 555                 560

Phe Asp Arg Asn Ser Ile Leu Gln Ala Leu Leu Val Thr Ala Asp Leu
                565                 570                 575

Leu Tyr Ile Gln Gly Ala Lys Arg Ile Leu Ser Pro Gln Ala Trp Val
            580                 585                 590

Pro Ile Phe Glu Ser Asp Lys Pro Lys Asp Lys Arg Ser Ile Lys Asp
        595                 600                 605

Glu Asp Tyr Val Glu Trp Arg Ala Lys Val Ala Lys Ile Pro Phe Asp
610                 615                 620

Thr Tyr Gly Ser Pro Tyr Gly Ser Ala His Gln Met Ser Ser Cys Arg
625                 630                 635                 640

Met Ser Gly Lys Gly Pro Lys Tyr Gly Ala Val Asp Thr Asp Gly Arg
                645                 650                 655

Leu Phe Glu Cys Ser Asn Val Tyr Val Ala Asp Ala Ser Leu Leu Pro
            660                 665                 670

Thr Ala Ser Gly Ala Asn Pro Met Val Thr Thr Met Thr Leu Ala Arg
        675                 680                 685

His Val Ala Leu Gly Leu Ala Asp Ser Leu Lys Thr Lys Ala Lys Leu
        690                 695                 700

<210> SEQ ID NO 9
<211> LENGTH: 704
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Ala Pro Phe Leu Pro Asp Gln Val Asp Tyr Lys His Val Asp Thr
1               5                   10                  15

Leu Met Leu Leu Cys Asp Gly Ile Ile His Glu Thr Thr Val Asp Gln
                20                  25                  30

Ile Lys Asp Val Ile Ala Pro Asp Phe Pro Ala Asp Lys Tyr Glu Glu
            35                  40                  45

Tyr Val Arg Thr Phe Thr Lys Pro Ser Glu Thr Pro Gly Phe Arg Glu
        50                  55                  60

Thr Val Tyr Asn Thr Val Asn Ala Asn Thr Thr Asp Ala Ile His Gln
65                  70                  75                  80
```

-continued

```
Phe Ile Ile Leu Thr Asn Val Leu Ala Ser Arg Val Leu Ala Pro Ala
                85                  90                  95
Leu Thr Asn Ser Leu Thr Pro Ile Lys Asp Met Ser Leu Glu Asp Arg
            100                 105                 110
Glu Lys Leu Leu Ala Ser Trp Arg Asp Ser Pro Ile Ala Ala Lys Arg
        115                 120                 125
Lys Leu Phe Arg Leu Val Ser Thr Leu Thr Leu Val Thr Phe Thr Arg
130                 135                 140
Leu Ala Asn Glu Leu His Leu Lys Ala Ile His Tyr Pro Gly Arg Glu
145                 150                 155                 160
Asp Arg Glu Lys Ala Tyr Glu Thr Gln Glu Ile Asp Pro Phe Lys Tyr
                165                 170                 175
Gln Phe Met Glu Lys Pro Lys Phe Asp Gly Ala Glu Leu Tyr Leu Pro
            180                 185                 190
Asp Ile Asp Val Ile Ile Ile Gly Ser Gly Ala Gly Ala Gly Val Val
        195                 200                 205
Ala His Thr Leu Ala Asn Asp Gly Phe Lys Ser Leu Val Leu Glu Lys
210                 215                 220
Gly Lys Tyr Phe Ser Asn Ser Glu Leu Asn Phe Asp Asp Lys Asp Gly
225                 230                 235                 240
Val Gln Glu Leu Tyr Gln Ser Gly Gly Thr Leu Thr Thr Val Asn Gln
                245                 250                 255
Gln Leu Phe Val Leu Ala Gly Ser Thr Phe Gly Gly Gly Thr Thr Val
            260                 265                 270
Asn Trp Ser Ala Cys Leu Lys Thr Pro Phe Lys Val Arg Lys Glu Trp
        275                 280                 285
Tyr Asp Glu Phe Gly Val Asp Phe Ala Ala Asp Glu Ala Tyr Asp Lys
290                 295                 300
Ala Gln Asp Tyr Val Trp Gln Gln Met Gly Ala Ser Thr Glu Gly Ile
305                 310                 315                 320
Thr His Ser Leu Ala Asn Glu Ile Ile Ile Glu Gly Gly Lys Lys Leu
                325                 330                 335
Gly Tyr Lys Ala Lys Val Leu Asp Gln Asn Ser Gly Gly His Pro Gln
            340                 345                 350
His Arg Cys Gly Phe Cys Tyr Leu Gly Cys Lys His Gly Ile Lys Gln
        355                 360                 365
Gly Ser Val Asn Asn Trp Phe Arg Asp Ala Ala His Gly Ser Gln
370                 375                 380
Phe Met Gln Gln Val Arg Val Leu Gln Ile Leu Asn Lys Lys Gly Ile
385                 390                 395                 400
Ala Tyr Gly Ile Leu Cys Glu Asp Val Val Thr Gly Ala Lys Phe Thr
                405                 410                 415
Ile Thr Gly Pro Lys Lys Phe Val Val Ala Ala Gly Ala Leu Asn Thr
            420                 425                 430
Pro Ser Val Leu Val Asn Ser Gly Phe Lys Asn Lys Asn Ile Gly Lys
        435                 440                 445
Asn Leu Thr Leu His Pro Val Ser Val Phe Gly Asp Phe Gly Lys
450                 455                 460
Asp Val Gln Ala Asp His Phe His Asn Ser Ile Met Thr Ala Leu Cys
465                 470                 475                 480
Ser Glu Ala Ala Asp Leu Asp Gly Lys Gly His Gly Cys Arg Ile Glu
                485                 490                 495
Thr Ile Leu Asn Ala Pro Phe Ile Gln Ala Ser Phe Leu Pro Trp Arg
```

```
                500             505             510
Gly Ser Asn Glu Ala Arg Arg Asp Leu Leu Arg Tyr Asn Asn Met Val
        515             520             525

Ala Met Leu Leu Leu Ser Arg Asp Thr Thr Ser Gly Ser Val Ser Ala
    530             535             540

His Pro Thr Lys Pro Glu Ala Leu Val Val Glu Tyr Asp Val Asn Lys
545             550             555             560

Phe Asp Arg Asn Ser Ile Leu Gln Ala Leu Leu Val Thr Ala Asp Leu
            565             570             575

Leu Tyr Ile Gln Gly Ala Lys Arg Ile Leu Ser Pro Gln Ala Trp Val
                580             585             590

Pro Ile Phe Glu Ser Asp Lys Pro Lys Asp Lys Arg Ser Ile Lys Asp
            595             600             605

Glu Asp Tyr Val Glu Trp Arg Ala Lys Val Ala Lys Ile Pro Phe Asp
        610             615             620

Thr Tyr Gly Ser Pro Tyr Gly Ser Ala His Gln Met Ser Ser Cys Arg
625             630             635             640

Met Ser Gly Lys Gly Pro Lys Tyr Gly Ala Val Asp Thr Asp Gly Arg
            645             650             655

Leu Phe Glu Cys Ser Asn Val Tyr Val Ala Asp Ala Ser Leu Leu Pro
        660             665             670

Thr Ala Ser Gly Ala Asn Pro Met Val Thr Thr Met Thr Leu Ala Arg
    675             680             685

His Val Ala Leu Gly Leu Ala Asp Ser Leu Lys Thr Lys Ala Lys Leu
    690             695             700
```

<210> SEQ ID NO 10
<211> LENGTH: 704
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Met Ala Pro Phe Leu Pro Asp Gln Val Asp Tyr Lys His Val Asp Thr
1               5                   10                  15

Leu Met Leu Leu Cys Asp Gly Ile Ile His Glu Thr Thr Val Asp Glu
            20                  25                  30

Ile Lys Asp Val Ile Ala Pro Asp Phe Pro Ala Asp Lys Tyr Glu Glu
        35                  40                  45

Tyr Val Arg Thr Phe Thr Lys Pro Ser Glu Thr Pro Gly Phe Arg Glu
    50                  55                  60

Thr Val Tyr Asn Thr Val Asn Ala Asn Thr Met Asp Ala Ile His Gln
65                  70                  75                  80

Phe Ile Ile Leu Thr Asn Val Leu Gly Ser Arg Val Leu Ala Pro Ala
                85                  90                  95

Leu Thr Asn Ser Leu Thr Pro Ile Lys Asp Met Ser Leu Glu Asp Arg
            100                 105                 110

Glu Lys Leu Leu Ala Ser Trp Arg Asp Ser Pro Ile Ala Ala Lys Arg
        115                 120                 125

Lys Leu Phe Arg Leu Val Ser Thr Leu Thr Leu Val Thr Phe Thr Arg
    130                 135                 140

Leu Ala Asn Glu Leu His Leu Lys Ala Ile His Tyr Pro Gly Arg Glu
145                 150                 155                 160
```

```
Asp Arg Glu Lys Ala Tyr Glu Thr Gln Glu Ile Asp Pro Phe Lys Tyr
            165                 170                 175
Gln Phe Leu Glu Lys Pro Lys Phe Tyr Gly Ala Glu Leu Tyr Leu Pro
        180                 185                 190
Asp Ile Asp Val Ile Ile Ile Gly Ser Gly Ala Gly Ala Gly Val Val
    195                 200                 205
Ala His Thr Leu Ala Asn Asp Gly Phe Lys Ser Leu Val Leu Glu Lys
210                 215                 220
Gly Lys Tyr Phe Ser Asn Ser Glu Leu Asn Phe Asp Asp Lys Asp Gly
225                 230                 235                 240
Val Gln Glu Leu Tyr Gln Ser Gly Gly Thr Leu Thr Thr Val Asn Gln
            245                 250                 255
Gln Leu Phe Val Leu Ala Gly Ser Thr Phe Gly Gly Gly Thr Thr Val
        260                 265                 270
Asn Trp Ser Ala Cys Leu Lys Thr Pro Phe Lys Val Arg Lys Glu Trp
    275                 280                 285
Tyr Asp Glu Phe Gly Val Asp Phe Ala Ala Asp Glu Ala Tyr Asp Lys
290                 295                 300
Ala Gln Asp Tyr Val Trp Gln Gln Met Gly Ala Ser Thr Glu Gly Ile
305                 310                 315                 320
Thr His Ser Leu Ala Asn Glu Ile Ile Ile Glu Gly Gly Lys Lys Leu
            325                 330                 335
Gly Tyr Lys Ala Lys Val Leu Asp Gln Asn Ser Gly Gly His Pro Gln
        340                 345                 350
His Arg Cys Gly Phe Cys Tyr Leu Gly Cys Lys His Gly Ile Lys Gln
    355                 360                 365
Gly Ser Val Asn Asn Trp Phe Arg Asp Ala Ala His Gly Ser Gln
370                 375                 380
Phe Met Gln Gln Val Arg Val Leu Gln Ile Leu Asn Lys Lys Gly Ile
385                 390                 395                 400
Ala Tyr Gly Ile Leu Cys Glu Asp Val Val Thr Gly Ala Lys Phe Thr
            405                 410                 415
Ile Thr Gly Pro Lys Lys Phe Val Val Ala Ala Gly Ala Leu Asn Thr
        420                 425                 430
Pro Ser Val Leu Val Asn Ser Gly Phe Lys Asn Lys Asn Ile Gly Lys
    435                 440                 445
Asn Leu Thr Leu His Pro Val Ser Val Val Phe Gly Asp Phe Gly Lys
450                 455                 460
Asp Val Gln Ala Asp His Phe His Asn Ser Ile Met Thr Ala Leu Cys
465                 470                 475                 480
Ser Glu Ala Ala Asp Leu Asp Gly Lys Gly His Gly Cys Arg Ile Glu
            485                 490                 495
Thr Ile Leu Asn Ala Pro Phe Ile Gln Ala Ser Phe Leu Pro Trp Arg
        500                 505                 510
Gly Ser Asn Glu Ala Arg Arg Asp Leu Leu Arg Tyr Asn Asn Met Val
    515                 520                 525
Ala Met Leu Leu Leu Ser Arg Asp Thr Thr Ser Gly Ser Val Ser Ala
530                 535                 540
His Pro Thr Lys Pro Glu Ala Leu Val Val Glu Tyr Asp Val Asn Lys
545                 550                 555                 560
Phe Asp Arg Asn Ser Ile Leu Gln Ala Leu Leu Val Thr Ala Asp Leu
            565                 570                 575
Leu Tyr Ile Gln Gly Ala Lys Arg Ile Leu Ser Pro Gln Ala Trp Val
```

```
            580                 585                 590
Pro Ile Phe Glu Ser Asp Lys Pro Lys Asp Lys Arg Ser Ile Lys Asp
            595                 600                 605

Glu Asp Tyr Val Glu Trp Arg Ala Lys Val Ala Lys Ile Pro Phe Asp
        610                 615                 620

Thr Tyr Gly Ser Pro Tyr Gly Ser Ala His Gln Met Ser Ser Cys Arg
625                 630                 635                 640

Met Ser Gly Lys Gly Pro Lys Tyr Gly Ala Val Asp Thr Asp Gly Arg
            645                 650                 655

Leu Phe Glu Cys Ser Asn Val Tyr Val Ala Asp Ala Ser Leu Leu Pro
        660                 665                 670

Thr Ala Ser Gly Ala Asn Pro Met Val Thr Thr Met Thr Leu Ala Arg
            675                 680                 685

His Val Ala Leu Gly Leu Ala Asp Ser Leu Lys Thr Lys Ala Lys Leu
        690                 695                 700

<210> SEQ ID NO 11
<211> LENGTH: 704
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Asn Thr Phe Leu Pro Asp Val Leu Glu Tyr Lys His Val Asp Thr
1               5                   10                  15

Leu Leu Leu Leu Cys Asp Gly Ile Ile His Thr Thr Val Asp Gln
            20                  25                  30

Ile Lys Asp Ala Ile Ala Pro Asp Phe Pro Glu Asp Gln Tyr Glu Glu
        35                  40                  45

Tyr Leu Lys Thr Phe Thr Lys Pro Ser Glu Thr Pro Gly Phe Arg Glu
    50                  55                  60

Ala Val Tyr Asp Thr Ile Asn Ala Thr Pro Thr Asp Ala Val His Met
65                  70                  75                  80

Cys Ile Val Leu Thr Thr Ala Leu Asp Ser Arg Ile Leu Ala Pro Thr
                85                  90                  95

Leu Thr Asn Ser Leu Thr Pro Ile Lys Asp Met Thr Leu Lys Glu Arg
            100                 105                 110

Glu Gln Leu Leu Ala Ser Trp Arg Asp Ser Pro Ile Ala Ala Lys Arg
        115                 120                 125

Arg Leu Phe Arg Leu Ile Ser Ser Leu Thr Leu Thr Thr Phe Thr Arg
    130                 135                 140

Leu Ala Ser Glu Leu His Leu Lys Ala Ile His Tyr Pro Gly Arg Asp
145                 150                 155                 160

Leu Arg Glu Lys Ala Tyr Glu Thr Gln Val Val Asp Pro Phe Arg Tyr
                165                 170                 175

Ser Phe Met Glu Lys Pro Lys Phe Asp Gly Ala Glu Leu Tyr Leu Pro
            180                 185                 190

Asp Ile Asp Val Ile Ile Gly Ser Gly Ala Gly Ala Gly Val Met
        195                 200                 205

Ala His Thr Leu Ala Asn Asp Gly Phe Lys Thr Leu Val Leu Glu Lys
    210                 215                 220

Gly Lys Tyr Phe Ser Asn Ser Glu Leu Asn Phe Asn Asp Ala Asp Gly
225                 230                 235                 240
```

```
Val Lys Glu Leu Tyr Gln Gly Lys Gly Ala Leu Ala Thr Thr Asn Gln
            245                 250                 255
Gln Met Phe Ile Leu Ala Gly Ser Thr Leu Gly Gly Thr Thr Val
        260                 265                 270
Asn Trp Ser Ala Cys Leu Lys Thr Pro Phe Lys Val Arg Lys Glu Trp
            275                 280                 285
Tyr Asp Glu Phe Gly Leu Glu Phe Ala Ala Asp Glu Ala Tyr Asp Lys
            290                 295                 300
Ala Gln Asp Tyr Val Trp Lys Gln Met Gly Ala Ser Thr Asp Gly Ile
305                 310                 315                 320
Thr His Ser Leu Ala Asn Glu Val Val Glu Gly Lys Lys Leu
            325                 330                 335
Gly Tyr Lys Ser Lys Glu Ile Glu Gln Asn Asn Gly Gly His Pro Asp
            340                 345                 350
His Pro Cys Gly Phe Cys Tyr Leu Gly Cys Lys Tyr Gly Ile Lys Gln
            355                 360                 365
Gly Ser Val Asn Asn Trp Phe Arg Asp Ala Ala Ala His Gly Ser Lys
            370                 375                 380
Phe Met Gln Gln Val Arg Val Val Gln Ile Leu Asn Lys Asn Gly Val
385                 390                 395                 400
Ala Tyr Gly Ile Leu Cys Glu Asp Val Glu Thr Gly Val Arg Phe Thr
                405                 410                 415
Ile Ser Gly Pro Lys Lys Phe Val Val Ser Ala Gly Ser Leu Asn Thr
            420                 425                 430
Pro Thr Val Leu Thr Asn Ser Gly Phe Lys Asn Lys His Ile Gly Lys
            435                 440                 445
Asn Leu Thr Leu His Pro Val Ser Thr Val Phe Gly Asp Phe Gly Arg
450                 455                 460
Asp Val Gln Ala Asp His Phe His Lys Ser Ile Met Thr Ser Leu Cys
465                 470                 475                 480
Tyr Glu Val Ala Asp Leu Asp Gly Lys Gly His Gly Cys Arg Ile Glu
                485                 490                 495
Thr Ile Leu Asn Ala Pro Phe Ile Gln Ala Ser Leu Leu Pro Trp Arg
            500                 505                 510
Gly Ser Asp Glu Val Arg Arg Asp Leu Leu Arg Tyr Asn Asn Met Val
            515                 520                 525
Ala Met Leu Leu Ile Thr Arg Asp Thr Thr Ser Gly Ser Val Ser Ala
            530                 535                 540
Asp Pro Lys Lys Pro Asp Ala Leu Ile Val Asp Tyr Glu Ile Asn Lys
545                 550                 555                 560
Phe Asp Lys Asn Ala Ile Leu Gln Ala Phe Leu Ile Thr Ser Asp Met
                565                 570                 575
Leu Tyr Ile Glu Gly Ala Lys Arg Ile Leu Ser Pro Gln Pro Trp Val
            580                 585                 590
Pro Ile Phe Glu Ser Asn Lys Pro Lys Glu Gln Arg Thr Ile Lys Asp
            595                 600                 605
Lys Asp Tyr Val Glu Trp Arg Ala Lys Ala Lys Ile Pro Phe Asp
            610                 615                 620
Thr Tyr Gly Ser Ala Tyr Gly Ser Ala His Gln Met Ser Thr Cys Arg
625                 630                 635                 640
Met Ser Gly Lys Gly Pro Lys Tyr Gly Ala Val Asp Thr Asp Gly Arg
                645                 650                 655
Leu Phe Glu Cys Ser Asn Val Tyr Val Ala Asp Ala Ser Val Leu Pro
```

```
                        660                 665                 670
Thr Ala Ser Gly Ala Asn Pro Met Ile Ser Thr Met Thr Phe Ala Arg
            675                 680                 685
Gln Ile Ala Leu Gly Leu Ala Asp Ser Leu Lys Thr Lys Pro Lys Leu
        690                 695                 700

<210> SEQ ID NO 12
<211> LENGTH: 704
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Asn Thr Phe Leu Pro Asp Val Leu Glu Tyr Lys His Val Asp Thr
1               5                   10                  15

Leu Leu Leu Leu Cys Asp Gly Ile Ile His Glu Thr Thr Val Asp Gln
            20                  25                  30

Ile Arg Asp Ala Ile Ala Pro Asp Phe Pro Glu Asp Gln Tyr Glu Glu
        35                  40                  45

Tyr Leu Lys Thr Phe Thr Lys Pro Ser Glu Thr Pro Gly Phe Arg Glu
    50                  55                  60

Ala Val Tyr Asp Thr Ile Asn Ser Thr Pro Thr Glu Ala Val His Met
65                  70                  75                  80

Cys Ile Val Leu Thr Thr Ala Leu Asp Ser Arg Ile Leu Ala Pro Thr
                85                  90                  95

Leu Thr Asn Ser Leu Thr Pro Ile Lys Asp Met Thr Leu Lys Glu Arg
            100                 105                 110

Glu Gln Leu Leu Ala Ala Trp Arg Asp Ser Pro Ile Ala Ala Lys Arg
        115                 120                 125

Arg Leu Phe Arg Leu Ile Ser Ser Leu Thr Leu Thr Thr Phe Thr Arg
    130                 135                 140

Leu Ala Ser Asp Leu His Leu Arg Ala Ile His Tyr Pro Gly Arg Asp
145                 150                 155                 160

Leu Arg Glu Lys Ala Tyr Glu Thr Gln Val Val Asp Pro Phe Arg Tyr
                165                 170                 175

Ser Phe Met Glu Lys Pro Lys Phe Asp Gly Thr Glu Leu Tyr Leu Pro
            180                 185                 190

Asp Ile Asp Val Ile Ile Ile Gly Ser Gly Ala Gly Ala Gly Val Met
        195                 200                 205

Ala His Thr Leu Ala Asn Asp Gly Tyr Lys Thr Leu Val Leu Glu Lys
    210                 215                 220

Gly Lys Tyr Phe Ser Asn Ser Glu Leu Asn Phe Asn Asp Ala Asp Gly
225                 230                 235                 240

Met Lys Glu Leu Tyr Gln Gly Lys Cys Ala Leu Thr Thr Thr Asn Gln
                245                 250                 255

Gln Met Phe Ile Leu Ala Gly Ser Thr Leu Gly Gly Gly Thr Thr Val
            260                 265                 270

Asn Trp Ser Ala Cys Leu Lys Thr Pro Phe Lys Val Arg Lys Glu Trp
        275                 280                 285

Tyr Asp Glu Phe Gly Leu Glu Phe Ala Ala Asp Glu Ala Tyr Asp Lys
    290                 295                 300

Ala Gln Asp Tyr Val Trp Lys Gln Met Gly Ala Ser Thr Glu Gly Ile
305                 310                 315                 320
```

Thr His Ser Leu Ala Asn Ala Val Val Glu Gly Gly Lys Lys Leu
                    325                 330                 335

Gly Tyr Lys Ser Lys Glu Ile Glu Gln Asn Asn Gly Gly His Pro Asp
                340                 345                 350

His Pro Cys Gly Phe Cys Tyr Leu Cys Lys Tyr Gly Ile Lys Gln
            355                 360                 365

Gly Ser Val Asn Asn Trp Phe Arg Asp Ala Ala His Gly Ser Lys
        370                 375                 380

Phe Met Gln Gln Val Arg Val Val Gln Ile Leu His Asn Lys Gly Val
385                 390                 395                 400

Ala Tyr Gly Ile Leu Cys Glu Asp Val Glu Thr Gly Val Lys Phe Thr
                405                 410                 415

Ile Ser Gly Pro Lys Lys Phe Val Val Ser Ala Gly Ser Leu Asn Thr
                420                 425                 430

Pro Thr Val Leu Thr Asn Ser Gly Phe Lys Asn Lys His Ile Gly Lys
            435                 440                 445

Asn Leu Thr Leu His Pro Val Ser Thr Val Phe Gly Asp Phe Gly Arg
    450                 455                 460

Asp Val Gln Ala Asp His Phe His Lys Ser Ile Met Thr Ser Leu Cys
465                 470                 475                 480

Tyr Glu Val Ala Asp Leu Asp Gly Lys Gly His Gly Cys Arg Ile Glu
                485                 490                 495

Thr Ile Leu Asn Ala Pro Phe Ile Gln Ala Ser Leu Leu Pro Trp Arg
            500                 505                 510

Gly Ser Asp Glu Val Arg Arg Asp Leu Leu Arg Tyr Asn Asn Met Val
        515                 520                 525

Ala Met Leu Leu Ile Thr Arg Asp Thr Thr Ser Gly Ser Val Ser Ala
530                 535                 540

Asp Pro Lys Lys Pro Asp Ala Leu Ile Val Asp Tyr Asp Ile Asn Lys
545                 550                 555                 560

Phe Asp Lys Asn Ala Ile Leu Gln Ala Phe Leu Ile Thr Ser Asp Met
                565                 570                 575

Leu Tyr Ile Glu Gly Ala Lys Arg Ile Leu Ser Pro Gln Ala Trp Val
                580                 585                 590

Pro Ile Phe Glu Ser Asn Lys Pro Lys Glu Gln Arg Thr Ile Lys Asp
            595                 600                 605

Lys Asp Tyr Val Glu Trp Arg Ala Lys Ala Ala Lys Ile Pro Phe Asp
        610                 615                 620

Thr Tyr Gly Ser Ala Tyr Gly Ser Ala His Gln Met Ser Thr Cys Arg
625                 630                 635                 640

Met Ser Gly Lys Gly Pro Lys Tyr Gly Ala Val Asp Thr Asp Gly Arg
                645                 650                 655

Leu Phe Glu Cys Ser Asn Val Tyr Val Ala Asp Ala Ser Val Leu Pro
            660                 665                 670

Thr Ala Ser Gly Ala Asn Pro Met Ile Ser Thr Met Thr Phe Ala Arg
        675                 680                 685

Gln Ile Ala Leu Gly Leu Ala Asp Ser Leu Lys Thr Lys Pro Lys Leu
    690                 695                 700

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic 6xHis tag

<400> SEQUENCE: 13

His His His His His His
1               5

<210> SEQ ID NO 14
<211> LENGTH: 419
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Val Ala Ala Ala Thr Ser Ala Phe Phe Pro Val Pro Ala Pro
1               5                   10                  15

Gly Thr Ser Pro Lys Pro Gly Lys Ser Gly Asn Trp Pro Ser Ser Leu
            20                  25                  30

Ser Pro Thr Phe Lys Pro Lys Ser Ile Pro Asn Ala Gly Phe Gln Val
        35                  40                  45

Lys Ala Asn Ala Ser Ala His Pro Lys Ala Asn Gly Ser Ala Val Asn
50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Thr Ala Ile Thr Thr Val Phe Val Ala Ala Glu Lys Gln Trp Thr Met
            100                 105                 110

Leu Asp Arg Lys Ser Lys Arg Pro Asp Met Leu Val Asp Ser Val Gly
        115                 120                 125

Leu Lys Ser Ile Val Arg Asp Gly Leu Val Ser Arg Gln Ser Phe Leu
130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ser Ile Asn His Cys Lys Ser Leu
                165                 170                 175

Gly Leu Leu Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
        195                 200                 205

Pro Thr Trp Gly Asp Thr Val Glu Ile Asn Thr Trp Phe Ser Gln Ser
    210                 215                 220

Gly Lys Ile Gly Met Ala Ser Asp Trp Leu Ile Ser Asp Cys Asn Thr
225                 230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
            260                 265                 270

Thr Pro His Phe Val Asp Ser Pro His Val Ile Glu Asp Asn Asp Gln
        275                 280                 285

Lys Leu His Lys Phe Asp Val Lys Thr Gly Asp Ser Ile Arg Lys Gly
    290                 295                 300

Leu Thr Pro Arg Trp Asn Asp Leu Asp Val Asn Gln His Val Ser Asn
305                 310                 315                 320

Val Lys Tyr Ile Gly Trp Ile Leu Glu Ser Met Pro Ile Glu Val Leu

```
                    325                 330                 335
Glu Thr Gln Glu Leu Cys Ser Leu Thr Val Glu Tyr Arg Arg Glu Cys
                340                 345                 350
Gly Met Asp Ser Val Leu Glu Ser Val Thr Ala Val Asp Pro Ser Glu
            355                 360                 365
Asn Gly Gly Arg Ser Gln Tyr Lys His Leu Leu Arg Leu Glu Asp Gly
        370                 375                 380
Thr Asp Ile Val Lys Ser Arg Thr Glu Trp Arg Pro Lys Asn Ala Gly
385                 390                 395                 400
Thr Asn Gly Ala Ile Ser Thr Ser Thr Ala Lys Thr Ser Asn Gly Asn
                405                 410                 415
Ser Ala Ser

<210> SEQ ID NO 15
<211> LENGTH: 2109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Ala Gln Ser Arg Gln Leu Phe Leu Phe Gly Asp Gln Thr Ala Asp
1               5                   10                  15
Phe Val Pro Lys Leu Arg Ser Leu Leu Ser Val Gln Asp Ser Pro Ile
            20                  25                  30
Leu Ala Ala Phe Leu Asp Gln Ser His Tyr Val Val Arg Ala Gln Met
        35                  40                  45
Leu Gln Ser Met Asn Thr Val Asp His Lys Leu Ala Arg Thr Ala Asp
    50                  55                  60
Leu Arg Gln Met Val Gln Lys Tyr Val Asp Gly Lys Leu Thr Pro Ala
65                  70                  75                  80
Phe Arg Thr Ala Leu Val Cys Leu Cys Gln Leu Gly Cys Phe Ile Arg
                85                  90                  95
Glu Tyr Glu Glu Ser Gly Asn Met Tyr Pro Gln Pro Ser Asp Ser Tyr
            100                 105                 110
Val Leu Gly Phe Cys Met Gly Ser Leu Ala Ala Val Ala Val Ser Cys
        115                 120                 125
Ser Arg Ser Leu Ser Glu Leu Leu Pro Ile Ala Val Gln Thr Val Leu
    130                 135                 140
Ile Ala Phe Arg Leu Gly Leu Cys Ala Leu Glu Met Arg Asp Arg Val
145                 150                 155                 160
Asp Gly Cys Ser Asp Asp Arg Gly Asp Pro Trp Ser Thr Ile Val Trp
                165                 170                 175
Gly Leu Asp Pro Gln Gln Ala Arg Asp Gln Ile Glu Val Phe Cys Arg
            180                 185                 190
Thr Thr Asn Val Pro Gln Thr Arg Arg Pro Trp Ile Ser Cys Ile Ser
        195                 200                 205
Lys Asn Ala Ile Thr Leu Ser Gly Ser Pro Ser Thr Leu Arg Ala Phe
    210                 215                 220
Cys Ala Met Pro Gln Met Ala Gln His Arg Thr Ala Pro Ile Pro Ile
225                 230                 235                 240
Cys Leu Pro Ala His Asn Gly Ala Leu Phe Thr Gln Ala Asp Ile Thr
                245                 250                 255
Thr Ile Leu Asp Thr Thr Pro Thr Thr Pro Trp Glu Gln Leu Pro Gly
```

```
                260             265             270
Gln Ile Pro Tyr Ile Ser His Val Thr Gly Asn Val Val Gln Thr Ser
            275             280             285
Asn Tyr Arg Asp Leu Ile Glu Val Ala Leu Ser Glu Thr Leu Leu Glu
        290             295             300
Gln Val Arg Leu Asp Leu Val Glu Thr Gly Leu Pro Arg Leu Leu Gln
305             310             315             320
Ser Arg Gln Val Lys Ser Val Thr Ile Val Pro Phe Leu Thr Arg Met
                325             330             335
Asn Glu Thr Met Ser Asn Ile Leu Pro Asp Ser Phe Ile Ser Thr Glu
            340             345             350
Thr Arg Thr Asp Thr Gly Arg Ala Ile Pro Ala Ser Gly Arg Pro Gly
        355             360             365
Ala Gly Lys Cys Lys Leu Ala Ile Val Ser Met Ser Gly Arg Phe Pro
        370             375             380
Glu Ser Pro Thr Thr Glu Ser Phe Trp Asp Leu Leu Tyr Lys Gly Leu
385             390             395             400
Asp Val Cys Lys Glu Val Pro Arg Arg Arg Trp Asp Ile Asn Thr His
            405             410             415
Val Asp Pro Ser Gly Lys Ala Arg Asn Lys Gly Ala Thr Lys Trp Gly
            420             425             430
Cys Trp Leu Asp Phe Ser Gly Asp Phe Asp Pro Arg Phe Phe Gly Ile
        435             440             445
Ser Pro Lys Glu Ala Pro Gln Met Asp Pro Ala Gln Arg Met Ala Leu
        450             455             460
Met Ser Thr Tyr Glu Ala Met Glu Arg Ala Gly Leu Val Pro Asp Thr
465             470             475             480
Thr Pro Ser Thr Gln Arg Asp Arg Ile Gly Val Phe His Gly Val Thr
            485             490             495
Ser Asn Asp Trp Met Glu Thr Asn Thr Ala Gln Asn Ile Asp Thr Tyr
            500             505             510
Phe Ile Thr Gly Gly Asn Arg Gly Phe Ile Pro Gly Arg Ile Asn Phe
        515             520             525
Cys Phe Glu Phe Ala Gly Pro Ser Tyr Thr Asn Asp Thr Ala Cys Ser
        530             535             540
Ser Ser Leu Ala Ala Ile His Leu Ala Cys Asn Ser Leu Trp Arg Gly
545             550             555             560
Asp Cys Asp Thr Ala Val Ala Gly Gly Thr Asn Met Ile Tyr Thr Pro
            565             570             575
Asp Gly His Thr Gly Leu Asp Lys Gly Phe Phe Leu Ser Arg Thr Gly
            580             585             590
Asn Cys Lys Pro Tyr Asp Asp Lys Ala Asp Gly Tyr Cys Arg Ala Glu
        595             600             605
Gly Val Gly Thr Val Phe Ile Lys Arg Leu Glu Asp Ala Leu Ala Asp
        610             615             620
Asn Asp Pro Ile Leu Gly Val Ile Leu Asp Ala Lys Thr Asn His Ser
625             630             635             640
Ala Met Ser Glu Ser Met Thr Arg Pro His Val Gly Ala Gln Ile Asp
            645             650             655
Asn Met Thr Ala Ala Leu Asn Thr Thr Gly Leu His Pro Asn Asp Phe
            660             665             670
Ser Tyr Ile Glu Met His Gly Thr Gly Thr Gln Val Gly Asp Ala Val
        675             680             685
```

-continued

```
Glu Met Glu Ser Val Leu Ser Val Phe Ala Pro Ser Glu Thr Ala Arg
690                 695                 700

Lys Ala Asp Gln Pro Leu Phe Val Gly Ser Ala Lys Ala Asn Val Gly
705                 710                 715                 720

His Gly Glu Gly Val Ser Gly Val Thr Ser Leu Ile Lys Val Leu Met
            725                 730                 735

Met Met Gln His Asp Thr Ile Pro Pro His Cys Gly Ile Lys Pro Gly
            740                 745                 750

Ser Lys Ile Asn Arg Asn Phe Pro Asp Leu Gly Ala Arg Asn Val His
            755                 760                 765

Ile Ala Phe Glu Pro Lys Pro Trp Pro Arg Thr His Thr Pro Arg Arg
770                 775                 780

Val Leu Ile Asn Asn Phe Ser Ala Ala Gly Gly Asn Thr Ala Leu Ile
785                 790                 795                 800

Val Glu Asp Ala Pro Glu Arg His Trp Pro Thr Glu Lys Asp Pro Arg
            805                 810                 815

Ser Ser His Ile Val Ala Leu Ser Ala His Val Gly Ala Ser Met Lys
            820                 825                 830

Thr Asn Leu Glu Arg Leu His Gln Tyr Leu Leu Lys Asn Pro His Thr
            835                 840                 845

Asp Leu Ala Gln Leu Ser Tyr Thr Thr Thr Ala Arg Arg Trp His Tyr
850                 855                 860

Leu His Arg Val Ser Val Thr Gly Ala Ser Val Glu Val Thr Arg
865                 870                 875                 880

Lys Leu Glu Met Ala Ile Gln Asn Gly Asp Gly Val Ser Arg Pro Lys
            885                 890                 895

Ser Lys Pro Lys Ile Leu Phe Ala Phe Thr Gly Gln Gly Ser Gln Tyr
            900                 905                 910

Ala Thr Met Gly Lys Gln Val Tyr Asp Ala Tyr Pro Ser Phe Arg Glu
            915                 920                 925

Asp Leu Glu Lys Phe Asp Arg Leu Ala Gln Ser His Gly Phe Pro Ser
            930                 935                 940

Phe Leu His Val Cys Thr Ser Pro Lys Gly Asp Val Glu Glu Met Ala
945                 950                 955                 960

Pro Val Val Val Gln Leu Ala Ile Thr Cys Leu Gln Met Ala Leu Thr
            965                 970                 975

Asn Leu Met Thr Ser Phe Gly Ile Arg Pro Asp Val Thr Val Gly His
            980                 985                 990

Ser Leu Gly Glu Phe Ala Ala Leu Tyr Ala Ala Gly Val Leu Ser Ala
            995                 1000                1005

Ser Asp Val Val Tyr Leu Val Gly Gln Arg Ala Glu Leu Leu Gln
    1010                1015                1020

Glu Arg Cys Gln Arg Gly Thr His Ala Met Leu Ala Val Lys Ala
    1025                1030                1035

Thr Pro Glu Ala Leu Ser Gln Trp Ile Gln Asp His Asp Cys Glu
    1040                1045                1050

Val Ala Cys Ile Asn Gly Pro Glu Asp Thr Val Leu Ser Gly Thr
    1055                1060                1065

Thr Lys Asn Val Ala Glu Val Gln Arg Ala Met Thr Asp Asn Gly
    1070                1075                1080

Ile Lys Cys Thr Leu Leu Lys Leu Pro Phe Ala Phe His Ser Ala
    1085                1090                1095
```

```
Gln Val Gln Pro Ile Leu Asp Asp Phe Glu Ala Leu Ala Gln Gly
    1100                1105                1110

Ala Thr Phe Ala Lys Pro Gln Leu Leu Ile Leu Ser Pro Leu Leu
    1115                1120                1125

Arg Thr Glu Ile His Glu Gln Gly Val Val Thr Pro Ser Tyr Val
    1130                1135                1140

Ala Gln His Cys Arg His Thr Val Asp Met Ala Gln Ala Leu Arg
    1145                1150                1155

Ser Ala Arg Glu Lys Gly Leu Ile Asp Asp Lys Thr Leu Val Ile
    1160                1165                1170

Glu Leu Gly Pro Lys Pro Leu Ile Ser Gly Met Val Lys Met Thr
    1175                1180                1185

Leu Gly Asp Lys Ile Ser Thr Leu Pro Thr Leu Ala Pro Asn Lys
    1190                1195                1200

Ala Ile Trp Pro Ser Leu Gln Lys Ile Leu Thr Ser Val Tyr Thr
    1205                1210                1215

Gly Gly Trp Asp Ile Asn Trp Lys Lys Tyr His Ala Pro Phe Ala
    1220                1225                1230

Ser Ser Gln Lys Val Val Asp Leu Pro Ser Tyr Gly Trp Asp Leu
    1235                1240                1245

Lys Asp Tyr Tyr Ile Pro Tyr Gln Gly Asp Trp Cys Leu His Arg
    1250                1255                1260

His Gln Gln Asp Cys Lys Cys Ala Ala Pro Gly His Glu Ile Lys
    1265                1270                1275

Thr Ala Asp Tyr Gln Val Pro Pro Glu Ser Thr Pro His Arg Pro
    1280                1285                1290

Ser Lys Leu Asp Pro Ser Lys Glu Ala Phe Pro Glu Ile Lys Thr
    1295                1300                1305

Thr Thr Thr Leu His Arg Val Val Glu Thr Thr Lys Pro Leu
    1310                1315                1320

Gly Ala Thr Leu Val Val Glu Thr Asp Ile Ser Arg Lys Asp Val
    1325                1330                1335

Asn Gly Leu Ala Arg Gly His Leu Val Asp Gly Ile Pro Leu Cys
    1340                1345                1350

Thr Pro Ser Phe Tyr Ala Asp Ile Ala Met Gln Val Gly Gln Tyr
    1355                1360                1365

Ser Met Gln Arg Leu Arg Ala Gly His Pro Gly Ala Gly Ala Ile
    1370                1375                1380

Asp Gly Leu Val Asp Val Ser Asp Met Val Val Asp Lys Ala Leu
    1385                1390                1395

Val Pro His Gly Lys Gly Pro Gln Leu Leu Arg Thr Thr Leu Thr
    1400                1405                1410

Met Glu Trp Pro Pro Lys Ala Ala Ala Thr Thr Arg Ser Ala Lys
    1415                1420                1425

Val Lys Phe Ala Thr Tyr Phe Ala Asp Gly Lys Leu Asp Thr Glu
    1430                1435                1440

His Ala Ser Cys Thr Val Arg Phe Thr Ser Asp Ala Gln Leu Lys
    1445                1450                1455

Ser Leu Arg Arg Ser Val Ser Glu Tyr Lys Thr His Ile Arg Gln
    1460                1465                1470

Leu His Asp Gly His Ala Lys Gly Gln Phe Met Arg Tyr Asn Arg
    1475                1480                1485

Lys Thr Gly Tyr Lys Leu Met Ser Ser Met Ala Arg Phe Asn Pro
```

-continued

```
            1490                1495                1500

Asp Tyr Met Leu Leu Asp Tyr Leu Val Leu Asn Glu Ala Glu Asn
    1505                1510                1515

Glu Ala Ala Ser Gly Val Asp Phe Ser Leu Gly Ser Ser Glu Gly
    1520                1525                1530

Thr Phe Ala Ala His Pro Ala His Val Asp Ala Ile Thr Gln Val
    1535                1540                1545

Ala Gly Phe Ala Met Asn Ala Asn Asp Asn Val Asp Ile Glu Lys
    1550                1555                1560

Gln Val Tyr Val Asn His Gly Trp Asp Ser Phe Gln Ile Tyr Gln
    1565                1570                1575

Pro Leu Asp Asn Ser Lys Ser Tyr Gln Val Tyr Thr Lys Met Gly
    1580                1585                1590

Gln Ala Lys Glu Asn Asp Leu Val His Gly Asp Val Val Val Leu
    1595                1600                1605

Asp Gly Glu Gln Ile Val Ala Phe Phe Arg Gly Leu Thr Leu Arg
    1610                1615                1620

Ser Val Pro Arg Gly Ala Leu Arg Val Val Leu Gln Thr Thr Val
    1625                1630                1635

Lys Lys Ala Asp Arg Gln Leu Gly Phe Lys Thr Met Pro Ser Pro
    1640                1645                1650

Pro Pro Pro Thr Thr Thr Met Pro Ile Ser Pro Tyr Lys Pro Ala
    1655                1660                1665

Asn Thr Gln Val Ser Ser Gln Ala Ile Pro Ala Glu Ala Thr His
    1670                1675                1680

Ser His Thr Pro Pro Gln Pro Lys His Ser Pro Val Pro Glu Thr
    1685                1690                1695

Ala Gly Ser Ala Pro Ala Ala Lys Gly Val Gly Val Ser Asn Glu
    1700                1705                1710

Lys Leu Asp Ala Val Met Arg Val Val Ser Glu Glu Ser Gly Ile
    1715                1720                1725

Ala Leu Glu Glu Leu Thr Asp Ser Asn Phe Ala Asp Met Gly
    1730                1735                1740

Ile Asp Ser Leu Ser Ser Met Val Ile Gly Ser Arg Phe Arg Glu
    1745                1750                1755

Asp Leu Gly Leu Asp Leu Gly Pro Glu Phe Ser Leu Phe Ile Asp
    1760                1765                1770

Cys Thr Thr Val Arg Ala Leu Lys Asp Phe Met Leu Gly Ser Gly
    1775                1780                1785

Asp Ala Gly Ser Gly Ser Asn Val Glu Asp Pro Pro Ser Ala
    1790                1795                1800

Thr Pro Gly Ile Asn Pro Glu Thr Asp Trp Ser Ser Ser Ala Ser
    1805                1810                1815

Asp Ser Ile Phe Ala Ser Glu Asp His Gly His Ser Ser Glu Ser
    1820                1825                1830

Gly Ala Asp Thr Gly Ser Pro Pro Ala Leu Asp Leu Lys Pro Tyr
    1835                1840                1845

Cys Arg Pro Ser Thr Ser Val Val Leu Gln Gly Leu Pro Met Val
    1850                1855                1860

Ala Arg Lys Thr Leu Phe Met Leu Pro Asp Gly Gly Gly Ser Ala
    1865                1870                1875

Phe Ser Tyr Ala Ser Leu Pro Arg Leu Lys Ser Asp Thr Ala Val
    1880                1885                1890
```

```
Val Gly Leu Asn Cys Pro Tyr Ala Arg Asp Pro Glu Asn Met Asn
    1895                1900                1905

Cys Thr His Gly Ala Met Ile Glu Ser Phe Cys Asn Glu Ile Arg
    1910                1915                1920

Arg Arg Gln Pro Arg Gly Pro Tyr His Leu Gly Gly Trp Ser Ser
    1925                1930                1935

Gly Gly Ala Phe Ala Tyr Val Val Ala Glu Ala Leu Val Asn Gln
    1940                1945                1950

Gly Glu Glu Val His Ser Leu Ile Ile Ile Asp Ala Pro Ile Pro
    1955                1960                1965

Gln Ala Met Glu Gln Leu Pro Arg Ala Phe Tyr Glu His Cys Asn
    1970                1975                1980

Ser Ile Gly Leu Phe Ala Thr Gln Pro Gly Ala Ser Pro Asp Gly
    1985                1990                1995

Ser Thr Glu Pro Pro Ser Tyr Leu Ile Pro His Phe Thr Ala Val
    2000                2005                2010

Val Asp Val Met Leu Asp Tyr Lys Leu Ala Pro Leu His Ala Arg
    2015                2020                2025

Arg Met Pro Lys Val Gly Ile Val Trp Ala Ala Asp Thr Val Met
    2030                2035                2040

Asp Glu Arg Asp Ala Pro Lys Met Lys Gly Met His Phe Met Ile
    2045                2050                2055

Gln Lys Arg Thr Glu Phe Gly Pro Asp Gly Trp Asp Thr Ile Met
    2060                2065                2070

Pro Gly Ala Ser Phe Asp Ile Val Arg Ala Asp Gly Ala Asn His
    2075                2080                2085

Phe Thr Leu Met Gln Lys Glu His Val Ser Ile Ile Ser Asp Leu
    2090                2095                2100

Ile Asp Arg Val Met Ala
    2105

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asp Tyr Lys Asp Asp Asp Asp Lys Gly
1               5

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Lys Pro Ile Pro Asn Pro Leu Leu Gly Leu Asp Ser Thr
1               5                   10

<210> SEQ ID NO 18
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 18

Glu Gln Lys Leu Ile Ser Glu Glu Asp Leu
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Pro Glu Leu Ala Pro Glu Asp Pro Glu Asp
1               5                   10

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Tyr Pro Tyr Asp Val Pro Asp Tyr Ala
1               5

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Tyr Thr Asp Ile Glu Met Asn Arg Leu Gly Lys
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: Any amino acid and this region may encompass
      1-3 residues

<400> SEQUENCE: 22

Cys Cys Xaa Xaa Xaa Cys Cys
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 23

Cys Cys Pro Gly Cys Cys
1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Leu Val Pro Arg Gly Ser
1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asp Asp Asp Asp Lys
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Glu Asn Leu Tyr Phe Gln Gly
1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Leu Glu Val Leu Phe Gln Gly Pro
1               5

<210> SEQ ID NO 28
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
atggtcatcc aagggaagag attggccgcc tcctctattc agc          43

<210> SEQ ID NO 29
<211> LENGTH: 29
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 29
gtaggcgtca caggaaagac tgcgtacca                                        29

<210> SEQ ID NO 30
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tatcaccaat gctggatgta aagaagtcgc g                                     31

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
aattgggcta ggaaaccggg gatgc                                            25

<210> SEQ ID NO 32
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cggtctaatg acggcgcatg atatcatagc cgaaacggtc gag                        43

<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
acttggctgg agtccatccc ttcggca                                          27

<210> SEQ ID NO 34
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ctgcccgagt ttgaagtatc tcaacttacc gccgacgcca tg                         42

<210> SEQ ID NO 35
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 35
tgagacgcgc tgcgcagggc                                                    20

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cgaggtgatc gagacgcaga tgc                                                23

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ttatgaagca ccagacatca gccccagc                                           28

<210> SEQ ID NO 38
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
atgggttccg ttagtaggga acatgagtca atc                                     33

<210> SEQ ID NO 39
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gttccttgtg tgagctcctg aataagactg catg                                    34

<210> SEQ ID NO 40
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ccatcaaaat cccctctat cacacgggca ctgggagcaa c                             41

<210> SEQ ID NO 41
<211> LENGTH: 27
<212> TYPE: DNA
<213> ORGANISM: Artificial Sequence
<220> FEATURE:
<223> OTHER INFORMATION: Description of Artificial Sequence: Synthetic
```

```
                              primer

<400> SEQUENCE: 41
cccacgcctt gcgcatctat aatcagg                                        27

<210> SEQ ID NO 42
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tgtccgaata ttctcctcgt tgtaggtagt ggatt                               35

<210> SEQ ID NO 43
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gcagtagtcg ataggtacac atccttgggg gttccatgac tgc                      43

<210> SEQ ID NO 44
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
agaggatcaa ggcattatac atgagtctgt ggaacttggg ctttcc                   46

<210> SEQ ID NO 45
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ttccccgtcc tccatggcct tatgc                                          25

<210> SEQ ID NO 46
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ggcctttgcg cgatacgctg gtctctcggg tcccat                              36

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 47
tcacgccatt tgttgaagca gggaatg                                              27

<210> SEQ ID NO 48
<211> LENGTH: 5016
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48

| | |
|---|---|
| atggtcatcc aagggaagag attggccgcc tcctctattc agcttctcgc aagctcgtta | 60 |
| gacgcgaaga agctttgtta tgagtatgac gagaggcaag ccccaggtgt aacccaaatc | 120 |
| accgaggagg cgcctacaga gcaaccgcct ctctctaccc ctccctcgct accccaaacg | 180 |
| cccaatattt cgcctataag tgcttcaaag atcgtgatcg acgatgtggc gctatctcga | 240 |
| gtgcaaattg ttcaggctct tgttgccaga agttgaaga cggcaattgc tcagcttcct | 300 |
| acatcaaagt caatcaaaga gttgtcgggt ggtcggtctt ctttgcagaa cgagctcgtg | 360 |
| ggggatatac acaacgagtt cagctccatc ccgatgcac cagagcagat cttgttgcgg | 420 |
| gactttggcg acgccaaccc aacagtgcaa ttggggaaaa cgtcctccgc ggcagttgcc | 480 |
| aaactaatct cgtccaagat gcctagtgac ttcaacgcca acgctattcg agcccaccta | 540 |
| gcaaacaagt ggggtctagg acccttgcga caaacagcgg tgttgctcta cgccattgcg | 600 |
| tcagaaccc catcgcgttt agcttcatcg agcagcgg aagagtactg gacaacgtg | 660 |
| tcatccatgt acgccgaatc gtgtggcatc accctccgcc cgagacaaga cactatgaat | 720 |
| gaagatgcta tggcatcgtc ggcgattgat ccggctgtgg tagccgagtt ttccaagggg | 780 |
| caccgtaggc tcggagttca acagttccaa gcgctagcag aatacttaca aattgatttg | 840 |
| tcggggtctc aagcctctca gtcggatgct ttggtggcgg aacttcagca gaaagtcgat | 900 |
| ctctggacgg ccgaaatgac ccccgagttt ctcgccggga tatcaccaat gttggatgta | 960 |
| aagaagtcgc gacgctatgg ctcgtggtgg aacatggcac ggcaggatgt cttggccttc | 1020 |
| tatcgccgtc cttcctacag tgaattcgtg gacgacgcct tggccttcaa agttttttc | 1080 |
| aatcgtctct gtaaccgagc tgatgaggcc ctcctcaaca tggtacgcag tcttttcctgt | 1140 |
| gacgcctact tcaagcaagg ttcttttgccc ggatatcatg ccgcctcgcg actccttgag | 1200 |
| caggccatca catccacagt ggcggattgc ccgaaggcac gcctcattct cccggcggtg | 1260 |
| ggcccccaca ccaccattac aaaggacggc acgattgaat acgcggaggc accgcgccag | 1320 |
| ggagtgagtg gtcccactgc gtacatccag tctctccgcc aaggcgcatc tttcattggt | 1380 |
| ctcaagtcag ccgacgtcga tactcagagc aacttgaccg acgctttgct tgacgccatg | 1440 |
| tgcttagcac tccataatgg aatctcgttt gttggtaaaa ccttttttggt gacgggagcg | 1500 |
| ggtcaggggt caataggagc gggagtggtg cgtctattgt tagagggagg agcccgagta | 1560 |
| ttggtgacga cgagcaggga gccggcgacg acatccagat acttccagca gatgtacgat | 1620 |
| aatcacggtg cgaagttctc cgagttgcgg gtagttcctt gcaatctagc cagcgcccaa | 1680 |
| gattgcgaag ggttgatccg gcacgtctac gatccccgtg ggctaaattg ggatttggat | 1740 |
| gccatccttc ccttcgctgc cgcgtccgac tacagcaccg agatgcatga cattcgggga | 1800 |
| cagagcgagt tgggccaccg gctaatgttg gtcaatgtct tccgcgtgtt ggggcatatc | 1860 |
| gtccactgta aacgagatgc cggggttgac tgccatccga cgcaggtgtt gttgccattg | 1920 |

-continued

```
tcgccaaatc acggcatctt cggtggcgat gggatgtatc cggagtcaaa gctagccctt    1980
gagagcttgt tccatcgcat ccgatcagag tcttggtcag accagttatc tatatgcggc    2040
gttcgtatcg gttggacccg gtcgaccggt ctaatgacgg cgcatgatat catagccgaa    2100
acggtcgagg aacacggaat acgcacattt tccgtggccg agatggcact caacatagcc    2160
atgttgttaa cccccgactt tgtggcccat tgtgaagatg gacctttgga tgccgatttc    2220
accggcagct tgggaacatt gggtagcatc cccggtttcc tagcccaatt gcaccagaaa    2280
gtccagttgg cagccgaggt gatccgtgcc gtgcaggccg aggatgagca tgagagattc    2340
ttgtctccgg gaacaaaacc taccttgcaa gcacccgtgg ccccaatgca cccccgcagt    2400
agccttcgtg taggctatcc ccgtctcccc gattatgagc aagagattcg cccgttgtcc    2460
ccacggttgg aaaggttgca agatccggcc aatgctgtgg tggtggtcgg gtactcggag    2520
ttggggccat ggggtagcgc gcgattacgg tgggaaatag agagccaggg ccagtggact    2580
tcagccggtt atgtcgaact tgcctggttg atgaacctca tccgccacgt caacgatgaa    2640
tcctacgtcg gctgggtgga tactcagacc ggaaagccag tgcgggatgg cgagatccag    2700
gcattgtacg gggaccacat tgacaaccac accggtatcc gtcctatcca gtccacctcg    2760
tacaacccag agcgcatgga ggtcttgcag gaggtcgctg tcgaggagga tttgcccgag    2820
tttgaagtat ctcaacttac cgccgacgcc atgcgtctcc gccatggagc taacgtttcc    2880
atccgcccca gtggaaatcc cgacgcatgc cacgtgaagc ttaaacgagg cgctgttatc    2940
cttgttccca agacagttcc ctttgtttgg ggatcgtgtg ccggtgagtt gccgaaggga    3000
tggactccag ccaagtacgg catccctgag aacctaattc atcaggtcga ccccgtcacg    3060
ctctatacaa tttgctgcgt ggcggaggca ttttacagtg ccggtataac tcaccctctt    3120
gaggtctttc gacacattca cctctcggaa ctaggcaact ttatcggatc ctccatgggt    3180
gggccgacga agactcgtca gctctaccga gatgtctact tcgaccatga gattccgtcg    3240
gatgttttgc aagacactta tctcaacaca cctgctgcct gggttaatat gctactcctt    3300
ggctgcacgg ggccgatcaa aactcccgtc ggcgcatgtg ccaccggggt cgagtcgatc    3360
gattccggct acgagtcaat catggcgggc aagacaaaga tgtgtcttgt gggtggctac    3420
gacgatttgc aggaggaggc atcgtatgga ttcgcacaac ttaaggccac ggtcaacgtt    3480
gaagaggaga tcgcctgcgg tcgacagccc tcggagatgt cgcgcccat ggctgagagt    3540 cgtgctggct ttgtcgaggc gcatggctgc ggtgtacagt tgttgtgtcg aggtgacatc    3600
gccttgcaaa tgggtcttcc tatctatgcg gtcattgcca gctcagccat ggccgccgac    3660
aagatcggtt cctcggtgcc agcaccgggc cagggcattc taagcttctc ccgtgagcgc    3720
gctcgatcca gtatgatatc cgtcacgtcg cgcccgagta gccgtagcag cacatcatct    3780
gaagtctcgg acaaatcatc cttgacctca atcacctcaa tcagcaatcc cgctcctcgt    3840
gcacaacgcg cccgatccac cactgatatg gctccgttgc gagcagcgct tgcgacttgg    3900
gggttgacta tcgacgactt ggatgtggcc tcattgcacg gcacctcgac gcgcggtaac    3960
gatctcaatg agcccgaggt gatcgagacg cagatgcgcc atttaggtcg cactcctggc    4020
cgccccttgt gggccatctg ccaaaagtca gtgacggac accctaaagc cccagcggcc    4080
gcatggatgc tcaatggatg cttgcaagta ttggactcgg ggttggtgcc gggcaaccgc    4140
aatcttgaca cgttggacga ggccttgcgc agcgcgtctc atctctgctt ccctacgcgc    4200
accgtgcagc tacgtgaggt caaggcattc ttgttgacct catttggctt cggacagaag    4260
```

```
gggggccaag tcgtcggcgt tgcccccaag tacttctttg ctacgctccc ccgccccgag    4320
gttgagggct actatcgcaa ggtgagggtt cgaaccgagg cgggtgatcg cgcctacgcc    4380
gcggcggtca tgtcgcaggc ggtggtgaag atccagacgc aaaacccgta cgacgagccg    4440 gatgccccc  gcattttct  cgatcccttg gcacgtatct cccaggatcc gtcgacgggc    4500
cagtatcggt ttcgttccga tgccactccc gccctcgatg atgatgcttt gccacctccc    4560
ggcgaaccca ccgagctagt gaagggcatc tcctccgcct ggatcgagga aaggtgcga    4620 ccgcatatgt ctcccggcgg cacggtgggc gtggacttgg ttcctctcgc ctccttcgac    4680
gcatacaaga atgccatctt tgttgagcgc aattatacgg taagggagcg cgattgggct    4740
gaaaagagtg cggatgtgcg cgcggcctat gccagtcggt ggtgtgcaaa agaggcggtg    4800
ttcaaatgtc tccagacaca ttcacagggc gcggggcag  ccatgaaaga gattgagatc    4860
gagcatggag gtaacggcgc accgaaagtc aagctccggg gtgctgcgca aacagcggcg    4920
cggcaacgag gattgaaagg agtgcaattg agcatcagct atggcgacga tgcggtgata    4980
gcggtggcgt tggggttgat gtctggtgct tcataa                              5016
```

<210> SEQ ID NO 49
<211> LENGTH: 5667
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49

```
atgggttccg ttagtaggga acatgagtca atccccatcc aggccgccca gagaggcgct      60
gcccggatct gcgctgcttt tggaggtcaa gggtctaaca atttggacgt gttaaaaggt     120
ctattggagt tatacaagcg gtatggccca gatttggatg agctactaga cgtggcatcc     180
aacacgcttt cgcagttggc atcttcccct gctgcaatag acgtccacga accctggggt     240
ttcgacctcc gacaatggtt gaccacaccg gaggttgctc ctagcaaaga aattcttgcc     300
ttgccaccac gaagctttcc cttaaatacg ttacttagct tggcgctcta ttgtgcaact     360
tgtcgagagc ttgaacttga tcctgggcaa tttcgatccc tccttcatag ttccacgggg     420
cattcccaag gcatattggc ggcggtggcc atcacccaag ccgagagctg gccaaccttt     480
tatgacgcct gcaggacggt gctccagatc tctttctgga ttggactcga ggcttacctc     540
ttcactccat cctccgccgc ctcggatgcc atgatccaag attgcatcga acatggcgag     600
ggccttcttt cctcaatgct aagtgtctcc gggctctccc gctcccaagt tgagcgagta     660
attgagcacg tcaataaagg gctcggagaa tgcaaccgat gggttcactt ggccttggtt     720
aactcccacg aaaagttcgt cttagcggga ccacctcaat ccttatgggc cgtttgtctt     780
catgtccgac ggatcagagc agacaatgac ctcgaccagt cgcgtatctt gttccgcaac     840
cgaaagccta tagtggatat attatttctt cccatatccg caccatttca cacaccgtac     900
ttggacggtg ttcaagatcg cgttatcgag gctttgagct ctgcttcgtt ggctctccat     960
tccatcaaaa tcccctcta  tcacacgggc actgggagca acctacaaga actacaacca    1020
catcagctaa tcccgactct tatccgcgcc attaccgtgg accaattgga ctggccgttg    1080
gtttgccggg gcttgaacgc aacgcacgtg ttggactttg gacctggaca acatgcagt     1140 cttattcagg agctcacaca aggaacaggt gtatcagtga tccagttgac tactcaatcg    1200
ggaccaaaac ccgttggagg ccatttggcg gcagtgaact gggaggccga gtttggctta    1260
```

-continued

```
cgacttcatg ccaatgtcca cggtgcagct aaattgcaca accgtatgac aacattgctt      1320
gggaagcctc ctgtgatggt agccggaatg acacctacta cggtgcgctg ggactttgtc      1380
gctgccgttg ctcaagctgg ataccacgtc gaattggctg gtggtggcta ccacgcagag      1440
cgccagttcg aggccgagat tcggcgcttg gcaactgcca tcccagcaga tcatggcatc      1500
acctgcaatc tcctctacgc caagcctacg acttttcct ggcagatctc tgtcatcaag       1560
gatttggtgc gccagggagt tcccgtggaa ggaatcacca tcggcgccgg catcccttct      1620
ccggaggtcg tccaagaatg tgtacagtcc atcggactca agcacatctc attcaagcct      1680
gggtctttcg aagccattca ccaagtcata cagatcgcgc gtacccatcc taacttttg      1740
atcgggttgc aatggaccgc aggacgaggg ggaggacatc attcctggga agacttccat      1800
ggacctattt tggcaaccta cgctcaaatc cgatcatgtc cgaatattct cctcgttgta      1860
ggtagtggat tcggtggagg cccggacacg tttccctacc tcacgggcca atgggcccag      1920
gcctttggct atccatgcat gcccttcgac ggagtgttgc tcggcagtcg catgatggtg      1980
gctcgggaag cccatacgtc agcccaggca aaacgcttga ttatagatgc gcaaggcgtg      2040
ggagatgcag attggcacaa gtctttcgat gagcctaccg gcggcgtagt gacggtcaac      2100
tcggaattcg gtcaacctat ccacgttcta gctactcgcg gagtgatgtt gtggaaagaa      2160
ctcgacaacc gggtcttttc aatcaaagac acttctaagc gcttagaata tttgcgcaac      2220
caccggcaag aaattgtgag ccgtcttaac gcagactttg cccgtccctg gtttgccgtt      2280
gacggacacg gacagaatgt ggagttggag gacatgacct acctcgaggt tctccgccgt      2340
ttgtgcgatc tcacgtatgt ttcccaccag aagcgatggg tagatccatc atatcgaata      2400
ttattgttgg acttcgttca tttgcttcga gaacgattcc aatgcgctat tgacaacccc      2460
ggcgaatatc cactcgacat catcgtccgg gtggaagaga gcttgaagga taaagcatac      2520
cgcacgcttt atccagaaga tgtctctctt ctaatgcatt tgttcagccg acgtgacatc      2580
aagcccgtac cattcatccc caggttggat gagcgttttg agacctggtt taaaaaagac      2640
tcattgtggc aatccgaaga tgtggaggcg gtaattggac aggacgtcca gcgaatcttc      2700
atcattcaag ggcctatggc cgttcagtac tcaatatccg acgatgagtc tgttaaagac      2760
attttacaca atatttgtaa tcattacgtg gaggctctac aggctgattc aagagaaact      2820
tctatcggcg atgtacactc gatcacgcaa aaacctctca gcgcgtttcc tgggctcaaa      2880
gtgacgacaa atagggtcca agggctctat aagttcgaga agtaggagc agtccccgaa       2940
atggacgttc tttttgagca tattgtcgga ttgtcgaagt catgggctcg acatgtttg       3000
atgagtaaat cggtctttag ggacggttct cgtttgcata accccattcg cgccgcactc      3060
cagctccagc gcggcgacac catcgaggtg cttttaacag cagactcgga aattcgcaag      3120
attcgactta tttcacccac gggggatggt ggatccactt ctaaggtcgt attagagata      3180
gtctctaacg acggacaaag agttttcgcc accttggccc ctaacatccc actcagcccc      3240
gagcccagcg tcgtctttg cttcaaggtc gaccagaagc cgaatgagtg gacccttgag      3300
gaggatgcgt ctggccgggc agagaggatc aaggcattat acatgagttt gtggaacttg      3360
ggctttccga acaaggcctc tgttttgggt cttaattcgc aattcacggg agaagaattg      3420
atgatcacaa cggacaagat tcgtgatttc gaaagggtat tgcggcaaac cagtcctctt      3480
cagttgcagt catggaaccc ccaaggatgt gtacctatcg actactgcgt ggtcatcgcc      3540
tggtctgctc ttaccaagcc tttgatggtc tcctctttga aatgcgacct cttggatttg      3600
ctccacagcg ctataagctt ccactatgct ccatctgtca aaccattgcg ggtgggcgat      3660
```

```
attgtcaaaa cctcatcccg tatcctagcg gtctcggtga gacctagggg aactatgttg    3720
acggtgtcgg cggacattca gcgccaggga caacatgtag tcactgtcaa atcagatttc    3780
tttctcggag gccccgtttt ggcatgtgaa acccctttcg aactcactga ggagcctgaa    3840
atggttgtcc atgtcgactc tgaagtgcgc cgtgctattt tacacagccg caagtggctc    3900
atgcgagaag atcgcgcgct agatttgcta gggaggcagc tcctcttcag attaaagagc    3960
gaaaaattgt tcaggccaga cggccagcta gcattgttac aggtaacagg ttccgtgttc    4020
agctacagcc ccgatgggtc aacgacagca ttcggtcgcg tatacttcga aagcgagtct    4080
tgtacaggga acgtggtgat ggacttcttg caccgctacg gtgcacctcg ggcgcagttg    4140
ttggagttgc aacatcccgg gtggacgggc acctctactg tggcagtaag aggtcctcga    4200
cgcagccaat cctacgcacg cgtctccctc gatcataatc ccatccatgt ttgtccggcc    4260
tttgcgcgat acgctggtct ctcgggtccc attgtccatg ggatggaaac ctctgccatg    4320
atgcgcagaa ttgccgaatg ggccatcgga gatgcagacc ggtctcggtt ccggagctgg    4380
catatcacct tgcaagcacc cgtccacccc aacgacccTt tgcgggtgga gttgcagcat    4440
aaggccatgg aggacgggga aatggttttg aaagtacaag catttaacga aaggacggaa    4500
gaacgcgtag cggaggcaga tgcccatgtt gagcaggaaa ctacggctta cgtcttctgt    4560
ggccagggca gtcaacgaca ggggatggga atggacttgt acgtcaactg tccggaggct    4620
aaagcgttgt gggctcgcgc cgacaagcat ttgtgggaga aatatgggtt ctccatcttg    4680
cacattgtgc aaaacaaccc tccagccctc actgttcact ttggcagcca gcagggcgc     4740
cgtattcgtg ccaactattt gcgcatgatg ggacagccac cgatagatgg tagacatccg    4800
cccatattga agggattgac gcggaattcg acctcgtaca ccttctccta ttcccagggg    4860
ttgttgatgt ccacccagtt cgcccagccc gcattggcgt tgatgaaat ggctcagttc     4920
gaatggctca aagcccaggg agtcgttcag aagggtgcgc ggttcgcggg acattcgttg    4980
ggagaatatg ccgcccttgg agcttgtgct tccttcctct catttgaaga tctcatatct    5040
ctcatctttt atcggggctt gaagatgcag aatgcgttgc cgcgcgatgc caacggccac    5100
accgactatg gaatgttggc tgccgatcca tcgcggatag gaaaaggttt cgaggaagcg    5160
agtttgaaat gtcttgtcca tatcattcaa caggagaccg gctggttcgt ggaagtcgtc    5220
aactacaaca tcaactcgca gcaatacgtc tgtgcaggcc atttccgagc cctttggatg    5280
ttgggtaaga tatgcgatga cctttcatgc caccctcaac cggagactgt tgaaggccaa    5340
gagctacggg ccatggtctg gaagcatgtc ccgacggtgg agcaggtgcc ccgcgaggat    5400
cgcatggaac gaggtcgagc gaccattccg ttgccgggga tcgatatccc ataccattcg    5460
accatgttac gagggagat  tgagcctTat cgtgaatatt tgtctgaacg tatcaaggtg    5520
ggggatgtga agccgtgcga attggtggga cgctggatcc ctaatgttgt tggccagcct    5580
ttctccgtcg ataagtctta cgttcagttg gtgcacggca tcacaggtag tcctcggctt    5640
cattccttgc ttcaacaaat ggcgtga                                        5667
```

<210> SEQ ID NO 50
<211> LENGTH: 12
<212> TYPE: DNA
<213> ORGANISM: Artificial Sequence
<220> FEATURE:
<223> OTHER INFORMATION: Description of Artificial Sequence: Synthetic binding motif oligonucleotide
<220> FEATURE:
<221> NAME/KEY: modified_base

```
<222> LOCATION: (4)..(9)
<223> OTHER INFORMATION: a, c, t, g, unknown or other

<400> SEQUENCE: 50
tcrnnnnnna cg                                                     12

<210> SEQ ID NO 51
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(14)
<223> OTHER INFORMATION: a, c, t, g, unknown or other

<400> SEQUENCE: 51
cggnnnnnnn nnnnccg                                                17

<210> SEQ ID NO 52
<211> LENGTH: 13
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(5)
<223> OTHER INFORMATION: a, c, t, g, unknown or other
<220> FEATURE:
<221> NAME/KEY: modified_base
<222> LOCATION: (9)..(10)
<223> OTHER INFORMATION: a, c, t, g, unknown or other

<400> SEQUENCE: 52
gaannttcnn gaa                                                    13

<210> SEQ ID NO 53
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (8)..(9)
<223> OTHER INFORMATION: a, c, t, g, unknown or other

<400> SEQUENCE: 53 tgatgtannt                                                        10

<210> SEQ ID NO 54
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(5)
<223> OTHER INFORMATION: a, c, t, g, unknown or other

<400> SEQUENCE: 54 ccnnnwwrgg                                                        10
```

```
<210> SEQ ID NO 55
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 55 wwwwsygggg                                                                10

<210> SEQ ID NO 56
<211> LENGTH: 13
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (8)..(9)
<223> OTHER INFORMATION: a, c, t, g, unknown or other

<400> SEQUENCE: 56
rmacccannc ayy                                                            13

<210> SEQ ID NO 57
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (6)..(7)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other

<400> SEQUENCE: 57
tycgtnnrna rtgaya                                                         16

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other

<400> SEQUENCE: 58
rrraararaa nanraraa                                                       18

<210> SEQ ID NO 59
<211> LENGTH: 18
<212> TYPE: DNA
<213> ORGANISM: Artificial Sequence
<220> FEATURE:
<223> OTHER INFORMATION: Description of Artificial Sequence: Synthetic
``` binding motif oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other

<400> SEQUENCE: 59
anagngagag agnggcag                                                     18

<210> SEQ ID NO 60
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(3)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other

<400> SEQUENCE: 60
tnnccwnttt ktttc                                                        15

<210> SEQ ID NO 61
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 61
aaaaararaa aarma                                                        15

<210> SEQ ID NO 62
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(14)
<223> OTHER INFORMATION: a, c, t, g, unknown or other

<400> SEQUENCE: 62
ykytyttytt nnnnky                                                       16

<210> SEQ ID NO 63
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 63
cgtccggcgc                                                              10

<210> SEQ ID NO 64
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 64
gaaaaagmaa aaaaa                                                        15

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other

<400> SEQUENCE: 65
ttttyyttyt tkyntynt                                                     18

<210> SEQ ID NO 66
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 66
catkyttttt tkyty                                                        15

<210> SEQ ID NO 67
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 67 cacgtgacya                                                              10

<210> SEQ ID NO 68
<211> LENGTH: 14
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(5)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other

```
<400> SEQUENCE: 68
cannnacaca sana                                                    14

<210> SEQ ID NO 69
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (7)..(8)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other

<400> SEQUENCE: 69
ggnanannar narggcn                                                 17

<210> SEQ ID NO 70
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(11)
<223> OTHER INFORMATION: a, c, t, g, unknown or other

<400> SEQUENCE: 70
tttkytktty nytttkty                                                18

<210> SEQ ID NO 71
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (16)..(16)
<223> OTHER INFORMATION: a, c, t, g, unknown or other

<400> SEQUENCE: 71
wttkttttty tttttnt                                                 17

<210> SEQ ID NO 72
<211> LENGTH: 11
<212> TYPE: DNA
<213> ORGANISM: Artificial Sequence
<220> FEATURE:
<223> OTHER INFORMATION: Description of Artificial Sequence: Synthetic
``` binding motif oligonucleotide

<400> SEQUENCE: 72
ttkttttytt c                                                          11

<210> SEQ ID NO 73
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(5)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other

<400> SEQUENCE: 73
aaannraang arraanar                                                   18

<210> SEQ ID NO 74
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other

<400> SEQUENCE: 74
gtgmaknmgr angng                                                      15

<210> SEQ ID NO 75
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other

<400> SEQUENCE: 75
nttwacaycc rtacayny                                                   18

<210> SEQ ID NO 76

```
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other

<400> SEQUENCE: 76
tttnctttky ttnytttt                                           18

<210> SEQ ID NO 77
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other

<400> SEQUENCE: 77
aaaranraaa naaarnaa                                           18

<210> SEQ ID NO 78
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 78
cacacacaca cacacac                                            17

<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 79
ttgcttgaac gsatgcca                                           18

<210> SEQ ID NO 80
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
```

```
<400> SEQUENCE: 80
yctttttttt yttyykg                                                17

<210> SEQ ID NO 81
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 81
rrsccgmcgm grcgcgcs                                               18

<210> SEQ ID NO 82
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other

<400> SEQUENCE: 82
aaanararnr aaaarrar                                               18

<210> SEQ ID NO 83
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 83
ggaagctgaa acgymwrr                                               18

<210> SEQ ID NO 84
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 84
ggagaggcat gatggggg                                               18

<210> SEQ ID NO 85
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(3)
<223> OTHER INFORMATION: a, c, t, g, unknown or other

<400> SEQUENCE: 85
``` ctnccttttct                                                         10

<210> SEQ ID NO 86
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 86
gaaarraaaa aamrmara                                                 18

<210> SEQ ID NO 87
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (8)..(9)
<223> OTHER INFORMATION: a, c, t, g, unknown or other

<400> SEQUENCE: 87
gngccrsnnt m                                                        11

<210> SEQ ID NO 88
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (13)..(13)
<223> OTHER INFORMATION: a, c, t, g, unknown or other

<400> SEQUENCE: 88
tttttyyttt tynktttt                                                 18

<210> SEQ ID NO 89
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (18)..(18)
<223> OTHER INFORMATION: a, c, t, g, unknown or other

<400> SEQUENCE: 89

```
yttctttttyt nyncnktn                                        18

<210> SEQ ID NO 90
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(2)
<223> OTHER INFORMATION: a, c, t, g, unknown or other

<400> SEQUENCE: 90
tnsykctttt cytty                                            15

<210> SEQ ID NO 91
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 91
sttnytttyn ttytyyyy                                         18

<210> SEQ ID NO 92
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(3)
<223> OTHER INFORMATION: a, c, t, g, unknown or other

<400> SEQUENCE: 92 yknttttwyyt c                                               11

<210> SEQ ID NO 93
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other
```

```
<400> SEQUENCE: 93
aaaananaar arnag                                                  15

<210> SEQ ID NO 94
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (13)..(13)
<223> OTHER INFORMATION: a, c, t, g, unknown or other

<400> SEQUENCE: 94
waaaaaagaa aanaaaar                                               18

<210> SEQ ID NO 95
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other

<400> SEQUENCE: 95
aaanggnara m                                                      11

<210> SEQ ID NO 96
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(12)
<223> OTHER INFORMATION: a, c, t, g, unknown or other

<400> SEQUENCE: 96
tyttcyagaa nnttcy                                                 16

<210> SEQ ID NO 97
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 97
cacacacaca cacacaca                                               18

<210> SEQ ID NO 98
<211> LENGTH: 11
<212> TYPE: DNA
<213> ORGANISM: Artificial Sequence
<220> FEATURE:
<223> OTHER INFORMATION: Description of Artificial Sequence: Synthetic
``` binding motif oligonucleotide

<400> SEQUENCE: 98
tttycacatg c                                                          11

<210> SEQ ID NO 99
<211> LENGTH: 14
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(3)
<223> OTHER INFORMATION: a, c, t, g, unknown or other

<400> SEQUENCE: 99
gnngcatgtg aaaa                                                       14

<210> SEQ ID NO 100
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other

<400> SEQUENCE: 100
gaaaanaaaa aaaarana                                                   18

<210> SEQ ID NO 101
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (13)..(13)
<223> OTHER INFORMATION: a, c, t, g, unknown or other

<400> SEQUENCE: 101
gaaaaaraar aanaa                                                      15

<210> SEQ ID NO 102
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (6)..(7)
<223> OTHER INFORMATION: a, c, t, g, unknown or other

<400> SEQUENCE: 102
yttktnnttt ttytyttt                                                   18

```
<210> SEQ ID NO 103
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (5)..(5)
<223> OTHER INFORMATION: a, c, t, g, unknown or other

<400> SEQUENCE: 103 gcagngcagg                                                                10

<210> SEQ ID NO 104
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(11)
<223> OTHER INFORMATION: a, c, t, g, unknown or other

<400> SEQUENCE: 104
tttytykttt nyyttttt                                                       18

<210> SEQ ID NO 105
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 105
tttccnaawn rggaaa                                                         16

<210> SEQ ID NO 106
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 106
yttyyttytt ttytyttc                                                       18

<210> SEQ ID NO 107
<211> LENGTH: 14
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 107
mtttttytyt yttc                                                           14
```

```
<210> SEQ ID NO 108
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (7)..(7)
<223> OTHER INFORMATION: a, c, t, g, unknown or other

<400> SEQUENCE: 108
tatacanagm krtatatg                                                 18

<210> SEQ ID NO 109
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other

<400> SEQUENCE: 109
tmtttntync ttntttwk                                                 18

<210> SEQ ID NO 110
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(4)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 110
ktnnttwtta ttccnc                                                   16

<210> SEQ ID NO 111
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(3)
<223> OTHER INFORMATION: a, c, t, g, unknown or other
<220> FEATURE:
<221> NAME/KEY: modified_base
<222> LOCATION: (8)..(8)
```

-continued

```
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other

<400> SEQUENCE: 111
rnnaaaanra naaraaat                                                 18

<210> SEQ ID NO 112
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 112
ttttttttcw ctttkyc                                                  17

<210> SEQ ID NO 113
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other

<400> SEQUENCE: 113
tttynytktt tynyttyt                                                 18

<210> SEQ ID NO 114
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(5)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other

<400> SEQUENCE: 114
ttynnttytt nytttyyy                                                 18

<210> SEQ ID NO 115
<211> LENGTH: 14
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
```

```
<222> LOCATION: (12)..(12)
<223> OTHER INFORMATION: a, c, t, g, unknown or other

<400> SEQUENCE: 115
tnygtgkryg tnyg                                                        14

<210> SEQ ID NO 116
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 116
ttyyyttttt yttttytt                                                    18

<210> SEQ ID NO 117
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 117
gamaaaaaar aaaar                                                       15

<210> SEQ ID NO 118
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (15)..(15)
<223> OTHER INFORMATION: a, c, t, g, unknown or other

<400> SEQUENCE: 118
cycgggaagc sammnccg                                                    18

<210> SEQ ID NO 119
<211> LENGTH: 13
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 119
grtgyayggr tgy                                                         13

<210> SEQ ID NO 120
<211> LENGTH: 14
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 120
kmaaraaaaa raar                                                        14

<210> SEQ ID NO 121
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 121
aygraaaara raaaaraa                                                   18

<210> SEQ ID NO 122
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (8)..(8)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other

<400> SEQUENCE: 122 ggakscentt tyngmrta                                                   18

<210> SEQ ID NO 123
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (6)..(6)
<223> OTHER INFORMATION: a, c, t, g, unknown or other

<400> SEQUENCE: 123
ttttcnkttt yttttc                                                     17

<210> SEQ ID NO 124
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 124
araagmagaa arraa                                                      15

<210> SEQ ID NO 125
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (12)..(12)
<223> OTHER INFORMATION: a, c, t, g, unknown or other

<400> SEQUENCE: 125
yttttctttt yntttt                                                     17
```

```
<210> SEQ ID NO 126
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(11)
<223> OTHER INFORMATION: a, c, t, g, unknown or other

<400> SEQUENCE: 126
arraraaagg n                                                                11

<210> SEQ ID NO 127
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other

<400> SEQUENCE: 127
ystnykntyt tnctcccm                                                         18

<210> SEQ ID NO 128
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other

<400> SEQUENCE: 128
garanaaaar nraaraaa                                                         18

<210> SEQ ID NO 129
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(4)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other
```

```
<400> SEQUENCE: 129
cynnggssan c                                                          11

<210> SEQ ID NO 130
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 130
cacacacaca cacaya                                                     16

<210> SEQ ID NO 131
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 131
cttytwttkt tktsa                                                      15

<210> SEQ ID NO 132
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 132
yttyyytytt tytyyttt                                                   18

<210> SEQ ID NO 133
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (16)..(16)
<223> OTHER INFORMATION: a, c, t, g, unknown or other

<400> SEQUENCE: 133
amaaaaaraa rwaranaa                                                   18

<210> SEQ ID NO 134
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (15)..(15)
<223> OTHER INFORMATION: a, c, t, g, unknown or other

<400> SEQUENCE: 134
araaaarraa aaagnraa                                                   18

<210> SEQ ID NO 135
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 135
raaraaaaar cmrsraaa                                                   18

<210> SEQ ID NO 136
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (10)..(10)
<223> OTHER INFORMATION: a, c, t, g, unknown or other

<400> SEQUENCE: 136
ttytktytyn tyykttty                                                   18

<210> SEQ ID NO 137
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 137
gaaaamaana aaanaaa                                                    18

<210> SEQ ID NO 138
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 138
yaanaraara aaanaam                                                    18

<210> SEQ ID NO 139
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
```

```
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other

<400> SEQUENCE: 139 tynttttty tttttntk                                                   18

<210> SEQ ID NO 140
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other

<400> SEQUENCE: 140
raaraaraaa naanrnaa                                                  18

<210> SEQ ID NO 141
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 141
cacacacaca cacacaca                                                  18

<210> SEQ ID NO 142
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (12)..(12)
<223> OTHER INFORMATION: a, c, t, g, unknown or other

<400> SEQUENCE: 142
raarrraaaa anaaamaa                                                  18

<210> SEQ ID NO 143
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 143
gccagaccta c                                                         11
```

```
<210> SEQ ID NO 144
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (14)..(14)
<223> OTHER INFORMATION: a, c, t, g, unknown or other

<400> SEQUENCE: 144
ttyttyttyt ttynytyt                                                 18

<210> SEQ ID NO 145
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 145
yksgcgcgyc kcgkcggs                                                 18

<210> SEQ ID NO 146
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 146
ttttyytttt yyyyktt                                                  17

<210> SEQ ID NO 147
<211> LENGTH: 13
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 147
ttcttktyyt ttt                                                      13

<210> SEQ ID NO 148
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 148
ttyttttyty ytttyttt                                                 18

<210> SEQ ID NO 149
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
```

```
<400> SEQUENCE: 149
ttgcttgaac ggatgcca                                                    18

<210> SEQ ID NO 150
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(3)
<223> OTHER INFORMATION: a, c, t, g, unknown or other

<400> SEQUENCE: 150
mgnmcaaaaa taaaas                                                      16

<210> SEQ ID NO 151
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (6)..(7)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other

<400> SEQUENCE: 151
tycgtnnrna rtgaya                                                      16

<210> SEQ ID NO 152
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 152
gtgtgtgtgt gtgtg                                                       15

<210> SEQ ID NO 153
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (9)..(9)
<223> OTHER INFORMATION: a, c, t, g, unknown or other

<400> SEQUENCE: 153
ytstysttnt tgytwtt                                                     17

<210> SEQ ID NO 154
<211> LENGTH: 15
<212> TYPE: DNA
<213> ORGANISM: Artificial Sequence
<220> FEATURE:
<223> OTHER INFORMATION: Description of Artificial Sequence: Synthetic
``` binding motif oligonucleotide

<400> SEQUENCE: 154
gcatgaccat ccacg                                                          15

<210> SEQ ID NO 155
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 155
gsgayarmgg amaaaaa                                                        17

<210> SEQ ID NO 156
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(11)
<223> OTHER INFORMATION: a, c, t, g, unknown or other

<400> SEQUENCE: 156
trccgagryw nsssgcgs                                                       18

<210> SEQ ID NO 157
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 157
cgtccggcgc                                                                10

<210> SEQ ID NO 158
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (13)..(14)
<223> OTHER INFORMATION: a, c, t, g, unknown or other

<400> SEQUENCE: 158
aarwtsgarg nanncsaa                                                       18

<210> SEQ ID NO 159
<211> LENGTH: 14
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:

```
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (11)..(12)
<223> OTHER INFORMATION: a, c, t, g, unknown or other

<400> SEQUENCE: 159
csnccaatgk nncs                                                              14

<210> SEQ ID NO 160
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(4)
<223> OTHER INFORMATION: a, c, t, g, unknown or other

<400> SEQUENCE: 160 gctnactaat                                                                   10

<210> SEQ ID NO 161
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 161 cacgtgacya                                                                   10

<210> SEQ ID NO 162
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (10)..(10)
<223> OTHER INFORMATION: a, c, t, g, unknown or other

<400> SEQUENCE: 162
cayamrtgyn c                                                                 11

<210> SEQ ID NO 163
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 163 tsgygrgasa                                                                   10

<210> SEQ ID NO 164
<211> LENGTH: 18
<212> TYPE: DNA
<213> ORGANISM: Artificial Sequence
<220> FEATURE:
<223> OTHER INFORMATION: Description of Artificial Sequence: Synthetic
```

```
         binding motif oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (6)..(8)
<223> OTHER INFORMATION: a, c, t, g, unknown or other

<400> SEQUENCE: 164
kncncnnnsc gctackgc                                                  18

<210> SEQ ID NO 165
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other

<400> SEQUENCE: 165
srnggcmcgg cnssg                                                     15

<210> SEQ ID NO 166
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (8)..(8)
<223> OTHER INFORMATION: a, c, t, g, unknown or other

<400> SEQUENCE: 166
tacyacanca cawga                                                     15

<210> SEQ ID NO 167
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other

<400> SEQUENCE: 167
ccytgnaytt cwncttc                                                   17

<210> SEQ ID NO 168
```

<211> LENGTH: 15
<212> TYPE: DNA
<213> ORGANISM: Artificial Sequence
<220> FEATURE:
<223> OTHER INFORMATION: Description of Artificial Sequence: Synthetic binding motif oligonucleotide
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other

<400> SEQUENCE: 168
gtgmaknmgr angng                                                    15

<210> SEQ ID NO 169
<211> LENGTH: 18
<212> TYPE: DNA
<213> ORGANISM: Artificial Sequence
<220> FEATURE:
<223> OTHER INFORMATION: Description of Artificial Sequence: Synthetic binding motif oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other

<400> SEQUENCE: 169
nttwacaycc rtacayny                                                 18

<210> SEQ ID NO 170
<211> LENGTH: 13
<212> TYPE: DNA
<213> ORGANISM: Artificial Sequence
<220> FEATURE:
<223> OTHER INFORMATION: Description of Artificial Sequence: Synthetic binding motif oligonucleotide
<220> FEATURE:
<221> NAME/KEY: modified_base
<222> LOCATION: (4)..(4)
<223> OTHER INFORMATION: a, c, t, g, unknown or other

<400> SEQUENCE: 170
aawnrtaaay arg                                                      13

<210> SEQ ID NO 171
<211> LENGTH: 16
<212> TYPE: DNA
<213> ORGANISM: Artificial Sequence
<220> FEATURE:
<223> OTHER INFORMATION: Description of Artificial Sequence: Synthetic binding motif oligonucleotide
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (8)..(8)
<223> OTHER INFORMATION: a, c, t, g, unknown or other

<400> SEQUENCE: 171

```
ggnaawangt aaacaa                                              16

<210> SEQ ID NO 172
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 172
sastkcwctc ktcgt                                               15

<210> SEQ ID NO 173
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 173
ttgcttgaac gsatgcca                                            18

<210> SEQ ID NO 174
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (5)..(7)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (12)..(13)
<223> OTHER INFORMATION: a, c, t, g, unknown or other

<400> SEQUENCE: 174
cggmnnncwn ynnccccg                                            17

<210> SEQ ID NO 175
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 175
rgargtsacg cakrttct                                            18

<210> SEQ ID NO 176
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 176
ggaagctgaa acgymwrr                                            18
```

```
<210> SEQ ID NO 177
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 177
aggtgatgga gtgctcag                                                 18

<210> SEQ ID NO 178
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other

<400> SEQUENCE: 178
gkctrrnrgg agangm                                                   16

<210> SEQ ID NO 179
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other

<400> SEQUENCE: 179
ngggsgntns ygtncga                                                  17

<210> SEQ ID NO 180
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(3)
<223> OTHER INFORMATION: a, c, t, g, unknown or other

<400> SEQUENCE: 180
```
agnawgtttt tgwcaama                                        18

<210> SEQ ID NO 181
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 181
kcksgcaggc wttkytct                                        18

<210> SEQ ID NO 182
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other

<400> SEQUENCE: 182
gnccsartng c                                               11

<210> SEQ ID NO 183
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (9)..(10)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other

<400> SEQUENCE: 183
sgcgmgggnn ccngaccg                                        18

<210> SEQ ID NO 184
<211> LENGTH: 14
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other

<400> SEQUENCE: 184

```
yctnattsgn cngs                                                    14

<210> SEQ ID NO 185
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other

<400> SEQUENCE: 185
tnttsmttny tttccknc                                                18

<210> SEQ ID NO 186
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (14)..(14)
<223> OTHER INFORMATION: a, c, t, g, unknown or other

<400> SEQUENCE: 186
ccacktksgs cctns                                                   15

<210> SEQ ID NO 187
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 187
crsgcywgkg c                                                       11

<210> SEQ ID NO 188
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other
```

<400> SEQUENCE: 188
naaraagcng ggcacnc                                                    17

<210> SEQ ID NO 189
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(12)
<223> OTHER INFORMATION: a, c, t, g, unknown or other

<400> SEQUENCE: 189
tyttcyagaa nnttcy                                                     16

<210> SEQ ID NO 190
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 190
cacacacaca cacacaca                                                   18

<210> SEQ ID NO 191
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 191
sckkcgckst ssttyaa                                                    17

<210> SEQ ID NO 192
<211> LENGTH: 14
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(3)
<223> OTHER INFORMATION: a, c, t, g, unknown or other

<400> SEQUENCE: 192
gnngcatgtg aaaa                                                       14

<210> SEQ ID NO 193
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 193
ctttttttyy tsgcc                                                      15

<210> SEQ ID NO 194

```
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (14)..(15)
<223> OTHER INFORMATION: a, c, t, g, unknown or other

<400> SEQUENCE: 194
gccggtmmcg sycnn                                              15

<210> SEQ ID NO 195
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(3)
<223> OTHER INFORMATION: a, c, t, g, unknown or other

<400> SEQUENCE: 195 annttttyt tkygc                                               15

<210> SEQ ID NO 196
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other

<400> SEQUENCE: 196
aaacntttat anataca                                            17

<210> SEQ ID NO 197
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other

<400> SEQUENCE: 197
caatntctnc k                                                  11

<210> SEQ ID NO 198
<211> LENGTH: 15
<212> TYPE: DNA
<213> ORGANISM: Artificial Sequence
```

```
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other

<400> SEQUENCE: 198
gnrrnanacg cgtnr                                                          15

<210> SEQ ID NO 199
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 199
tttccnaawn rggaaa                                                         16

<210> SEQ ID NO 200
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
atggtcatcc aagggaagag attggccgcc tcctctattc agc                            43

<210> SEQ ID NO 201
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
gtaggcgtca caggaaagac tgcgtacca                                           29

<210> SEQ ID NO 202
<211> LENGTH: 31
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 202
tatcaccaat gctggatgta aagaagtcgc g                                      31

<210> SEQ ID NO 203
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
aattgggcta ggaaaccggg gatgc                                             25

<210> SEQ ID NO 204
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
cggtctaatg acggcgcatg atatcatagc cgaaacggtc gag                         43

<210> SEQ ID NO 205
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
acttggctgg agtccatccc ttcggca                                           27

<210> SEQ ID NO 206
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
ctgcccgagt ttgaagtatc tcaacttacc gccgacgcca tg                          42

<210> SEQ ID NO 207
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
tgagacgcgc tgcgcagggc                                                   20

<210> SEQ ID NO 208
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 208
cgaggtgatc gagacgcaga tgc                                              23

<210> SEQ ID NO 209
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
ttatgaagca ccagacatca gccccagc                                         28

<210> SEQ ID NO 210
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
gtactagtaa aaaaatggtc atccaaggga agagattggc cgcctcctct attcagc         57

<210> SEQ ID NO 211
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
gtcccgggct attatgaagc accagacatc agccccagc                             39

<210> SEQ ID NO 212
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
tacccgggct attagtgatg gtggtgatgg tgtgaagcac cagacatcag ccccagc         57

<210> SEQ ID NO 213
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
atgggttccg ttagtaggga acatgagtca atc                                   33

<210> SEQ ID NO 214
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
```

```
gttccttgtg tgagctcctg aataagactg catg                          34
```

<210> SEQ ID NO 215
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215

```
ccatcaaaat ccccctctat cacacgggca ctgggagcaa c                  41
```

<210> SEQ ID NO 216
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216

```
cccacgcctt gcgcatctat aatcagg                                  27
```

<210> SEQ ID NO 217
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217

```
tgtccgaata ttctcctcgt tgtaggtagt ggatt                         35
```

<210> SEQ ID NO 218
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218

```
gcagtagtcg ataggtacac atccttgggg gttccatgac tgc                43
```

<210> SEQ ID NO 219
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219

```
agaggatcaa ggcattatac atgagtctgt ggaacttggg ctttcc             46
```

<210> SEQ ID NO 220
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220

```
ttccccgtcc tccatggcct tatgc                                          25
```

<210> SEQ ID NO 221
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221

```
ggcctttgcg cgatacgctg gtctctcggg tcccat                              36
```

<210> SEQ ID NO 222
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222

```
tcacgccatt tgttgaagca gggaatg                                        27
```

<210> SEQ ID NO 223
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223

```
gtactagtaa aaaatgggt tccgttagta gggaacatga gtcaatc                   47
```

<210> SEQ ID NO 224
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224

```
gtgtttaaac ctatcacgcc atttgttgaa gcagggaatg                          40
```

<210> SEQ ID NO 225
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225

```
ggtttaaacc tatcagtgat ggtggtgatg gtgcgccatt tgttgaagca gggaatgaa     59
```

<210> SEQ ID NO 226
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226

```
atgacccaaa agactataca gcaggtccca aga                                 33
```

<210> SEQ ID NO 227
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
tatggtgcat cgaatgttgt ttgcctgg                                28

<210> SEQ ID NO 228
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 228
aaaatgcgtg agcactttgt ccagcgc                                 27

<210> SEQ ID NO 229
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
cgacgtaatt gacgttgtca acatgccg                                28

<210> SEQ ID NO 230
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
catctcgggt tcccatcact ccctgagtat gac                          33

<210> SEQ ID NO 231
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
gacaaagaag ctggacaccg cagccttggg attccacgaa c                 41

<210> SEQ ID NO 232
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
gatctgcctt gtcggtggct atgacgacct tcagcctgag gagtca            46

<210> SEQ ID NO 233
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 233
ttaacggatg atagaggcca acggccaaag acaccacttg cgtacac                47

<210> SEQ ID NO 234
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 234
cacacaacta gtaaaaaaat gacccaaaag actatacagc aggtcccaag a            51

<210> SEQ ID NO 235
<211> LENGTH: 59
<212> TYPE: DNA
<213> ORGANISM: Artificial Sequence
<220> FEATURE:
<223> OTHER INFORMATION: Description of Artificial Sequence: Synthetic primer

<400> SEQUENCE: 235
tgtgtgcccg ggttaacgga tgatagaggc caacggccaa agacaccact tgcgtacac   59

<210> SEQ ID NO 236
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 236
tacccgggct attagtgatg gtggtgatgg tgacggatga tagaggccaa c            51

<210> SEQ ID NO 237
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 237
atgactccat caccgtttct cgatgctgt                                    29

<210> SEQ ID NO 238
<211> LENGTH: 50
<212> TYPE: DNA
<213> ORGANISM: Artificial Sequence
<220> FEATURE:
<223> OTHER INFORMATION: Description of Artificial Sequence: Synthetic primer

<400> SEQUENCE: 238
cacatgggta gcatcgttca ttgcccaaca caaagcgggc cagttaactc              50

```
<210> SEQ ID NO 239
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
gtcgagctaa gagtgactga tgccattggc                                        30

<210> SEQ ID NO 240
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 240
cgtaattcag cttctgaacc tgagcccagg                                        30

<210> SEQ ID NO 241
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 241
ctttgcccgg ccgtggttcg c                                                 21

<210> SEQ ID NO 242
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 242
cccccaagct cgacaacggg c                                                 21

<210> SEQ ID NO 243
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 243
ttctcaaaat gcaccggact gattacttgg a                                      31

<210> SEQ ID NO 244
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 244
cccattcctc tctcctgcgt gccctggccg gtaaagacgt at                          42

<210> SEQ ID NO 245
```

```
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 245
ccctccttcg atggacttgt ccgggcaaac gaccggttgc gaatggagat                50

<210> SEQ ID NO 246
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 246
ctacctattc tcttcaaccc gccgtaacag c                                    31

<210> SEQ ID NO 247
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
cacacaacta gtaaaaaaat gactccatca ccgtttctcg atgctgt                   47

<210> SEQ ID NO 248
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 248
tgtgtgcccg ggctacctat tctcttcaac ccgccgtaac agc                       43

<210> SEQ ID NO 249
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 249
tgtgtgcccg ggctatcagt gatggtggtg atggtgccta ttctcttcaa c              51

<210> SEQ ID NO 250
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 250
cacacagctc ttctagaatg gtcatccaag ggaagag                              37

<210> SEQ ID NO 251
<211> LENGTH: 28
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 251
agtatcgacg tcggctgact tgagacca                                      28

<210> SEQ ID NO 252
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 252
ccatcacatc cacagtggcg g                                             21

<210> SEQ ID NO 253
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 253
aaccaggcaa gttcgacata accggc                                        26

<210> SEQ ID NO 254
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 254
gtaggctatc cccgtctccc cgattatg                                      28

<210> SEQ ID NO 255
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 255
tgattgaggt caaggatgat ttgtccgaga                                    30

<210> SEQ ID NO 256
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 256
tcttcctatc tatgcggtca ttgccagct                                     29

<210> SEQ ID NO 257
<211> LENGTH: 39
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 257
cacacagctc ttcctttta tgaagcacca gacatcaac                              39

<210> SEQ ID NO 258
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 258
cacacagctc ttcctttta gtgatggtgg tgatggtgtg aagcaccaga catcaacccc       60
aacg                                                                  64

<210> SEQ ID NO 259
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 259
cacacagctc ttctagaatg ggttccgtta gtaggga                               37

<210> SEQ ID NO 260
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 260
caaatccttg atgacagaga tctgccagga                                       30

<210> SEQ ID NO 261
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 261
gctgggactt tgtcgctgcc gttgctcaag ctggat                                36

<210> SEQ ID NO 262
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 262
actgctccta ctttctcgaa cttatagagc ccttg                                 35

<210> SEQ ID NO 263
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 263
atatccgacg atgagtctgt                                                    20

<210> SEQ ID NO 264
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 264
atggacaatg ggacccgaga                                                    20

<210> SEQ ID NO 265
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 265
ggacttcttg caccgctacg                                                    20

<210> SEQ ID NO 266
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 266
cacacagctc ttccttttca cgccatttgt tgaagcaaag                              40

<210> SEQ ID NO 267
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 267
cacacagctc ttccttttca gtgatggtgg tgatggtgcg ccatttgttg aagca             55

<210> SEQ ID NO 268
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 268
gattactgca gcagtattag tcttc                                              25

<210> SEQ ID NO 269
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 269
gtcgaaaact tcatcggcaa ag                                             22

<210> SEQ ID NO 270
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 270
cacgatatta tcgccacata cttc                                           24

<210> SEQ ID NO 271
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 271
cgggacgatc gagatcgtgg atacg                                          25

<210> SEQ ID NO 272
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 272
caggatatta tcgccacata catc                                           24

<210> SEQ ID NO 273
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 273
ctggacgatt gagcgcttgg atacg                                          25

<210> SEQ ID NO 274
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 274
cgtcttctcc atcgtttgcc caagag                                         26

<210> SEQ ID NO 275
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 275
ggtccctgac aaagttaccg agtg                                           24

<210> SEQ ID NO 276
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 276
cgtcttctcc atcgtttgct caggag                                         26

<210> SEQ ID NO 277
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 277
gatccaacac gacgttaccg agcg                                           24

<210> SEQ ID NO 278
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 278
ggtatgtcgt tgtgccagtg ttg                                            23

<210> SEQ ID NO 279
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 279
cccacgcttg ggttcttgga gtggtc                                         26

<210> SEQ ID NO 280
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 280
ggtatattgt tgtgcctgtg ttg                                            23

<210> SEQ ID NO 281
<211> LENGTH: 26
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 281
ccgacgcttg ggttcttgga gctgtc                                          26

<210> SEQ ID NO 282
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 282
ggaaggatga ggtggtgcag tac                                             23

<210> SEQ ID NO 283
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 283
gtcttgtgac aagtttggaa actc                                            24

<210> SEQ ID NO 284
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 284
gaaagaatga ggtggtgcaa tac                                             23

<210> SEQ ID NO 285
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 285
gtcctgtgac aagctaggga attc                                            24

<210> SEQ ID NO 286
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 286
ctatcgtggg atgtgatctg tgtcg                                           25

<210> SEQ ID NO 287
<211> LENGTH: 25
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 287
ctcgaatctc ttgacactga actcg                                         25

<210> SEQ ID NO 288
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 288
aacgacaaga ttagattggt tgaga                                         25

<210> SEQ ID NO 289
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 289
gtcgagtttg aagtgtgtgt ctaag                                         25

<210> SEQ ID NO 290
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 290
agatctcata tggctccatt tttgcccgac caggtcgact acaaacacgt c             51

<210> SEQ ID NO 291
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 291
atctggatcc tcattactac aacttggctt tggtcttcaa ggagtctgcc aaacctaac    59

<210> SEQ ID NO 292
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 292
acatctggat cctcattact acaacttggc cttggtct                           38

<210> SEQ ID NO 293
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 293
cacacagctc ttctagaatg gctccatttt tgcccgacca ggtcgac        47

<210> SEQ ID NO 294
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 294
cacacagctc ttcctttcta caacttggct ttggtcttca aggagtctgc        50

<210> SEQ ID NO 295
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 295
gtctactgat tcccctttgt c        21

<210> SEQ ID NO 296
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 296
ttctcgttgt acccgtcgca        20

<210> SEQ ID NO 297
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 297
cacacacata tgcgacgggt acaacgagaa tt        32

<210> SEQ ID NO 298
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 298
cacacaacgc gtagacgaag ccgttcttca ag        32

<210> SEQ ID NO 299
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 299
atgatctgcc atgccgaact c                                                    21

<210> SEQ ID NO 300
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 300
agcgagttcg gcatggcaga tcatcatg                                             28

<210> SEQ ID NO 301
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 301
cacacactgc agttgtccaa tgtaataatt tt                                        32

<210> SEQ ID NO 302
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 302
cacacatcta gacccgggct cttcttctga ataggcaatt gataaactta cttatc             56

<210> SEQ ID NO 303
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 303
gagcccgggt ctagatgtgt gctcttccaa agtacggtgt tgttgaca                      48

<210> SEQ ID NO 304
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 304
cacacacata tgaattctgt actggtagag ctaaatt                                  37

<210> SEQ ID NO 305
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 305

-continued gagctccaat tgtaatattt cggg                                        24

<210> SEQ ID NO 306
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 306
gtcgacctaa attcgcaact atcaa                                       25

<210> SEQ ID NO 307
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 307
gaattcacat ggctaatttg gcctcggttc cacaacgcac tcagcattaa aaa         53

<210> SEQ ID NO 308
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 308
gagctcccct gcaaacaggg aaacacttgt catctgattt                       40

<210> SEQ ID NO 309
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 309
cacctcgctc ttccagctgt catgtctatt caatgcttcg a                     41

<210> SEQ ID NO 310
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 310
cacacagcat gctaatgttt atatcgttga cggtgaaa                         38

<210> SEQ ID NO 311
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 311
cacaaagcgg aagagcaaat tttgtattct cagtaggatt tcatc            45

<210> SEQ ID NO 312
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 312
cacacagcat gcaaacttaa gggtgttgta gatatccc                    38

<210> SEQ ID NO 313
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 313
cacacacccg ggatcgacag tcgattacgt aatccatatt attt             44

<210> SEQ ID NO 314
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 314
cacacagcat gcaaacttaa gggtgttgta gatatccc                    38

<210> SEQ ID NO 315
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 315
cacacagagc tcacagtcga ttacgtaatc cat                         33

<210> SEQ ID NO 316
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 316
cacatctaga gcatgcaaac ttaagggtgt tgta                        34

<210> SEQ ID NO 317
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 317
ttaatgcctt ctcaagacaa                                        20

<210> SEQ ID NO 318
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 318
ggttttccca gtcacgacgt                                              20

<210> SEQ ID NO 319
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 319
ccttgctaat tttcttctgt atagc                                        25

<210> SEQ ID NO 320
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 320
ttctcgttgt acccgtcgca                                              20

<210> SEQ ID NO 321
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 321
cacacaactt cagagttgcc                                              20

<210> SEQ ID NO 322
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 322
tcgccacctc tgacttgagc                                              20

<210> SEQ ID NO 323
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
aattgaacat cagaagagga                                              20

<210> SEQ ID NO 324
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
cctgaaattt ccaaatggtg tctaa                                          25

<210> SEQ ID NO 325
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325 tttttgtgc gcaagtacac                                                 20

<210> SEQ ID NO 326
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
caacttgacg tgagaaacct                                                20

<210> SEQ ID NO 327
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
agatgctcgt tttacaccct                                                20

<210> SEQ ID NO 328
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
acacagcttt gatgttctct                                                20

BIOLOGICAL METHODS FOR PREPARING ADIPIC ACID

RELATED PATENT APPLICATIONS

This patent application is a continuation application of U.S. patent application Ser. No. 13/245,777 filed on Sep. 26, 2011, entitled BIOLOGICAL METHODS FOR PREPARING ADIPIC ACID, naming Stephen Picataggio and Tom Beardslee as inventors, which is a continuation application which claims the benefit of international patent application no. PCT/US2010/040837 filed on Jul. 1, 2010, entitled BIOLOGICAL METHODS FOR PREPARING ADIPIC ACID, naming Stephen Picataggio and Tom Beardslee as inventors, which claims the benefit of U.S. provisional patent application No. 61/222,902 filed on Jul. 2, 2009, entitled BIOLOGICAL METHODS FOR PREPARING ADIPIC ACID, naming Stephen Picataggio as inventor. The entire content of the foregoing patent application is incorporated herein by reference, including, without limitation, all text, tables and drawings.

FIELD

The technology relates in part to biological methods for producing adipic acid and engineered microorganisms capable of such production.

BACKGROUND

Microorganisms employ various enzyme-driven biological pathways to support their own metabolism and growth. A cell synthesizes native proteins, including enzymes, in vivo from deoxyribonucleic acid (DNA). DNA first is transcribed into a complementary ribonucleic acid (RNA) that comprises a ribonucleotide sequence encoding the protein. RNA then directs translation of the encoded protein by interaction with various cellular components, such as ribosomes. The resulting enzymes participate as biological catalysts in pathways involved in production of molecules by the organism.

These pathways can be exploited for the harvesting of the naturally produced products. The pathways also can be altered to increase production or to produce different products that may be commercially valuable. Advances in recombinant molecular biology methodology allow researchers to isolate DNA from one organism and insert it into another organism, thus altering the cellular synthesis of enzymes or other proteins. Such genetic engineering can change the biological pathways within the host organism, causing it to produce a desired product. Microorganic industrial production can minimize the use of caustic chemicals and the production of toxic byproducts, thus providing a "clean" source for certain compounds.

SUMMARY

Provided herein are engineered microorganisms that produce six-carbon organic molecules such as adipic acid, methods for manufacturing such microorganisms and methods for using them to produce adipic acid and other six-carbon organic molecules.

Thus, provided herein in some embodiments are engineered microorganisms capable of producing adipic acid, or produce adipic acid, which microorganisms comprise one or more altered activities selected from the group consisting of aldehyde dehydrogenase activity (e.g., 6-oxohexanoic acid dehydrogenase activity, omega oxo fatty acid dehydrogenase activity), fatty alcohol oxidase activity (e.g., 6-hydroxyhexanoic acid dehydrogenase activity, omega hydroxyl fatty acid dehydrogenase activity), hexanoate synthase activity and monooxygenase activity. In certain embodiments, the microorganism comprises a genetic modification that adds or increases the aldehyde dehydrogenase activity (e.g., 6-oxohexanoic acid dehydrogenase activity, omega oxo fatty acid dehydrogenase activity), fatty alcohol oxidase activity (e.g., 6-hydroxyhexanoic acid dehydrogenase activity, omega hydroxyl fatty acid dehydrogenase activity), hexanoate synthase activity, monooxygenase activity, monooxygenase reductase activity, fatty alcohol oxidase activity, acyl-CoA ligase activity, acyl-CoA oxidase activity, enoyl-CoA hydratase activity, 3-hydroxyacyl-CoA dehydrogenase activity, and/or acetyl-CoA C-acyltransferase activity. Also provided in some embodiments, are engineered microorganisms that produce adipic acid, which microorganisms comprise an altered monooxygenase activity. Provided also herein in some embodiments are engineered microorganisms that include a genetic modification that reduces the acyl-CoA oxidase activity.

In some embodiments, an engineered microorganism includes a genetic modification that includes multiple copies of a polynucleotide that encodes a polypeptide having aldehyde dehydrogenase activity (e.g., 6-oxohexanoic acid dehydrogenase activity, omega oxo fatty acid dehydrogenase activity), fatty alcohol oxidase activity (e.g., 6-hydroxyhexanoic acid dehydrogenase activity, omega hydroxyl fatty acid dehydrogenase activity), hexanoate synthase activity, monooxygenase activity, monooxygenase reductase activity, fatty alcohol oxidase activity, acyl-CoA ligase activity, acyl-CoA oxidase activity, enoyl-CoA hydratase activity, 3-hydroxyacyl-CoA dehydrogenase activity, and/or acetyl-CoA C-acyltransferase activity. In some embodiments, 2, 3, 4, 5, 6, 7, 8, 9 or 10 or more copies of the particular polynucleotide are present in the microbe. In certain embodiments, an engineered microorganism includes a heterologous promoter (and/or 5'UTR) in functional connection with a polynucleotide that encodes a polypeptide having aldehyde dehydrogenase activity (e.g., 6-oxohexanoic acid dehydrogenase activity, omega oxo fatty acid dehydrogenase activity), fatty alcohol oxidase activity (e.g., 6-hydroxyhexanoic acid dehydrogenase activity, omega hydroxyl fatty acid dehydrogenase activity), hexanoate synthase activity, monooxygenase activity, monooxygenase reductase activity, fatty alcohol oxidase activity, acyl-CoA ligase activity, acyl-CoA oxidase activity, enoyl-CoA hydratase activity, 3-hydroxyacyl-CoA dehydrogenase activity, and/or acetyl-CoA C-acyltransferase activity. In some embodiments, the promoter is a POX4 or POX5 promoter or monooxygenase promoter from a yeast (e.g., *Candida* yeast strain (e.g., *C. tropicalis* strain)), or other promoter. Examples of promoters that can be utilized are described herein. The promoter sometimes is exogenous or endogenous with respect to the microbe.

Also provided herein is an engineered microorganism that produces adipic acid, where the microorganism includes an altered monooxygenase activity. In certain embodiments, an engineered microorganism comprises a genetic modification that alters a monooxygenase activity. In some embodiments, an engineered microorganism includes a genetic modification that alters a monooxygenase activity selected from the group consisting of CYP52A15 activity, CYP52A16 activity, or CYP52A15 activity and CYP52A16 activity. In some embodiments, the monooxygenase activity is encoded by a CYP52A15 polynucleotide, a CYP52A16 polynucleotide, or CYP52A15 and CYP52A16 polynucleotides. In some embodiments, the genetic modification increases monooxygenase activity. In certain embodiments, the genetic modification increases the copy number of an endogenous polynucleotide that encodes a polypeptide having the monooxygenase activity (e.g., 2, 3, 4, 5, 6, 7, 8, 9, 10 or more copies of the polynucleotide). In certain embodiments, an engineered microorganism comprises a polynucleotide that includes a promoter (e.g., promoter and/or 5'UTR) and encodes a polypeptide having a monooxygenase activity. The promoter may be exogenous or endogenous with respect to the microbe. An engineered microorganism in certain embodiments comprises a heterologous polynucleotide encoding a polypeptide having monooxygenase activity. In related embodiments, the heterologous polynucleotide is from a yeast, such as a *Candida* yeast in certain embodiments (e.g., *C. tropicalis*).

In certain embodiments, an engineered microorganism comprises a genetic modification that alters monooxygenase reductase activity. In some embodiments, the genetic modification increases the copy number of an endogenous polynucleotide that encodes a polypeptide having monooxygenase reductase activity (e.g., 2, 3, 4, 5, 6, 7, 8, 9, 10 or more copies of the polynucleotide). An engineered microorganism in certain embodiments comprises a heterologous promoter (e.g., endogenous or exogenous promoter with respect to the microbe) in functional connection with a polynucleotide that encodes a polypeptide having monooxygenase reductase activity. In some embodiments, the polynucleotide is from a yeast, and in certain embodiments the yeast is a *Candida* yeast (e.g., *C. tropicalis*).

An engineered microorganism in some embodiments comprises an altered thioesterase activity. In some embodiments, an engineered microorganism comprises a genetic modification that alters the thioesterase activity, and in certain embodiments, the engineered microorganism comprises a genetic alteration that adds or increases a thioesterase activity. In some embodiments, the engineered microorganism comprises a heterologous polynucleotide encoding a polypeptide having thioesterase activity.

An engineered microorganism in some embodiments comprises an altered fatty alcohol oxidase activity. In some embodiments, an engineered microorganism comprises a genetic modification that alters the fatty alcohol oxidase activity, and in certain embodiments, the engineered microorganism comprises a genetic alteration that adds or increases a fatty alcohol oxidase activity. In some embodiments, the genetic modification increases the copy number of an endogenous polynucleotide that encodes a polypeptide having fatty alcohol oxidase activity (e.g., 2, 3, 4, 5, 6, 7, 8, 9, 10 or more copies of the polynucleotide). An engineered microorganism in certain embodiments comprises a heterologous promoter (e.g., endogenous or exogenous promoter with respect to the microbe) in functional connection with a polynucleotide that encodes a polypeptide having fatty alcohol oxidase activity. In some embodiments, the engineered microorganism comprises a heterologous polynucleotide encoding a polypeptide having fatty alcohol oxidase activity. In some embodiments, the polynucleotide is from a yeast, and in certain embodiments the yeast is *Candida* (e.g., a *C. tropicalis* strain).

An engineered microorganism in some embodiments comprises an altered 6-oxohexanoic acid dehydrogenase activity or an altered omega oxo fatty acid dehydrogenase activity. In some embodiments, an engineered microorganism comprises a genetic modification that adds or increases 6-oxohexanoic acid dehydrogenase activity or omega oxo fatty acid dehydrogenase activity, and in certain embodiments, an engineered microorganism comprises a heterologous polynucleotide encoding a polypeptide having 6-oxohexanoic acid dehydrogenase activity or omega oxo fatty acid dehydrogenase activity. In related embodiments, the heterologous polynucleotide sometimes is from a bacterium, such as an *Acinetobacter, Nocardia, Pseudomonas* or *Xanthobacter* bacterium in some embodiments.

An engineered microorganism in some embodiments comprises an altered 6-hydroxyhexanoic acid dehydrogenase activity or an altered omega hydroxyl fatty acid dehydrogenase activity. In some embodiments, an engineered microorganism comprises a genetic modification that adds or increases the 6-hydroxyhexanoic acid dehydrogenase activity or omega hydroxyl fatty acid dehydrogenase activity, and in certain embodiments, an engineered microorganism comprises a heterologous polynucleotide encoding a polypeptide having 6-hydroxyhexanoic acid dehydrogenase activity or omega hydroxyl fatty acid dehydrogenase activity. In related embodiments, the heterologous polynucleotide is from a bacterium, such as an *Acinetobacter, Nocardia, Pseudomonas* or *Xanthobacter* bacterium in some embodiments.

An engineered microorganism in some embodiments comprises an altered hexanoate synthase activity. In some embodiments, an engineered microorganism comprises a genetic modification that alters hexanoate synthase activity. In certain embodiments, an engineered microorganism includes a genetic alteration that adds or increases hexanoate synthase activity. In some embodiments, an engineered microorganism comprises a heterologous polynucleotide encoding a polypeptide having hexanoate synthase activity. In certain embodiments, the hexanoate synthase activity is provided by a polypeptide having hexanoate synthase activity. In certain embodiments, the hexanoate synthase activity is provided by a polypeptide having hexanoate synthase subunit A activity, hexanoate synthase subunit B activity, or hexanoate synthase subunit A activity and hexanoate synthase subunit B activity. In some embodiments, the heterologous polynucleotide is from a fungus, such as an *Aspergillus* fungus in certain embodiments (e.g., *A. parasiticus, A. nidulans*).

In certain embodiments, an engineered microorganism comprises a genetic modification that results in substantial (e.g., primary) hexanoate usage by monooxygenase activity. In related embodiments, the genetic modification reduces a polyketide synthase activity.

An engineered microorganism in some embodiments is a non-prokaryotic organism, and sometimes is a eukaryote. A eukaryote can be a yeast in some embodiments, such as a *Candida* yeast (e.g., *C. tropicalis*), for example. In certain embodiments a eukaryote is a fungus, such as a *Yarrowia* fungus (e.g., *Y. lipolytica*) or *Aspergillus* fungus (e.g., *A. parasiticus* or *A. nidulans*), for example.

In some embodiments, an engineered microorganism comprises a genetic modification that reduces 6-hydroxyhexanoic acid conversion. In related embodiments, the genetic modification reduces 6-hydroxyhexanoic acid dehydrogenase activity or omega hydroxyl fatty acid dehydrogenase activity.

In certain embodiments, an engineered microorganism comprises a genetic modification that reduces beta-oxidation activity, and in some embodiments, the genetic modification renders beta-oxidation activity undetectable (e.g., completely blocked beta-oxidation activity). In certain embodiments, the genetic modification partially reduces beta-oxidation activity. In some embodiments, an engineered microorganism comprises a genetic modification that increases omega-oxidation activity. In some embodiments, an engineered microorganism comprises one or more genetic modifications that alter a reverse activity in a beta oxidation pathway, an omega oxidation pathway, or a beta oxidation and omega oxidation pathway, thereby increasing carbon flux through the respective pathways, due to the reduction in one or more reverse enzymatic activities.

A fatty acid-CoA derivative, or dicarboxylic acid-CoA derivative, can be converted to a trans-2,3-dehydroacyl-CoA derivative by the activity of acyl-CoA oxidase (e.g., also known as or referred to as acyl-CoA oxidoreductase and fatty acyl-coenzyme A oxidase), in many organisms. In some embodiments, an engineered microorganism comprises a genetic modification that alters the specificity of and/or reduces the activity of an acyl-CoA oxidase activity. In certain embodiments, the genetic modification disrupts an acyl-CoA oxidase activity. In some embodiments, the genetic modification includes disrupting a polynucleotide that encodes a polypeptide having an acyl-CoA oxidase activity. In certain embodiments, the genetic modification includes disrupting a promoter and/or 5'UTR in functional connection with a polynucleotide that encodes a polypeptide having the acyl-CoA oxidase activity. In some embodiments, the polypeptide having acyl-CoA activity is a POX polypeptide. In certain embodiments, the POX polypeptide is a POX4 polypeptide, a POX5 polypeptide, or a POX4 polypeptide and POX5 polypeptide. In certain embodiments, the genetic modification disrupts an acyl-CoA activity by disrupting a POX4 nucleotide sequence, a POX5 nucleotide sequence, or a POX4 and POX5 nucleotide sequence.

An engineered microorganism can include a heterologous polynucleotide that encodes a polypeptide providing an activity described above, and the heterologous polynucleotide can be from any suitable microorganism. Examples of microorganisms are described herein (e.g., *Candida* yeast, *Saccharomyces* yeast, *Yarrowia* yeast, *Pseudomonas* bacteria, *Bacillus* bacteria, *Clostridium* bacteria, *Eubacterium* bacteria and others include *Megasphaera* bacteria.

Also provided in some embodiments are methods for manufacturing adipic acid, which comprise culturing an engineered microorganism described herein under culture conditions in which the cultured microorganism produces adipic acid. In some embodiments, the host microorganism from which the engineered microorganism is generated does not produce a detectable amount of adipic acid. In certain embodiments, the culture conditions comprise fermentation conditions, introduction of biomass, introduction of glucose, introduction of a paraffin (e.g., plant or petroleum based, such as hexane or coconut oil, for example) and/or combinations thereof. In some embodiments, the adipic acid is produced with a yield of greater than about 0.3 grams per gram of glucose added. In related embodiments, a method comprises purifying the adipic acid from the cultured microorganisms and or modifying the adipic acid, thereby producing modified adipic acid. In certain embodiments, a method comprises placing the cultured microorganisms, the adipic acid or the modified adipic acid in a container, and optionally, shipping the container.

Provided also in certain embodiments are methods for manufacturing 6-hydroxyhexanoic acid, which comprise culturing an engineered microorganism described herein under culture conditions in which the cultured microorganism produces 6-hydroxyhexanoic acid. In some embodiments, the host microorganism from which the engineered microorganism is generated does not produce a detectable amount of 6-hydroxyhexanoic acid. In certain embodiments, the culture conditions comprise fermentation conditions, introduction of biomass, introduction of glucose, and/or introduction of hexane. In some embodiments, the 6-hydroxyhexanoic acid is produced with a yield of greater than about 0.3 grams per gram of glucose added. In related embodiments, a method comprises purifying the 6-hydroxyhexanoic acid from the cultured microorganisms and or modifying the 6-hydroxyhexanoic acid, thereby producing modified 6-hydroxyhexanoic acid. In certain embodiments, a method comprises placing the cultured microorganisms, the 6-hydroxyhexanoic acid or the modified 6-hydroxyhexanoic acid in a container, and optionally, shipping the container.

Also provided in some embodiments are methods for preparing an engineered microorganism that produces adipic acid, which comprise: (a) introducing a genetic modification to a host organism that adds or increases monooxygenase activity, thereby producing engineered microorganisms having detectable and/or increased monooxygenase activity; and (b) selecting for engineered microorganisms that produce adipic acid. Provided also herein in some embodiments are methods for preparing an engineered microorganism that produces adipic acid, which comprise: (a) culturing a host organism with hexane as a nutrient source, thereby producing engineered microorganisms having detectable monooxygenase activity; and (b) selecting for engineered microorganisms that produce adipic acid. In some embodiments the monooxygenase activity is incorporation of a hydroxyl moiety into a six-carbon molecule, and in certain embodiments, the six-carbon molecule is hexanoate. In related embodiments, a method comprises selecting the engineered microorganisms that have a detectable amount of the monooxygenase activity. In some embodiments, a method comprises introducing a genetic modification that adds or increases a hexanoate synthase activity, thereby producing engineered microorganisms, and selecting for engineered microorganisms having detectable and/or increased hexanoate synthase activity. In related embodiments, the genetic modification encodes a polypeptide having a hexanoate synthase subunit A activity, a hexanoate synthase subunit B activity, or a hexanoate synthase subunit A activity and a hexanoate synthase subunit B activity.

In some embodiments, a method comprises introducing a genetic modification that adds or increases an aldehyde dehydrogenase activity (e.g., 6-oxohexanoic acid dehydrogenase activity, omega oxo fatty acid dehydrogenase), thereby producing engineered microorganisms, and selecting for engineered microorganisms having detectable and/or increased 6-oxohexanoic acid dehydrogenase activity or omega oxo fatty acid dehydrogenase relative to the host microorgansim. In certain embodiments, a method for preparing microorganisms that produce adipic acid includes selecting for engineered microorganisms having one or more detectable and/or increased activities selected from the group consisting of an aldehyde dehydrogenase activity (e.g., 6-oxohexanoic acid dehydrogenase activity, omega oxo fatty acid dehydrogenase), fatty alcohol oxidase activity (e.g., 6-hydroxyhexanoic acid dehydrogenase activity, omega hydroxyl-fatty acid dehydrogenase), hexanoate synthase activity, monooxygenase activity, monooxygenase reductase activity, fatty alcohol oxidase activity, acyl-CoA ligase activity, acyl-CoA oxidase activity, enoyl-CoA hydratase activity, 3-hydroxyacyl-CoA dehydrogenase activity, and/or acetyl-CoA C-acyltransferase activity.

In certain embodiments, a method comprises introducing a genetic modification that adds or increases a fatty alcohol oxidase activity (e.g., 6-hydroxyhexanoic acid dehydrogenase activity, omega hydroxyl fatty acid dehydrogenase activity) thereby producing engineered microorganisms, and selecting for engineered microorganisms having a detectable and/or increased 6-hydroxyhexanoic acid dehydrogenase activity or omega hydroxyl fatty acid dehydrogenase activity relative to the host microorganism. In some embodiments, a method comprises introducing a genetic modification that adds or increases a thioesterase activity, thereby producing engineered microorganisms, and selecting for engineered microorganisms having a detectable and/or increased thioesterase activity relative to the host microorganism.

In certain embodiments, a method comprises introducing a genetic modification that reduces 6-hydroxyhexanoic acid conversion, thereby producing engineered microorganisms, and selecting for engineered microorganisms having reduced 6-hydroxyhexanoic acid conversion relative to the host microorganism. In some embodiments, a method comprises introducing a genetic modification that reduces beta-oxidation activity, thereby producing engineered microorganisms, and selecting for engineered microorganisms having reduced beta-oxidation activity relative to the host microorganism. In certain embodiments, a method comprises introducing a genetic modification that results in substantial hexanoate usage by the monooxygenase activity, thereby producing engineered microorganisms, and selecting for engineered microorganisms in which substantial hexanoate usage is by the monooxygenase activity relative to the host microorganism. In some embodiments, a method comprises introducing a genetic modification that increases omega-oxidation activity, thereby producing engineered microorganisms, and selecting for engineered microorganisms having increased omega-oxidation activity relative to the host microorganism.

Provided also herein in certain embodiments are methods for preparing a microorganism that produces adipic acid, which comprise: (a) introducing one or more genetic modifications to a host organism that add or increase one or more activities selected from the group consisting of 6-oxohexanoic acid dehydrogenase activity, omega oxo fatty acid dehydrogenase activity, 6-hydroxyhexanoic acid dehydrogenase activity, omega hydroxyl fatty acid dehydrogenase activity, hexanoate synthase activity, monooxygenase activity, monooxygenase reductase activity, fatty alcohol oxidase activity, acyl-CoA ligase activity, acyl-CoA oxidase activity, enoyl-CoA hydratase activity, 3-hydroxyacyl-CoA dehydrogenase activity, and/or acetyl-CoA C-acyltransferase activity, thereby producing engineered microorganisms, and (b) selecting for engineered microorganisms that produce adipic acid. In some embodiments, a method comprises selecting for engineered microorganisms having one or more detectable and/or increased activities selected from the group consisting of 6-oxohexanoic acid dehydrogenase activity, 6-hydroxyhexanoic acid dehydrogenase activity, hexanoate synthase activity, monooxygenase activity, monooxygenase reductase activity, fatty alcohol oxidase activity, acyl-CoA ligase activity, acyl-CoA oxidase activity, enoyl-CoA hydratase activity, 3-hydroxyacyl-CoA dehydrogenase activity, and/or acetyl-CoA C-acyltransferase activity, relative to the host microorganism.

In certain embodiments, a method comprises introducing a genetic modification that reduces 6-hydroxyhexanoic acid conversion, thereby producing engineered microorganisms, and selecting for engineered microorganisms having reduced 6-hydroxyhexanoic acid conversion relative to the host microorganism. In some embodiments, a method comprises introducing a genetic modification that reduces beta-oxidation activity, thereby producing engineered microorganisms, and selecting for engineered microorganisms having reduced beta-oxidation activity relative to the host microorganism. In certain embodiments, a method comprises introducing a genetic modification that results in substantial hexanoate usage by the monooxygenase activity, thereby producing engineered microorganisms, and selecting for engineered microorganisms in which substantial hexanoate usage is by the monooxygenase activity relative to the host microorganism.

Also provided in some embodiments are methods for preparing a microorganism that produces 6-hydroxyhexanoic acid, which comprise: (a) introducing one or more genetic modifications to a host organism that add or increase one or more activities selected from the group consisting of 6-oxohexanoic acid dehydrogenase activity, hexanoate synthase activity, monooxygenase activity, monooxygenase reductase activity, fatty alcohol oxidase activity, acyl-CoA ligase activity, acyl-CoA oxidase activity, enoyl-CoA hydratase activity, 3-hydroxyacyl-CoA dehydrogenase activity, and/or acetyl-CoA C-acyltransferase activity, thereby producing engineered microorganisms, (b) introducing a genetic modification to the host organism that reduces 6-hydroxyhexanoic acid conversion, and (c) selecting for engineered microorganisms that produce 6-hydroxyhexanoic acid. In certain embodiments, a method comprises selecting for engineered microorganisms having reduced 6-hydroxyhexanoic acid conversion relative to the host microorganism. In some embodiments, a method comprises selecting for engineered microorganisms having one or more detectable and/or increased activities selected from the group consisting of aldehyde dehydrogenase activity (e.g., 6-oxohexanoic acid dehydrogenase activity, omega oxo fatty acid dehydrogenase activity), fatty alcohol oxidase activity (e.g., 6-hydroxyhexanoic acid dehydrogenase activity, omega hydroxyl fatty acid dehydrogenase activity), hexanoate synthase activity, monooxygenase activity, monooxygenase reductase activity, fatty alcohol oxidase activity, acyl-CoA ligase activity, acyl-CoA oxidase activity, enoyl-CoA hydratase activity, 3-hydroxyacyl-CoA dehydrogenase activity, and/or acetyl-CoA C-acyltransferase activity, relative to the host microorganism. In certain embodiments, a method comprises introducing a genetic modification that reduces beta-oxidation activity, thereby producing engineered microorganisms, and selecting for engineered microorganisms having reduced beta-oxidation activity relative to the host microorganism. In some embodiments, a method comprises introducing a genetic modification that results in substantial hexanoate usage by the monooxygenase activity, thereby producing engineered microorganisms, and selecting for engineered microorganisms in which substantial hexanoate usage is by the monooxygenase activity relative to the host microorganism.

Also provided are methods that include contacting an engineered microorganism with a feedstock including one or more polysaccharides, wherein the engineered microorganism includes: (a) a genetic alteration that blocks beta oxidation activity, and (b) a genetic alteration that adds or increases a monooxygenase activity or a genetic alteration that adds or increases a hexanoate synthetase activity, and culturing the engineered microorganism under conditions in which adipic acid is produced. In some embodiments, the engineered microorganism comprises a genetic alteration that adds or increases hexanoate synthetase activity. In certain embodiments, the engineered microorganism comprises a heterologous polynucleotide encoding a polypeptide having hexanoate synthase subunit A activity, and in some embodiments the engineered microorganism comprises a heterologous polynucleotide encoding a polypeptide having hexanoate synthase subunit B activity. In certain embodiments, the heterologous polynucleotide independently is selected from a fungus. In some embodiments, the fungus is an *Aspergillus* fungus, and in certain embodiments the *Aspergillus* fungus is *A. parasiticus*. In some embodiments, wherein the microorganism is a *Candida* yeast, and in certain embodiments, the microorganism is a *C. tropicalis* strain.

Provided also are methods that include contacting an engineered microorganism with a feedstock comprising one or more paraffins, wherein the engineered microorganism comprises a genetic alteration that partially blocks beta oxidation activity and culturing the engineered microorganism under conditions in which adipic acid is produced. In certain embodiments, the microorganism comprises a genetic alteration that increases a monooxygenase activity. In some embodiments, the microorganism is a *Candida* yeast, and in certain embodiments, the microorganism is a *C. tropicalis* strain.

In some embodiments, the genetic alteration that increases monooxygenase activity comprises a genetic alteration that increases Cytochrome P450 reductase activity. In certain embodiments, the genetic alteration increases the number of copies of a polynucleotide that encodes a polypeptide having the Cytochrome P450 reductase activity. In some embodiments, the genetic alteration places a promoter and/or 5'UTR in functional connection with a polynucleotide that encodes a polypeptide having the Cytochrome P450 reductase activity. In certain embodiments, the monooxygenase activity is a CYP52A15 activity, CYP52A16 activity, or a CYP52A15 activity and CYP52A16 activity. In some embodiments, the genetic alteration increases the number of copies of a polynucleotide that encodes a polypeptide having the monooxygenase activity. In certain embodiments, the genetic alteration places a promoter and/or 5'UTR in functional connection with a polynucleotide that encodes a polypeptide having the monooxygenase activity.

In certain embodiments, the genetic alteration that blocks beta oxidation activity disrupts acyl-CoA oxidase activity. In some embodiments, the genetic alteration disrupts POX4 and/or POX5 activity. In certain embodiments, the genetic alteration disrupts a polynucleotide that encodes a polypeptide having the acyl-CoA oxidase activity. In some embodiments, the genetic alteration disrupts a promoter and/or 5'UTR in functional connection with a polynucleotide that encodes a polypeptide having the acyl-CoA oxidase activity.

In some embodiments, the feedstock comprises a 6-carbon sugar. In certain embodiments, the feedstock comprises a 5-carbon sugar. In certain embodiments, the adipic acid is produced at a level of about 80% or more of theoretical yield. In some embodiments, the amount of adipic acid produced is detected. In certain embodiments, the adipic acid produced is isolated (e.g., partially or completely purified). In some embodiments, the culture conditions comprise fermenting the engineered microorganism.

Provided also herein are engineered microorganisms in contact with a feedstock. In some embodiments, the feedstock includes a saccharide. In certain embodiments, the saccharide is a monosaccharide, polysaccharide, or a mixture of a monosaccharide and polysaccharide. In some embodiments, the feedstock includes a paraffin. In certain embodiments, the paraffin is a saturated paraffin, unsaturated paraffin, substituted paraffin, branched paraffin, linear paraffin, or combination thereof.

In some embodiments, the paraffin includes about 1 to about 60 carbon atoms (e.g., between about 1 carbon atom, about 2 carbon atoms, about 3 carbon atoms, about 4 carbon atoms, about 5 carbon atoms, about 6 carbon atoms, about 7 carbon atoms, about 8 carbon atoms, about 9 carbon atoms, about 10 carbon atoms, about 12 carbon atoms, about 14 carbon atoms, about 16 carbon atoms, about 18 carbon atoms, about 20 carbon atoms, about 22 carbon atoms, about 24 carbon atoms, about 26 carbon atoms, about 28 carbon atoms, about 30 carbon atoms, about 32 carbon atoms, about 34 carbon atoms, about 36 carbon atoms, about 38 carbon atoms, about 40 carbon atoms, about 42 carbon atoms, about 44 carbon atoms, about 46 carbon atoms, about 48 carbon atoms, about 50 carbon atoms, about 52 carbon atoms, about 54 carbon atoms, about 56 carbon atoms, about 58 carbon atoms and about 60 carbon atoms). In certain embodiments, the paraffin is in a mixture of paraffins. In some embodiments, the paraffins in the mixture of paraffins have a mean number of carbon atoms of about 8 carbon atoms to about 18 carbon atoms (e.g., about 8 carbon atoms, about 9 carbon atoms, about 10 carbon atoms, about 11 carbon atoms, about 12 carbon atoms, about 13 carbon atoms, about 14 carbon atoms, about 15 carbon atoms, about 16 carbon atoms, about 17 carbon atoms or about 18 carbon atoms). In certain embodiments, the paraffin is in a wax, and in some embodiments, the paraffin is in an oil. In certain embodiments, the paraffin is from a petroleum product, and in some embodiments, the petroleum product is a petroleum distillate. In certain embodiments, the paraffin is from a plant or plant product.

Also provided herein, is an isolated polynucleotide selected from the group including a polynucleotide having a nucleotide sequence 96% or more (e.g., 96% or more, 97% or more, 98% or more, 99% or more, or 100%) identical to the nucleotide sequence of SEQ ID NO: 1, a polynucleotide having a nucleotide sequence that encodes a polypeptide of SEQ ID NO: 8, and a polynucleotide having a portion of a nucleotide sequence 96% or more identical to the nucleotide sequence of SEQ ID NO: 1 and encodes a polypeptide having fatty alcohol oxidase activity.

Also provided herein, is an isolated polynucleotide selected from the group including a polynucleotide having a nucleotide sequence 98% or more (e.g., 98% or more, 99% or more, or 100%) identical to the nucleotide sequence of SEQ ID NO: 2, a polynucleotide having a nucleotide sequence that encodes a polypeptide of SEQ ID NO:10, and a polynucleotide having a portion of a nucleotide sequence 98% or more identical to the nucleotide sequence of SEQ ID NO: 2 and encodes a polypeptide having fatty alcohol oxidase activity.

Also provided herein, is an isolated polynucleotide selected from the group including a polynucleotide having a nucleotide sequence 95% or more (e.g., 95% or more, 96% or more, 97% or more, 98% or more, 99% or more, or 100%) identical to the nucleotide sequence of SEQ ID NO: 3, a polynucleotide having a nucleotide sequence that encodes a polypeptide of SEQ ID NO: 9, and a polynucleotide having a portion of a nucleotide sequence 95% or more identical to the nucleotide sequence of SEQ ID NO: 3 and encodes a polypeptide having fatty alcohol oxidase activity.

Also provided herein, is an isolated polynucleotide selected from the group including a polynucleotide having a nucleotide sequence 83% or more (e.g., 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, or 100%) identical to the nucleotide sequence of SEQ ID NO: 4, a polynucleotide having a nucleotide sequence that encodes a polypeptide of SEQ ID NO: 11, and a polynucleotide having a portion of a nucleotide sequence 83% or more identical to the nucleotide sequence of SEQ ID NO: 3 and encodes a polypeptide having fatty alcohol oxidase activity.

Also provided herein, is an isolated polynucleotide selected from the group including a polynucleotide having a nucleotide sequence 82% or more (e.g., 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, or 100%) identical to the nucleotide sequence of SEQ ID NO: 5, a polynucleotide having a nucleotide sequence that encodes a polypeptide of SEQ ID NO: 12, and a polynucleotide having a portion of a nucleotide sequence 82% or more identical to the nucleotide sequence of SEQ ID NO: 3 and encodes a polypeptide having fatty alcohol oxidase activity.

In certain embodiments, an expression vector includes a polynucleotide sequence of SEQ ID NOs: 1 to 5. In some embodiments, an integration vector includes a polynucleotide sequence of SEQ ID NOs: 1 to 5. In certain embodiments, a microorganism includes an expression vector, an integration vector, or an expression vector and an integration vector that includes a polynucleotide sequence of SEQ ID NOs: 1 to 5. In some embodiments, a culture includes a microorganism that includes an expression vector, an integration vector, or an expression vector and an integration vector that includes a polynucleotide sequence of SEQ ID NOs: 1 to 5. In certain embodiments, a fermentation device includes a microorganism that includes an expression vector, an integration vector, or an expression vector and an integration vector that includes a polynucleotide sequence of SEQ ID NOs: 1 to 5. Also provided herein is a polypeptide encoded by a polynucleotide sequence of SEQ ID NOs: 1 to 5 or produced by an expression vector that includes a polynucleotide sequence of SEQ ID NOs: 1 to 5. Provided also herein is an antibody that specifically binds to a polypeptide encoded by a polynucleotide sequence of SEQ ID NOs: 1 to 5 or produced by an expression vector that includes a polynucleotide sequence of SEQ ID NOs: 1 to 5.

Certain embodiments are described further in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

FIG. 11B shows a common intermediate from the metabolism of fats and sugars entering the omega oxidation pathway to ultimately produce adipic acid.

FIG. 16 depicts a plasmid diagram for inserting a heterologous HEXA gene into S. cerevisiae.

FIG. 17 depicts a plasmid diagram for inserting a heterologous HEXB gene into S. cerevisiae.

FIG. 18 depicts a plasmid diagram for inserting a heterologous HEXA-6×His gene into S. cerevisiae.

FIG. 19 depicts a plasmid diagram for inserting a heterologous HEXB-6×His gene into S. cerevisiae.

FIG. 20 depicts a plasmid diagram for inserting a heterologous STCJ gene into S. cerevisiae.

FIG. 21 depicts a plasmid diagram for inserting a heterologous STCK gene into S. cerevisiae.

FIG. 22 depicts a plasmid diagram for inserting a heterologous STCJ-6×His gene into S. cerevisiae.

FIG. 23 depicts a plasmid diagram for inserting a heterologous STCK-6×His gene into S. cerevisiae.

FIG. 24 depicts a plasmid diagram for inserting a heterologous alternative genetic code (AGC) HEXA gene into C. tropicalis.

FIG. 25 depicts a plasmid diagram for inserting a heterologous AGC-HEXB gene into C. tropicalis.

FIG. 26 depicts a plasmid diagram for inserting a heterologous AGC-HEXA-6×His gene into C. tropicalis.

FIG. 27 depicts a plasmid diagram for inserting a heterologous AGC-HEXB-6×His gene into C. tropicalis.

FIG. 28 depicts a diagram of a plasmid used for cloning the POX5 gene from C. tropicalis.

FIG. 29 depicts a diagram of a plasmid used for cloning the POX4 gene from C. tropicalis.

FIG. 30 illustrates a plasmid constructed for use of URA selection in C. tropicalis.

FIG. 31 depicts a plasmid containing the PGK promoter and terminator from C. tropicalis.

FIG. 32 depicts a plasmid used for integration of the CPR gene in C. tropicalis.

FIG. 33 depicts a plasmid used for integration of the CYP52A15 gene in C. tropicalis.

FIG. 34 depicts a plasmid used for integration of the CYP52A16 gene in C. tropicalis.

DETAILED DESCRIPTION

Figure 1:
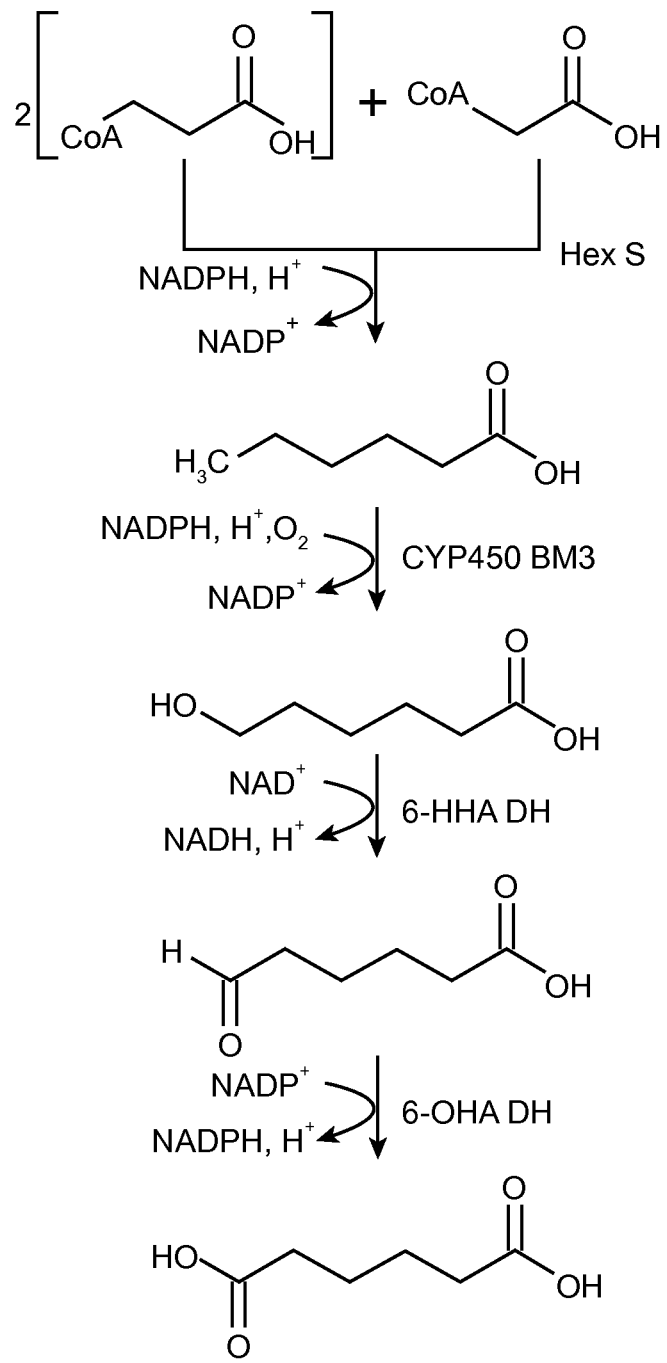
FIG. 1 depicts a metabolic pathway for making adipic acid. The pathway can be engineered into a eukaryotic microorganism to generate a microorganism capable of producing adipic acid.
Figure 2:
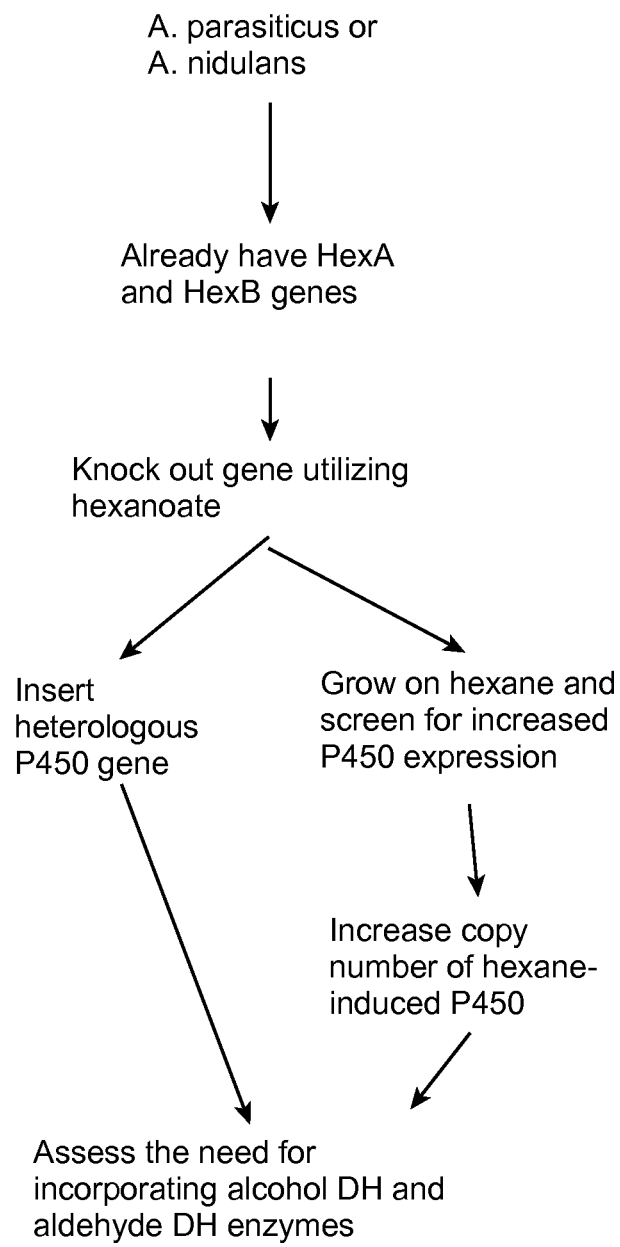
FIG. 2 depicts an embodiment for a method of generating an adipic acid producing microorganism. The method comprises expressing one or more genes catalyzing the omega oxidation of fatty acids to dicarboxylic acids in a host microorganism that produces hexanoate. In the method depicted, the host organism, for example *A. parasiticus* or *A. nidulans*, endogenously includes HEXA and HEXB (or STCJ and STCK) genes. In one embodiment the method comprises knocking out or otherwise disabling the gene coding for diversion of hexanoate into an endogenous pathway such as mycotoxin production. Certain embodiments of the method further comprise inserting a heterologous cytochrome P450 gene. Some embodiments of the method comprise growing the culture on hexane and screening for increased P450 expression. The copy number of hexanoate induced P450 may in certain embodiments be increased. In some embodiments the microorganism may be altered to increase the flux of six carbon substrate through the final two oxidation steps.
Figure 3:
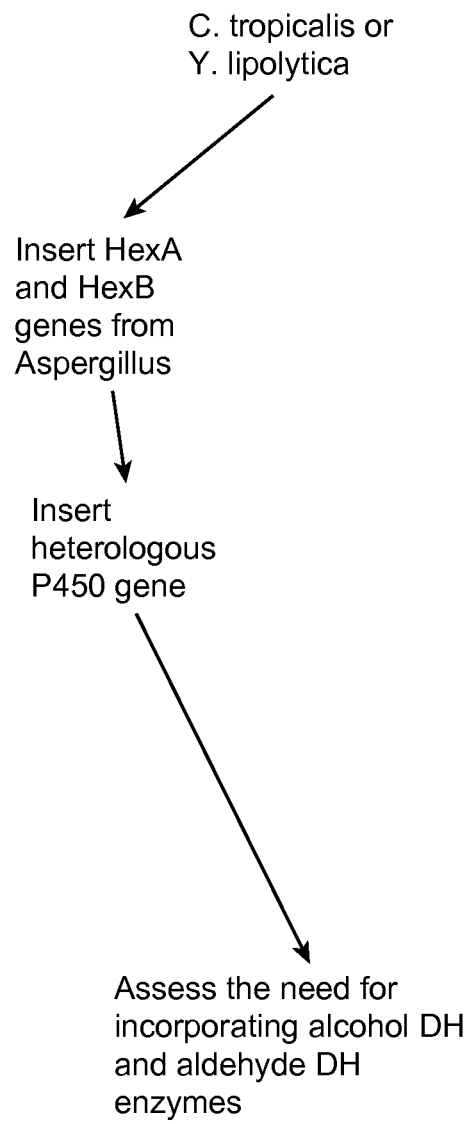
FIG. 3 depicts an embodiment for a method of generating an adipic acid producing organism. The method comprises expressing one or more genes encoding hexanoate synthase in a host microorganism that produces dicarboxylic acids via an omega-oxidation pathway. Such microorganisms may include, without limitation, *C. tropicalis* and *C. maltosa*. As depicted, the method comprises inserting HEXA and HEXB genes into the host microorganism. The genes may be isolated from *Aspergillus*, or another appropriate organism. In some embodiments, the genes are synthesized from an alternative sequence as described herein to produce the amino acid sequence of the donor mircroorganism enzyme through a non-standard translation mechanism of *C. tropicalis*. In some embodiments the method comprises inserting a heterologous cytochrome P450 gene into the host organism. In certain embodiments the microorganism may be altered to increase the flux of a six-carbon substrate through the final two oxidation steps.

Adipic acid is a six-carbon organic molecule that is a chemical intermediate in manufacturing processes used to make certain polyamides, polyurethanes and plasticizers, all of which have wide applications in producing items such as carpets, coatings, adhesives, elastomers, food packaging, and lubricants, for example. Some large-scale processes for making adipic acid include (i) liquid phase oxidation of ketone alcohol oil (KA oil); (ii) air oxidation/hydration of cyclohexane with boric acid to make cyclohexanol, followed by oxidation with nitric acid; and (iii) hydrocyanation of butadiene to a pentenenitrile mixture, followed by hydroisomerization of adiponitrile, followed by hydrogenation. Each of the latter processes requires use of noxious chemicals and/or solvents, some require high temperatures, and all require significant energy input. In addition, some of the processes emit toxic byproducts (such as nitrous oxide) and give rise to environmental concerns.

Provided herein are methods for producing adipic acid and other organic chemical intermediates using biological systems. Such production systems may have significantly less environmental impact and could be economically competitive with current manufacturing systems. Thus, provided herein are methods for manufacturing adipic acid by engineered microorganisms. In some embodiments microorganisms are engineered to contain at least one heterologous gene encoding an enzyme, where the enzyme is a member of a novel pathway engineered into the microorganism. In certain embodiments, an organism may be selected for elevated activity of a native enzyme.

Microorganisms

A microorganism selected often is suitable for genetic manipulation and often can be cultured at cell densities useful for industrial production of a target product. A microorganism selected often can be maintained in a fermentation device.

The term "engineered microorganism" as used herein refers to a modified microorganism that includes one or more activities distinct from an activity present in a microorganism utilized as a starting point (hereafter a "host microorganism"). An engineered microorganism includes a heterologous polynucleotide in some embodiments, and in certain embodiments, an engineered organism has been subjected to selective conditions that alter an activity, or introduce an activity, relative to the host microorganism. Thus, an engineered microorganism has been altered directly or indirectly by a human being. A host microorganism sometimes is a native microorganism, and at times is a microorganism that has been engineered to a certain point.

In some embodiments an engineered microorganism is a single cell organism, often capable of dividing and proliferating. A microorganism can include one or more of the following features: aerobe, anaerobe, filamentous, non-filamentous, monoploid, dipoid, auxotrophic and/or non-auxotrophic. In certain embodiments, an engineered microorganism is a prokaryotic microorganism (e.g., bacterium), and in certain embodiments, an engineered microorganism is a non-prokaryotic microorganism. In some embodiments, an engineered microorganism is a eukaryotic microorganism (e.g., yeast, fungi, amoeba).

Any suitable yeast may be selected as a host microorganism, engineered microorganism or source for a heterologous polynucleotide. Yeast include, but are not limited to, *Yarrowia* yeast (e.g., *Y. lipolytica* (formerly classified as *Candida lipolytica*)), *Candida* yeast (e.g., *C. revkaufi, C. pulcherrima, C. tropicalis, C. utilis*), *Rhodotorula* yeast (e.g., *R. glutinus, R. graminis*), *Rhodosporidium* yeast (e.g., *R. toruloides*), *Saccharomyces* yeast (e.g., *S. cerevisiae, S. bayanus, S. pastorianus, S. carlsbergensis*), *Cryptococcus* yeast, *Trichosporon* yeast (e.g., *T. pullans, T. cutaneum*), *Pichia* yeast (e.g., *P. pastoris*) and *Lipomyces* yeast (e.g., *L. starkeyii, L. lipoferus*). In some embodiments, a yeast is a *Y. lipolytica* strain that includes, but is not limited to, ATCC20362, ATCC8862, ATCC18944, ATCC20228, ATCC76982 and LGAM S(7)1 strains (Papanikolaou S., and Aggelis G., Bioresour. Technol. 82(1):43-9 (2002)). In certain embodiments, a yeast is a *C. tropicalis* strain that includes, but is not limited to, ATCC20336, ATCC20913, SU-2 (ura3-/ura3-), ATCC20962, H5343 (beta oxidation blocked; U.S. Pat. No. 5,648,247) strains.

Any suitable fungus may be selected as a host microorganism, engineered microorganism or source for a heterologous polynucleotide. Non-limiting examples of fungi include, but are not limited to, *Aspergillus* fungi (e.g., *A. parasiticus, A. nidulans*), *Thraustochytrium* fungi, *Schizochytrium* fungi and *Rhizopus* fungi (e.g., *R. arrhizus, R. oryzae, R. nigricans*). In some embodiments, a fungus is an *A. parasiticus* strain that includes, but is not limited to, strain ATCC24690, and in certain embodiments, a fungus is an *A. nidulans* strain that includes, but is not limited to, strain ATCC38163.

Any suitable prokaryote may be selected as a host microorganism, engineered microorganism or source for a heterologous polynucleotide. A Gram negative or Gram positive bacteria may be selected. Examples of bacteria include, but are not limited to, *Bacillus* bacteria (e.g., *B. subtilis, B. megaterium*), *Acinetobacter* bacteria, *Norcardia* baceteria, *Xanthobacter* bacteria, *Escherichia* bacteria (e.g., *E. coli* (e.g., strains DH10B, Stbl2, DH5-alpha, DB3, DB3.1), DB4, DB5, JDP682 and ccdA-over (e.g., U.S. application Ser. No. 09/518,188))), *Streptomyces* bacteria, *Erwinia* bacteria, *Klebsiella* bacteria, *Serratia* bacteria (e.g., *S. marcessans*), *Pseudomonas* bacteria (e.g., *P. aeruginosa*), *Salmonella* bacteria (e.g., *S. typhimurium, S. typhi*), *Megasphaera* bacteria (e.g., *Megasphaera elsdenii*). Bacteria also include, but are not limited to, photosynthetic bacteria (e.g., green non-sulfur bacteria (e.g., *Choroflexus* bacteria (e.g., *C. aurantiacus*), *Chloronema* bacteria (e.g., *C. gigateum*)), green sulfur bacteria (e.g., *Chlorobium* bacteria (e.g., *C. limicola*), *Pelodictyon* bacteria (e.g., *P. luteolum*), purple sulfur bacteria (e.g., *Chromatium* bacteria (e.g., *C. okenii*)), and purple non-sulfur bacteria (e.g., *Rhodospirillum* bacteria (e.g., *R. rubrum*), *Rhodobacter* bacteria (e.g., *R. sphaeroides, R. capsulatus*), and *Rhodomicrobium* bacteria (e.g., *R. vanellii*)).

Cells from non-microbial organisms can be utilized as a host microorganism, engineered microorganism or source for a heterologous polynucleotide. Examples of such cells, include, but are not limited to, insect cells (e.g., *Drosophila* (e.g., *D. melanogaster*), *Spodoptera* (e.g., *S. frugiperda* Sf9 or Sf21 cells) and *Trichoplusa* (e.g., High-Five cells); nematode cells (e.g., *C. elegans* cells); avian cells; amphibian cells (e.g., *Xenopus laevis* cells); reptilian cells; and mammalian cells (e.g., NIH3T3, 293, CHO, COS, VERO, C127, BHK, Per-C6, Bowes melanoma and HeLa cells).

Microorganisms or cells used as host organisms or source for a heterologous polynucleotide are commercially available. Microoganisms and cells described herein, and other suitable microorganisms and cells are available, for example, from Invitrogen Corporation, (Carlsbad, Calif.), American Type Culture Collection (Manassas, Va.), and Agricultural Research Culture Collection (NRRL; Peoria, Ill.).

Host microorganisms and engineered microorganisms may be provided in any suitable form. For example, such microorganisms may be provided in liquid culture or solid culture (e.g., agar-based medium), which may be a primary culture or may have been passaged (e.g., diluted and cultured) one or more times. Microorganisms also may be provided in frozen form or dry form (e.g., lyophilized). Microorganisms may be provided at any suitable concentration.

Carbon Processing Pathways and Activities

Figure 9:
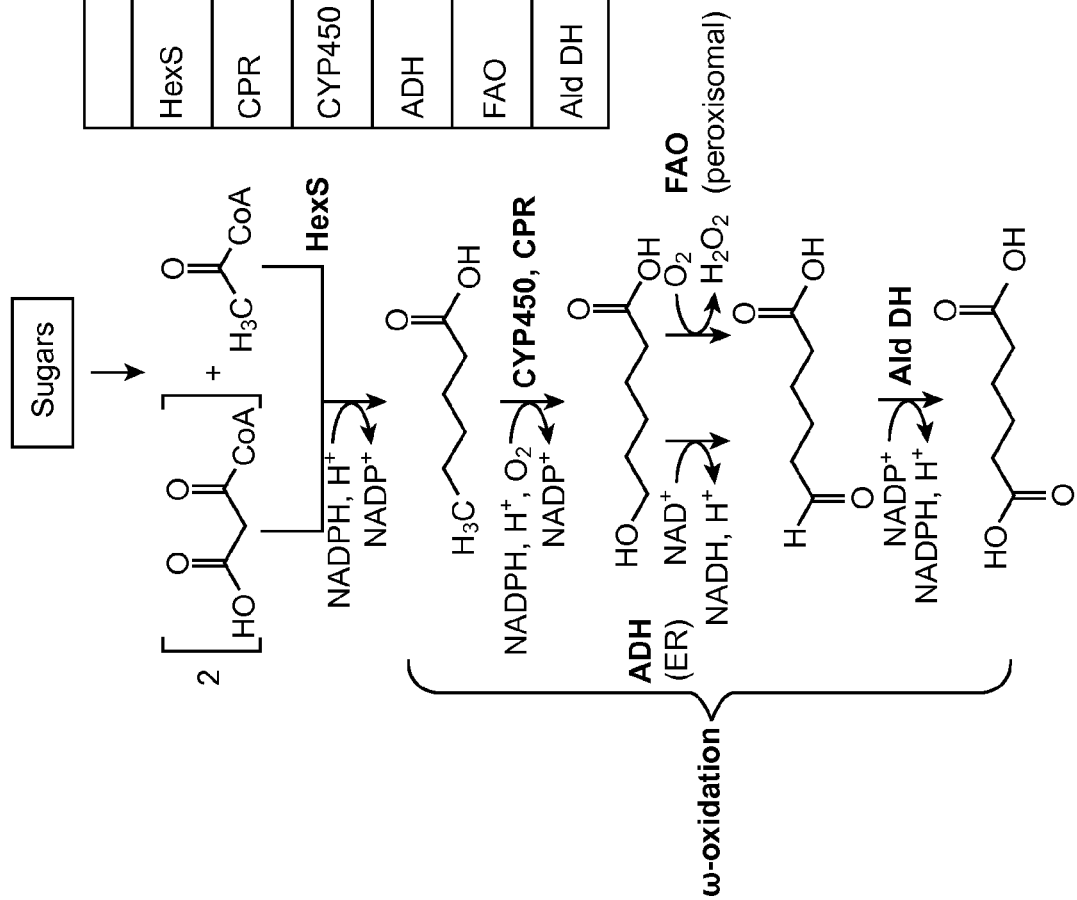
FIG. 9 depicts a metabolic pathway for making adipic acid from saccharide or polysaccharide carbon sources, similar to the pathway depicted in FIG. 1, with additional activities that aid in metabolism of, or enhance metabolism of, pathway intermediates, thereby potentially increasing the yield of adipic acid. The additional activities are a monooxygenase reductase activity (cytochrome P450 reductase or CPR) and a fatty alcohol oxidase activity (FAO). Part, or all, of the pathway can be engineered into a eukaryotic microorganism to generate a microorganism capable of producing adipic acid.

FIGS. 1 and 9 depict an embodiment of a biological pathway for making adipic acid, using a sugar as the carbon source starting material. Any suitable sugar can be used as the feedstock for the organism, (e.g., 6-carbon sugars (e.g., glucose, fructose), 5-carbon sugars (e.g., xylose), the like or combinations thereof). The sugars are initially metabolized using naturally occurring and/or engineered pathways to yield malonyl CoA, which is depicted as the molecule entering the omega oxidation pathway shown in FIG. 9. As depicted, the enzyme hexanoate synthase converts two molecules of malonyl CoA and one molecule of acetyl CoA to one molecule of hexanoic acid. In some embodiments a cytochrome P450 enzyme converts hexanoic acid to 6-hydroxyhexanoic acid, which may be oxidized to 6-oxohexanoic acid via 6-hydroxyhexanoic acid dehydrogenase, or fatty alcohol oxidase. 6-oxohexanoic acid may be converted to adipic acid by 6-oxohexanoic acid dehydrogenase.

A hexanoate synthase enzyme (HexS) is coded by hexonate synthase subunit alpha (HEXA) and hexanoate synthase subunit beta (HEXB) genes. In some embodiments, the HexS enzyme is endogenous to the host microorganism. In certain embodiments, HEXA and HEXB genes may be isolated from a suitable organism (e.g., *Aspergillus parasiticus*). In some embodiments, HEXA and HEXB orthologs, such as STCJ and STCK, also may be isolated from suitable organisms (e.g., *Aspergillus nidulans*).

Hexanoate is omega-hydroxylated by the enzyme cytochrome P450, thereby generating a six carbon alcohol, in some embodiments. In certain embodiments, the cytochrome P450 enzyme is endogenous to the host microorganism. In some embodiments the cytochrome P450 gene is isolated from *Bacillus megaterium* and codes for a single subunit, soluble, cytoplasmic enzyme. Soluble or membrane bound cytochrome P450 from certain host organisms is specific for 6-carbon substrates and may be used in some embodiments.

Cytochrome P450 is reduced by the activity of cytochrome P450 reductase (CPR), thereby recycling cytochrome P450 to allow further enzymatic activity. In certain embodiments, the CPR enzyme is endogenous to the host microorganism. In some embodiments, host CPR activity can be increased by increasing the number of copies of a CPR gene (e.g., 2, 3, 4, 5, 6, 7, 8, 9, 10 or more copies of the gene), by increasing the activity of a promoter that regulates transcription of a CPR gene, or by increasing the number of copies of a CPR gene and increasing the activity of a promoter that regulates transcription of a CPR gene, thereby increasing the production of target product (e.g., adipic acid) via increased recycling of cytochrome P450. In certain embodiments, the promoter can be a heterologous promoter (e.g., endogenous or exogenous promoter). In some embodiments, the CPR gene is heterologous and exogenous and can be isolated from any suitable organism. Non-limiting examples of organisms from which a CPR gene can be isolated include *C. tropicalis, S. cerevisiae* and *Bacillus megaterium*.

Oxidation of the alcohol to an aldehyde may be performed by an enzyme in the fatty alcohol oxidase family (e.g., 6-hydroxyhexanoic acid dehydrogenase, omega hydroxyl fatty acid dehydrogenase), or an enzyme in the aldehyde dehydrogenase family (e.g., 6-oxohexanoic acid dehydrogenase, omega oxo fatty acid dehydrogenase). The enzyme 6-oxohexanoic acid dehydrogenase or omega oxo fatty acid dehydrogenase may oxidize the aldehyde to the carboxylic acid adipic acid. In some embodiments, the enzymes 6-hydroxyhexanoic acid dehydrogenase, omega hydroxyl fatty acid dehydrogenase, fatty alcohol oxidase, 6-oxohexanoic acid dehydrogenase, or omega oxo fatty acid dehydrogenase, exist in a host organism. Flux through these two steps may sometimes be augmented by increasing the copy number of the enzymes, or by increasing the activity of the promoter transcribing the genes. In some embodiments alcohol and aldehyde dehydrogenases specific for six carbon substrates may be isolated from another organism, for example *Acinetobacter, Candida, Saccharomyces* or *Pseudomonas* and inserted into the host organism.

Figure 10:
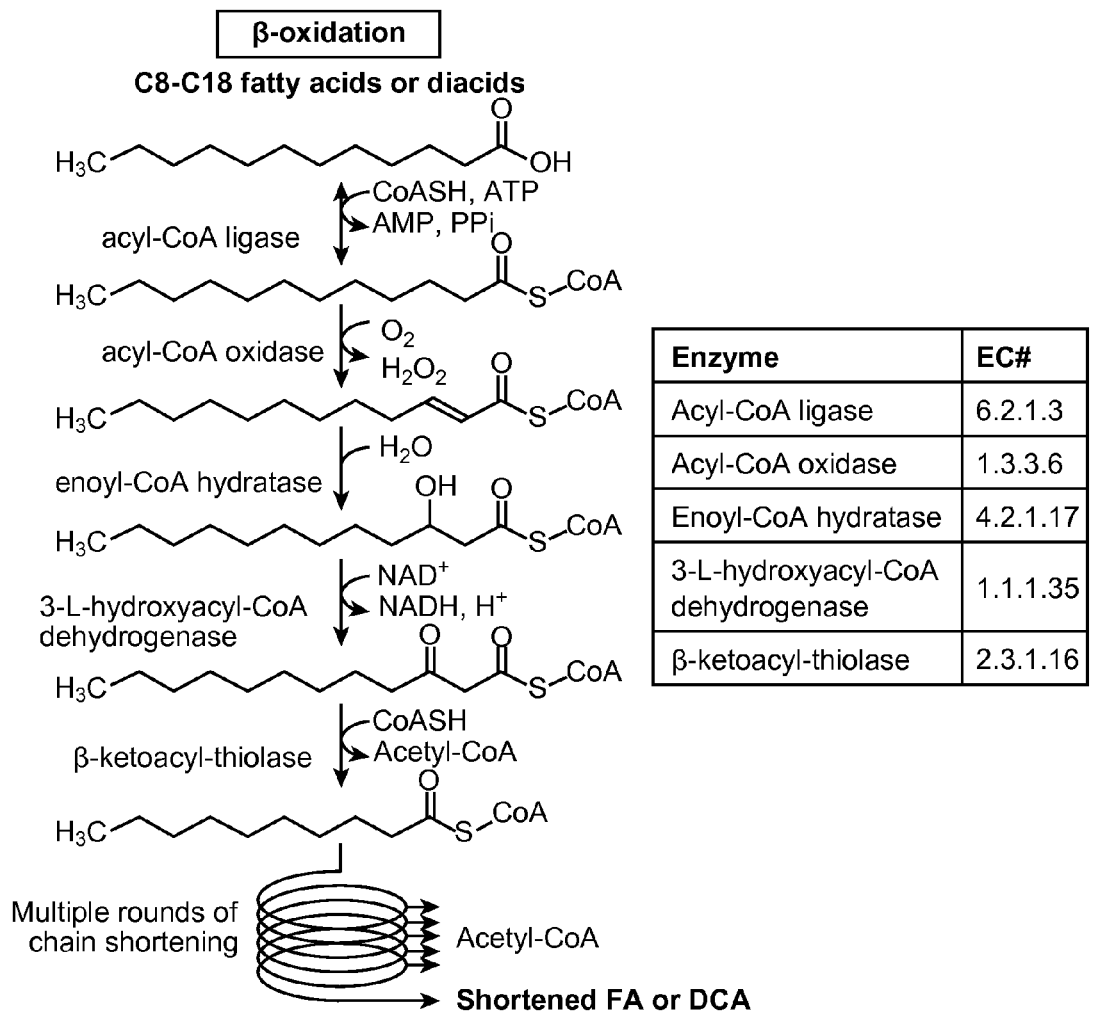
FIG. 10 depicts a non-limiting example of a metabolic pathway for making adipic acid from paraffins, fats, oils, fatty acids or dicarboxylic acids, as described in FIG. 2. Part, or all, of the pathway can be engineered (e.g., added, altered to increase or decrease copy number, or increase or decrease promoter activity, depending on the desired effect) into a microorganism, depending on the activities already present in the host organism, to generate a microorganism capable of producing adipic acid.
Figure 11A:
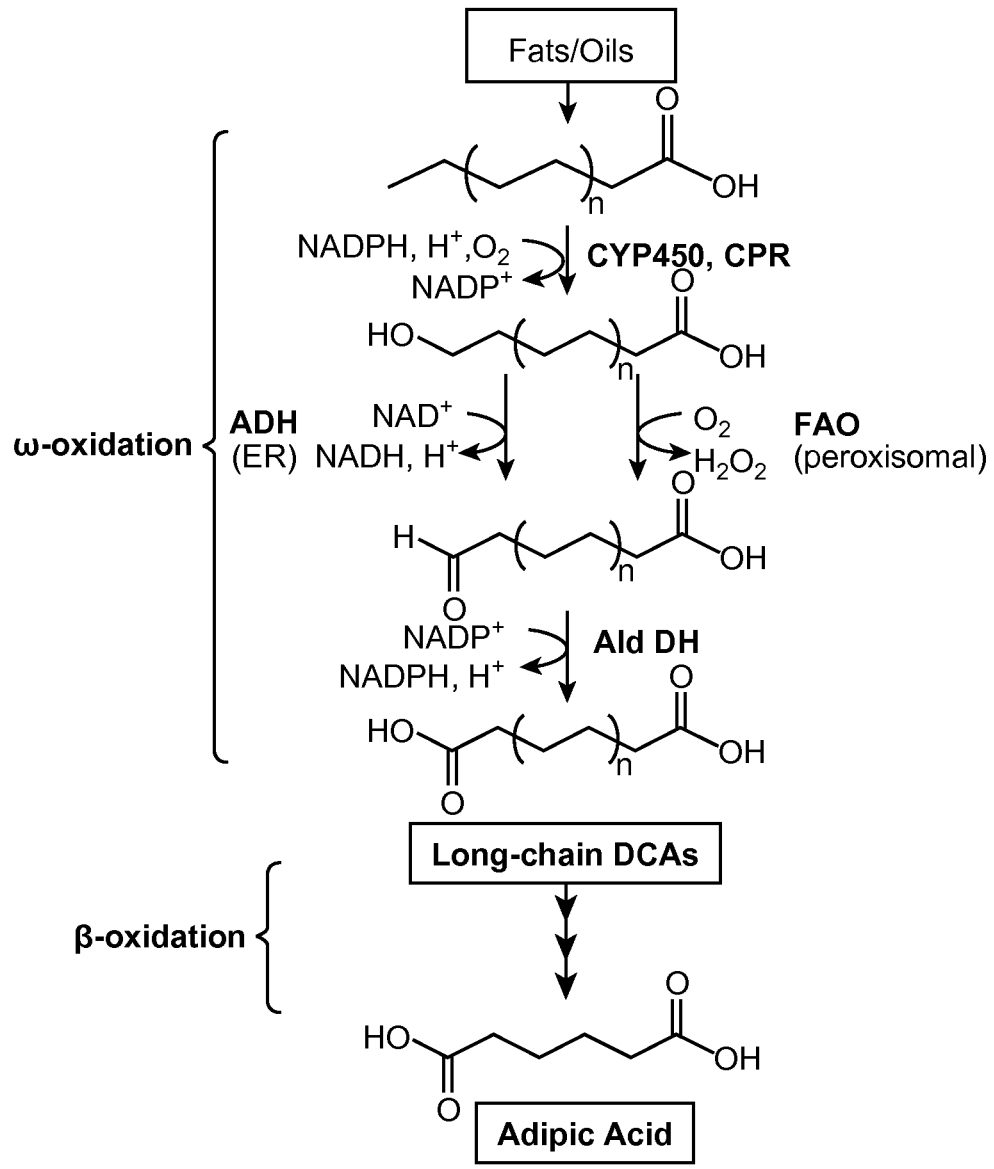
FIGS. 11A and 11B depict omega and beta oxidation pathways useful for producing adipic acid from various carbon sources. Adipic acid can be produced from paraffins, fats, oils and intermediates of sugar metabolism, using omega oxidation, as shown in FIG. 11A. Adipic acid also can be produced from long chain fatty acids or dicarboxylic acids using beta oxidation, as shown in FIG. 11A.

FIG. 10 depicts an embodiment of a biological pathway for making adipic acid, using fats, oils, dicarboxylic acids, paraffins (e.g., linear, branched, substituted, saturated, unsaturated, the like and combinations thereof), fatty alcohols, fatty acids, or the like, as the carbon source starting material. Any suitable fatty alcohol, fatty acid, paraffin, dicarboxylic acid, fat or oil can be used as the feedstock for the organism, (e.g., hexane, hexanoic acid, oleic acid, coconut oil, the like or combinations thereof). Carbon sources with longer chain lengths (e.g., 8 carbons or greater in length) can be metabolized using naturally occurring and/or engineered pathways to yield molecules that can be further metabolized using the beta oxidation pathway shown in FIG. 10 and the lower portion of FIG. 11A. In some embodiments, the activities in the pathway shown in FIG. 10 also can be engineered (e.g., as described herein) to enhance metabolism and target product formation. The enzyme acyl-CoA ligase converts a long chain fatty alcohol, fatty acid or dicarboxylic acid and 1 molecule of acetyl-CoA into an acyl-CoA derivative of the long chain fatty alcohol, fatty acid or dicarboxylic acid with the conversion of ATP to AMP and inorganic phosphate, as depicted in the first step of the reaction in FIG. 10. The term "beta oxidation pathway" as used herein, refers to a series of enzymatic activities utilized to metabolize fatty alcohols, fatty acids, or dicarboxylic acids. The activities utilized to metabolize fatty alcohols, fatty acids, or dicarboxylic acids include, but are not limited to, acyl-CoA ligase activity, acyl-CoA oxidase activity, enoyl-CoA hydratase activity, 3-hydroxyacyl-CoA dehydrogenase activity and acetyl-CoA C-acyltransferase activity. The term "beta oxidation activity" refers to any of the activities in the beta oxidation pathway utilized to metabolize fatty alcohols, fatty acids or dicarboxylic acids. The term "omega oxidation activity" refers to any of the activities in the omega oxidation pathway utilized to metabolize fatty alcohols, fatty acids, dicarboxylic acids, or sugars.

In certain embodiments, an Acyl-CoA ligase enzyme converts a long chain fatty alcohol, fatty acid or dicarboxylic acid into the acyl-CoA derivative, which may be oxidized to yield a trans-2,3-dehydroacyl-CoA derivative, by the activity of Acyl CoA oxidase (e.g., also known as acyl-CoA oxidoreductase and fatty acyl-coenzyme A oxidase). The trans-2,3-dehydroacyl-CoA derivative long chain fatty alcohol, fatty acid or dicarboxylic acid may be further converted to 3-hydroxyacyl-CoA by the activity of enoyl-CoA hydratase. 3-hydroxyacyl-CoA can be converted to 3-oxoacyl-CoA by the activity of 3-hydroxyacyl-CoA dehydrogenase. 3-oxoacyl-CoA may be converted to an acyl-CoA molecule, shortened by 2 carbons and an acetyl-CoA, by the activity of Acetyl-CoA C-acyltransferase (e.g., also known as beta-ketothiolase and β-ketothiolase). In some embodiments, acyl-CoA molecules may be repeatedly shortened by beta oxidation until a desired carbon chain length is generated (e.g., 6 carbons, adipic acid). The shortened fatty acid can be further processed using omega oxidation to yield adipic acid.

An acyl-CoA ligase enzyme sometimes is encoded by the host organism and can be added to generate an engineered organism. In some embodiments, host acyl-CoA ligase activity can be increased by increasing the number of copies of an acyl-CoA ligase gene, by increasing the activity of a promoter that regulates transcription of an acyl-CoA ligase gene, or by increasing the number copies of the gene and by increasing the activity of a promoter that regulates transcription of the gene, thereby increasing production of target product (e.g., adipic acid) due to increased carbon flux through the pathway. In certain embodiments, the acyl-CoA ligase gene can be isolated from any suitable organism. Non-limiting examples of organisms that include, or can be used as donors for, acyl-CoA ligase enzymes include *Candida, Saccharomyces*, or *Yarrowia*.

An enoyl-CoA hydratase enzyme catalyzes the addition of a hydroxyl group and a proton to the unsaturated β-carbon on a fatty-acyl CoA and sometimes is encoded by the host organism and sometimes can be added to generate an engineered organism. In certain embodiments, the enoyl-CoA hydratase activity is unchanged in a host or engineered organism. In some embodiments, the host enoyl-CoA hydratase activity can be increased by increasing the number of copies of an enoyl-CoA hydratase gene, by increasing the activity of a promoter that regulates transcription of an enoyl-CoA hydratase gene, or by increasing the number copies of the gene and by increasing the activity of a promoter that regulates transcription of the gene, thereby increasing the production of target product (e.g., adipic acid) due to increased carbon flux through the pathway. In certain embodiments, the enoyl-CoA hydratase gene can be isolated from any suitable organism. Non-limiting examples of organisms that include, or can be used as donors for, enoyl-CoA hydratase enzymes include *Candida, Saccharomyces*, or *Yarrowia*.

3-hydroxyacyl-CoA dehydrogenase enzyme catalyzes the formation of a 3-ketoacyl-CoA by removal of a hydrogen from the newly formed hydroxyl group created by the activity of enoyl-CoA hydratase. In some embodiments, the activity is encoded by the host organism and sometimes can be added or increased to generate an engineered organism. In certain embodiments, the 3-hydroxyacyl-CoA activity is unchanged in a host or engineered organism. In some embodiments, the host 3-hydroxyacyl-CoA dehydrogenase activity can be increased by increasing the number of copies of a 3-hydroxyacyl-CoA dehydrogenase gene, by increasing the activity of a promoter that regulates transcription of a 3-hydroxyacyl-CoA dehydrogenase gene, or by increasing the number copies of the gene and by increasing the activity of a promoter that regulates transcription of the gene, thereby increasing production of target product (e.g., adipic acid) due to increased carbon flux through the pathway. In certain embodiments, the 3-hydroxyacyl-CoA dehydrogenase gene can be isolated from any suitable organism. Non-limiting examples of organisms that include, or can be used as donors for, 3-hydroxyacyl-CoA dehydrogenase enzymes include *Candida*, *Saccharomyces*, or *Yarrowia*.

An Acetyl-CoA C-acyltransferase (e.g., β-ketothiolase) enzyme catalyzes the formation of a fatty acyl-CoA shortened by 2 carbons by cleavage of the 3-ketoacyl-CoA by the thiol group of another molecule of CoA. The thiol is inserted between C-2 and C-3, which yields an acetyl CoA molecule and an acyl CoA molecule that is two carbons shorter. An Acetyl-CoA C-acyltransferase sometimes is encoded by the host organism and sometimes can be added to generate an engineered organism. In certain embodiments, the acetyl-CoA C-acyltransferase activity is unchanged in a host or engineered organism. In some embodiments, the host acetyl-CoA C-acyltransferase activity can be increased by increasing the number of copies of an acetyl-CoA C-acyltransferase gene, or by increasing the activity of a promoter that regulates transcription of an acetyl-CoA C-acyltransferase gene, thereby increasing the production of target product (e.g., adipic acid) due to increased carbon flux through the pathway. In certain embodiments, the acetyl-CoA C-acyltransferase gene can be isolated from any suitable organism. Non-limiting examples of organisms that include, or can be used as donors for, acetyl-CoA C-acyltransferase enzymes include *Candida*, *Saccharomyces*, or *Yarrowia*.

A microorganism may be modified and engineered to include or regulate one or more activities in an adipic acid pathway. The term "activity" as used herein refers to the functioning of a microorganism's natural or engineered biological pathways to yield various products including adipic acid and its precursors. Adipic acid producing activity can be provided by any non-mammalian source in certain embodiments. Such sources include, without limitation, eukaryotes such as yeast and fungi and prokaryotes such as bacteria. In some embodiments, a reverse activity in a pathway described herein can be altered (e.g., disrupted, reduced) to increase carbon flux through a beta oxidation pathway, an omega oxidation pathway, or a beta oxidation and omega oxidation pathway, towards the production of target product (e.g., adipic acid). In some embodiments, a genetic modification disrupts an activity in the beta oxidation pathway, or disrupts a polynucleotide that encodes a polypeptide that carries out a forward reaction in the beta oxidation pathway, which renders beta oxidation activity undetectable. The term "undetectable" as used herein refers to an amount of an analyte that is below the limits of detection, using detection methods or assays known (e.g., described herein). In certain embodiments, the genetic modification partially reduces beta oxidation activity. The term "partially reduces beta oxidation activity" as used here refers to a level of activity in an engineered organism that is lower than the level of activity found in the host or starting organism.

An activity within an engineered microorganism provided herein can include one or more (e.g., 1, 2, 3, 4, 5, 6, 7, 8, 9, 10 or all) of the following activities: 6-oxohexanoic acid dehydrogenase activity; 6-hydroxyhexanoic acid dehydrogenase activity; hexanoate synthase activity; cytochrome P450 activity; cytochrome P450 reductase activity; fatty alcohol oxidase activity; acyl-CoA ligase activity, acyl-CoA oxidase activity; enoyl-CoA hydratase activity, 3-hydroxyacyl-CoA dehydrogenase activity, and thioesterase activity (e.g., acetyl-CoA C-acyltransferase, beta-ketothiolase). In certain embodiments, one or more (e.g., 1, 2, 3, 4, 5, 6, 7, 8, 9, 10 or all) of the foregoing activities is altered by way of a genetic modification. In some embodiments, one or more (e.g., 1, 2, 3, 4, 5, 6, 7, 8, 9, 10 or all) of the foregoing activities is altered by way of (i) adding a heterologous polynucleotide that encodes a polypeptide having the activity, and/or (ii) altering or adding a regulatory sequence that regulates the expression of a polypeptide having the activity.

The term "6-oxohexanoic acid dehydrogenase activity" as used herein refers to conversion of 6-oxohexanoic acid to adipic acid. The 6-oxohexanoic acid dehydrogenase activity can be provided by a polypeptide. In some embodiments, the polypeptide is encoded by a heterologous nucleotide sequence introduced to a host microorganism. In certain embodiments, an endogenous polypeptide having the 6-oxohexanoic acid dehydrogenase activity is identified in the host microorganism, and the host microorganism is genetically altered to increase the amount of the polypeptide produced (e.g., a heterologous promoter is introduced in operable linkage with a polynucleotide that encodes the polypeptide; the copy number of a polynucleotide that encodes the polypeptide is increased (e.g., by introducing a plasmid that includes the polynucleotide)). Nucleic acid sequences conferring 6-oxohexanoic acid dehydrogenase activity can be obtained from a number of sources, including *Actinobacter, Norcardia, Pseudomonas* and *Xanthobacter* bacteria. Examples of an amino acid sequence of a polypeptide having 6-oxohexanoic acid dehyrdogenase activity, and a nucleotide sequence of a polynucleotide that encodes the polypeptide, are presented herein. Presence, absence or amount of 6-oxohexanoic acid dehydrogenase activity can be detected by any suitable method known in the art. For an example of a detection method for alcohol oxidase or alcohol dehydrogenase activity (see Appl Environ Microbiol 70: 4872). In some embodiments, 6-oxohexanoic acid dehydrogenase activity is not altered in a host microorganism, and in certain embodiments, the activity is added or increased in the engineered microorganism relative to the host microorganism.

The term "omega oxo fatty acid dehydrogenase activity" as used herein refers to conversion of an omega oxo fatty acid to a dicarboxylic acid. The omega oxo fatty acid dehydrogenase activity can be provided by a polypeptide. In some embodiments, the polypeptide is encoded by a heterologous nucleotide sequence introduced to a host microorganism. In certain embodiments, an endogenous polypeptide having the omega oxo fatty acid dehydrogenase activity is identified in the host microorganism, and the host microorganism is genetically altered to increase the amount of the polypeptide produced (e.g., a heterologous promoter is introduced in operable linkage with a polynucleotide that encodes the polypeptide; the copy number of a polynucleotide that encodes the polypeptide is increased (e.g., by introducing a plasmid that includes the polynucleotide)). Nucleic acid sequences conferring omega oxo fatty acid dehydrogenase activity can be obtained from a number of sources, including *Actinobacter, Norcardia, Pseudomonas* and *Xanthobacter* bacteria. Examples of an amino acid sequence of a polypeptide having omega oxo fatty acid dehydrogenase activity and a nucleotide sequence of a polynucleotide that encodes the polypeptide, are presented herein. Presence, absence or amount of omega oxo fatty acid dehydrogenase activity can be detected by any suitable method known in the art. In some embodiments, omega oxo fatty acid dehydrogenase activity is not altered in a host microorganism, and in certain embodiments, the activity is added or increased in the engineered microorganism relative to the host microorganism.

The term "6-hydroxyhexanoic acid dehydrogenase activity" as used herein refers to conversion of 6-hydroxyhexanoic acid to 6-oxohexanoic acid. The 6-hydroxyhexanoic acid dehydrogenase activity can be provided by a polypeptide. In some embodiments, the polypeptide is encoded by a heterologous nucleotide sequence introduced to a host microorganism. In certain embodiments, an endogenous polypeptide having the 6-hydroxyhexanoic acid dehydrogenase activity is identified in the host microorganism, and the host microorganism is genetically altered to increase the amount of the polypeptide produced (e.g., a heterologous promoter is introduced in operable linkage with a polynucleotide that encodes the polypeptide; the copy number of a polynucleotide that encodes the polypeptide is increased (e.g., by introducing a plasmid that includes the polynucleotide)). Nucleic acid sequences conferring 6-hydroxohexanoic acid dehydrogenase activity can be obtained from a number of sources, including *Actinobacter, Norcardia, Pseudomonas*, and *Xanthobacter*. Examples of an amino acid sequence of a polypeptide having 6-hydroxyhexanoic acid dehydrogenase activity, and a nucleotide sequence of a polynucleotide that encodes the polypeptide, are presented herein. Presence, absence or amount of 6-hydroxyhexanoic acid dehydrogenase activity can be detected by any suitable method known in the art. An example of such a method is described in Methods in Enzymology, 188: 176. In some embodiments, 6-hydroxyhexanoic acid dehydrogenase activity is not altered in a host microorganism, and in certain embodiments, the activity is added or increased in the engineered microorganism relative to the host microorganism.

The term "omega hydroxyl fatty acid dehydrogenase activity" as used herein refers to conversion of an omega hydroxyl fatty acid to an omega oxo fatty acid. The omega hydroxyl fatty acid dehydrogenase activity can be provided by a polypeptide. In some embodiments, the polypeptide is encoded by a heterologous nucleotide sequence introduced to a host microorganism. In certain embodiments, an endogenous polypeptide having the omega hydroxyl fatty acid dehydrogenase activity is identified in the host microorganism, and the host microorganism is genetically altered to increase the amount of the polypeptide produced (e.g., a heterologous promoter is introduced in operable linkage with a polynucleotide that encodes the polypeptide; the copy number of a polynucleotide that encodes the polypeptide is increased (e.g., by introducing a plasmid that includes the polynucleotide)). Nucleic acid sequences conferring omega hydroxyl fatty acid dehydrogenase activity can be obtained from a number of sources, including *Actinobacter, Norcardia, Pseudomonas* and *Xanthobacter* bacteria. Examples of an amino acid sequence of a polypeptide having omega hydroxyl fatty acid dehydrogenase activity and a nucleotide sequence of a polynucleotide that encodes the polypeptide, are presented herein. Presence, absence or amount of omega hydroxyl fatty acid dehydrogenase activity can be detected by any suitable method known in the art. In some embodiments, omega hydroxyl fatty acid dehydrogenase activity is not altered in a host microorganism, and in certain embodiments, the activity is added or increased in the engineered microorganism relative to the host microorganism.

The term "hexanoate synthase activity" as used herein refers to conversion of acetyl-CoA and malonyl-CoA to hexanoic acid. Hexanoate synthase activity may be provided by an enzyme that includes one or two subunits (referred to hereafter as "subunit A" and/or "subunit B"). The hexanoate synthase activity can be provided by a polypeptide. In some embodiments, the polypeptide is encoded by a heterologous nucleotide sequence introduced to a host microorganism. Nucleic acid sequences conferring hexonate synthase activity can be obtained from a number of sources, including *Aspergillus parisiticus*, for example. Examples of an amino acid sequence of a polypeptide having hexanoate synthase activity, and a nucleotide sequence of a polynucleotide that encodes the polypeptide, are presented herein. In some embodiments, hexanoate synthase activity is not altered in a host microorganism, and in certain embodiments, the activity is added or increased in the engineered microorganism relative to the host microorganism.

Presence, absence or amount of hexanoate synthase activity can be detected by any suitable method known in the art. An example of such a method is described in Hexanoate synthase+thioesterase (Chemistry and Biology 9: 981-988). Briefly, an indicator strain may be prepared. An indicator strain may be *Bacillus subtilis* containing a reporter gene (beta-galactosidase, green fluorescent protein, etc.) under control of the promoter regulated by LiaR, for example. An indicator strain also may be *Candida tropicalis* containing either the LiaR regulatable promoter from *Bacillus subtilis* or the alkane inducible promoter for the native gene for the peroxisomal 3-ketoacyl coenzyme A thiolase gene (CT-T3A), for example. Mutants with an improved functionality of HexS, thereby producing more hexanoic acid, can be plated onto a lawn of indicator strain. Upon incubation and growth of both the test mutant and the indicator strain, the appearance of a larger halo, which correlates to the induction of the reporter strain compared to control strains, indicates a mutant with improved activity. In alternative approach, mutants are grown in conditions favoring production of hexanoyl CoA or hexanoic acid and lysed. Cell lysates are treated with proteases which may release hexanoic acid from the PKS. Clarified lysates may be spotted onto lawns of indicator strains to assess improved production. In another alternative approach, indicator strains are grown under conditions suitable to support expression of the reporter gene when induced by hexanoic acid. Dilutions of a known concentration of hexanoic acid are used to determine a standard curve. Lysates of the test strain grown under conditions favoring production of hexanoic acid are prepared and dilutions of the lysate added to the indicator strain. Indicator strains with lysates are placed under identical conditions as used to determine the standard curve. The lysate dilutions that minimally support induction can be used to determine, quantitatively, the amount produced when compared to the standard curve.

The term "monooxygenase activity" as used herein refers to inserting one atom of oxygen from $O_2$ into an organic substrate (RH) and reducing the other oxygen atom to water. In some embodiments, monooxygenase activity refers to incorporation of an oxygen atom onto a six-carbon organic substrate. In certain embodiments, monooxygenase activity refers to conversion of hexanoate to 6-hydroxyhexanoic acid. Monooxygenase activity can be provided by any suitable polypeptide, such as a cytochrome P450 polypeptide (hereafter "CYP450") in certain embodiments. Nucleic acid sequences conferring CYP450 activity can be obtained from a number of sources, including *Bacillus megaterium* and may be induced in organisms including but not limited to *Candida tropicalis, Yarrowia lipolytica, Aspergillus nidulans*, and *Aspergillus parasiticus*. Examples of oligonucleotide sequences utilized to isolate a polynucleotide sequence encoding a polypeptide having CYP450 activity (e.g., CYP52A15 activity, CYP52A16 activity, or CYP52A15 activity and CYP52A16 activity) are presented herein. In some embodiments, monooxygenase activity is not altered in a host microorganism, and in certain embodiments, the activity is added or increased in the engineered microorganism relative to the host microorganism.

Presence, absence or amount of cytochrome P450 activity can be detected by any suitable method known in the art. For example, detection can be performed by assaying a reaction containing cytochrome P450 (CYP52A family) and NADPH-cytochrome P450 reductase (see Appl Environ Microbiol 69: 5983 and 5992). Briefly, cells are grown under standard conditions and harvested for production of microsomes, which are used to detect CYP activity. Microsomes are prepared by lysing cells in Tris-buffered sucrose (10 mM Tris-HCl pH 7.5, 1 mM EDTA, 0.25M sucrose). Differential centrifugation is performed first at 25,000×g then at 100,000×g to pellet cell debris then microsomes, respectively. The microsome pellet is resuspended in 0.1 M phosphate buffer (pH 7.5), 1 mM EDTA to a final concentration of approximately 10 mg protein/mL. A reaction mixture containing approximately 0.3 mg microsomes, 0.1 mM sodium hexanoate, 0.7 mM NADPH, 50 mM Tris-HCl pH 7.5 in 1 mL is initiated by the addition of NADPH and incubated at 37° C. for 10 minutes. The reaction is terminated by addition of 0.25 mL 5M HCl and 0.25 mL 2.5 ug/mL 10-hydroxydecanoic acid is added as an internal standard (3.3 nmol). The mixture is extracted with 4.5 mL diethyl ether under NaCl-saturated conditions. The organic phase is transferred to a new tube and evaporated to dryness. The residue is dissolved in acetonitrile containing 10 mM 3-bromomethyl-7-methoxy-1,4-benzoxazin-2-one (BrMB) and 0.1 mL of 15 mg/mL 18-crown-6 in acetonitril saturated with $K_2CO_3$. The solution is incubated at 40° C. for 30 minutes before addition of 0.05 mL 2% acetic acid. The fluorescently labeled omega-hydroxy fatty acids are resolved via HPLC with detection at 430 nm and excitation at 355 nm (Yamada et al., 1991, AnalBiochem 199: 132-136). Optionally, specifically induced CYP gene(s) may be detected by Northern blotting and/or quantitative RT-PCR. (Craft et al., 2003, AppEnvironMicro 69: 5983-5991).

The term "monooxygenase reductase activity" as used herein refers to the transfer of an electron from NAD(P)H, FMN, or FAD by way of an electron transfer chain, reducing the ferric heme iron of cytochrome P450 to the ferrous state. The term "monooxygenase reductase activity" as used herein also can refer to the transfer of a second electron via the electron transport system, reducing a dioxygen adduct to a negatively charged peroxo group. In some embodiments, a monooxygenase activity can donate electrons from the two-electron donor NAD(P)H to the heme of cytochrome P450 (e.g., monooxygenase activity) in a coupled two-step reaction in which NAD(P)H can bind to the NAD(P)H-binding domain of the polypeptide having the monooxygenase reductase activity and electrons are shuttled from NAD(P)H through FAD and FMN to the heme of the monooxygenase activity, thereby regenerating an active monooxygenase activity (e.g., cytochrome P450). Monooxygenase reductase activity can be provided by any suitable polypeptide, such as a cytochrome P450 reductase polypeptide (hereafter "CPR") in certain embodiments. Nucleic acid sequences conferring CPR activity can be obtained from and/or induced in a number of sources, including but not limited to *Bacillus megaterium, Candida tropicalis, Yarrowia lipolytica, Aspergillus nidulans*, and *Aspergillus parasiticus*. Examples of oligonucleotide sequences utilized to isolate a polynucleotide sequence encoding a polypeptide having CPR activity are presented herein. In some embodiments, monooxygenase reductase activity is not altered in a host microorganism, and in certain embodiments, the activity is added or increased in the engineered microorganism relative to the host microorganism.

Presence, absence or amount of CPR activity can be detected by any suitable method known in the art. For example, an engineered microorganism having an increased number of genes encoding a CPR activity, relative to the host microorganism, could be detected using quantitative nucleic acid detection methods (e.g., southern blotting, PCR, primer extension, the like and combinations thereof). An engineered microorganism having increased expression of genes encoding a CPR activity, relative to the host microorganism, could be detected using quantitative expression based analysis (e.g., RT-PCR, western blot analysis, northern blot analysis, the like and combinations thereof). Alternately, an enzymatic assay can be used to detect Cytochrome P450 reductase activity, where the enzyme activity alters the optical absorbance at 550 nanometers of a substrate solution (Masters, B. S. S., Williams, C. H., Kamin, H. (1967) Methods in Enzymology, X, 565-573).

The term "fatty alcohol oxidase activity" as used herein refers to inserting one atom of oxygen from $O_2$ into an organic substrate and reducing the other oxygen atom to peroxide. Fatty alcohol oxidase activity sometimes also is referred to as "long-chain-alcohol oxidase activity", "long-chain-alcohol:oxygen oxidoreductase activity", "fatty alcohol:oxygen oxidoreductase activity" and "long-chain fatty acid oxidase activity". In some embodiments, fatty alcohol oxidase activity refers to incorporation of an oxygen atom onto a six-carbon organic substrate. In certain embodiments, fatty alcohol oxidase activity refers to the conversion of 6-hydroxyhexanoic acid into 6-oxohexanoic acid. In some embodiments, fatty alcohol oxidase activity refers to the conversion of an omega hydroxyl fatty acid into an omega oxo fatty acid. A Fatty alcohol oxidase (FAO) activity can be provided by any suitable polypeptide, such as a fatty alcohol oxidase peptide, a long-chain-alcohol oxidase peptide, a long-chain-alcohol:oxygen oxidoreductase peptide, a fatty alcohol:oxygen oxidoreductase peptide and a long-chain fatty acid oxidase peptide. Nucleic acid sequences conferring FAO activity can be obtained from a number of sources, including but not limited to *Candida tropicalis, Candida cloacae, Yarrowia lipolytica*, and *Arabidopsis thaliana*. Examples of amino acid sequences of polypeptides having FAO activity, and nucleotide sequences of polynucleotides that encode the polypeptides, are presented herein. In some embodiments, fatty alcohol oxidase activity is not altered in a host microorganism, and in certain embodiments, the activity is added or increased in the engineered microorganism relative to the host microorganism.

Presence, absence or amount of FAO activity can be detected by any suitable method known in the art. For example, an engineered microorganism having an increased number of genes encoding an FAO activity, relative to the host microorganism, could be detected using quantitative nucleic acid detection methods (e.g., southern blotting, PCR, primer extension, the like and combinations thereof). An engineered microorganism having increased expression of genes encoding an FAO activity, relative to the host microorganism, could be detected using quantitative expression based analysis (e.g., RT-PCR, western blot analysis, northern blot analysis, the like and combinations thereof). Alternately, an enzymatic assay can be used to detect fatty alcohol oxidase activity as described in Eirich et al, 2004, or as modified in the Examples herein.

The term "acyl-CoA oxidase activity" as used herein refers to the oxidation of a long chain fatty-acyl-CoA to a trans-2,3-dehydroacyl-CoA fatty alcohol. In some embodiments, the acyl-CoA activity is from a peroxisome. In certain embodiments, the acyl-CoA oxidase activity is a peroxisomal acyl-CoA oxidase (POX) activity, carried out by a POX polypeptide. In some embodiments the acyl-CoA oxidase activity is encoded by the host organism and sometimes can be altered to generate an engineered organism. Acyl-CoA oxidase activity is encoded by the POX4 and POX5 genes of *C. tropicalis*. In certain embodiments, endogenous acyl-CoA oxidase activity can be increased. In some embodiments, acyl-CoA oxidase activity of the POX4 polypeptide or the POX5 polypeptide can be altered independently of each other (e.g., increase activity of POX4 alone, POX5 alone, increase one and disrupt the other, and the like). Increasing the activity of one POX activity, while disrupting the activity of another POX activity, may alter the specific activity of acyl-CoA oxidase with respect to carbon chain length, while maintaining or increasing overall flux through the beta oxidation pathway, in certain embodiments.

Figure 15A:
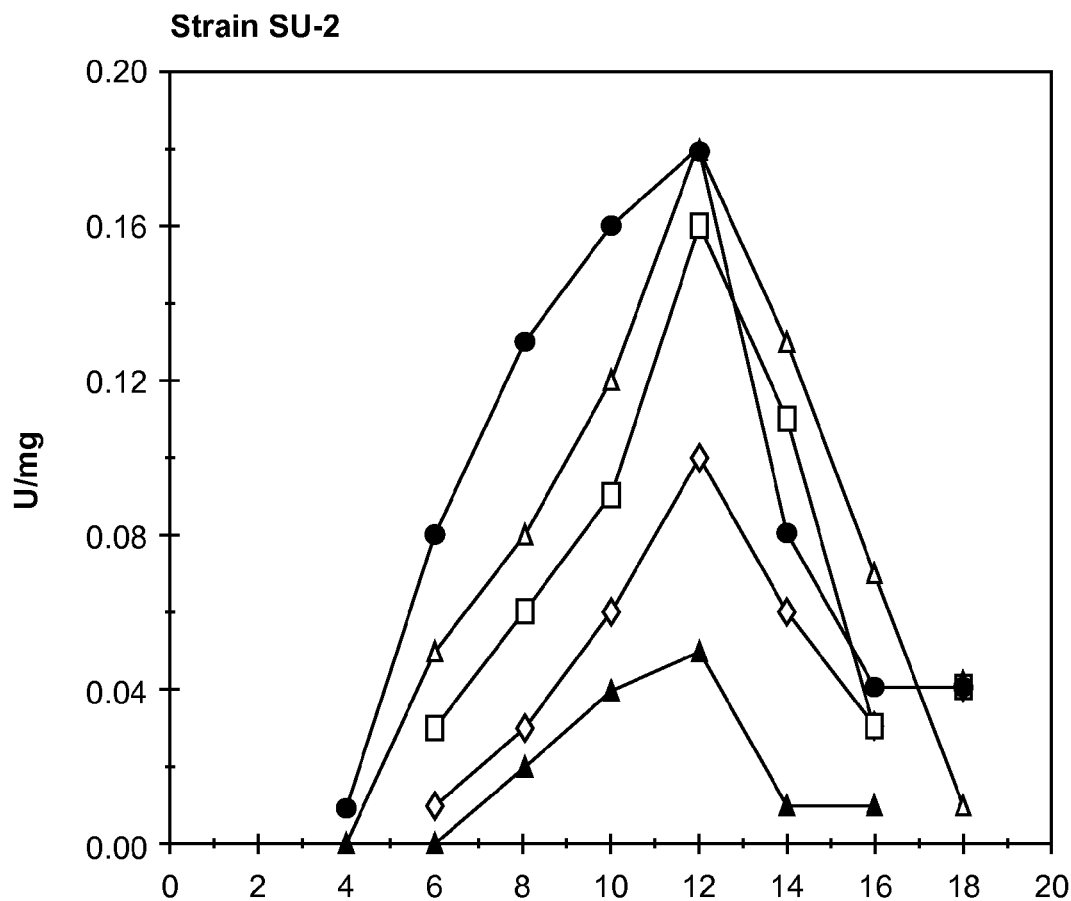
FIGS. 15A-15C illustrate results of acyl-CoA oxidase (POX) enzymatic activity assays on substrates of various carbon lengths, using acyl-CoA enzyme preparations from Candida tropicalis strains with no POX genes disrupted (see FIG. 15A), POX4 genes disrupted (see FIG. 15C) or POX5 genes disrupted (see FIG. 15B). Experimental results and conditions are given in the Detailed Description and Examples sections.
Figure 15B:
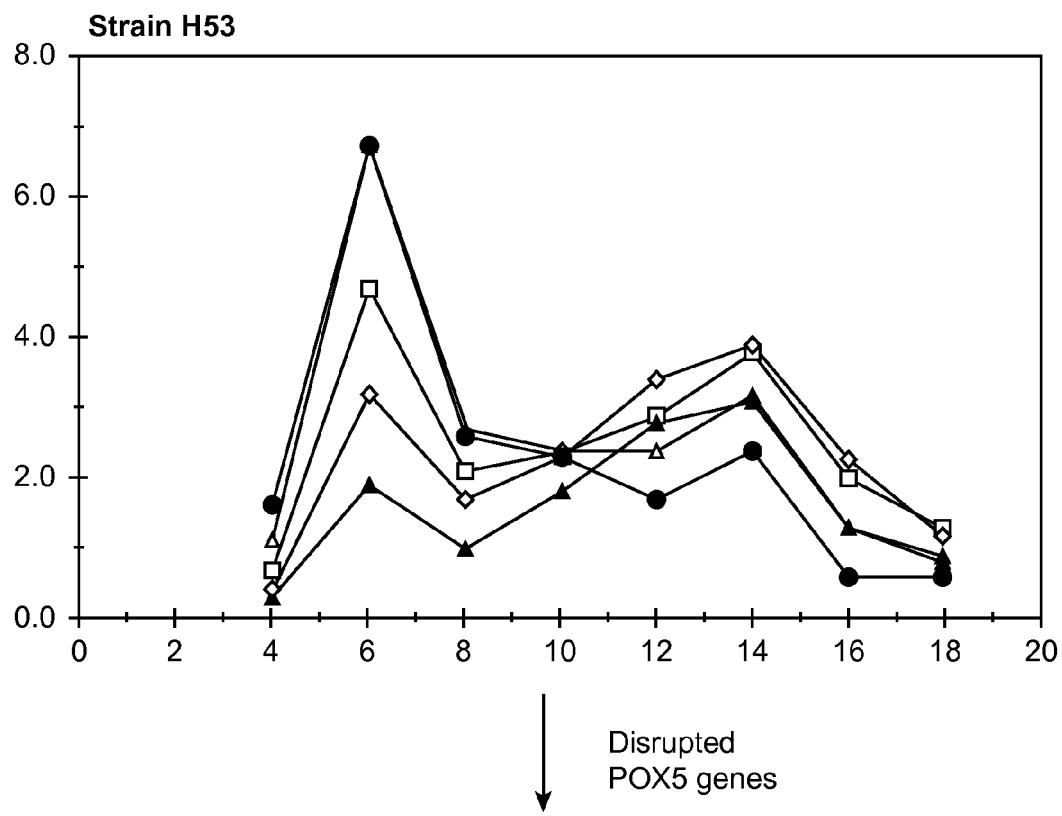
Figure 15C:
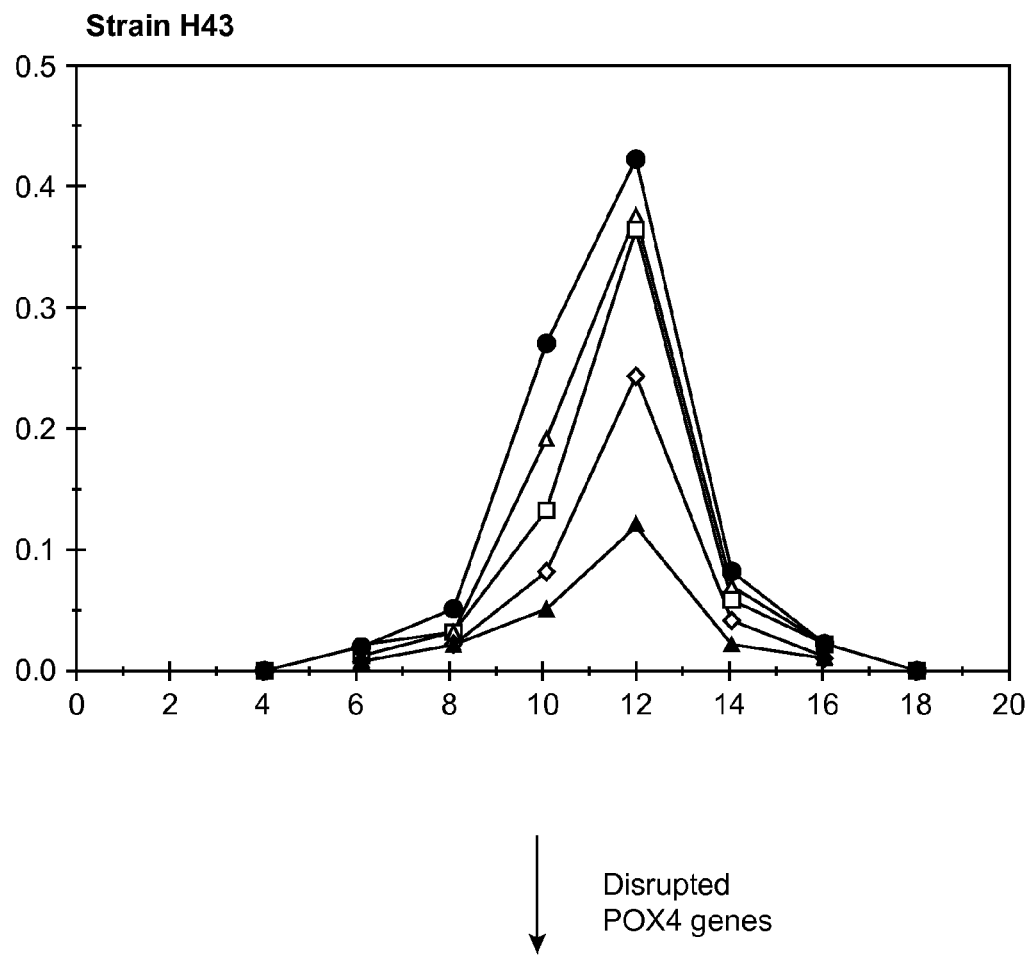
Figure 16:
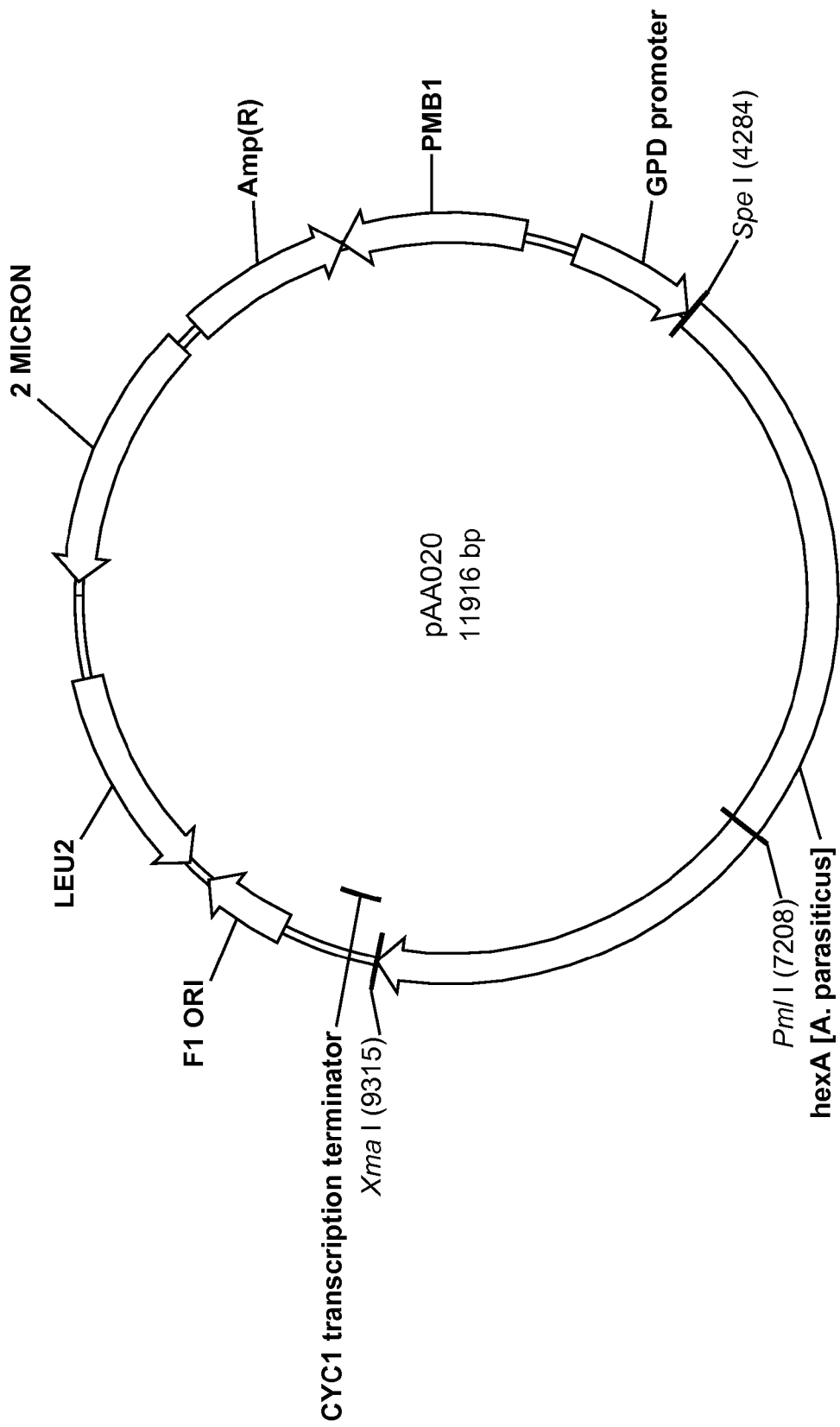
FIGS. 16-34 illustrate various plasmids for cloning, expression, or integration of various activities described herein, into a host organism or engineered organism.
Figure 17:
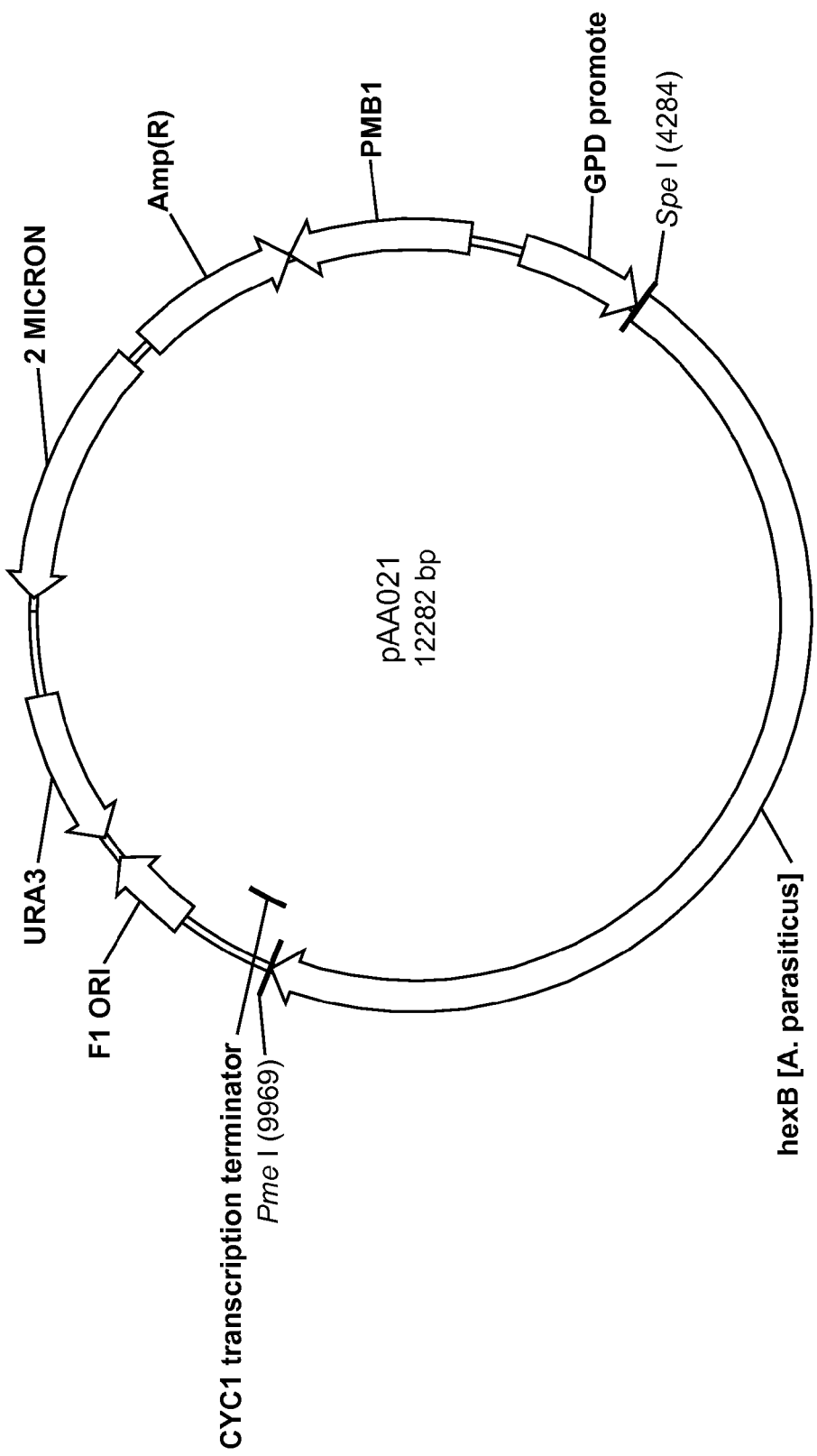
Figure 18:
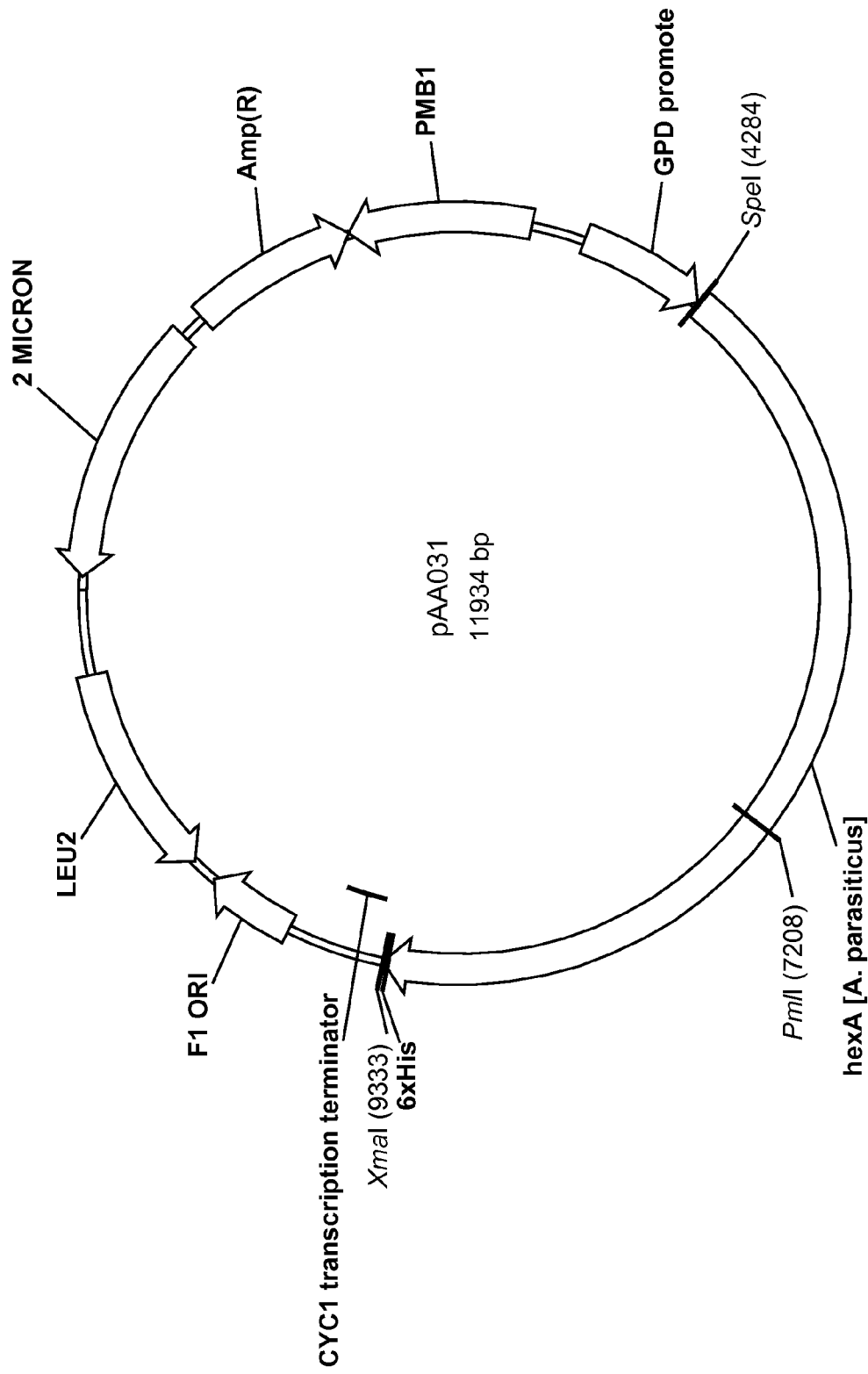
Figure 19:
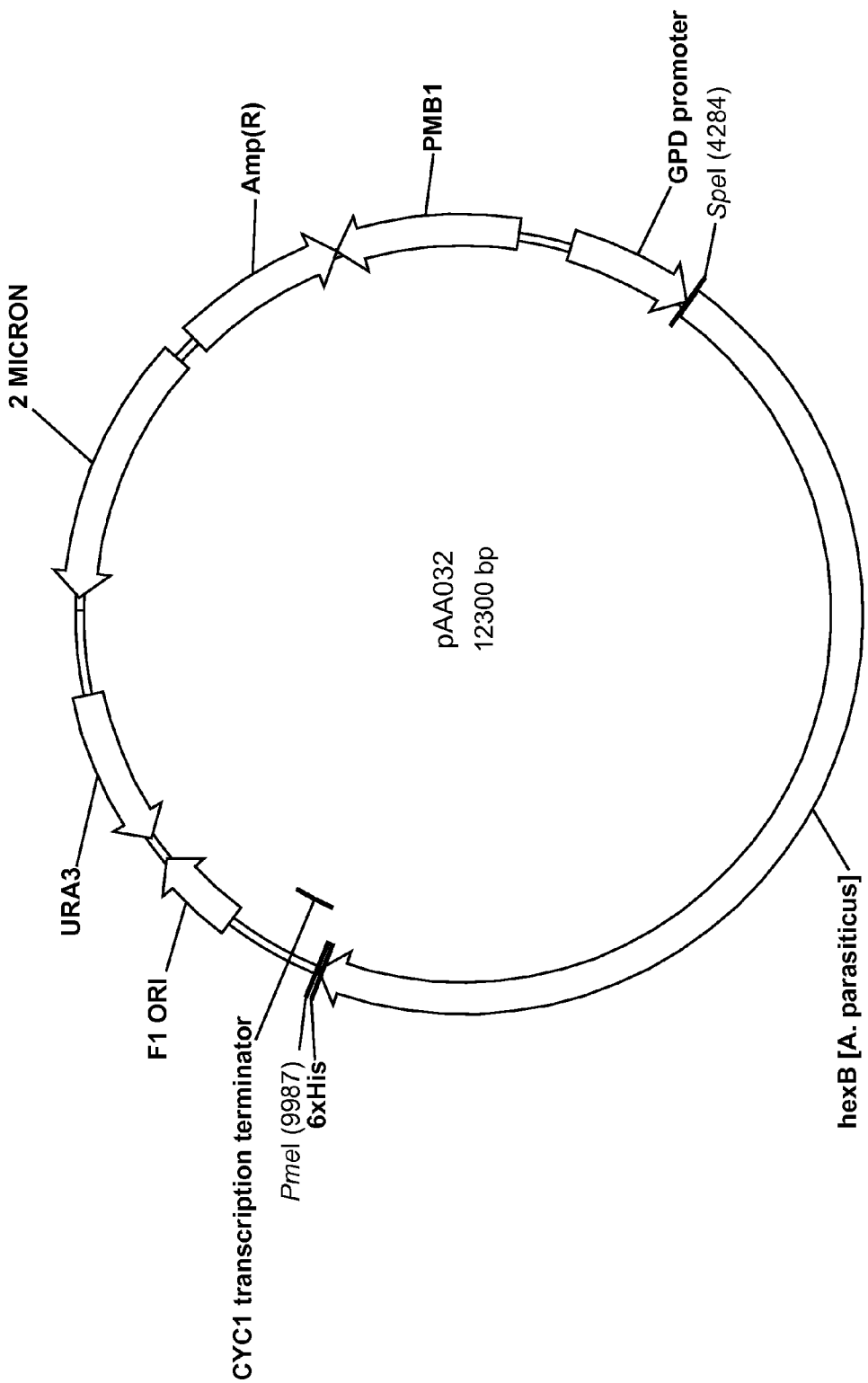
Figure 20:
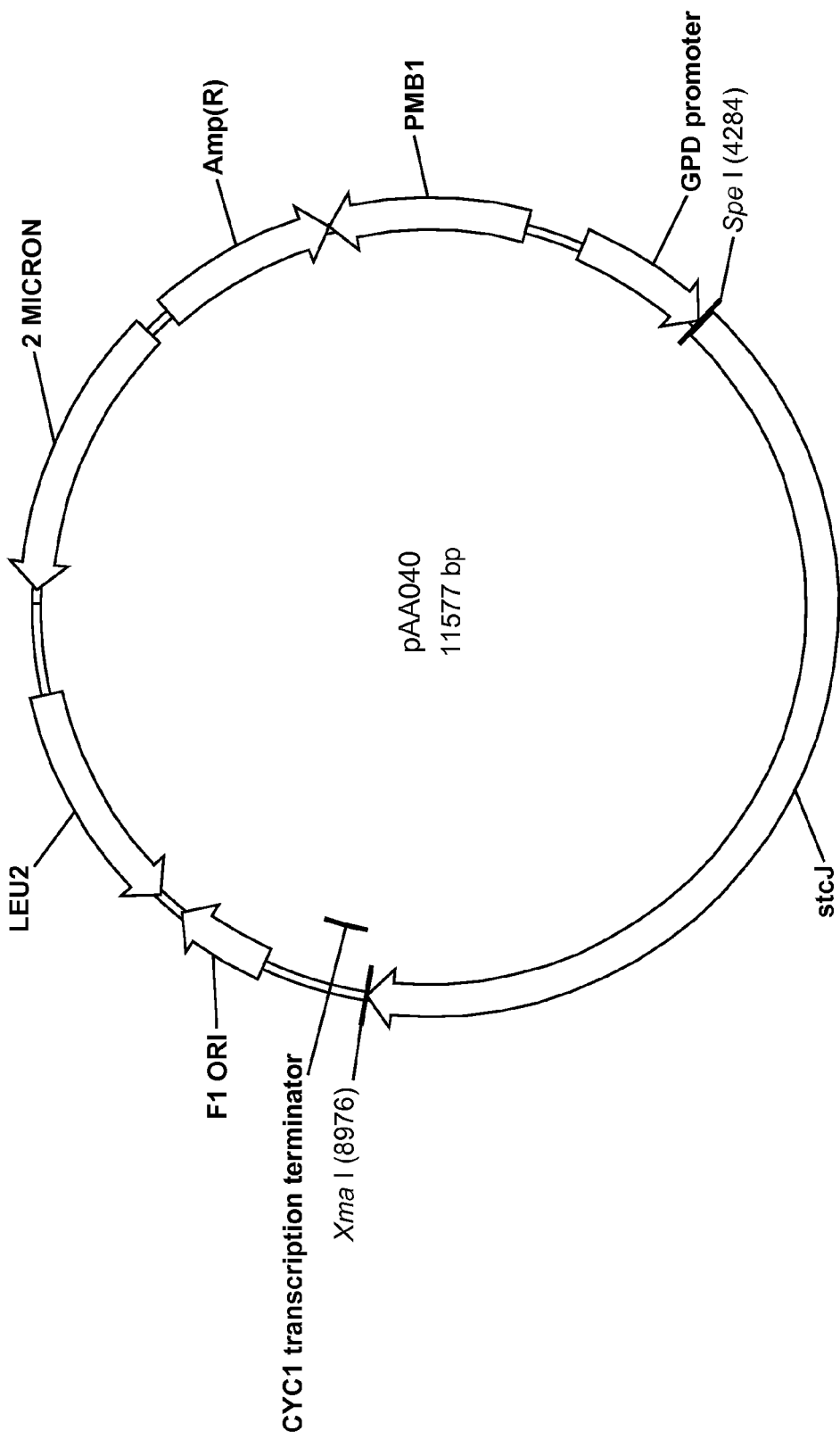
Figure 21:
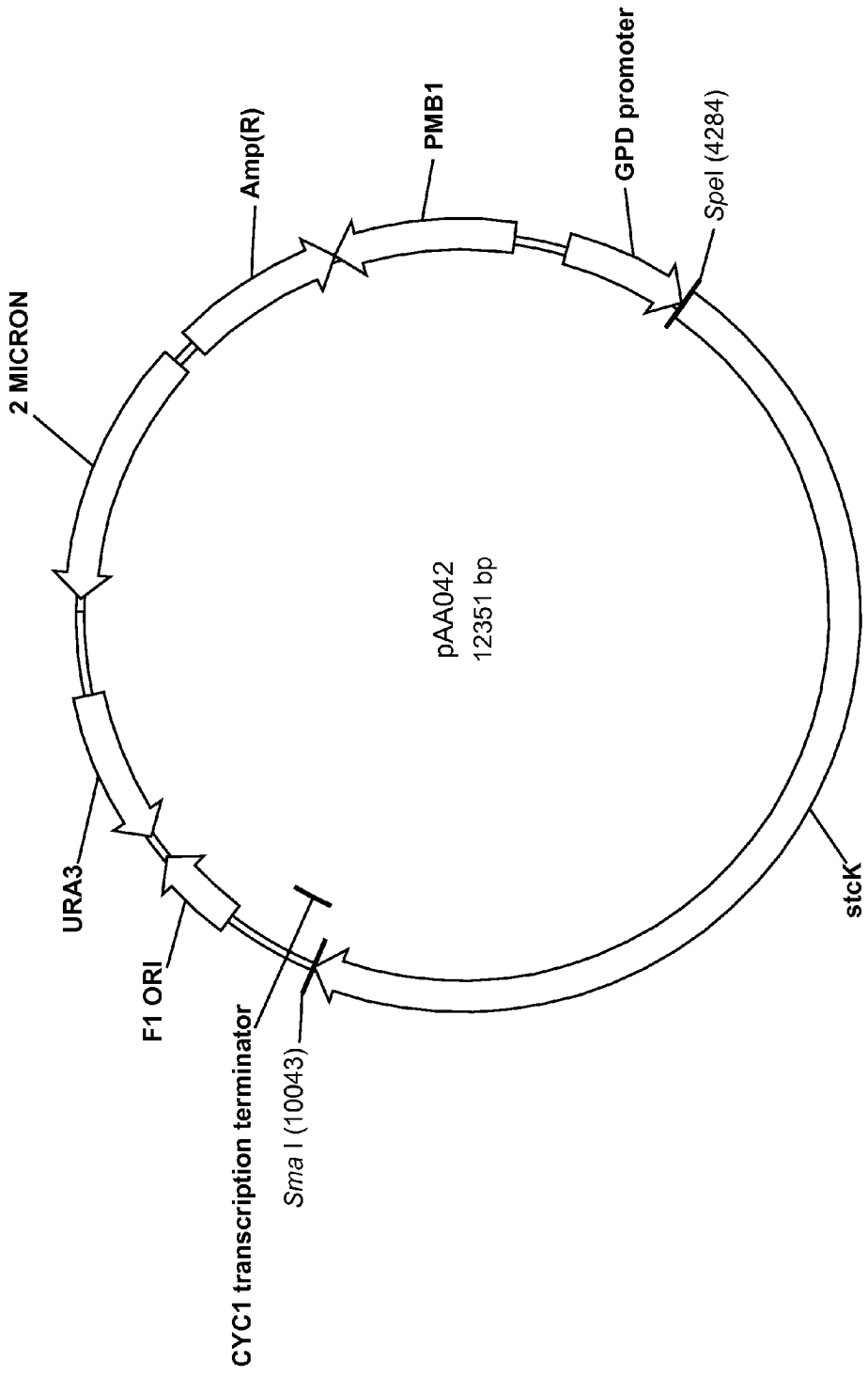
Figure 22:
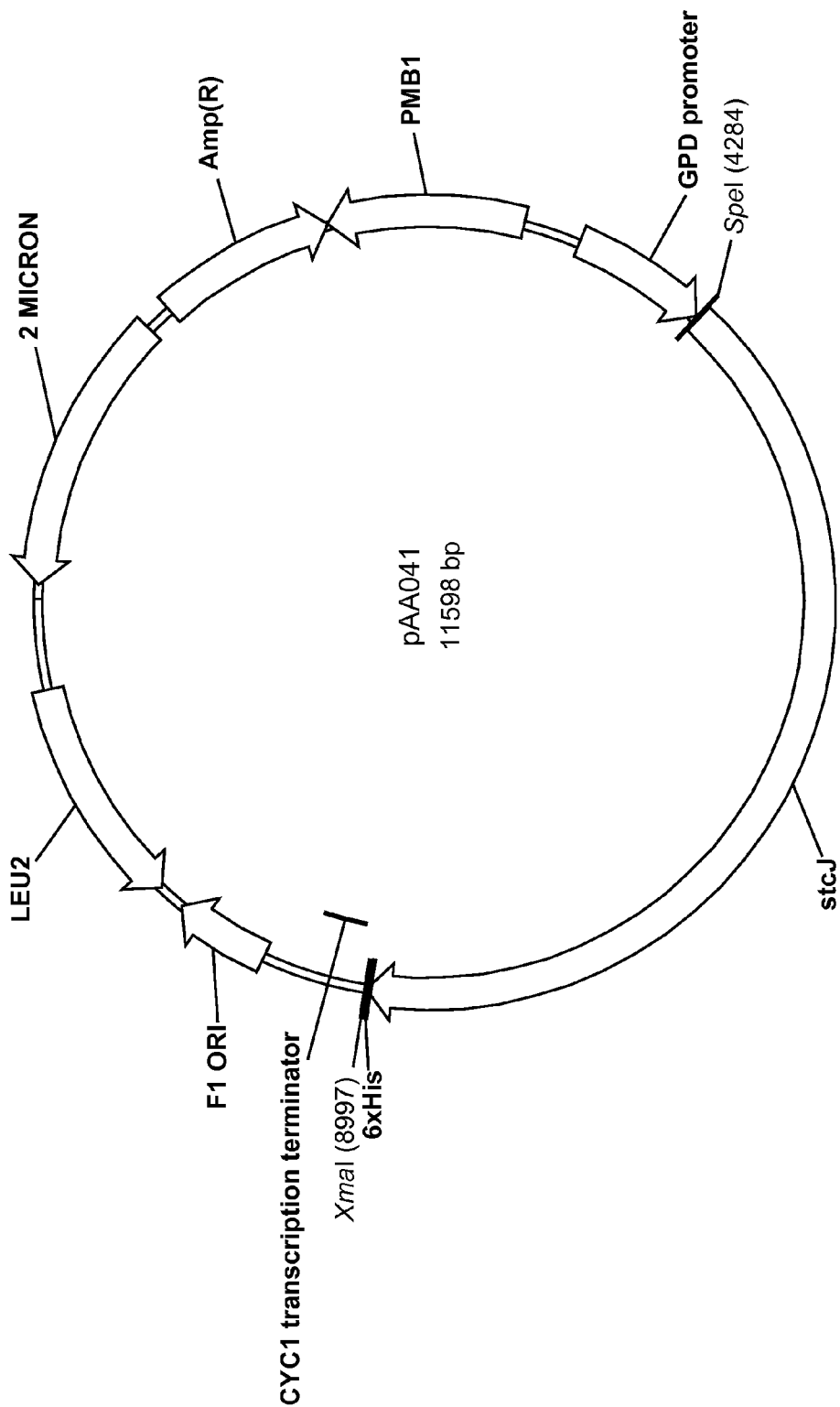
Figure 23:
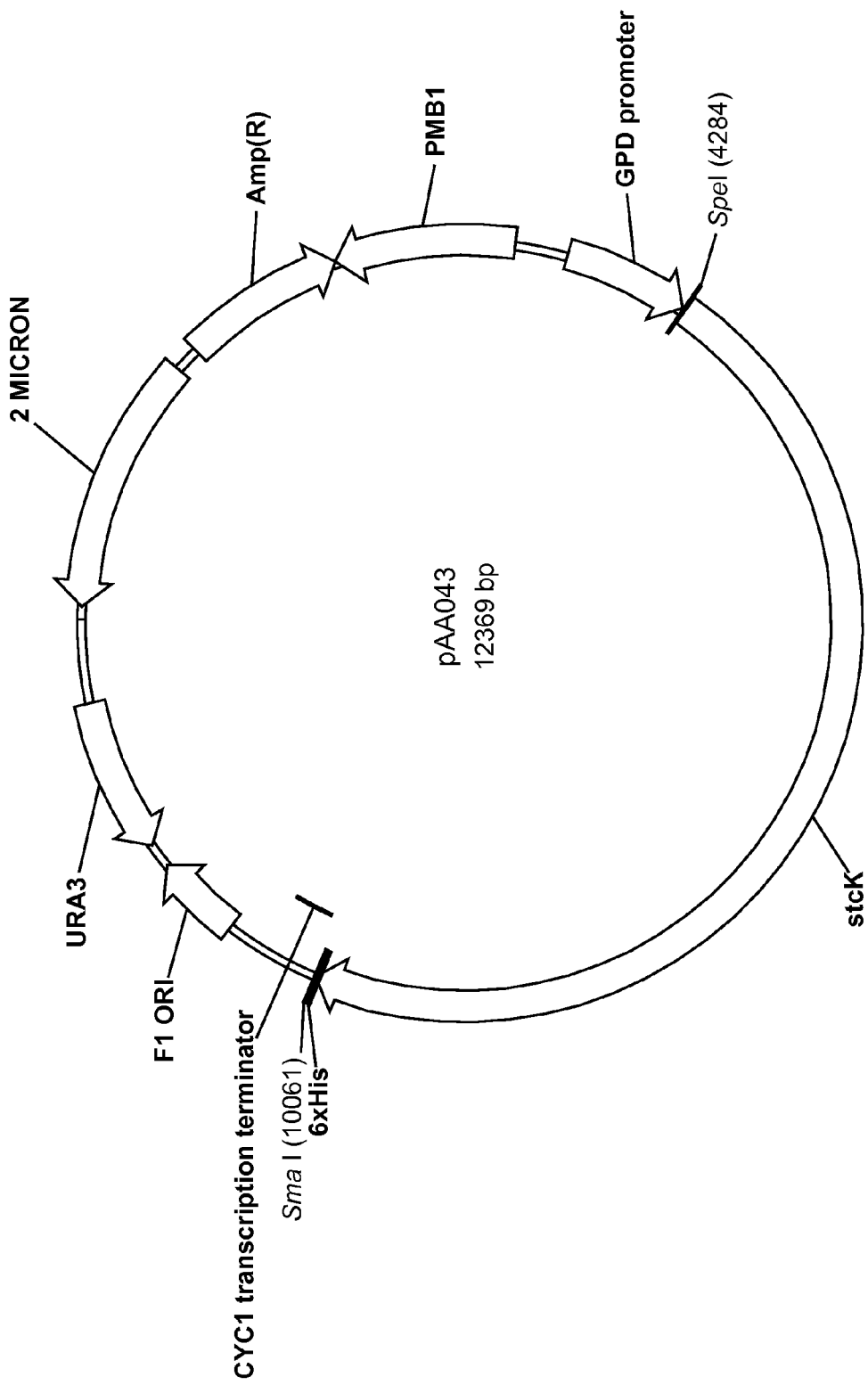
Figure 24:
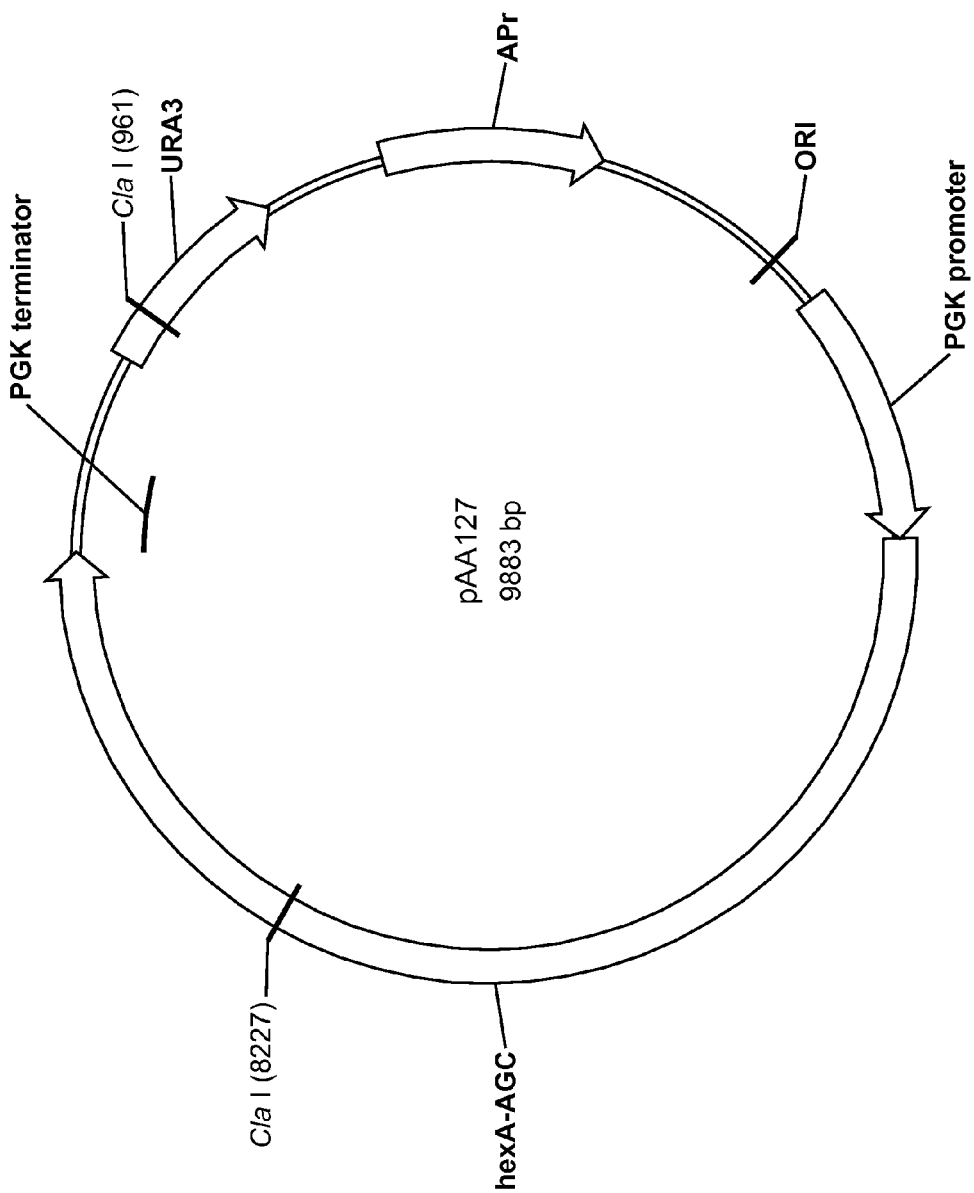
Figure 25:
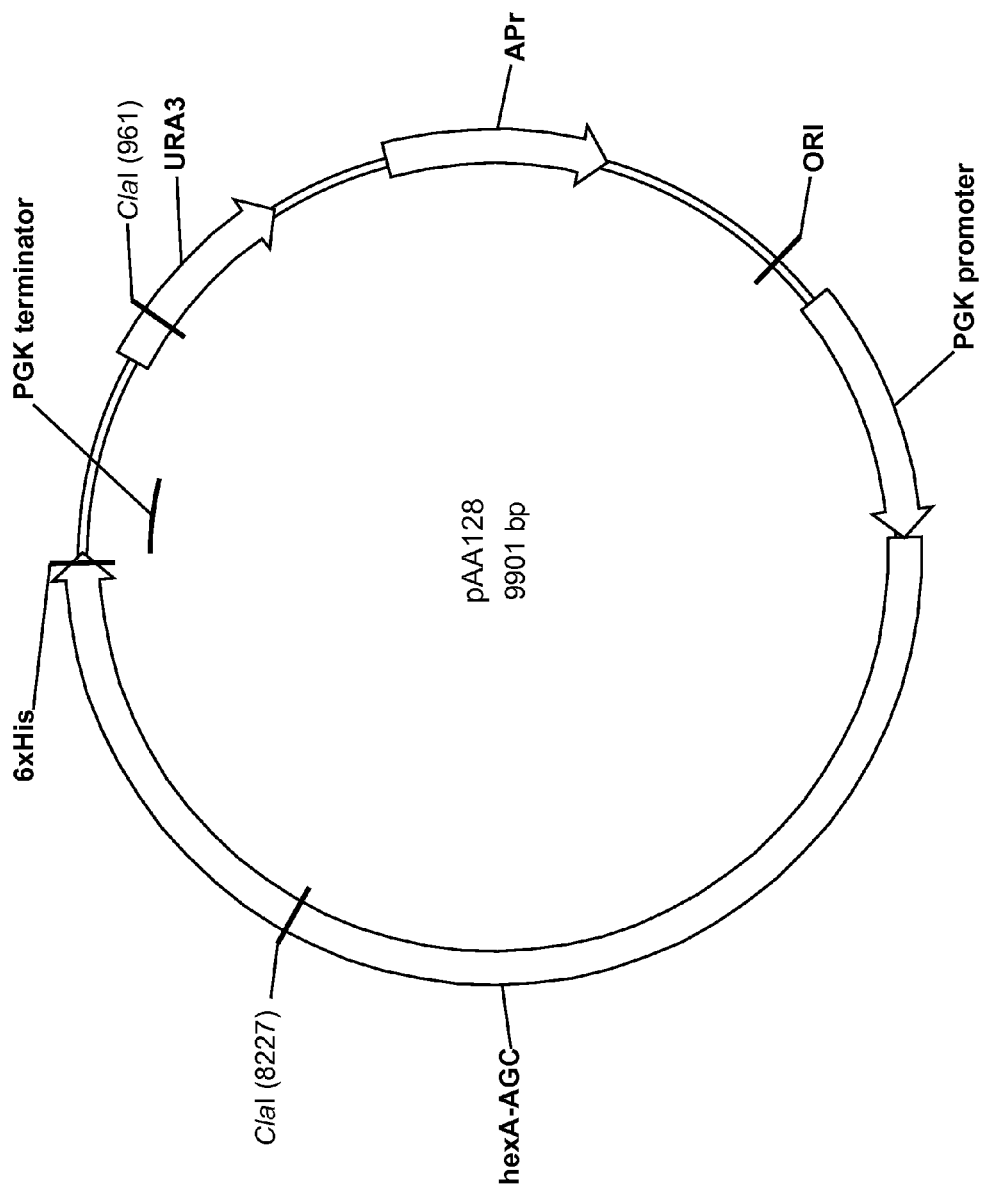
Figure 26:
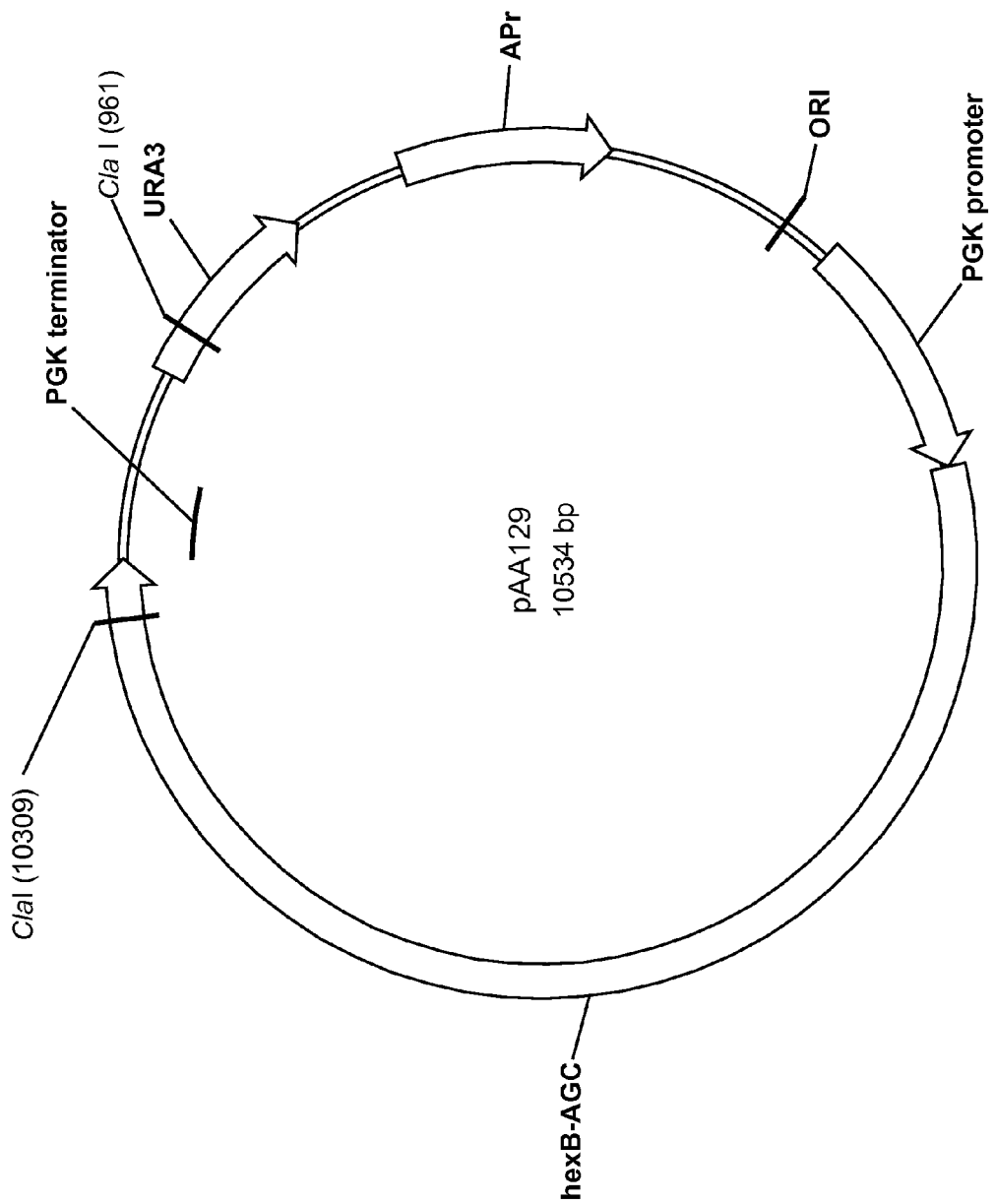
Figure 27:
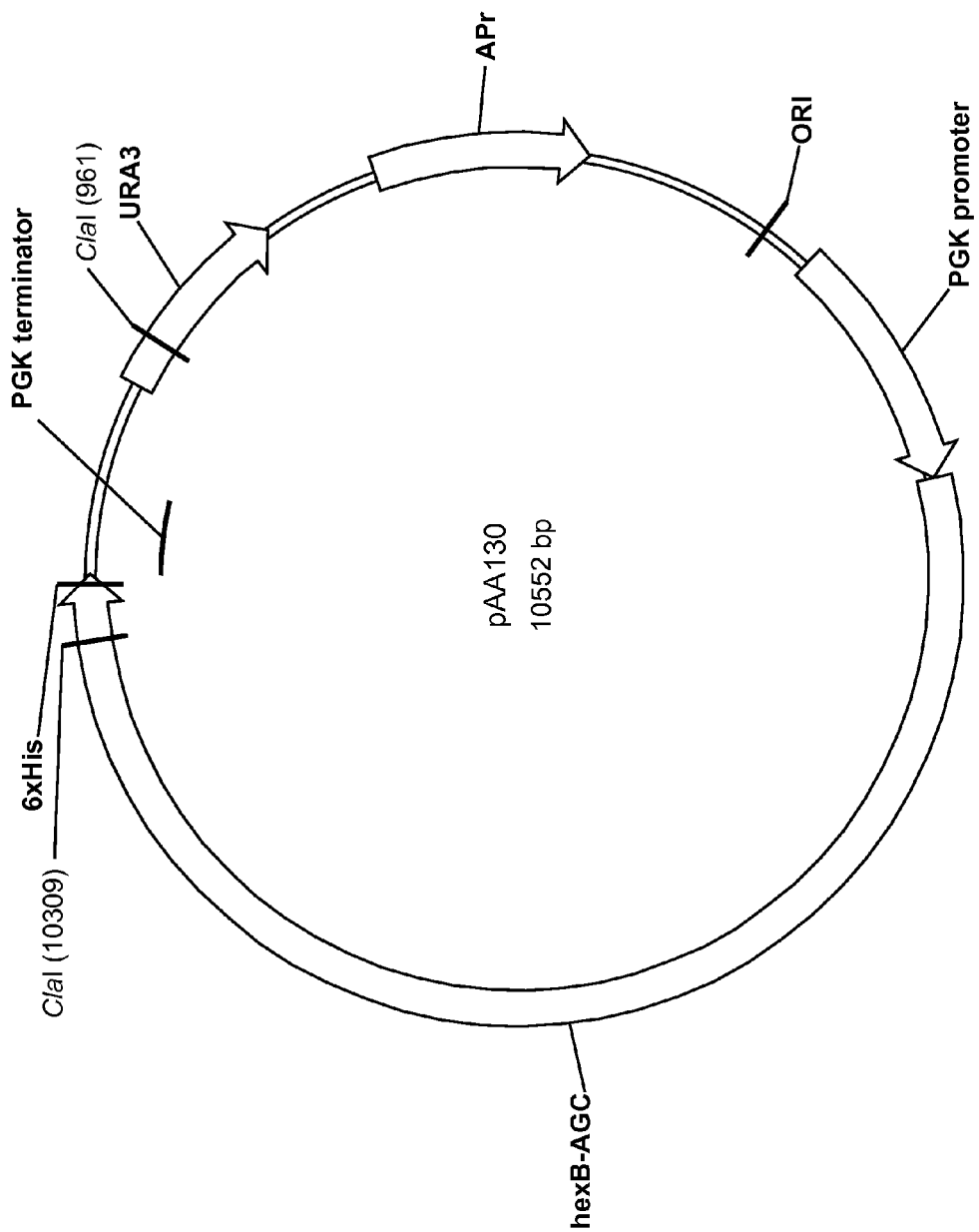

FIGS. 15A-15C graphically illustrate the units of acyl-CoA oxidase activity expressed as units (U) per milligram of protein (Y axis) in various strains of *Candida tropicalis* induced by feedstocks of specific chain length (Picataggio et al. 1991 Molecular and Cellular Biology 11: 4333-4339). Isolated protein was assayed for acyl-CoA oxidase activity using carbon chains of various length (X axis). The X and Y axes in FIGS. 15A-15C represent substantially similar data. FIG. 15A illustrates acyl-CoA oxidase activity as measured in a strain having a full complement of POX genes (e.g., POX4 and POX5 are active). FIG. 15B illustrates acyl-CoA oxidase activity as measured in a strain having a disrupted POX5 gene. The activity encoded by the functional POX4 gene exhibits a higher specific activity for acyl-CoA molecules with shorter carbon chain lengths (e.g., less than 10 carbons). The results of the POX5 disrupted strain also are presented numerically in the table in FIG. 15B. FIG. 15C illustrates acyl-CoA oxidase activity as measured in a strain having a disrupted POX4 gene. The activity encoded by the functional POX5 gene exhibits a narrow peak of high specific activity for acyl-CoA molecules 12 carbons in length, with a lower specific activity for molecules 10 carbons in length. The results of the POX4 disrupted strain are presented numerically in the table in FIG. 15C.

In certain embodiments, host acyl-CoA oxidase activity of one of the POX genes can be increased by genetically altering (e.g., increasing) the amount of the polypeptide produced (e.g., a strongly transcribed or constitutively expressed heterologous promoter is introduced in operable linkage with a polynucleotide that encodes the polypeptide; the copy number of a polynucleotide that encodes the polypeptide is increased (e.g., by introducing a plasmid that includes the polynucleotide, integration of additional copies in the host genome)). In some embodiments, the host acyl-CoA oxidase activity can be decreased by disruption (e.g., knockout, insertion mutagenesis, the like and combinations thereof) of an acyl-CoA oxidase gene, or by decreasing the activity of the promoter (e.g., addition of repressor sequences to the promoter or 5'UTR) which transcribes an acyl-CoA oxidase gene.

A noted above, disruption of nucleotide sequences encoding POX4, POX 5, or POX4 and POX5 sometimes can alter pathway efficiency, specificity and/or specific activity with respect to metabolism of carbon chains of different lengths (e.g., carbon chains including fatty alcohols, fatty acids, paraffins, dicarboxylic acids of between about 1 and about 60 carbons in length). In some embodiments, the nucleotide sequence of POX4, POX5, or POX4 and POX5 is disrupted with a URA3 nucleotide sequence encoding a selectable marker, and introduced to a host microorganism, thereby generating an engineered organism deficient in POX4, POX5 or POX4 and POX5 activity. Nucleic acid sequences encoding POX4 and POX5 can be obtained from a number of sources, including *Candida tropicalis*, for example. Examples of POX4 and POX5 amino acid sequences and nucleotide sequences of polynucleotides that encode the polypeptides, are presented herein.

Presence, absence or amount of POX4 and/or POX5 activity can be detected by any suitable method known in the art. For example, using enzymatic assays as described in Shimizu et al, 1979, and as described herein in the Examples. Alternatively, nucleic acid sequences representing native and/or disrupted POX4 and POX5 sequences also can be detected using nucleic acid detection methods (e.g., PCR, primer extension, nucleic acid hybridization, the like and combinations thereof), or quantitative expression based analysis (e.g., RT-PCR, western blot analysis, northern blot analysis, the like and combinations thereof), where the engineered organism exhibits decreased RNA and/or polypeptide levels as compared to the host organism.

The term "thioesterase activity" as used herein refers to removal of Coenzyme A from hexanoate. The thioesterase activity can be provided by a polypeptide. In some embodiments, the polypeptide is encoded by a heterologous nucleotide sequence introduced to a host microorganism. Nucleic acid sequences conferring thioesterase activity can be obtained from a number of sources, including *Cuphea lanceolata*. Examples of such polypeptides include, without limitation, acyl-(ACP) thioesterase type B from *Cuphea lanceolata*, encoded by the nucleotide sequences referenced by accession number CAB60830 at the World Wide Web Uniform Resource Locator (URL) ncbi.nlm.nih.gov of the National Center for Biotechnology Information (NCBI).

Presence, absence or amount of thioesterase activity can be detected by any suitable method known in the art. An example of such a method is described Chemistry and Biology 9: 981-988. In some embodiments, thioesterase activity is not altered in a host microorganism, and in certain embodiments, the activity is added or increased in the engineered microorganism relative to the host microorganism. In some embodiments, a polypeptide having thioesterase activity is linked to another polypeptide (e.g., a hexanoate synthase A or hexanoate synthase B polypeptide). A non-limiting example of an amino acid sequence (one letter code sequence) for a polypeptide having thioesterase activity is provided hereafter:

```
MVAAAATSAFFPVPAPGTSPKPGKSGNWPSSLSPTFKPKSIPNAGFQVKA

NASAHPKANGSAVNLKSGSLNTQEDTSSSPPPRAFLNQLPDWSMLLTAIT

TVFVAAEKQWTMLDRKSKRPDMLVDSVGLKSIVRDGLVSRQSFLIRSYEI

GADRTASIETLMNHLQETSINHCKSLGLLNDGFGRTPGMCKNDLIWVLTK

MQIMVNRYPTWGDTVEINTWFSQSGKIGMASDWLISDCNTGEILIRATSV

WAMMNQKTRRFSRLPYEVRQELTPHFVDSPHVIEDNDQKLHKFDVKTGDS

IRKGLTPRWNDLDVNQHVSNVKYIGWILESMPIEVLETQELCSLTVEYRR

ECGMDSVLESVTAVDPSENGGRSQYKHLLRLEDGTDIVKSRTEWRPKNAG

TNGAISTSTAKTSNGNSAS
```

The term "a genetic modification that results in substantial hexanoate usage by monooxygenase activity" as used herein refers to a genetic alteration of a host microorganism that reduces an endogenous activity that converts hexanoate to another product. In some embodiments, an endogenous activity that converts hexanoate to a toxin (e.g., in fungus) is reduced. In certain embodiments, a polyketide synthase activity is reduced. Such alterations can advantageously increase yields of end products, such as adipic acid.

The term "polyketide synthase activity" as used herein refers to the alteration of hexanoic acid by the polyketide synthase enzyme (PKS) as a step in the production of other products including mycotoxin. The PKS activity can be provided by a polypeptide. Examples of such polypeptides include, without limitation, an *Aspergillus parasiticus* enzyme referenced by accession number AAS66004 at the World Wide Web Uniform Resource Locator (URL) ncbi.nlm.nih.gov of the National Center for Biotechnology Information (NCBI). In certain embodiments, a PKS enzyme uses hexanoic acid generated by hexanoate synthase as a substrate and a component of the *Aspergillus* NorS multienzyme complex, a closely associated gene cluster involved in the synthesis of various products including mytoxin. Accordingly, a PKS activity sometimes is altered to free hexanoic acid for an engineered adipic acid pathway. In some embodiments PKS activity is diminished or blocked. In certain embodiments the PKS enzyme is engineered to substitute thioesterase activity for PKS activity. Presence, absence, or amount of PKS activity can be detected by any suitable method known in the art, such as that described in Watanabe C and Townsend C (2002) Initial characterization of a type I fatty acid synthase and polyketide synthase multienzyme complex N or S in the biosynthesis of aflatoxin B1. Chemistry and Biology 9: 981-988. A non-limiting example of an amino acid sequence (one letter code sequence) of a polypeptide having polyketide synthase activity is provided hereafter:

```
MAQSRQLFLFGDQTADEVPKLRSLLSVQDSPILAAFLDQSHYVVRAQMLQ

SMNTVDHKLARTADLRQMVQKYVDGKLTPAFRTALVCLCQLGCFIREYEE

SGNMYPQPSDSYVLGFCMGSLAAVAVSCSRSLSELLPIAVQTVLIAFRLG

LCALEMRDRVDGCSDDRGDPWSTIVWGLDPQQARDQIEVFCRTTNVPQTR

RPWISCISKNAITLSGSPSTLRAFCAMPQMAQHRTAPIPICLPAHNGALF

TQADITTILDTTPTTPWEQLPGQIPYISHVTGNVVQTSNYRDLIEVALSE

TLLEQVRLDLVETGLPRLLQSRQVKSVTIVPFLTRMNETMSNILPDSFIS

TETRTDTGRAIPASGRPGAGKCKLAIVSMSGRFPESPTTESFWDLLYKGL

DVCKEVPRRRWDINTHVDPSGKARNKGATKWGCWLDFSGDFDPRFFGISP

KEAPQMDPAQRMALMSTYEAMERAGLVPDTTPSTQRDRIGVFHGVTSNDW

METNTAQNIDTYFITGGNRGFIPGRINFCFEFAGPSYTNDTACSSSLAAI

HLACNSLWRGDCDTAVAGGTNMIYTPDGHTGLDKGFFLSRTGNCKPYDDK

ADGYCRAEGVGTVFIKRLEDALADNDPILGVILDAKTNHSAMSESMTRPH

VGAQIDNMTAALNTTGLHPNDFSYIEMHGTGTQVGDAVEMESVLSVFAPS

ETARKADQPLFVGSAKANVGHGEGVSGVTSLIKVLMMMQHDTIPPHCGIK
PGSKINRNFPDLGARNVHIAFEPKPWPRTHTPRRVLINNFSAAGGNTALI
VEDAPERHWPTEKDPRSSHIVALSAHVGASMKTNLERLHQYLLKNPHTDL
AQLSYTTTARRWHYLHRVSVTGASVEEVTRKLEMAIQNGDGVSRPKSKPK
ILFAFTGQGSQYATMGKQVYDAYPSFREDLEKEDRLAQSHGEPSFLHVCT
SPKGDVEEMAPVVVQLAITCLQMALTNLMTSFGIRPDVTVGHSLGEFAAL
YAAGVLSASDVVYLVGQRAELLQERCQRGTHAMLAVKATPEALSQWIQDH
DCEVACINGPEDTVLSGTTKNVAEVQRAMTDNGIKCTLLKLPFAFHSAQV
QPILDDFEALAQGATFAKPQLLILSPLLRTEIHEQGVVTPSYVAQHCRHT
```

-continued

```
VDMAQALRSAREKGLIDDKTLVIELGPKPLISGMVKMTLGDKISTLPTLA
PNKAIWPSLQKILTSVYTGGWDINWKKYHAPFASSQKVVDLPSYGWDLKD
YYIPYQGDWCLHRHQQDCKCAAPGHEIKTADYQVPPESTPHRPSKLDPSK
EAFPEIKTTTTLHRVVEETTKPLGATLVVETDISRKDVNGLARGHLVDGI
PLCTPSFYADIAMQVGQYSMQRLRAGHPGAGAIDGLVDVSDMVVDKALVP
HGKGPQLLRTTLTMEWPPKAAATTRSAKVKFATYFADGKLDTEHASCTVR
FTSDAQLKSLRRSVSEYKTHIRQLHDGHAKGQFMRYNRKTGYKLMSSMAR
FNPDYMLLDYLVLNEAENEAASGVDFSLGSSEGTFAAHPAHVDAITQVAG
FAMNANDNVDIEKQVYVNHGWDSFQIYQPLDNSKSYQVYTKMGQAKENDL
VHGDVVVLDGEQIVAFFRGLTLRSVPRGALRVVLQTTVKKADRQLGFKTM
PSPPPPTTTMPISPYKPANTQVSSQAIPAEATHSHTPPQPKHSPVPETAG
SAPAAKGVGVSNEKLDAVMRVVSEESGIALEELTDDSNFADMGIDSLSSM
VIGSRFREDLGLDLGPEFSLFIDCTTVRALKDFMLGSGDAGSGSNVEDPP
PSATPGINPETDWSSSASDSIFASEDHGHSSESGADTGSPPALDLKPYCR
PSTSVVLQGLPMVARKTLFMLPDGGGSAFSYASLPRLKSDTAVVGLNCPY
ARDPENMNCTHGAMIESFCNEIRRRQPRGPYHLGGWSSGGAFAYVVAEAL
VNQGEEVHSLIIIDAPIPQAMEQLPRAFYEHCNSIGLFATQPGASPDGST
EPPSYLIPHFTAVVDVMLDYKLAPLHARRMPKVGIVWAADTVMDERDAPK
MKGMHFMIQKRTEFGPDGWDTIMPGASFDIVRADGANHFTLMQKEHVSII
SDLIDRVMA
```

The terms "a genetic modification that reduces 6-hydroxyhexanoic acid conversion" or "a genetic modification that reduces omega hydroxyl fatty acid conversion" as used herein refer to genetic alterations of a host microorganism that reduce an endogenous activity that converts 6-hydroxyhexanoic acid to another product. In some embodiments, an endogenous 6-hydroxyhexanoic acid dehydrogenase activity is reduced. Such alterations can advantageously increase the amount of 6-hydroxyhexanoic acid, which can be purified and further processed.

The term "a genetic modification that reduces beta-oxidation activity" as used herein refers to a genetic alteration of a host microorganism that reduces an endogenous activity that oxidizes a beta carbon of carboxylic acid containing organic molecules. In certain embodiments, the organic molecule is a six carbon molecule, and sometimes contains one or two carboxylic acid moieties located at a terminus of the molecule (e.g., adipic acid). Such alterations can advantageously increase yields of end products, such as adipic acid.

Polynucleotides and Polypeptides

A nucleic acid (e.g., also referred to herein as nucleic acid reagent, target nucleic acid, target nucleotide sequence, nucleic acid sequence of interest or nucleic acid region of interest) can be from any source or composition, such as DNA, cDNA, gDNA (genomic DNA), RNA, siRNA (short inhibitory RNA), RNAi, tRNA or mRNA, for example, and can be in any form (e.g., linear, circular, supercoiled, single-stranded, double-stranded, and the like). A nucleic acid can also comprise DNA or RNA analogs (e.g., containing base analogs, sugar analogs and/or a non-native backbone and the like). It is understood that the term "nucleic acid" does not refer to or infer a specific length of the polynucleotide chain, thus polynucleotides and oligonucleotides are also included in the definition. Deoxyribonucleotides include deoxyadenosine, deoxycytidine, deoxyguanosine and deoxythymidine. For RNA, the uracil base is uridine.

A nucleic acid sometimes is a plasmid, phage, autonomously replicating sequence (ARS), centromere, artificial chromosome, yeast artificial chromosome (e.g., YAC) or other nucleic acid able to replicate or be replicated in a host cell. In certain embodiments a nucleic acid can be from a library or can be obtained from enzymatically digested, sheared or sonicated genomic DNA (e.g., fragmented) from an organism of interest. In some embodiments, nucleic acid subjected to fragmentation or cleavage may have a nominal, average or mean length of about 5 to about 10,000 base pairs, about 100 to about 1,000 base pairs, about 100 to about 500 base pairs, or about 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000 or 10000 base pairs. Fragments can be generated by any suitable method in the art, and the average, mean or nominal length of nucleic acid fragments can be controlled by selecting an appropriate fragment-generating procedure by the person of ordinary skill. In some embodiments, the fragmented DNA can be size selected to obtain nucleic acid fragments of a particular size range.

Nucleic acid can be fragmented by various methods known to the person of ordinary skill, which include without limitation, physical, chemical and enzymic processes. Examples of such processes are described in U.S. Patent Application Publication No. 20050112590 (published on May 26, 2005, entitled "Fragmentation-based methods and systems for sequence variation detection and discovery," naming Van Den Boom et al.). Certain processes can be selected by the person of ordinary skill to generate non-specifically cleaved fragments or specifically cleaved fragments. Examples of processes that can generate non-specifically cleaved fragment sample nucleic acid include, without limitation, contacting sample nucleic acid with apparatus that expose nucleic acid to shearing force (e.g., passing nucleic acid through a syringe needle; use of a French press); exposing sample nucleic acid to irradiation (e.g., gamma, x-ray, UV irradiation; fragment sizes can be controlled by irradiation intensity); boiling nucleic acid in water (e.g., yields about 500 base pair fragments) and exposing nucleic acid to an acid and base hydrolysis process.

Nucleic acid may be specifically cleaved by contacting the nucleic acid with one or more specific cleavage agents. The term "specific cleavage agent" as used herein refers to an agent, sometimes a chemical or an enzyme that can cleave a nucleic acid at one or more specific sites. Specific cleavage agents often will cleave specifically according to a particular nucleotide sequence at a particular site. Examples of enzymic specific cleavage agents include without limitation endonucleases (e.g., DNase (e.g., DNase I, II); RNase (e.g., RNase E, F, H, P); Cleavase™ enzyme; Taq DNA polymerase; E. coli DNA polymerase I and eukaryotic structure-specific endonucleases; murine FEN-1 endonucleases; type I, II or III restriction endonucleases such as Acc I, Afl III, Alu I, Alw44 I, Apa I, Asn I, Ava I, Ava II, BamH I, Ban II, Bcl I, Bgl I. Bgl II, Bln I, Bsm I, BssH II, BstE II, Cfo I, Cla I, Dde I, Dpn I, Dra I, EclX I, EcoR I, EcoR I, EcoR II, EcoR V, Hae II, Hae II, Hind III, Hind III, Hpa I, Hpa II, Kpn I, Ksp I, Mlu I, MluN I, Msp I, Nci I, Nco I, Nde I, Nde II, Nhe I, Not I, Nru I, Nsi I, Pst I, Pvu I, Pvu II, Rsa I, Sac I, Sal I, Sau3A I, Sca I, ScrF I, Sfi I, Sma I, Spe I, Sph I, Ssp I, Stu I, Sty I, Swa I, Taq I, Xba I, Xho I); glycosylases (e.g., uracil-DNA glycolsylase (UDG), 3-methyladenine DNA glycosylase, 3-methyladenine DNA glycosylase II, pyrimidine hydrate-DNA glycosylase, FaPy-DNA glycosylase, thymine mismatch-DNA glycosylase, hypoxanthine-DNA glycosylase, 5-Hydroxymethyluracil DNA glycosylase (HmUDG), 5-Hydroxymethylcytosine DNA glycosylase, or 1,N6-etheno-adenine DNA glycosylase); exonucleases (e.g., exonuclease III); ribozymes, and DNAzymes. Sample nucleic acid may be treated with a chemical agent, or synthesized using modified nucleotides, and the modified nucleic acid may be cleaved. In non-limiting examples, sample nucleic acid may be treated with (i) alkylating agents such as methylnitrosourea that generate several alkylated bases, including N3-methyladenine and N3-methylguanine, which are recognized and cleaved by alkyl purine DNA-glycosylase; (ii) sodium bisulfite, which causes deamination of cytosine residues in DNA to form uracil residues that can be cleaved by uracil N-glycosylase; and (iii) a chemical agent that converts guanine to its oxidized form, 8-hydroxyguanine, which can be cleaved by formamidopyrimidine DNA N-glycosylase. Examples of chemical cleavage processes include without limitation alkylation, (e.g., alkylation of phosphorothioate-modified nucleic acid); cleavage of acid lability of P3'-N5'-phosphoroamidate-containing nucleic acid; and osmium tetroxide and piperidine treatment of nucleic acid.

As used herein, the term "complementary cleavage reactions" refers to cleavage reactions that are carried out on the same nucleic acid using different cleavage reagents or by altering the cleavage specificity of the same cleavage reagent such that alternate cleavage patterns of the same target or reference nucleic acid or protein are generated. In certain embodiments, nucleic acids of interest may be treated with one or more specific cleavage agents (e.g., 1, 2, 3, 4, 5, 6, 7, 8, 9, 10 or more specific cleavage agents) in one or more reaction vessels (e.g., nucleic acid of interest is treated with each specific cleavage agent in a separate vessel).

A nucleic acid suitable for use in the embodiments described herein sometimes is amplified by any amplification process known in the art (e.g., PCR, RT-PCR and the like). Nucleic acid amplification may be particularly beneficial when using organisms that are typically difficult to culture (e.g., slow growing, require specialize culture conditions and the like). The terms "amplify", "amplification", "amplification reaction", or "amplifying" as used herein refer to any in vitro processes for multiplying the copies of a target sequence of nucleic acid. Amplification sometimes refers to an "exponential" increase in target nucleic acid. However, "amplifying" as used herein can also refer to linear increases in the numbers of a select target sequence of nucleic acid, but is different than a one-time, single primer extension step. In some embodiments, a limited amplification reaction, also known as pre-amplification, can be performed. Pre-amplification is a method in which a limited amount of amplification occurs due to a small number of cycles, for example 10 cycles, being performed. Pre-amplification can allow some amplification, but stops amplification prior to the exponential phase, and typically produces about 500 copies of the desired nucleotide sequence(s). Use of pre-amplification may also limit inaccuracies associated with depleted reactants in standard PCR reactions.

In some embodiments, a nucleic acid reagent sometimes is stably integrated into the chromosome of the host organism, or a nucleic acid reagent can be a deletion of a portion of the host chromosome, in certain embodiments (e.g., genetically modified organisms, where alteration of the host genome confers the ability to selectively or preferentially maintain the desired organism carrying the genetic modification). Such nucleic acid reagents (e.g., nucleic acids or genetically modified organisms whose altered genome confers a selectable trait to the organism) can be selected for their ability to guide production of a desired protein or nucleic acid molecule. When desired, the nucleic acid reagent can be altered such that codons encode for (i) the same amino acid, using a different tRNA than that specified in the native sequence, or (ii) a different amino acid than is normal, including unconventional or unnatural amino acids (including detectably labeled amino acids). As described herein, the term "native sequence" refers to an unmodified nucleotide sequence as found in its natural setting (e.g., a nucleotide sequence as found in an organism).

A nucleic acid or nucleic acid reagent can comprise certain elements often selected according to the intended use of the nucleic acid. Any of the following elements can be included in or excluded from a nucleic acid reagent. A nucleic acid reagent, for example, may include one or more or all of the following nucleotide elements: one or more promoter elements, one or more 5' untranslated regions (5'UTRs), one or more regions into which a target nucleotide sequence may be inserted (an "insertion element"), one or more target nucleotide sequences, one or more 3' untranslated regions (3'UTRs), and one or more selection elements. A nucleic acid reagent can be provided with one or more of such elements and other elements may be inserted into the nucleic acid before the nucleic acid is introduced into the desired organism. In some embodiments, a provided nucleic acid reagent comprises a promoter, 5'UTR, optional 3'UTR and insertion element(s) by which a target nucleotide sequence is inserted (i.e., cloned) into the nucleic acid reagent. In certain embodiments, a provided nucleic acid reagent comprises a promoter, insertion element(s) and optional 3'UTR, and a 5' UTR/target nucleotide sequence is inserted with an optional 3'UTR. The elements can be arranged in any order suitable for expression in the chosen expression system (e.g., expression in a chosen organism, or expression in a cell free system, for example), and in some embodiments a nucleic acid reagent comprises the following elements in the 5' to 3' direction: (1) promoter element, 5'UTR, and insertion element(s); (2) promoter element, 5'UTR, and target nucleotide sequence; (3) promoter element, 5'UTR, insertion element(s) and 3'UTR; and (4) promoter element, 5'UTR, target nucleotide sequence and 3'UTR.

A promoter element typically is required for DNA synthesis and/or RNA synthesis. A promoter element often comprises a region of DNA that can facilitate the transcription of a particular gene, by providing a start site for the synthesis of RNA corresponding to a gene. Promoters generally are located near the genes they regulate, are located upstream of the gene (e.g., 5' of the gene), and are on the same strand of DNA as the sense strand of the gene, in some embodiments. In some embodiments, a promoter element can be isolated from a gene or organism and inserted in functional connection with a polynucleotide sequence to allow altered and/or regulated expression. A non-native promoter (e.g., promoter not normally associated with a given nucleic acid sequence) used for expression of a nucleic acid often is referred to as a heterologous promoter. In certain embodiments, a heterologous promoter and/or a 5'UTR can be inserted in functional connection with a polynucleotide that encodes a polypeptide having a desired activity as described herein. The terms "operably linked" and "in functional connection with" as used herein with respect to promoters, refer to a relationship between a coding sequence and a promoter element. The promoter is operably linked or in functional connection with the coding sequence when expression from the coding sequence via transcription is regulated, or controlled by, the promoter element. The terms "operably linked" and "in functional connection with" are utilized interchangeably herein with respect to promoter elements.

A promoter often interacts with a RNA polymerase. A polymerase is an enzyme that catalyses synthesis of nucleic acids using a preexisting nucleic acid reagent. When the template is a DNA template, an RNA molecule is transcribed before protein is synthesized. Enzymes having polymerase activity suitable for use in the present methods include any polymerase that is active in the chosen system with the chosen template to synthesize protein. In some embodiments, a promoter (e.g., a heterologous promoter) also referred to herein as a promoter element, can be operably linked to a nucleotide sequence or an open reading frame (ORF). Transcription from the promoter element can catalyze the synthesis of an RNA corresponding to the nucleotide sequence or ORF sequence operably linked to the promoter, which in turn leads to synthesis of a desired peptide, polypeptide or protein.

Promoter elements sometimes exhibit responsiveness to regulatory control. Promoter elements also sometimes can be regulated by a selective agent. That is, transcription from promoter elements sometimes can be turned on, turned off, up-regulated or down-regulated, in response to a change in environmental, nutritional or internal conditions or signals (e.g., heat inducible promoters, light regulated promoters, feedback regulated promoters, hormone influenced promoters, tissue specific promoters, oxygen and pH influenced promoters, promoters that are responsive to selective agents (e.g., kanamycin) and the like, for example). Promoters influenced by environmental, nutritional or internal signals frequently are influenced by a signal (direct or indirect) that binds at or near the promoter and increases or decreases expression of the target sequence under certain conditions.

Non-limiting examples of selective or regulatory agents that can influence transcription from a promoter element used in embodiments described herein include, without limitation, (1) nucleic acid segments that encode products that provide resistance against otherwise toxic compounds (e.g., antibiotics); (2) nucleic acid segments that encode products that are otherwise lacking in the recipient cell (e.g., essential products, tRNA genes, auxotrophic markers); (3) nucleic acid segments that encode products that suppress the activity of a gene product; (4) nucleic acid segments that encode products that can be readily identified (e.g., phenotypic markers such as antibiotics (e.g., β-lactamase), β-galactosidase, green fluorescent protein (GFP), yellow fluorescent protein (YFP), red fluorescent protein (RFP), cyan fluorescent protein (CFP), and cell surface proteins); (5) nucleic acid segments that bind products that are otherwise detrimental to cell survival and/or function; (6) nucleic acid segments that otherwise inhibit the activity of any of the nucleic acid segments described in Nos. 1-5 above (e.g., antisense oligonucleotides); (7) nucleic acid segments that bind products that modify a substrate (e.g., restriction endonucleases); (8) nucleic acid segments that can be used to isolate or identify a desired molecule (e.g., specific protein binding sites); (9) nucleic acid segments that encode a specific nucleotide sequence that can be otherwise non-functional (e.g., for PCR amplification of subpopulations of molecules); (10) nucleic acid segments that, when absent, directly or indirectly confer resistance or sensitivity to particular compounds; (11) nucleic acid segments that encode products that either are toxic or convert a relatively non-toxic compound to a toxic compound (e.g., Herpes simplex thymidine kinase, cytosine deaminase) in recipient cells; (12) nucleic acid segments that inhibit replication, partition or heritability of nucleic acid molecules that contain them; and/or (13) nucleic acid segments that encode conditional replication functions, e.g., replication in certain hosts or host cell strains or under certain environmental conditions (e.g., temperature, nutritional conditions, and the like). In some embodiments, the regulatory or selective agent can be added to change the existing growth conditions to which the organism is subjected (e.g., growth in liquid culture, growth in a fermentor, growth on solid nutrient plates and the like for example).

In some embodiments, regulation of a promoter element can be used to alter (e.g., increase, add, decrease or substantially eliminate) the activity of a peptide, polypeptide or protein (e.g., enzyme activity for example). For example, a microorganism can be engineered by genetic modification to express a nucleic acid reagent that can add a novel activity (e.g., an activity not normally found in the host organism) or increase the expression of an existing activity by increasing transcription from a homologous or heterologous promoter operably linked to a nucleotide sequence of interest (e.g., homologous or heterologous nucleotide sequence of interest), in certain embodiments. In some embodiments, a microorganism can be engineered by genetic modification to express a nucleic acid reagent that can decrease expression of an activity by decreasing or substantially eliminating transcription from a homologous or heterologous promoter operably linked to a nucleotide sequence of interest, in certain embodiments.

In some embodiments the activity can be altered using recombinant DNA and genetic techniques known to the artisan. Methods for engineering microorganisms are further described herein. Tables herein provide non-limiting lists of yeast promoters that are up-regulated by oxygen, yeast promoters that are down-regulated by oxygen, yeast transcriptional repressors and their associated genes, DNA binding motifs as determined using the MEME sequence analysis software. Potential regulator binding motifs can be identified using the program MEME to search intergenic regions bound by regulators for overrepresented sequences. For each regulator, the sequences of intergenic regions bound with p-values less than 0.001 were extracted to use as input for motif discovery. The MEME software was run using the following settings: a motif width ranging from 6 to 18 bases, the "zoops" distribution model, a $6^{th}$ order Markov background model and a discovery limit of 20 motifs. The discovered sequence motifs were scored for significance by two criteria: an E-value calculated by MEME and a specificity score. The motif with the best score using each metric is shown for each regulator. All motifs presented are derived from datasets generated in rich growth conditions with the exception of a previously published dataset for epitope-tagged Gal4 grown in galactose.

In some embodiments, the altered activity can be found by screening the organism under conditions that select for the desired change in activity. For example, certain microorganisms can be adapted to increase or decrease an activity by selecting or screening the organism in question on a media containing substances that are poorly metabolized or even toxic. An increase in the ability of an organism to grow a substance that is normally poorly metabolized would result in an increase in the growth rate on that substance, for example. A decrease in the sensitivity to a toxic substance might be manifested by growth on higher concentrations of the toxic substance, for example. Genetic modifications that are identified in this manner sometimes are referred to as naturally occurring mutations or the organisms that carry them can sometimes be referred to as naturally occurring mutants. Modifications obtained in this manner are not limited to alterations in promoter sequences. That is, screening microorganisms by selective pressure, as described above, can yield genetic alterations that can occur in non-promoter sequences, and sometimes also can occur in sequences that are not in the nucleotide sequence of interest, but in a related nucleotide sequences (e.g., a gene involved in a different step of the same pathway, a transport gene, and the like). Naturally occurring mutants sometimes can be found by isolating naturally occurring variants from unique environments, in some embodiments.

In addition to the regulated promoter sequences, regulatory sequences, and coding polynucleotides provided herein, a nucleic acid reagent may include a polynucleotide sequence 80% or more identical to the foregoing (or to the complementary sequences). That is, a nucleotide sequence that is at least 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more identical to a nucleotide sequence described herein can be utilized. The term "identical" as used herein refers to two or more nucleotide sequences having substantially the same nucleotide sequence when compared to each other. One test for determining whether two nucleotide sequences or amino acids sequences are substantially identical is to determine the percent of identical nucleotide sequences or amino acid sequences shared.

Calculations of sequence identity can be performed as follows. Sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is sometimes 30% or more, 40% or more, 50% or more, often 60% or more, and more often 70% or more, 80% or more, 90% or more, or 100% of the length of the reference sequence. The nucleotides or amino acids at corresponding nucleotide or polypeptide positions, respectively, are then compared among the two sequences. When a position in the first sequence is occupied by the same nucleotide or amino acid as the corresponding position in the second sequence, the nucleotides or amino acids are deemed to be identical at that position. The percent identity between the two sequences is a function of the number of identical positions shared by the sequences, taking into account the number of gaps, and the length of each gap, introduced for optimal alignment of the two sequences.

Comparison of sequences and determination of percent identity between two sequences can be accomplished using a mathematical algorithm. Percent identity between two amino acid or nucleotide sequences can be determined using the algorithm of Meyers & Miller, CABIOS 4: 11-17 (1989), which has been incorporated into the ALIGN program (version 2.0), using a PAM120 weight residue table, a gap length penalty of 12 and a gap penalty of 4. Also, percent identity between two amino acid sequences can be determined using the Needleman & Wunsch, J. Mol. Biol. 48: 444-453 (1970) algorithm which has been incorporated into the GAP program in the GCG software package (available at the http address www.gcg.com), using either a Blossum 62 matrix or a PAM250 matrix, and a gap weight of 16, 14, 12, 10, 8, 6, or 4 and a length weight of 1, 2, 3, 4, 5, or 6. Percent identity between two nucleotide sequences can be determined using the GAP program in the GCG software package (available at http address www.gcg.com), using a NWSgapdna.CMP matrix and a gap weight of 40, 50, 60, 70, or 80 and a length weight of 1, 2, 3, 4, 5, or 6. A set of parameters often used is a Blossum 62 scoring matrix with a gap open penalty of 12, a gap extend penalty of 4, and a frameshift gap penalty of 5.

Sequence identity can also be determined by hybridization assays conducted under stringent conditions. As use herein, the term "stringent conditions" refers to conditions for hybridization and washing. Stringent conditions are known to those skilled in the art and can be found in Current Protocols in Molecular Biology, John Wiley & Sons, N.Y., 6.3.1-6.3.6 (1989). Aqueous and non-aqueous methods are described in that reference and either can be used. An example of stringent hybridization conditions is hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions is hybridization in 6× sodium chloride/sodium citrate (SSC) at about 45° C., followed by one or more washes in 0.2×SSC, 0.1% SDS at 60° C. Often, stringent hybridization conditions are hybridization in 6× sodium chloride/sodium citrate (SSC) at about 45° C., followed by one or more washes in 0.2×SSC, 0.1% SDS at 65° C. More often, stringency conditions are 0.5M sodium phosphate, 7% SDS at 65° C., followed by one or more washes at 0.2×SSC, 1% SDS at 65° C.

As noted above, nucleic acid reagents may also comprise one or more 5' UTR's, and one or more 3'UTR's. A 5' UTR may comprise one or more elements endogenous to the nucleotide sequence from which it originates, and sometimes includes one or more exogenous elements. A 5' UTR can originate from any suitable nucleic acid, such as genomic DNA, plasmid DNA, RNA or mRNA, for example, from any suitable organism (e.g., virus, bacterium, yeast, fungi, plant, insect or mammal). The artisan may select appropriate elements for the 5' UTR based upon the chosen expression system (e.g., expression in a chosen organism, or expression in a cell free system, for example). A 5' UTR sometimes comprises one or more of the following elements known to the artisan: enhancer sequences (e.g., transcriptional or translational), transcription initiation site, transcription factor binding site, translation regulation site, translation initiation site, translation factor binding site, accessory protein binding site, feedback regulation agent binding sites, Pribnow box, TATA box, -35 element, E-box (helix-loop-helix binding element), ribosome binding site, replicon, internal ribosome entry site (IRES), silencer element and the like. In some embodiments, a promoter element may be isolated such that all 5' UTR elements necessary for proper conditional regulation are contained in the promoter element fragment, or within a functional subsequence of a promoter element fragment.

A 5'UTR in the nucleic acid reagent can comprise a translational enhancer nucleotide sequence. A translational enhancer nucleotide sequence often is located between the promoter and the target nucleotide sequence in a nucleic acid reagent. A translational enhancer sequence often binds to a ribosome, sometimes is an 18S rRNA-binding ribonucleotide sequence (i.e., a 40S ribosome binding sequence) and sometimes is an internal ribosome entry sequence (IRES). An IRES generally forms an RNA scaffold with precisely placed RNA tertiary structures that contact a 40S ribosomal subunit via a number of specific intermolecular interactions. Examples of ribosomal enhancer sequences are known and can be identified by the artisan (e.g., Mignone et al., Nucleic Acids Research 33: D141-D146 (2005); Paulous et al., Nucleic Acids Research 31: 722-733 (2003); Akbergenov et al., Nucleic Acids Research 32: 239-247 (2004); Mignone et al., Genome Biology 3(3): reviews 0004.1-0001.10 (2002); Gallie, Nucleic Acids Research 30: 3401-3411 (2002); Shaloiko et al., http address www.interscience.wiley.com, DOI: 10.1002/bit.20267; and Gallie et al., Nucleic Acids Research 15: 3257-3273 (1987)).

A translational enhancer sequence sometimes is a eukaryotic sequence, such as a Kozak consensus sequence or other sequence (e.g., hydroid polyp sequence, GenBank accession no. U07128). A translational enhancer sequence sometimes is a prokaryotic sequence, such as a Shine-Dalgarno consensus sequence. In certain embodiments, the translational enhancer sequence is a viral nucleotide sequence. A translational enhancer sequence sometimes is from a 5' UTR of a plant virus, such as Tobacco Mosaic Virus (TMV), Alfalfa Mosaic Virus (AMV); Tobacco Etch Virus (ETV); Potato Virus Y (PVY); Turnip Mosaic (poty) Virus and Pea Seed Borne Mosaic Virus, for example. In certain embodiments, an omega sequence about 67 bases in length from TMV is included in the nucleic acid reagent as a translational enhancer sequence (e.g., devoid of guanosine nucleotides and includes a 25 nucleotide long poly (CAA) central region).

A 3' UTR may comprise one or more elements endogenous to the nucleotide sequence from which it originates and sometimes includes one or more exogenous elements. A 3' UTR may originate from any suitable nucleic acid, such as genomic DNA, plasmid DNA, RNA or mRNA, for example, from any suitable organism (e.g., a virus, bacterium, yeast, fungi, plant, insect or mammal). The artisan can select appropriate elements for the 3' UTR based upon the chosen expression system (e.g., expression in a chosen organism, for example). A 3' UTR sometimes comprises one or more of the following elements known to the artisan: transcription regulation site, transcription initiation site, transcription termination site, transcription factor binding site, translation regulation site, translation termination site, translation initiation site, translation factor binding site, ribosome binding site, replicon, enhancer element, silencer element and polyadenosine tail. A 3' UTR often includes a polyadenosine tail and sometimes does not, and if a polyadenosine tail is present, one or more adenosine moieties may be added or deleted from it (e.g., about 5, about 10, about 15, about 20, about 25, about 30, about 35, about 40, about 45 or about 50 adenosine moieties may be added or subtracted).

In some embodiments, modification of a 5' UTR and/or a 3' UTR can be used to alter (e.g., increase, add, decrease or substantially eliminate) the activity of a promoter. Alteration of the promoter activity can in turn alter the activity of a peptide, polypeptide or protein (e.g., enzyme activity for example), by a change in transcription of the nucleotide sequence(s) of interest from an operably linked promoter element comprising the modified 5' or 3' UTR. For example, a microorganism can be engineered by genetic modification to express a nucleic acid reagent comprising a modified 5' or 3' UTR that can add a novel activity (e.g., an activity not normally found in the host organism) or increase the expression of an existing activity by increasing transcription from a homologous or heterologous promoter operably linked to a nucleotide sequence of interest (e.g., homologous or heterologous nucleotide sequence of interest), in certain embodiments. In some embodiments, a microorganism can be engineered by genetic modification to express a nucleic acid reagent comprising a modified 5' or 3' UTR that can decrease the expression of an activity by decreasing or substantially eliminating transcription from a homologous or heterologous promoter operably linked to a nucleotide sequence of interest, in certain embodiments.

A nucleotide reagent sometimes can comprise a target nucleotide sequence. A "target nucleotide sequence" as used herein encodes a nucleic acid, peptide, polypeptide or protein of interest, and may be a ribonucleotide sequence or a deoxyribonucleotide sequence. A target nucleic acid sometimes is an untranslated ribonucleic acid and sometimes is a translated ribonucleic acid. An untranslated ribonucleic acid may include, but is not limited to, a small interfering ribonucleic acid (siRNA), a short hairpin ribonucleic acid (shRNA), other ribonucleic acid capable of RNA interference (RNAi), an antisense ribonucleic acid, or a ribozyme. A translatable target nucleotide sequence (e.g., a target ribonucleotide sequence) sometimes encodes a peptide, polypeptide or protein, which are sometimes referred to herein as "target peptides," "target polypeptides" or "target proteins."

Any peptides, polypeptides or proteins, or an activity catalyzed by one or more peptides, polypeptides or proteins may be encoded by a target nucleotide sequence and may be selected by a user. Representative proteins include enzymes (e.g., hexanoate synthase, thioesterase, monooxygenase, monooxygenase reductase, fatty alcohol oxidase, 6-oxohexanoic acid deydrogenase, 6-hydroxyhexanoic acid dehydrogenase and the like, for example), antibodies, serum proteins (e.g., albumin), membrane bound proteins, hormones (e.g., growth hormone, erythropoietin, insulin, etc.), cytokines, etc., and include both naturally occurring and exogenously expressed polypeptides. Representative activities (e.g., enzymes or combinations of enzymes which are functionally associated to provide an activity) include hexanoate synthase activity, thioesterase activity, monooxygenase activity, 6-oxohexanoic acid deydrogenase activity, 6-hydroxyhexanoic acid dehydrogenase activity, beta-oxidation activity and the like, for example. The term "enzyme" as used herein refers to a protein which can act as a catalyst to induce a chemical change in other compounds, thereby producing one or more products from one or more substrates.

Specific polypeptides (e.g., enzymes) useful for embodiments described herein are listed herein. The term "protein" as used herein refers to a molecule having a sequence of amino acids linked by peptide bonds. This term includes fusion proteins, oligopeptides, peptides, cyclic peptides, polypeptides and polypeptide derivatives, whether native or recombinant, and also includes fragments, derivatives, homologs, and variants thereof. A protein or polypeptide sometimes is of intracellular origin (e.g., located in the nucleus, cytosol, or interstitial space of host cells in vivo) and sometimes is a cell membrane protein in vivo. In some embodiments (described above, and in further detail hereafter in Engineering and Alteration Methods), a genetic modification can result in a modification (e.g., increase, substantially increase, decrease or substantially decrease) of a target activity.

A translatable nucleotide sequence generally is located between a start codon (AUG in ribonucleic acids and ATG in deoxyribonucleic acids) and a stop codon (e.g., UAA (ochre), UAG (amber) or UGA (opal) in ribonucleic acids and TAA, TAG or TGA in deoxyribonucleic acids), and sometimes is referred to herein as an "open reading frame" (ORF). A translatable nucleotide sequence (e.g., ORF) sometimes is encoded differently in one organism (e.g., most organisms encode CTG as leucine) than in another organism (e.g., C. tropicalis encodes CTG as serine). In some embodiments, a translatable nucleotide sequence is altered to correct alternate genetic code (e.g., codon usage) differences between a nucleotide donor organism and an nucleotide recipient organism (e.g., engineered organism). In certain embodiments, a translatable nucleotide sequence is altered to improve; (i) codon usage, (ii) transcriptional efficiency, (iii) translational efficiency, (iv) the like, and combinations thereof.

A nucleic acid reagent sometimes comprises one or more ORFs. An ORF may be from any suitable source, sometimes from genomic DNA, mRNA, reverse transcribed RNA or complementary DNA (cDNA) or a nucleic acid library comprising one or more of the foregoing, and is from any organism species that contains a nucleic acid sequence of interest, protein of interest, or activity of interest. Non-limiting examples of organisms from which an ORF can be obtained include bacteria, yeast, fungi, human, insect, nematode, bovine, equine, canine, feline, rat or mouse, for example.

A nucleic acid reagent sometimes comprises a nucleotide sequence adjacent to an ORF that is translated in conjunction with the ORF and encodes an amino acid tag. The tag-encoding nucleotide sequence is located 3' and/or 5' of an ORF in the nucleic acid reagent, thereby encoding a tag at the C-terminus or N-terminus of the protein or peptide encoded by the ORF. Any tag that does not abrogate in vitro transcription and/or translation may be utilized and may be appropriately selected by the artisan. Tags may facilitate isolation and/or purification of the desired ORF product from culture or fermentation media.

A tag sometimes specifically binds a molecule or moiety of a solid phase or a detectable label, for example, thereby having utility for isolating, purifying and/or detecting a protein or peptide encoded by the ORF. In some embodiments, a tag comprises one or more of the following elements: FLAG (e.g., DYKDDDDKG), V5 (e.g., GKPIPNPLLGLDST), c-MYC (e.g., EQKLISEEDL), HSV (e.g., QPELAPEDPED), influenza hemaglutinin, HA (e.g., YPYDVPDYA), VSV-G (e.g., YTDIEMNRLGK), bacterial glutathione-S-transferase, maltose binding protein, a streptavidin- or avidin-binding tag (e.g., pcDNA™6 BioEase™ Gateway® Biotinylation System (Invitrogen)), thioredoxin, β-galactosidase, VSV-glycoprotein, a fluorescent protein (e.g., green fluorescent protein or one of its many color variants (e.g., yellow, red, blue)), a polylysine or polyarginine sequence, a polyhistidine sequence (e.g., His6) or other sequence that chelates a metal (e.g., cobalt, zinc, copper), and/or a cysteine-rich sequence that binds to an arsenic-containing molecule. In certain embodiments, a cysteine-rich tag comprises the amino acid sequence CC-Xn-CC, wherein X is any amino acid and n is 1 to 3, and the cysteine-rich sequence sometimes is CCPGCC. In certain embodiments, the tag comprises a cysteine-rich element and a polyhistidine element (e.g., CCPGCC and His6).

A tag often conveniently binds to a binding partner. For example, some tags bind to an antibody (e.g., FLAG) and sometimes specifically bind to a small molecule. For example, a polyhistidine tag specifically chelates a bivalent metal, such as copper, zinc and cobalt; a polylysine or polyarginine tag specifically binds to a zinc finger; a glutathione S-transferase tag binds to glutathione; and a cysteine-rich tag specifically binds to an arsenic-containing molecule. Arsenic-containing molecules include LUMIO™ agents (Invitrogen, California), such as FlAsH™ (EDT2[4',5'-bis(1,3,2-dithioarsolan-2-yl)fluorescein-(1,2-ethanedithiol)2]) and ReAsH reagents (e.g., U.S. Pat. No. 5,932,474 to Tsien et al., entitled "Target Sequences for Synthetic Molecules;" U.S. Pat. No. 6,054,271 to Tsien et al., entitled "Methods of Using Synthetic Molecules and Target Sequences;" U.S. Pat. Nos. 6,451,569 and 6,008,378; published U.S. Patent Application 2003/0083373, and published PCT Patent Application WO 99/21013, all to Tsien et al. and all entitled "Synthetic Molecules that Specifically React with Target Sequences"). Such antibodies and small molecules sometimes are linked to a solid phase for convenient isolation of the target protein or target peptide.

A tag sometimes comprises a sequence that localizes a translated protein or peptide to a component in a system, which is referred to as a "signal sequence" or "localization signal sequence" herein. A signal sequence often is incorporated at the N-terminus of a target protein or target peptide, and sometimes is incorporated at the C-terminus. Examples of signal sequences are known to the artisan, are readily incorporated into a nucleic acid reagent, and often are selected according to the organism in which expression of the nucleic acid reagent is performed. A signal sequence in some embodiments localizes a translated protein or peptide to a cell membrane. Examples of signal sequences include, but are not limited to, a nucleus targeting signal (e.g., steroid receptor sequence and N-terminal sequence of SV40 virus large T antigen); mitochondrial targeting signal (e.g., amino acid sequence that forms an amphipathic helix); peroxisome targeting signal (e.g., C-terminal sequence in YFG from *S. cerevisiae*); and a secretion signal (e.g., N-terminal sequences from invertase, mating factor alpha, PHO5 and SUC2 in *S. cerevisiae*; multiple N-terminal sequences of *B. subtilis* proteins (e.g., Tjalsma et al., Microbiol. Molec. Biol. Rev. 64: 515-547 (2000)); alpha amylase signal sequence (e.g., U.S. Pat. No. 6,288,302); pectate lyase signal sequence (e.g., U.S. Pat. No. 5,846,818); precollagen signal sequence (e.g., U.S. Pat. No. 5,712,114); OmpA signal sequence (e.g., U.S. Pat. No. 5,470,719); lam beta signal sequence (e.g., U.S. Pat. No. 5,389,529); *B. brevis* signal sequence (e.g., U.S. Pat. No. 5,232,841); and *P. pastoris* signal sequence (e.g., U.S. Pat. No. 5,268,273)).

A tag sometimes is directly adjacent to the amino acid sequence encoded by an ORF (i.e., there is no intervening sequence) and sometimes a tag is substantially adjacent to an ORF encoded amino acid sequence (e.g., an intervening sequence is present). An intervening sequence sometimes includes a recognition site for a protease, which is useful for cleaving a tag from a target protein or peptide. In some embodiments, the intervening sequence is cleaved by Factor Xa (e.g., recognition site I (E/D)GR), thrombin (e.g., recognition site LVPRGS), enterokinase (e.g., recognition site DDDDK), TEV protease (e.g., recognition site ENLYFQG) or PreScission™ protease (e.g., recognition site LEVLFQGP), for example.

An intervening sequence sometimes is referred to herein as a "linker sequence," and may be of any suitable length selected by the artisan. A linker sequence sometimes is about 1 to about 20 amino acids in length, and sometimes about 5 to about 10 amino acids in length. The artisan may select the linker length to substantially preserve target protein or peptide function (e.g., a tag may reduce target protein or peptide function unless separated by a linker), to enhance disassociation of a tag from a target protein or peptide when a protease cleavage site is present (e.g., cleavage may be enhanced when a linker is present), and to enhance interaction of a tag/target protein product with a solid phase. A linker can be of any suitable amino acid content, and often comprises a higher proportion of amino acids having relatively short side chains (e.g., glycine, alanine, serine and threonine).

A nucleic acid reagent sometimes includes a stop codon between a tag element and an insertion element or ORF, which can be useful for translating an ORF with or without the tag. Mutant tRNA molecules that recognize stop codons (described above) suppress translation termination and thereby are designated "suppressor tRNAs." Suppressor tRNAs can result in the insertion of amino acids and continuation of translation past stop codons (e.g., U.S. Patent Application No. 60/587,583, filed Jul. 14, 2004, entitled "Production of Fusion Proteins by Cell-Free Protein Synthesis,"; Eggertsson, et al., (1988) Microbiological Review 52(3):354-374, and Engleerg-Kukla, et al. (1996) in *Escherichia coli* and *Salmonella* Cellular and Molecular Biology, Chapter 60, pps 909-921, Neidhardt, et al. eds., ASM Press, Washington, D.C.). A number of suppressor tRNAs are known, including but not limited to, supE, supP, supD, supF and supZ suppressors, which suppress the termination of translation of the amber stop codon; supB, gIT, supL, supN, supC and supM suppressors, which suppress the function of the ochre stop codon and glyT, trpT and Su-9 suppressors, which suppress the function of the opal stop codon. In general, suppressor tRNAs contain one or more mutations in the anti-codon loop of the tRNA that allows the tRNA to base pair with a codon that ordinarily functions as a stop codon. The mutant tRNA is charged with its cognate amino acid residue and the cognate amino acid residue is inserted into the translating polypeptide when the stop codon is encountered. Mutations that enhance the efficiency of termination suppressors (i.e., increase stop codon read-through) have been identified. These include, but are not limited to, mutations in the uar gene (also known as the prfA gene), mutations in the ups gene, mutations in the sueA, sueB and sueC genes, mutations in the rpsD (ramA) and rpsE (spcA) genes and mutations in the rpIL gene.

Thus, a nucleic acid reagent comprising a stop codon located between an ORF and a tag can yield a translated ORF alone when no suppressor tRNA is present in the translation system, and can yield a translated ORF-tag fusion when a suppressor tRNA is present in the system. Suppressor tRNA can be generated in cells transfected with a nucleic acid encoding the tRNA (e.g., a replication incompetent adenovirus containing the human tRNA-Ser suppressor gene can be transfected into cells, or a YAC containing a yeast or bacterial tRNA suppressor gene can be transfected into yeast cells, for example). Vectors for synthesizing suppressor tRNA and for translating ORFs with or without a tag are available to the artisan (e.g., Tag-On-Demand™ kit (Invitrogen Corporation, California); Tag-On-Demand™ Suppressor Supernatant Instruction Manual, Version B, 6 Jun. 2003, at http address www.invitrogen.com/content/sfs/manuals/tagondemand_supernatant_man.pdf; Tag-On-Demand™ Gateway® Vector Instruction Manual, Version B, 20 Jun. 2003 at http address www.invitrogen.com/content/sfs/manuals/tagondemand_vectors_man.pdf; and Capone et al., Amber, ochre and opal suppressor tRNA genes derived from a human serine tRNA gene. EMBO J. 4:213, 1985).

Any convenient cloning strategy known in the art may be utilized to incorporate an element, such as an ORF, into a nucleic acid reagent. Known methods can be utilized to insert an element into the template independent of an insertion element, such as (1) cleaving the template at one or more existing restriction enzyme sites and ligating an element of interest and (2) adding restriction enzyme sites to the template by hybridizing oligonucleotide primers that include one or more suitable restriction enzyme sites and amplifying by polymerase chain reaction (described in greater detail herein). Other cloning strategies take advantage of one or more insertion sites present or inserted into the nucleic acid reagent, such as an oligonucleotide primer hybridization site for PCR, for example, and others described herein. In some embodiments, a cloning strategy can be combined with genetic manipulation such as recombination (e.g., recombination of a nucleic acid reagent with a nucleic acid sequence of interest into the genome of the organism to be modified, as described further herein). In some embodiments, the cloned ORF(s) can produce (directly or indirectly) adipic acid, by engineering a microorganism with one or more ORFs of interest, which microorganism comprises one or more altered activities selected from the group consisting of 6-oxohexanoic acid dehydrogenase activity, 6-hydroxyhexanoic acid dehydrogenase activity, hexanoate synthase activity and monooxygenase activity.

In some embodiments, the nucleic acid reagent includes one or more recombinase insertion sites. A recombinase insertion site is a recognition sequence on a nucleic acid molecule that participates in an integration/recombination reaction by recombination proteins. For example, the recombination site for Cre recombinase is loxP, which is a 34 base pair sequence comprised of two 13 base pair inverted repeats (serving as the recombinase binding sites) flanking an 8 base pair core sequence (e.g., FIG. 1 of Sauer, B., Curr. Opin. Biotech. 5:521-527 (1994)). Other examples of recombination sites include attB, attP, attL, and attR sequences, and mutants, fragments, variants and derivatives thereof, which are recognized by the recombination protein A Int and by the auxiliary proteins integration host factor (IHF), FIS and excisionase (Xis) (e.g., U.S. Pat. Nos. 5,888,732; 6,143,557; 6,171,861; 6,270,969; 6,277,608; and 6,720,140; U.S. patent application Ser. Nos. 09/517,466, filed Mar. 2, 2000, and 09/732,914, filed Aug. 14, 2003, and in U.S. patent publication no. 2002-0007051-A1; Landy, Curr. Opin. Biotech. 3:699-707 (1993)).

Examples of recombinase cloning nucleic acids are in Gateway® systems (Invitrogen, California), which include at least one recombination site for cloning a desired nucleic acid molecules in vivo or in vitro. In some embodiments, the system utilizes vectors that contain at least two different site-specific recombination sites, often based on the bacteriophage lambda system (e.g., att1 and att2), and are mutated from the wild-type (att0) sites. Each mutated site has a unique specificity for its cognate partner att site (i.e., its binding partner recombination site) of the same type (for example attB1 with attP1, or attL1 with attR1) and will not cross-react with recombination sites of the other mutant type or with the wild-type att0 site. Different site specificities allow directional cloning or linkage of desired molecules thus providing desired orientation of the cloned molecules. Nucleic acid fragments flanked by recombination sites are cloned and subcloned using the Gateway® system by replacing a selectable marker (for example, ccdB) flanked by att sites on the recipient plasmid molecule, sometimes termed the Destination Vector. Desired clones are then selected by transformation of a ccdB sensitive host strain and positive selection for a marker on the recipient molecule. Similar strategies for negative selection (e.g., use of toxic genes) can be used in other organisms such as thymidine kinase (TK) in mammals and insects.

A recombination system useful for engineering yeast is outlined briefly. The system makes use of the URA3 gene (e.g., for *S. cerevisieae* and *C. albicans*, for example) or URA4 and URA5 genes (e.g., for *S. pombe*, for example) and toxicity of the nucleotide analogue 5-Fluoroorotic acid (5-FOA). The URA3 or URA4 and URA5 genes encode orotine-5'-monophosphate (OMP) dicarboxylase. Yeast with an active URA3 or URA4 and URA5 gene (phenotypically Ura+) convert 5-FOA to fluorodeoxyuridine, which is toxic to yeast cells. Yeast carrying a mutation in the appropriate gene(s) or having a knock out of the appropriate gene(s) can grow in the presence of 5-FOA, if the media is also supplemented with uracil.

A nucleic acid engineering construct can be made which may comprise the URA3 gene or cassette (for *S. cerevisieae*), flanked on either side by the same nucleotide sequence in the same orientation. The URA3 cassette comprises a promoter, the URA3 gene and a functional transcription terminator. Target sequences which direct the construct to a particular nucleic acid region of interest in the organism to be engineered are added such that the target sequences are adjacent to and abut the flanking sequences on either side of the URA3 cassette. Yeast can be transformed with the engineering construct and plated on minimal media without uracil. Colonies can be screened by PCR to determine those transformants that have the engineering construct inserted in the proper location in the genome. Checking insertion location prior to selecting for recombination of the ura3 cassette may reduce the number of incorrect clones carried through to later stages of the procedure. Correctly inserted transformants can then be replica plated on minimal media containing 5-FOA to select for recombination of the URA3 cassette out of the construct, leaving a disrupted gene and an identifiable footprint (e.g., nucleic acid sequence) that can be use to verify the presence of the disrupted gene. The technique described is useful for disrupting or "knocking out" gene function, but also can be used to insert genes or constructs into a host organisms genome in a targeted, sequence specific manner.

In certain embodiments, a nucleic acid reagent includes one or more topoisomerase insertion sites. A topoisomerase insertion site is a defined nucleotide sequence recognized and bound by a site-specific topoisomerase. For example, the nucleotide sequence 5'-(C/T)CCTT-3' is a topoisomerase recognition site bound specifically by most poxvirus topoisomerases, including vaccinia virus DNA topoisomerase I. After binding to the recognition sequence, the topoisomerase cleaves the strand at the 3'-most thymidine of the recognition site to produce a nucleotide sequence comprising 5'-(C/T)CCTT-PO4-TOPO, a complex of the topoisomerase covalently bound to the 3' phosphate via a tyrosine in the topoisomerase (e.g., Shuman, J. Biol. Chem. 266:11372-11379, 1991; Sekiguchi and Shuman, Nucl. Acids Res. 22:5360-5365, 1994; U.S. Pat. No. 5,766,891; PCT/US95/16099; and PCT/US98/12372). In comparison, the nucleotide sequence 5'-GCAACTT-3' is a topoisomerase recognition site for type IA *E. coli* topoisomerase III. An element to be inserted often is combined with topoisomerase-reacted template and thereby incorporated into the nucleic acid reagent (e.g., World Wide Web URL invitrogen.com/downloads/F-13512_Topo_Flyer.pdf; World Wide Web URL invitrogen.com/content/sfs/brochures/710_021849%20_B_TOPOCloning_bro.pdf; TOPO TA Cloning® Kit and Zero Blunt® TOPO® Cloning Kit product information).

A nucleic acid reagent sometimes contains one or more origin of replication (ORI) elements. In some embodiments, a template comprises two or more ORIs, where one functions efficiently in one organism (e.g., a bacterium) and another functions efficiently in another organism (e.g., a eukaryote, like yeast for example). In some embodiments, an ORI may function efficiently in one species (e.g., *S. cerevisieae*, for example) and another ORI may function efficiently in a different species (e.g., *S. pombe*, for example). A nucleic acid reagent also sometimes includes one or more transcription regulation sites.

A nucleic acid reagent can include one or more selection elements (e.g., elements for selection of the presence of the nucleic acid reagent, and not for activation of a promoter element which can be selectively regulated). Selection elements often are utilized using known processes to determine whether a nucleic acid reagent is included in a cell. In some embodiments, a nucleic acid reagent includes two or more selection elements, where one functions efficiently in one organism and another functions efficiently in another organism. Examples of selection elements include, but are not limited to, (1) nucleic acid segments that encode products that provide resistance against otherwise toxic compounds (e.g., antibiotics); (2) nucleic acid segments that encode products that are otherwise lacking in the recipient cell (e.g., essential products, tRNA genes, auxotrophic markers); (3) nucleic acid segments that encode products that suppress the activity of a gene product; (4) nucleic acid segments that encode products that can be readily identified (e.g., phenotypic markers such as antibiotics (e.g., β-lactamase), β-galactosidase, green fluorescent protein (GFP), yellow fluorescent protein (YFP), red fluorescent protein (RFP), cyan fluorescent protein (CFP), and cell surface proteins); (5) nucleic acid segments that bind products that are otherwise detrimental to cell survival and/or function; (6) nucleic acid segments that otherwise inhibit the activity of any of the nucleic acid segments described in Nos. 1-5 above (e.g., antisense oligonucleotides); (7) nucleic acid segments that bind products that modify a substrate (e.g., restriction endonucleases); (8) nucleic acid segments that can be used to isolate or identify a desired molecule (e.g., specific protein binding sites); (9) nucleic acid segments that encode a specific nucleotide sequence that can be otherwise non-functional (e.g., for PCR amplification of subpopulations of molecules); (10) nucleic acid segments that, when absent, directly or indirectly confer resistance or sensitivity to particular compounds; (11) nucleic acid segments that encode products that either are toxic or convert a relatively non-toxic compound to a toxic compound (e.g., Herpes simplex thymidine kinase, cytosine deaminase) in recipient cells; (12) nucleic acid segments that inhibit replication, partition or heritability of nucleic acid molecules that contain them; and/or (13) nucleic acid segments that encode conditional replication functions, e.g., replication in certain hosts or host cell strains or under certain environmental conditions (e.g., temperature, nutritional conditions, and the like).

A nucleic acid reagent is of any form useful for in vivo transcription and/or translation. A nucleic acid sometimes is a plasmid, such as a supercoiled plasmid, sometimes is a yeast artificial chromosome (e.g., YAC), sometimes is a linear nucleic acid (e.g., a linear nucleic acid produced by PCR or by restriction digest), sometimes is single-stranded and sometimes is double-stranded. A nucleic acid reagent sometimes is prepared by an amplification process, such as a polymerase chain reaction (PCR) process or transcription-mediated amplification process (TMA). In TMA, two enzymes are used in an isothermal reaction to produce amplification products detected by light emission (see, e.g., Biochemistry 1996 Jun. 25; 35(25):8429-38 and http address www.devicelink.com/ivdt/archive/00/11/007.html). Standard PCR processes are known (e.g., U.S. Pat. Nos. 4,683,202; 4,683,195; 4,965,188; and 5,656,493), and generally are performed in cycles. Each cycle includes heat denaturation, in which hybrid nucleic acids dissociate; cooling, in which primer oligonucleotides hybridize; and extension of the oligonucleotides by a polymerase (i.e., Taq polymerase). An example of a PCR cyclical process is treating the sample at 95° C. for 5 minutes; repeating forty-five cycles of 95° C. for 1 minute, 59° C. for 1 minute, 10 seconds, and 72° C. for 1 minute 30 seconds; and then treating the sample at 72° C. for 5 minutes. Multiple cycles frequently are performed using a commercially available thermal cycler. PCR amplification products sometimes are stored for a time at a lower temperature (e.g., at 4° C.) and sometimes are frozen (e.g., at −20° C.) before analysis.

In some embodiments, a nucleic acid reagent, protein reagent, protein fragment reagent or other reagent described herein is isolated or purified. The term "isolated" as used herein refers to material removed from its original environment (e.g., the natural environment if it is naturally occurring, or a host cell if expressed exogenously), and thus is altered "by the hand of man" from its original environment. The term "purified" as used herein with reference to molecules does not refer to absolute purity. Rather, "purified" refers to a substance in a composition that contains fewer substance species in the same class (e.g., nucleic acid or protein species) other than the substance of interest in comparison to the sample from which it originated. "Purified," if a nucleic acid or protein for example, refers to a substance in a composition that contains fewer nucleic acid species or protein species other than the nucleic acid or protein of interest in comparison to the sample from which it originated. Sometimes, a protein or nucleic acid is "substantially pure," indicating that the protein or nucleic acid represents at least 50% of protein or nucleic acid on a mass basis of the composition. Often, a substantially pure protein or nucleic acid is at least 75% on a mass basis of the composition, and sometimes at least 95% on a mass basis of the composition.

Engineering and Alteration Methods

Methods and compositions (e.g., nucleic acid reagents) described herein can be used to generate engineered microorganisms. As noted above, the term "engineered microorganism" as used herein refers to a modified organism that includes one or more activities distinct from an activity present in a microorganism utilized as a starting point for modification (e.g., host microorganism or unmodified organism). Engineered microorganisms typically arise as a result of a genetic modification, usually introduced or selected for, by one of skill in the art using readily available techniques. Non-limiting examples of methods useful for generating an altered activity include, introducing a heterologous polynucleotide (e.g., nucleic acid or gene integration, also referred to as "knock in"), removing an endogenous polynucleotide, altering the sequence of an existing endogenous nucleic acid sequence (e.g., site-directed mutagenesis), disruption of an existing endogenous nucleic acid sequence (e.g., knock outs and transposon or insertion element mediated mutagenesis), selection for an altered activity where the selection causes a change in a naturally occurring activity that can be stably inherited (e.g., causes a change in a nucleic acid sequence in the genome of the organism or in an epigenetic nucleic acid that is replicated and passed on to daughter cells), PCR-based mutagenesis, and the like. The term "mutagenesis" as used herein refers to any modification to a nucleic acid (e.g., nucleic acid reagent, or host chromosome, for example) that is subsequently used to generate a product in a host or modified organism. Non-limiting examples of mutagenesis include, deletion, insertion, substitution, rearrangement, point mutations, suppressor mutations and the like. Mutagenesis methods are known in the art and are readily available to the artisan. Non-limiting examples of mutagenesis methods are described herein and can also be found in Maniatis, T., E. F. Fritsch and J. Sambrook (1982) *Molecular Cloning: a Laboratory Manual*; Cold Spring Harbor Laboratory, Cold Spring Harbor, N.Y. Another non-limiting example of mutagenesis can be conducted using a Stratagene (San Diego, Calif.) "QuickChange" kit according to the manufacturer's instructions.

The term "genetic modification" as used herein refers to any suitable nucleic acid addition, removal or alteration that facilitates production of a target product (e.g., adipic acid, 6-hydroxyhexanoic acid) in an engineered microorganism. Genetic modifications include, without limitation, insertion of one or more nucleotides in a native nucleic acid of a host organism in one or more locations, deletion of one or more nucleotides in a native nucleic acid of a host organism in one or more locations, modification or substitution of one or more nucleotides in a native nucleic acid of a host organism in one or more locations, insertion of a non-native nucleic acid into a host organism (e.g., insertion of an autonomously replicating vector), and removal of a non-native nucleic acid in a host organism (e.g., removal of a vector).

The term "heterologous polynucleotide" as used herein refers to a nucleotide sequence not present in a host microorganism in some embodiments. In certain embodiments, a heterologous polynucleotide is present in a different amount (e.g., different copy number) than in a host microorganism, which can be accomplished, for example, by introducing more copies of a particular nucleotide sequence to a host microorganism (e.g., the particular nucleotide sequence may be in a nucleic acid autonomous of the host chromosome or may be inserted into a chromosome). A heterologous polynucleotide is from a different organism in some embodiments, and in certain embodiments, is from the same type of organism but from an outside source (e.g., a recombinant source).

In some embodiments, an organism engineered using the methods and nucleic acid reagents described herein can produce adipic acid. In certain embodiments, an engineered microorganism described herein that produces adipic acid may comprise one or more altered activities selected from the group consisting of 6-oxohexanoic acid dehydrogenase activity, omega oxo fatty acid dehydrogenase activity, 6-hydroxyhexanoic acid dehydrogenase activity, omega hydroxyl fatty acid dehydrogenase activity, hexanoate synthase activity and monooxygenase activity. In some embodiments, an engineered microorganism as described herein may comprise a genetic modification that adds or increases the 6-oxohexanoic acid dehydrogenase activity, omega oxo fatty acid dehydrogenase activity, 6-hydroxyhexanoic acid dehydrogenase activity, omega hydroxyl fatty acid dehydrogenase activity, hexanoate synthase activity and monooxygenase activity.

In certain embodiments, an engineered microorganism described herein can comprise an altered thioesterase activity. In some embodiments, the engineered microorganism may comprise a genetic alteration that adds or increases a thioesterase activity. In some embodiments, the engineered microorganism comprising a genetic alteration that adds or increases a thioesterase activity, may further comprise a heterologous polynucleotide encoding a polypeptide having thioesterase activity.

The term "altered activity" as used herein refers to an activity in an engineered microorganism that is added or modified relative to the host microorganism (e.g., added, increased, reduced, inhibited or removed activity). An activity can be altered by introducing a genetic modification to a host microorganism that yields an engineered microorganism having added, increased, reduced, inhibited or removed activity.

An added activity often is an activity not detectable in a host microorganism. An increased activity generally is an activity detectable in a host microorganism that has been increased in an engineered microorganism. An activity can be increased to any suitable level for production of a target product (e.g., adipic acid, 6-hydroxyhexanoic acid), including but not limited to less than 2-fold (e.g., about 10% increase to about 99% increase; about 20%, 30%, 40%, 50%, 60%, 70%, 80%, 90% increase), 2-fold, 3-fold, 4-fold, 5-fold, 6-fold, 7-fold, 8-fold, 9-fold, of 10-fold increase, or greater than about 10-fold increase. A reduced or inhibited activity generally is an activity detectable in a host microorganism that has been reduced or inhibited in an engineered microorganism. An activity can be reduced to undetectable levels in some embodiments, or detectable levels in certain embodiments. An activity can be decreased to any suitable level for production of a target product (e.g., adipic acid, 6-hydroxyhexanoic acid), including but not limited to less than 2-fold (e.g., about 10% decrease to about 99% decrease; about 20%, 30%, 40%, 50%, 60%, 70%, 80%, 90% decrease), 2-fold, 3-fold, 4-fold, 5-fold, 6-fold, 7-fold, 8-fold, 9-fold, of 10-fold decrease, or greater than about 10-fold decrease.

An altered activity sometimes is an activity not detectable in a host organism and is added to an engineered organism. An altered activity also may be an activity detectable in a host organism and is increased in an engineered organism. An activity may be added or increased by increasing the number of copies of a polynucleotide that encodes a polypeptide having a target activity, in some embodiments. In certain embodiments an activity can be added or increased by inserting into a host microorganism a heterologous polynucleotide that encodes a polypeptide having the added activity. In certain embodiments, an activity can be added or increased by inserting into a host microorganism a heterologous polynucleotide that is (i) operably linked to another polynucleotide that encodes a polypeptide having the added activity, and (ii) up regulates production of the polynucleotide. Thus, an activity can be added or increased by inserting or modifying a regulatory polynucleotide operably linked to another polynucleotide that encodes a polypeptide having the target activity. In certain embodiments, an activity can be added or increased by subjecting a host microorganism to a selective environment and screening for microorganisms that have a detectable level of the target activity. Examples of a selective environment include, without limitation, a medium containing a substrate that a host organism can process and a medium lacking a substrate that a host organism can process.

An altered activity sometimes is an activity detectable in a host organism and is reduced, inhibited or removed (i.e., not detectable) in an engineered organism. An activity may be reduced or removed by decreasing the number of copies of a polynucleotide that encodes a polypeptide having a target activity, in some embodiments. In some embodiments, an activity can be reduced or removed by (i) inserting a polynucleotide within a polynucleotide that encodes a polypeptide having the target activity (disruptive insertion), and/or (ii) removing a portion of or all of a polynucleotide that encodes a polypeptide having the target activity (deletion or knock out, respectively). In certain embodiments, an activity can be reduced or removed by inserting into a host microorganism a heterologous polynucleotide that is (i) operably linked to another polynucleotide that encodes a polypeptide having the target activity, and (ii) down regulates production of the polynucleotide. Thus, an activity can be reduced or removed by inserting or modifying a regulatory polynucleotide operably linked to another polynucleotide that encodes a polypeptide having the target activity.

An activity also can be reduced or removed by (i) inhibiting a polynucleotide that encodes a polypeptide having the activity or (ii) inhibiting a polynucleotide operably linked to another polynucleotide that encodes a polypeptide having the activity. A polynucleotide can be inhibited by a suitable technique known in the art, such as by contacting an RNA encoded by the polynucleotide with a specific inhibitory RNA (e.g., RNAi, siRNA, ribozyme). An activity also can be reduced or removed by contacting a polypeptide having the activity with a molecule that specifically inhibits the activity (e.g., enzyme inhibitor, antibody). In certain embodiments, an activity can be reduced or removed by subjecting a host microorganism to a selective environment and screening for microorganisms that have a reduced level or removal of the target activity.

In some embodiments, an untranslated ribonucleic acid, or a cDNA can be used to reduce the expression of a particular activity or enzyme. For example, a microorganism can be engineered by genetic modification to express a nucleic acid reagent that reduces the expression of an activity by producing an RNA molecule that is partially or substantially homologous to a nucleic acid sequence of interest which encodes the activity of interest. The RNA molecule can bind to the nucleic acid sequence of interest and inhibit the nucleic acid sequence from performing its natural function, in certain embodiments. In some embodiments, the RNA may alter the nucleic acid sequence of interest which encodes the activity of interest in a manner that the nucleic acid sequence of interest is no longer capable of performing its natural function (e.g., the action of a ribozyme for example).

In certain embodiments, nucleotide sequences sometimes are added to, modified or removed from one or more of the nucleic acid reagent elements, such as the promoter, 5'UTR, target sequence, or 3'UTR elements, to enhance, potentially enhance, reduce, or potentially reduce transcription and/or translation before or after such elements are incorporated in a nucleic acid reagent. In some embodiments, one or more of the following sequences may be modified or removed if they are present in a 5'UTR: a sequence that forms a stable secondary structure (e.g., quadruplex structure or stem loop stem structure (e.g., EMBL sequences X12949, AF274954, AF139980, AF152961, S95936, U194144, AF116649 or substantially identical sequences that form such stem loop stem structures)); a translation initiation codon upstream of the target nucleotide sequence start codon; a stop codon upstream of the target nucleotide sequence translation initiation codon; an ORF upstream of the target nucleotide sequence translation initiation codon; an iron responsive element (IRE) or like sequence; and a 5' terminal oligopyrimidine tract (TOP, e.g., consisting of 5-15 pyrimidines adjacent to the cap). A translational enhancer sequence and/or an internal ribosome entry site (IRES) sometimes is inserted into a 5'UTR (e.g., EMBL nucleotide sequences J04513, X87949, M95825, M12783, AF025841, AF013263, AF006822, M17169, M13440, M22427, D14838 and M17446 and substantially identical nucleotide sequences). An AU-rich element (ARE, e.g., AUUUA repeats) and/or splicing junction that follows a nonsense codon sometimes is removed from or modified in a 3'UTR. A polyadenosine tail sometimes is inserted into a 3'UTR if none is present, sometimes is removed if it is present, and adenosine moieties sometimes are added to or removed from a polyadenosine tail present in a 3'UTR. Thus, some embodiments are directed to a process comprising: determining whether any nucleotide sequences that increase, potentially increase, reduce or potentially reduce translation efficiency are present in the elements, and adding, removing or modifying one or more of such sequences if they are identified. Certain embodiments are directed to a process comprising: determining whether any nucleotide sequences that increase or potentially increase translation efficiency are not present in the elements, and incorporating such sequences into the nucleic acid reagent.

In some embodiments, an activity can be altered by modifying the nucleotide sequence of an ORF. An ORF sometimes is mutated or modified (for example, by point mutation, deletion mutation, insertion mutation, PCR based mutagenesis and the like) to alter, enhance or increase, reduce, substantially reduce or eliminate the activity of the encoded protein or peptide. The protein or peptide encoded by a modified ORF sometimes is produced in a lower amount or may not be produced at detectable levels, and in other embodiments, the product or protein encoded by the modified ORF is produced at a higher level (e.g., codons sometimes are modified so they are compatible with tRNA's preferentially used in the host organism or engineered organism). To determine the relative activity, the activity from the product of the mutated ORF (or cell containing it) can be compared to the activity of the product or protein encoded by the unmodified ORF (or cell containing it).

In some embodiments, an ORF nucleotide sequence sometimes is mutated or modified to alter the triplet nucleotide sequences used to encode amino acids (e.g., amino acid codon triplets, for example). Modification of the nucleotide sequence of an ORF to alter codon triplets sometimes is used to change the codon found in the original sequence to better match the preferred codon usage of the organism in which the ORF or nucleic acid reagent will be expressed. The codon usage, and therefore the codon triplets encoded by a nucleic acid sequence, in bacteria may be different from the preferred codon usage in eukaryotes, like yeast or plants for example. Preferred codon usage also may be different between bacterial species. In certain embodiments an ORF nucleotide sequences sometimes is modified to eliminate codon pairs and/or eliminate mRNA secondary structures that can cause pauses during translation of the mRNA encoded by the ORF nucleotide sequence. Translational pausing sometimes occurs when nucleic acid secondary structures exist in an mRNA, and sometimes occurs due to the presence of codon pairs that slow the rate of translation by causing ribosomes to pause. In some embodiments, the use of lower abundance codon triplets can reduce translational pausing due to a decrease in the pause time needed to load a charged tRNA into the ribosome translation machinery. Therefore, to increase transcriptional and translational efficiency in bacteria (e.g., where transcription and translation are concurrent, for example) or to increase translational efficiency in eukaryotes (e.g., where transcription and translation are functionally separated), the nucleotide sequence of a nucleotide sequence of interest can be altered to better suit the transcription and/or translational machinery of the host and/or genetically modified microorganism. In certain embodiments, slowing the rate of translation by the use of lower abundance codons, which slow or pause the ribosome, can lead to higher yields of the desired product due to an increase in correctly folded proteins and a reduction in the formation of inclusion bodies.

Codons can be altered and optimized according to the preferred usage by a given organism by determining the codon distribution of the nucleotide sequence donor organism and comparing the distribution of codons to the distribution of codons in the recipient or host organism. Techniques described herein (e.g., site directed mutagenesis and the like) can then be used to alter the codons accordingly. Comparisons of codon usage can be done by hand, or using nucleic acid analysis software commercially available to the artisan.

Modification of the nucleotide sequence of an ORF also can be used to correct codon triplet sequences that have diverged in different organisms. For example, certain yeast (e.g., C. tropicalis and C. maltosa) use the amino acid triplet CUG (e.g., CTG in the DNA sequence) to encode serine. CUG typically encodes leucine in most organisms. In order to maintain the correct amino acid in the resultant polypeptide or protein, the CUG codon must be altered to reflect the organism in which the nucleic acid reagent will be expressed. Thus, if an ORF from a bacterial donor is to be expressed in either Candida yeast strain mentioned above, the heterologous nucleotide sequence must first be altered or modified to the appropriate leucine codon. Therefore, in some embodiments, the nucleotide sequence of an ORF sometimes is altered or modified to correct for differences that have occurred in the evolution of the amino acid codon triplets between different organisms. In some embodiments, the nucleotide sequence can be left unchanged at a particular amino acid codon, if the amino acid encoded is a conservative or neutral change in amino acid when compared to the originally encoded amino acid.

In some embodiments, an activity can be altered by modifying translational regulation signals, like a stop codon for example. A stop codon at the end of an ORF sometimes is modified to another stop codon, such as an amber stop codon described above. In some embodiments, a stop codon is introduced within an ORF, sometimes by insertion or mutation of an existing codon. An ORF comprising a modified terminal stop codon and/or internal stop codon often is translated in a system comprising a suppressor tRNA that recognizes the stop codon. An ORF comprising a stop codon sometimes is translated in a system comprising a suppressor tRNA that incorporates an unnatural amino acid during translation of the target protein or target peptide. Methods for incorporating unnatural amino acids into a target protein or peptide are known, which include, for example, processes utilizing a heterologous tRNA/synthetase pair, where the tRNA recognizes an amber stop codon and is loaded with an unnatural amino acid (e.g., World Wide Web URL iupac.org/news/prize/2003/wang.pdf).

Depending on the portion of a nucleic acid reagent (e.g., Promoter, 5' or 3' UTR, ORI, ORF, and the like) chosen for alteration (e.g., by mutagenesis, introduction or deletion, for example) the modifications described above can alter a given activity by (i) increasing or decreasing feedback inhibition mechanisms, (ii) increasing or decreasing promoter initiation, (iii) increasing or decreasing translation initiation, (iv) increasing or decreasing translational efficiency, (v) modifying localization of peptides or products expressed from nucleic acid reagents described herein, or (vi) increasing or decreasing the copy number of a nucleotide sequence of interest, (vii) expression of an anti-sense RNA, RNAi, siRNA, ribozyme and the like. In some embodiments, alteration of a nucleic acid reagent or nucleotide sequence can alter a region involved in feedback inhibition (e.g., 5' UTR, promoter and the like). A modification sometimes is made that can add or enhance binding of a feedback regulator and sometimes a modification is made that can reduce, inhibit or eliminate binding of a feedback regulator.

In certain embodiments, alteration of a nucleic acid reagent or nucleotide sequence can alter sequences involved in transcription initiation (e.g., promoters, 5' UTR, and the like). A modification sometimes can be made that can enhance or increase initiation from an endogenous or heterologous promoter element. A modification sometimes can be made that removes or disrupts sequences that increase or enhance transcription initiation, resulting in a decrease or elimination of transcription from an endogenous or heterologous promoter element.

In some embodiments, alteration of a nucleic acid reagent or nucleotide sequence can alter sequences involved in translational initiation or translational efficiency (e.g., 5' UTR, 3' UTR, codon triplets of higher or lower abundance, translational terminator sequences and the like, for example). A modification sometimes can be made that can increase or decrease translational initiation, modifying a ribosome binding site for example. A modification sometimes can be made that can increase or decrease translational efficiency. Removing or adding sequences that form hairpins and changing codon triplets to a more or less preferred codon are non-limiting examples of genetic modifications that can be made to alter translation initiation and translation efficiency.

In certain embodiments, alteration of a nucleic acid reagent or nucleotide sequence can alter sequences involved in localization of peptides, proteins or other desired products (e.g., adipic acid, for example). A modification sometimes can be made that can alter, add or remove sequences responsible for targeting a polypeptide, protein or product to an intracellular organelle, the periplasm, cellular membranes, or extracellularly. Transport of a heterologous product to a different intracellular space or extracellularly sometimes can reduce or eliminate the formation of inclusion bodies (e.g., insoluble aggregates of the desired product).

In some embodiments, alteration of a nucleic acid reagent or nucleotide sequence can alter sequences involved in increasing or decreasing the copy number of a nucleotide sequence of interest. A modification sometimes can be made that increases or decreases the number of copies of an ORF stably integrated into the genome of an organism or on an epigenetic nucleic acid reagent. Non-limiting examples of alterations that can increase the number of copies of a sequence of interest include, adding copies of the sequence of interest by duplication of regions in the genome (e.g., adding additional copies by recombination or by causing gene amplification of the host genome, for example), cloning additional copies of a sequence onto a nucleic acid reagent, or altering an ORI to increase the number of copies of an epigenetic nucleic acid reagent. Non-limiting examples of alterations that can decrease the number of copies of a sequence of interest include, removing copies of the sequence of interest by deletion or disruption of regions in the genome, removing additional copies of the sequence from epigenetic nucleic acid reagents, or altering an ORI to decrease the number of copies of an epigenetic nucleic acid reagent.

In certain embodiments, increasing or decreasing the expression of a nucleotide sequence of interest can also be accomplished by altering, adding or removing sequences involved in the expression of an anti-sense RNA, RNAi, siRNA, ribozyme and the like. The methods described above can be used to modify expression of anti-sense RNA, RNAi, siRNA, ribozyme and the like.

The methods and nucleic acid reagents described herein can be used to generate genetically modified microorganisms with altered activities in cellular processes involved in adipic acid synthesis. In some embodiments, an engineered microorganism described herein may comprise a heterologous polynucleotide encoding a polypeptide having 6-oxohexanoic acid dehydrogenase activity, and in certain embodiments, an engineered microorganism described herein may comprise a heterologous polynucleotide encoding a polypeptide having omega oxo fatty acid dehydrogenase activity. In some embodiments, an engineered microorganism described herein may comprise a heterologous polynucleotide encoding a polypeptide having 6-hydroxyhexanoic acid dehydrogenase activity, and in certain embodiments, an engineered microorganism described herein may comprise a heterologous polynucleotide encoding a polypeptide having omega hydroxyl fatty acid dehydrogenase activity. In some embodiments, the heterologous polynucleotide can be from a bacterium. In some embodiments, the bacterium can be an *Acinetobacter, Nocardia, Pseudomonas* or *Xanthobacter* bacterium.

In certain embodiments, an engineered microorganism described herein may comprise a heterologous polynucleotide encoding a polypeptide having hexanoate synthase subunit A activity. In some embodiments, an engineered microorganism described herein may comprise a heterologous polynucleotide encoding a polypeptide having hexanoate synthase subunit B activity. In certain embodiments, the heterologous polynucleotide independently is selected from a fungus. In some embodiments, the fungus can be an *Aspergillus* fungus. In certain embodiments, the *Aspergillus* fungus is *A. parasiticus*.

In some embodiments, an engineered microorganism described herein may comprise a heterologous polynucleotide encoding a polypeptide having monooxygenase activity. In certain embodiments, the heterologous polynucleotide can be from a bacterium. In some embodiments, the bacterium can be a *Bacillus* bacterium. In certain embodiments, the *Bacillus* bacterium is *B. megaterium*.

In some embodiments, an engineered microorganism described herein may comprise a genetic modification that results in primary hexanoate usage by monooxygenase activity. In certain embodiments, the genetic modification can reduce a polyketide synthase activity. In some embodiments, the engineered microorganism can be a eukaryote. In certain embodiments, the eukaryote can be a yeast. In some embodiments, the eukaryote may be a fungus. In certain embodiments, the yeast can be a *Candida* yeast. In some embodiments, the *Candida* yeast may be *C. troplicalis*. In certain embodiments, the fungus can be a *Yarrowia* fungus. In some embodiments the *Yarrowia* fungus may be *Y. lipolytica*. In certain embodiments, the fungus can be an *Aspergillus* fungus. In some embodiments, the *Aspergillus* fungus may be *A. parasiticus* or *A. nidulans*.

In certain embodiments, an engineered microorganism described herein may comprise a genetic modification that reduces 6-hydroxyhexanoic acid conversion. In some embodiments, the genetic modification can reduce 6-hydroxyhexanoic acid dehydrogenase activity. In certain embodiments, an engineered microorganism described herein may comprise a genetic modification that reduces beta-oxidation activity. In some embodiments, the genetic modification can reduce a target activity described herein.

Engineered microorganisms that produce adipic acid, as described herein, can comprise an altered monooxygenase activity, in certain embodiments. In some embodiments, the engineered microorganism described herein may comprise a genetic modification that alters the monooxygenase activity. In certain embodiments, the genetic modification can result in substantial hexanoate usage by the monooxygenase activity. In some embodiments, the genetic modification can reduce a polyketide synthase activity. In certain embodiments, the engineered microorganism described herein can comprise a heterologous polynucleotide encoding a polypeptide having monooxygenase activity. In certain embodiments, the heterologous polynucleotide can be from a bacterium. In some embodiments, the bacterium can be a *Bacillus* bacterium. In certain embodiments, the *Bacillus* bacterium is *B. megaterium*.

In some embodiments, the engineered microorganism described herein may comprise an altered hexanoate synthase activity. In certain embodiments, the altered hexanoate synthase activity is an altered hexanoate synthase subunit A activity, altered hexanoate synthase subunit B activity, or altered hexanoate synthase subunit A activity and altered hexanoate synthase subunit B activity. In some embodiments, the engineered microorganism may comprise a genetic alteration that adds or increases hexanoate synthase activity. In certain embodiments, the engineered microorganism may comprise a heterologous polynucleotide encoding a polypeptide having hexanoate synthase activity. In some embodiments, the heterologous polynucleotide can be from a fungus. In certain embodiments, the fungus can be an *Aspergillus* fungus. In some embodiments, the *Aspergillus* fungus is *A. parasiticus*.

Engineered microorganisms that produce adipic acid, as described herein, can comprise an altered thioesterase activity, in certain embodiments. In some embodiments, the engineered microorganism may comprise a genetic modification that adds or increases the thioesterase activity. In certain embodiments, the engineered microorganism may comprise a heterologous polynucleotide encoding a polypeptide having thioesterase activity.

In some embodiments, the engineered microorganism with an altered thioesterase activity may comprise an altered 6-oxohexanoic acid dehydrogenase activity, or an altered omega oxo fatty acid dehydrogenase activity. In certain embodiments, the engineered microorganism with an altered thioesterase activity may comprise a genetic modification that adds or increases 6-oxohexanoic acid dehydrogenase activity, or a genetic modification that adds or increases omega oxo fatty acid dehydrogenase activity. In some embodiments, the engineered microorganism may comprise a heterologous polynucleotide encoding a polypeptide having altered 6-oxohexanoic acid dehydrogenase activity, and in some embodiments, the engineered microorganism may comprise a heterologous polynucleotide encoding a polypeptide having altered omega oxo fatty acid dehydrogenase activity. In certain embodiments, the heterologous polynucleotide can be from a bacterium. In some embodiments, the bacterium can be an *Acinetobacter, Nocardia, Pseudomonas* or *Xanthobacter* bacterium.

Engineered microorganisms that produce adipic acid, as described herein, can comprise an altered 6-hydroxyhexanoic acid dehydrogenase activity, in certain embodiments, and in some embodiments, can comprise an altered omega hydroxyl fatty acid dehydrogenase activity. In certain embodiments, the engineered microorganism may comprise a genetic modification that adds or increases the 6-hydroxyhexanoic acid dehydrogenase activity and in some embodiments the engineered microorganism may comprise a genetic modification that adds or increases the omega hydroxyl fatty acid dehydrogenase activity. In certain embodiments, the engineered microorganism may comprise a heterologous polynucleotide encoding a polypeptide having altered 6-hydroxyhexanoic acid dehydrogenase activity, and in some embodiments, the engineered microorganism may comprise a heterologous polynucleotide encoding a polypeptide having altered omega hydroxyl fatty acid dehydrogenase activity. In some embodiments, the heterologous polynucleotide is from a bacterium. In certain embodiments, the bacterium can be an *Acinetobacter, Nocardia, Pseudomonas* or *Xanthobacter* bacterium. In some embodiments, the engineered microorganism can be a eukaryote. In certain embodiments, the eukaryote can be a yeast. In some embodiments, the eukaryote may be a fungus. In certain embodiments, the yeast can be a *Candida* yeast. In some embodiments, the *Candida* yeast may be *C. troplicalis*. In certain embodiments, the fungus can be a *Yarrowia* fungus. In some embodiments the *Yarrowia* fungus may be *Y. lipolytica*. In certain embodiments, the fungus can be an *Aspergillus* fungus. In some embodiments, the *Aspergillus* fungus may be *A. parasiticus* or *A. nidulans*.

In some embodiments, an engineered microorganism as described above may comprise a genetic modification that reduces 6-hydroxyhexanoic acid conversion. In certain embodiments, the genetic modification can reduce 6-hydroxyhexanoic acid dehydrogenase activity. In some embodiments the genetic may reduce beta-oxidation activity. In certain embodiments, the genetic modification may reduce a target activity described herein.

Engineered microorganisms can be prepared by altering, introducing or removing nucleotide sequences in the host genome or in stably maintained epigenetic nucleic acid reagents, as noted above. The nucleic acid reagents use to alter, introduce or remove nucleotide sequences in the host genome or epigenetic nucleic acids can be prepared using the methods described herein or available to the artisan.

Nucleic acid sequences having a desired activity can be isolated from cells of a suitable organism using lysis and nucleic acid purification procedures described in a known reference manual (e.g., Maniatis, T., E. F. Fritsch and J. Sambrook (1982) *Molecular Cloning: a Laboratory Manual*; Cold Spring Harbor Laboratory, Cold Spring Harbor, N.Y.) or using commercially available cell lysis and DNA purification reagents and kits. In some embodiments, nucleic acids used to engineer microorganisms can be provided for conducting methods described herein after processing of the organism containing the nucleic acid. For example, the nucleic acid of interest may be extracted, isolated, purified or amplified from a sample (e.g., from an organism of interest or culture containing a plurality of organisms of interest, like yeast or bacteria for example). The term "isolated" as used herein refers to nucleic acid removed from its original environment (e.g., the natural environment if it is naturally occurring, or a host cell if expressed exogenously), and thus is altered "by the hand of man" from its original environment. An isolated nucleic acid generally is provided with fewer non-nucleic acid components (e.g., protein, lipid) than the amount of components present in a source sample. A composition comprising isolated sample nucleic acid can be substantially isolated (e.g., about 90%, 91%, 92%, 93%, 94%, 95%, 96%, 97%, 98%, 99% or greater than 99% free of non-nucleic acid components). The term "purified" as used herein refers to sample nucleic acid provided that contains fewer nucleic acid species than in the sample source from which the sample nucleic acid is derived. A composition comprising sample nucleic acid may be substantially purified (e.g., about 90%, 91%, 92%, 93%, 94%, 95%, 96%, 97%, 98%, 99% or greater than 99% free of other nucleic acid species). The term "amplified" as used herein refers to subjecting nucleic acid of a cell, organism or sample to a process that linearly or exponentially generates amplicon nucleic acids having the same or substantially the same nucleotide sequence as the nucleotide sequence of the nucleic acid in the sample, or portion thereof. As noted above, the nucleic acids used to prepare nucleic acid reagents as described herein can be subjected to fragmentation or cleavage.

Amplification of nucleic acids is sometimes necessary when dealing with organisms that are difficult to culture. Where amplification may be desired, any suitable amplification technique can be utilized. Non-limiting examples of methods for amplification of polynucleotides include, polymerase chain reaction (PCR); ligation amplification (or ligase chain reaction (LCR)); amplification methods based on the use of Q-beta replicase or template-dependent polymerase (see US Patent Publication Number US20050287592); helicase-dependant isothermal amplification (Vincent et al., "Helicase-dependent isothermal DNA amplification". EMBO reports 5 (8): 795-800 (2004)); strand displacement amplification (SDA); thermophilic SDA nucleic acid sequence based amplification (3SR or NASBA) and transcription-associated amplification (TAA). Non-limiting examples of PCR amplification methods include standard PCR, AFLP-PCR, Allele-specific PCR, Alu-PCR, Asymmetric PCR, Colony PCR, Hot start PCR, Inverse PCR (IPCR), In situ PCR (ISH), Intersequence-specific PCR (ISSR-PCR), Long PCR, Multiplex PCR, Nested PCR, Quantitative PCR, Reverse Transcriptase PCR(RT-PCR), Real Time PCR, Single cell PCR, Solid phase PCR, combinations thereof, and the like. Reagents and hardware for conducting PCR are commercially available.

Protocols for conducting the various type of PCR listed above are readily available to the artisan. PCR conditions can be dependent upon primer sequences, target abundance, and the desired amount of amplification, and therefore, one of skill in the art may choose from a number of PCR protocols available (see, e.g., U.S. Pat. Nos. 4,683,195 and 4,683,202; and PCR Protocols: A Guide to Methods and Applications, Innis et al., eds, 1990. PCR often is carried out as an automated process with a thermostable enzyme. In this process, the temperature of the reaction mixture is cycled through a denaturing region, a primer-annealing region, and an extension reaction region automatically. Machines specifically adapted for this purpose are commercially available. A non-limiting example of a PCR protocol that may be suitable for embodiments described herein is, treating the sample at 95° C. for 5 minutes; repeating forty-five cycles of 95° C. for 1 minute, 59° C. for 1 minute, 10 seconds, and 72° C. for 1 minute 30 seconds; and then treating the sample at 72° C. for 5 minutes. Additional PCR protocols are described in the example section. Multiple cycles frequently are performed using a commercially available thermal cycler. Suitable isothermal amplification processes known and selected by the person of ordinary skill in the art also may be applied, in certain embodiments. In some embodiments, nucleic acids encoding polypeptides with a desired activity can be isolated by amplifying the desired sequence from an organism having the desired activity using oligonucleotides or primers designed based on sequences described herein.

Amplified, isolated and/or purified nucleic acids can be cloned into the recombinant DNA vectors described in Figures herein or into suitable commercially available recombinant DNA vectors. Cloning of nucleic acid sequences of interest into recombinant DNA vectors can facilitate further manipulations of the nucleic acids for preparation of nucleic acid reagents, (e.g., alteration of nucleotide sequences by mutagenesis, homologous recombination, amplification and the like, for example). Standard cloning procedures (e.g., enzymic digestion, ligation, and the like) are known (e.g., described in Maniatis, T., E. F. Fritsch and J. Sambrook (1982) *Molecular Cloning: a Laboratory Manual*; Cold Spring Harbor Laboratory, Cold Spring Harbor, N.Y.).

In some embodiments, nucleic acid sequences prepared by isolation or amplification can be used, without any further modification, to add an activity to a microorganism and thereby create a genetically modified or engineered microorganism. In certain embodiments, nucleic acid sequences prepared by isolation or amplification can be genetically modified to alter (e.g., increase or decrease, for example) a desired activity. In some embodiments, nucleic acids, used to add an activity to an organism, sometimes are genetically modified to optimize the heterologous polynucleotide sequence encoding the desired activity (e.g., polypeptide or protein, for example). The term "optimize" as used herein can refer to alteration to increase or enhance expression by preferred codon usage. The term optimize can also refer to modifications to the amino acid sequence to increase the activity of a polypeptide or protein, such that the activity exhibits a higher catalytic activity as compared to the "natural" version of the polypeptide or protein.

Nucleic acid sequences of interest can be genetically modified using methods known in the art. Mutagenesis techniques are particularly useful for small scale (e.g., 1, 2, 5, 10 or more nucleotides) or large scale (e.g., 50, 100, 150, 200, 500, or more nucleotides) genetic modification. Mutagenesis allows the artisan to alter the genetic information of an organism in a stable manner, either naturally (e.g., isolation using selection and screening) or experimentally by the use of chemicals, radiation or inaccurate DNA replication (e.g., PCR mutagenesis). In some embodiments, genetic modification can be performed by whole scale synthetic synthesis of nucleic acids, using a native nucleotide sequence as the reference sequence, and modifying nucleotides that can result in the desired alteration of activity. Mutagenesis methods sometimes are specific or targeted to specific regions or nucleotides (e.g., site-directed mutagenesis, PCR-based site-directed mutagenesis, and in vitro mutagenesis techniques such as transplacement and in vivo oligonucleotide site-directed mutagenesis, for example). Mutagenesis methods sometimes are non-specific or random with respect to the placement of genetic modifications (e.g., chemical mutagenesis, insertion element (e.g., insertion or transposon elements) and inaccurate PCR based methods, for example).

Site directed mutagenesis is a procedure in which a specific nucleotide or specific nucleotides in a DNA molecule are mutated or altered. Site directed mutagenesis typically is performed using a nucleic acid sequence of interest cloned into a circular plasmid vector. Site-directed mutagenesis requires that the wild type sequence be known and used a platform for the genetic alteration. Site-directed mutagenesis sometimes is referred to as oligonucleotide-directed mutagenesis because the technique can be performed using oligonucleotides which have the desired genetic modification incorporated into the complement a nucleotide sequence of interest. The wild type sequence and the altered nucleotide are allowed to hybridize and the hybridized nucleic acids are extended and replicated using a DNA polymerase. The double stranded nucleic acids are introduced into a host (e.g., E. coli, for example) and further rounds of replication are carried out in vivo. The transformed cells carrying the mutated nucleic acid sequence are then selected and/or screened for those cells carrying the correctly mutagenized sequence. Cassette mutagenesis and PCR-based site-directed mutagenesis are further modifications of the site-directed mutagenesis technique. Site-directed mutagenesis can also be performed in vivo (e.g., transplacement "pop-in pop-out", In vivo site-directed mutagenesis with synthetic oligonucleotides and the like, for example).

PCR-based mutagenesis can be performed using PCR with oligonucleotide primers that contain the desired mutation or mutations. The technique functions in a manner similar to standard site-directed mutagenesis, with the exception that a thermocycler and PCR conditions are used to replace replication and selection of the clones in a microorganism host. As PCR-based mutagenesis also uses a circular plasmid vector, the amplified fragment (e.g., linear nucleic acid molecule) containing the incorporated genetic modifications can be separated from the plasmid containing the template sequence after a sufficient number of rounds of thermocycler amplification, using standard electrophorectic procedures. A modification of this method uses linear amplification methods and a pair of mutagenic primers that amplify the entire plasmid. The procedure takes advantage of the E. coli Dam methylase system which causes DNA replicated in vivo to be sensitive to the restriction endonucleases DpnI. PCR synthesized DNA is not methylated and is therefore resistant to DpnI. This approach allows the template plasmid to be digested, leaving the genetically modified, PCR synthesized plasmids to be isolated and transformed into a host bacteria for DNA repair and replication, thereby facilitating subsequent cloning and identification steps. A certain amount of randomness can be added to PCR-based sited directed mutagenesis by using partially degenerate primers.

Recombination sometimes can be used as a tool for mutagenesis. Homologous recombination allows the artisan to specifically target regions of known sequence for insertion of heterologous nucleotide sequences using the host organisms natural DNA replication and repair enzymes. Homologous recombination methods sometimes are referred to as "pop in pop out" mutagenesis, transplacement, knock out mutagenesis or knock in mutagenesis. Integration of a nucleic acid sequence into a host genome is a single cross over event, which inserts the entire nucleic acid reagent (e.g., pop in). A second cross over event excises all but a portion of the nucleic acid reagent, leaving behind a heterologous sequence, often referred to as a "footprint" (e.g., pop out). Mutagenesis by insertion (e.g., knock in) or by double recombination leaving behind a disrupting heterologous nucleic acid (e.g., knock out) both server to disrupt or "knock out" the function of the gene or nucleic acid sequence in which insertion occurs. By combining selectable markers and/or auxotrophic markers with nucleic acid reagents designed to provide the appropriate nucleic acid target sequences, the artisan can target a selectable nucleic acid reagent to a specific region, and then select for recombination events that "pop out" a portion of the inserted (e.g., "pop in") nucleic acid reagent.

Such methods take advantage of nucleic acid reagents that have been specifically designed with known target nucleic acid sequences at or near a nucleic acid or genomic region of interest. Popping out typically leaves a "foot print" of left over sequences that remain after the recombination event. The left over sequence can disrupt a gene and thereby reduce or eliminate expression of that gene. In some embodiments, the method can be used to insert sequences, upstream or downstream of genes that can result in an enhancement or reduction in expression of the gene. In certain embodiments, new genes can be introduced into the genome of a host organism using similar recombination or "pop in" methods. An example of a yeast recombination system using the ura3 gene and 5-FOA were described briefly above and further detail is presented herein.

A method for modification is described in Alani et al., "A method for gene disruption that allows repeated use of URA3 selection in the construction of multiply disrupted yeast strains", Genetics 116(4):541-545 August 1987. The original method uses a Ura3 cassette with 1000 base pairs (bp) of the same nucleotide sequence cloned in the same orientation on either side of the URA3 cassette. Targeting sequences of about 50 bp are added to each side of the construct. The double stranded targeting sequences are complementary to sequences in the genome of the host organism. The targeting sequences allow site-specific recombination in a region of interest. The modification of the original technique replaces the two 1000 bp sequence direct repeats with two 200 bp direct repeats. The modified method also uses 50 bp targeting sequences. The modification reduces or eliminates recombination of a second knock out into the 1000 bp repeat left behind in a first mutagenesis, therefore allowing multiply knocked out yeast. Additionally, the 200 bp sequences used herein are uniquely designed, self-assembling sequences that leave behind identifiable footprints. The technique used to design the sequences incorporate design features such as low identity to the yeast genome, and low identity to each other. Therefore a library of the self-assembling sequences can be generated to allow multiple knockouts in the same organism, while reducing or eliminating the potential for integration into a previous knockout.

As noted above, the URA3 cassette makes use of the toxicity of 5-FOA in yeast carrying a functional URA3 gene. Uracil synthesis deficient yeast are transformed with the modified URA3 cassette, using standard yeast transformation protocols, and the transformed cells are plated on minimal media minus uracil. In some embodiments, PCR can be used to verify correct insertion into the region of interest in the host genome, and certain embodiments the PCR step can be omitted. Inclusion of the PCR step can reduce the number of transformants that need to be counter selected to "pop out" the URA3 cassette. The transformants (e.g., all or the ones determined to be correct by PCR, for example) can then be counter-selected on media containing 5-FOA, which will select for recombination out (e.g., popping out) of the URA3 cassette, thus rendering the yeast ura3 deficient again, and resistant to 5-FOA toxicity. Targeting sequences used to direct recombination events to specific regions are presented herein. A modification of the method described above can be used to integrate genes in to the chromosome, where after recombination a functional gene is left in the chromosome next to the 200 bp footprint.

In some embodiments, other auxotrophic or dominant selection markers can be used in place of URA3 (e.g., an auxotrophic selectable marker), with the appropriate change in selection media and selection agents. Auxotrophic selectable markers are used in strains deficient for synthesis of a required biological molecule (e.g., amino acid or nucleoside, for example). Non-limiting examples of additional auxotrophic markers include; HIS3, TRP1, LEU2, LEU2-d, and LYS2. Certain auxotrophic markers (e.g., URA3 and LYS2) allow counter selection to select for the second recombination event that pops out all but one of the direct repeats of the recombination construct. HIS3 encodes an activity involved in histidine synthesis. TRP1 encodes an activity involved in tryptophan synthesis. LEU2 encodes an activity involved in leucine synthesis. LEU2-d is a low expression version of LEU2 that selects for increased copy number (e.g., gene or plasmid copy number, for example) to allow survival on minimal media without leucine. LYS2 encodes an activity involved in lysine synthesis, and allows counter selection for recombination out of the LYS2 gene using alpha-amino adipate (α-amino adipate).

Dominant selectable markers are useful because they also allow industrial and/or prototrophic strains to be used for genetic manipulations. Additionally, dominant selectable markers provide the advantage that rich medium can be used for plating and culture growth, and thus growth rates are markedly increased. Non-limiting examples of dominant selectable markers include; Tn903 kan$^r$, Cm$^r$, Hyg$^r$, CUP1, and DHFR. Tn903 kan$^r$ encodes an activity involved in kanamycin antibiotic resistance (e.g., typically neomycin phosphotransferase II or NPTII, for example). Cm$^r$ encodes an activity involved in chloramphenicol antibiotic resistance (e.g., typically chloramphenicol acetyl transferase or CAT, for example). Hyg$^r$ encodes an activity involved in hygromycin resistance by phosphorylation of hygromycin B (e.g., hygromycin phosphotransferase, or HPT). CUP1 encodes an activity involved in resistance to heavy metal (e.g., copper, for example) toxicity. DHFR encodes a dihydrofolate reductase activity which confers resistance to methotrexate and sulfanilamde compounds.

In contrast to site-directed or specific mutagenesis, random mutagenesis does not require any sequence information and can be accomplished by a number of widely different methods. Random mutagenesis often is used to create mutant libraries that can be used to screen for the desired genotype or phenotype. Non-limiting examples of random mutagenesis include; chemical mutagenesis, UV-induced mutagenesis, insertion element or transposon-mediated mutagenesis, DNA shuffling, error-prone PCR mutagenesis, and the like.

Chemical mutagenesis often involves chemicals like ethyl methanesulfonate (EMS), nitrous acid, mitomycin C, N-methyl-N-nitrosourea (MNU), diepoxybutane (DEB), 1, 2, 7, 8-diepoxyoctane (DEO), methyl methane sulfonate (MMS), N-methyl-N'-nitro-N-nitrosoguanidine (MNNG), 4-nitroquinoline 1-oxide (4-NQO), 2-methyloxy-6-chloro-9(3-[ethyl-2-chloroethyl]-aminopropylamino)-acridinedihydrochloride (ICR-170), 2-amino purine (2AP), and hydroxylamine (HA), provided herein as non-limiting examples. These chemicals can cause base-pair substitutions, frameshift mutations, deletions, transversion mutations, transition mutations, incorrect replication, and the like. In some embodiments, the mutagenesis can be carried out in vivo. Sometimes the mutagenic process involves the use of the host organisms DNA replication and repair mechanisms to incorporate and replicate the mutagenized base or bases. Another type of chemical mutagenesis involves the use of base-analogs. The use of base-analogs cause incorrect base pairing which in the following round of replication is corrected to a mismatched nucleotide when compared to the starting sequence. Base analog mutagenesis introduces a small amount of non-randomness to random mutagenesis, because specific base analogs can be chose which can be incorporated at certain nucleotides in the starting sequence. Correction of the mispairing typically yields a known substitution. For example, Bromo-deoxyuridine (BrdU) can be incorporated into DNA and replaces T in the sequence. The host DNA repair and replication machinery can sometime correct the defect, but sometimes will mispair the BrdU with a G. The next round of replication then causes a G-C transversion from the original A-T in the native sequence.

Ultra violet (UV) induced mutagenesis is caused by the formation of thymidine dimers when UV light irradiates chemical bonds between two adjacent thymine residues. Excision repair mechanism of the host organism correct the lesion in the DNA, but occasionally the lesion is incorrectly repaired typically resulting in a C to T transition.

Insertion element or transposon-mediated mutagenesis makes use of naturally occurring or modified naturally occurring mobile genetic elements. Transposons often encode accessory activities in addition to the activities necessary for transposition (e.g., movement using a transposase activity, for example). In many examples, transposon accessory activities are antibiotic resistance markers (e.g., see Tn903 kan$^r$ described above, for example). Insertion elements typically only encode the activities necessary for movement of the nucleic acid sequence. Insertion element and transposon mediated mutagenesis often can occur randomly, however specific target sequences are known for some transposons. Mobile genetic elements like IS elements or Transposons (Tn) often have inverted repeats, direct repeats or both inverted and direct repeats flanking the region coding for the transposition genes. Recombination events catalyzed by the transposase cause the element to remove itself from the genome and move to a new location, leaving behind a portion of an inverted or direct repeat. Classic examples of transposons are the "mobile genetic elements" discovered in maize. Transposon mutagenesis kits are commercially available which are designed to leave behind a 5 codon insert (e.g., Mutation Generation System kit, Finnzymes, World Wide Web URL finnzymes.us, for example). This allows the artisan to identify the insertion site, without fully disrupting the function of most genes.

DNA shuffling is a method which uses DNA fragments from members of a mutant library and reshuffles the fragments randomly to generate new mutant sequence combinations. The fragments are typically generated using DNaseI, followed by random annealing and re-joining using self priming PCR. The DNA overhanging ends, from annealing of random fragments, provide "primer" sequences for the PCR process. Shuffling can be applied to libraries generated by any of the above mutagenesis methods.

Error prone PCR and its derivative rolling circle error prone PCR uses increased magnesium and manganese concentrations in conjunction with limiting amounts of one or two nucleotides to reduce the fidelity of the Taq polymerase. The error rate can be as high as 2% under appropriate conditions, when the resultant mutant sequence is compared to the wild type starting sequence. After amplification, the library of mutant coding sequences must be cloned into a suitable plasmid. Although point mutations are the most common types of mutation in error prone PCR, deletions and frameshift mutations are also possible. There are a number of commercial error-prone PCR kits available, including those from Stratagene and Clontech (e.g., World Wide Web URL strategene.com and World Wide Web URL clontech.com, respectively, for example). Rolling circle error-prone PCR is a variant of error-prone PCR in which wild-type sequence is first cloned into a plasmid, then the whole plasmid is amplified under error-prone conditions.

As noted above, organisms with altered activities can also be isolated using genetic selection and screening of organisms challenged on selective media or by identifying naturally occurring variants from unique environments. For example, 2-Deoxy-D-glucose is a toxic glucose analog. Growth of yeast on this substance yields mutants that are glucose-deregulated. A number of mutants have been isolated using 2-Deoxy-D-glucose including transport mutants, and mutants that ferment glucose and galactose simultaneously instead of glucose first then galactose when glucose is depleted. Similar techniques have been used to isolate mutant microorganisms that can metabolize plastics (e.g., from landfills), petrochemicals (e.g., from oil spills), and the like, either in a laboratory setting or from unique environments.

Similar methods can be used to isolate naturally occurring mutations in a desired activity when the activity exists at a relatively low or nearly undetectable level in the organism of choice, in some embodiments. The method generally consists of growing the organism to a specific density in liquid culture, concentrating the cells, and plating the cells on various concentrations of the substance to which an increase in metabolic activity is desired. The cells are incubated at a moderate growth temperature, for 5 to 10 days. To enhance the selection process, the plates can be stored for another 5 to 10 days at a low temperature. The low temperature sometimes can allow strains that have gained or increased an activity to continue growing while other strains are inhibited for growth at the low temperature. Following the initial selection and secondary growth at low temperature, the plates can be replica plated on higher or lower concentrations of the selection substance to further select for the desired activity.

A native, heterologous or mutagenized polynucleotide can be introduced into a nucleic acid reagent for introduction into a host organism, thereby generating an engineered microorganism.

Standard recombinant DNA techniques (restriction enzyme digests, ligation, and the like) can be used by the artisan to combine the mutagenized nucleic acid of interest into a suitable nucleic acid reagent capable of (i) being stably maintained by selection in the host organism, or (ii) being integrating into the genome of the host organism. As noted above, sometimes nucleic acid reagents comprise two replication origins to allow the same nucleic acid reagent to be manipulated in bacterial before final introduction of the final product into the host organism (e.g., yeast or fungus for example). Standard molecular biology and recombinant DNA methods are known (e.g., described in Maniatis, T., E. F. Fritsch and J. Sambrook (1982) *Molecular Cloning: a Laboratory Manual*; Cold Spring Harbor Laboratory, Cold Spring Harbor, N.Y.).

Nucleic acid reagents can be introduced into microorganisms using various techniques. Non-limiting examples of methods used to introduce heterologous nucleic acids into various organisms include; transformation, transfection, transduction, electroporation, ultrasound-mediated transformation, particle bombardment and the like. In some instances the addition of carrier molecules (e.g., bis-benzimdazolyl compounds, for example, see U.S. Pat. No. 5,595,899) can increase the uptake of DNA in cells typically though to be difficult to transform by conventional methods. Conventional methods of transformation are known (e.g., described in Maniatis, T., E. F. Fritsch and J. Sambrook (1982) *Molecular Cloning: a Laboratory Manual*; Cold Spring Harbor Laboratory, Cold Spring Harbor, N.Y.).

Culture, Production and Process Methods

Engineered microorganisms often are cultured under conditions that optimize yield of a target molecule (e.g., six-carbon target molecule). Non-limiting examples of such target molecules are adipic acid and 6-hydroxyhexanoic acid. Culture conditions often optimize activity of one or more of the following activities: 6-oxohexanoic acid dehydrogenase activity, omega oxo fatty acid dehydrogenase activity, 6-hydroxyhexanoic acid dehydrogenase activity, omega hydroxyl fatty acid dehydrogenase activity, hexanoate synthase, monooxygenase, monooxygenase reductase, fatty alcohol oxidase, acyl-CoA ligase, acyl-CoA oxidase, enoyl-CoA hydratase, 3-hydroxyacyl-CoA dehydrogenase, and/or acetyl-CoA C-acyltransferase activities. In general, non-limiting examples of conditions that may be optimized include the type and amount of carbon source, the type and amount of nitrogen source, the carbon-to-nitrogen ratio, the oxygen level, growth temperature, pH, length of the biomass production phase, length of target product accumulation phase, and time of cell harvest.

Culture media generally contain a suitable carbon source. Carbon sources useful for culturing microorganisms and/or fermentation processes sometimes are referred to as feedstocks. The term "feedstock" as used herein refers to a composition containing a carbon source that is provided to an organism, which is used by the organism to produce energy and metabolic products useful for growth. A feedstock may be a natural substance, a "man-made substance," a purified or isolated substance, a mixture of purified substances, a mixture of unpurified substances or combinations thereof. A feedstock often is prepared by and/or provided to an organism by a person, and a feedstock often is formulated prior to administration to the organism. A carbon source may include, but is not limited to including, one or more of the following substances: monosaccharides (e.g., also referred to as "saccharides," which include 6-carbon sugars (e.g., glucose, fructose), 5-carbon sugars (e.g., xylose and other pentoses) and the like), disaccharides (e.g., lactose, sucrose), oligosaccharides (e.g., glycans, homopolymers of a monosaccharide), polysaccharides (e.g., starch, cellulose, heteropolymers of monosaccharides or mixtures thereof), sugar alcohols (e.g., glycerol), and renewable feedstocks (e.g., cheese whey permeate, cornsteep liquor, sugar beet molasses, barley malt).

Carbon sources also can be selected from one or more of the following non-limiting examples: paraffin (e.g., saturated paraffin, unsaturated paraffin, substituted paraffin, linear paraffin, branched paraffin, or combinations thereof); alkanes (e.g., hexane), alkenes or alkynes, each of which may be linear, branched, saturated, unsaturated, substituted or combinations thereof (described in greater detail below); linear or branched alcohols (e.g., hexanol); fatty acids (e.g., about 1 carbon to about 60 carbons, including free fatty acids, soap stock, for example); esters of fatty acids; monoglycerides; diglycerides; triglycerides, phospholipids. Non-limiting commercial sources of products for preparing feedstocks include plants or plant products (e.g., vegetable oils (e.g., almond oil, canola oil, cocoa butter, coconut oil, corn oil, cottonseed oil, flaxseed oil, grape seed oil, illipe, olive oil, palm oil, palm olein, palm kernel oil, safflower oil, peanut oil, soybean oil, sesame oil, shea nut oil, sunflower oil walnut oil, the like and combinations thereof) and animal fats (e.g., beef tallow, butterfat, lard, cod liver oil). A carbon source may include a petroleum product and/or a petroleum distillate (e.g., diesel, fuel oils, gasoline, kerosene, paraffin wax, paraffin oil, petrochemicals).

The term "paraffin" as used herein refers to the common name for alkane hydrocarbons, independent of the source (e.g., plant derived, petroleum derived, chemically synthesized, fermented by a microorganism), or carbon chain length. A carbon source sometimes comprises a paraffin, and in some embodiments, a paraffin is predominant in a carbon source (e.g., about 75%, 80%, 85%, 90% or 95% paraffin). A paraffin sometimes is saturated (e.g., fully saturated), sometimes includes one or more unsaturations (e.g., about 1, 2, 3, 4, 5, 6, 7, 8, 9, 10 unsaturations) and sometimes is substituted with one or more non-hydrogen substituents. Non-limiting examples of non-hydrogen substituents include halo, acetyl, $=O$, $=N-CN$, $=N-OR$, $=NR$, $OR$, $NR_2$, $SR$, $SO_2R$, $SO_2NR_2$, $NRSO_2R$, $NRCONR_2$, $NRCOOR$, $NRCOR$, $CN$, $COOR$, $CONR_2$, $OOCR$, $COR$, and $NO_2$, where each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R is optionally substituted with halo, $=O$, $=N-CN$, $=N-OR'$, $=NR'$, $OR'$, $NR'_2$, $SR'$, $SO_2R'$, $SO_2NR'_2$, $NR'SO_2R'$, $NR'CONR'_2$, $NR'COOR'$, $NR'COR'$, $CN$, $COOR'$, $CONR'_2$, $OOCR'$, $COR'$, and $NO_2$, where each R' is independently H, C1-C8 alkyl, C2-C8 heteroalkyl, C1-C8 acyl, C2-C8 heteroacyl, C6-C10 aryl or C5-C10 heteroaryl.

In some embodiments a feedstock is selected according to the genotype and/or phenotype of the engineered microorganism to be cultured. For example, a feedstock rich in 12-carbon fatty acids, 12-carbon dicarboxylic acids or 12-carbon paraffins, or a mixture of 10-carbon and 12-carbon compounds can be useful for culturing yeast strains harboring an alteration that partially blocks beta oxidation by disrupting POX4 activity, as described herein. Non-limiting examples of carbon sources having 10 and/or 12 carbons include fats (e.g., coconut oil, palm kernel oil), paraffins (e.g., alkanes, alkenes, or alkynes) having 10 or 12 carbons, (e.g., decane, dodecane (also referred to as adakane12, bihexyl, dihexyl and duodecane), alkene and alkyne derivatives), fatty acids (decanoic acid, dodecanoic acid), fatty alcohols (decanol, dodecanol), the like, non-toxic substituted derivatives or combinations thereof.

A carbon source sometimes comprises an alkyl, alkenyl or alkynyl compound or molecule (e.g., a compound that includes an alkyl, alkenyl or alkynyl moiety (e.g., alkane, alkene, alkyne)). In certain embodiments, an alkyl, alkenyl or alkynyl molecule, or combination thereof, is predominant in a carbon source (e.g., about 75%, 80%, 85%, 90% or 95% of such molecules). As used herein, the terms "alkyl," "alkenyl" and "alkynyl" include straight-chain (referred to herein as "linear"), branched-chain (referred to herein as "non-linear"), cyclic monovalent hydrocarbyl radicals, and combinations of these, which contain only C and H atoms when they are unsubstituted. Non-limiting examples of alkyl moieties include methyl, ethyl, isobutyl, cyclohexyl, cyclopentylethyl, 2-propenyl, 3-butynyl, and the like. An alkyl that contains only C and H atoms and is unsubstituted sometimes is referred to as "saturated." An alkenyl or alkynyl generally is "unsaturated" as it contains one or more double bonds or triple bonds, respectively. An alkenyl can include any number of double bonds, such as 1, 2, 3, 4 or 5 double bonds, for example. An alkynyl can include any number of triple bonds, such as 1, 2, 3, 4 or 5 triple bonds, for example. Alkyl, alkenyl and alkynyl molecules sometimes contain between about 2 to about 60 carbon atoms (C). For example, an alkyl, alkenyl and alkynyl molecule can include about 1 carbon atom, about 2 carbon atoms, about 3 carbon atoms, about 4 carbon atoms, about 5 carbon atoms, about 6 carbon atoms, about 7 carbon atoms, about 8 carbon atoms, about 9 carbon atoms, about 10 carbon atoms, about 12 carbon atoms, about 14 carbon atoms, about 16 carbon atoms, about 18 carbon atoms, about 20 carbon atoms, about 22 carbon atoms, about 24 carbon atoms, about 26 carbon atoms, about 28 carbon atoms, about 30 carbon atoms, about 32 carbon atoms, about 34 carbon atoms, about 36 carbon atoms, about 38 carbon atoms, about 40 carbon atoms, about 42 carbon atoms, about 44 carbon atoms, about 46 carbon atoms, about 48 carbon atoms, about 50 carbon atoms, about 52 carbon atoms, about 54 carbon atoms, about 56 carbon atoms, about 58 carbon atoms or about 60 carbon atoms. In some embodiments, paraffins can have a mean number of carbon atoms of between about 8 to about 18 carbon atoms (e.g., about 8 carbon atoms, about 9 carbon atoms, about 10 carbon atoms, about 11 carbon atoms, about 12 carbon atoms, about 13 carbon atoms, about 14 carbon atoms, about 15 carbon atoms, about 16 carbon atoms, about 17 carbon atoms and about 18 carbon atoms). A single group can include more than one type of multiple bond, or more than one multiple bond. Such groups are included within the definition of the term "alkenyl" when they contain at least one carbon-carbon double bond, and are included within the term "alkynyl" when they contain at least one carbon-carbon triple bond. Alkyl, alkenyl and alkynyl molecules include molecules that comprise an alkyl, alkenyl and/or alkynyl moiety, and include molecules that consist of an alkyl, alkenyl or alkynyl moiety (i.e., alkane, alkene and alkyne molecules).

Alkyl, alkenyl and alkynyl substituents sometimes contain 1-20C (alkyl) or 2-20C (alkenyl or alkynyl). They can contain about 8-14C or about 10-14C in some embodiments. A single group can include more than one type of multiple bond, or more than one multiple bond. Such groups are included within the definition of the term "alkenyl" when they contain at least one carbon-carbon double bond, and are included within the term "alkynyl" when they contain at least one carbon-carbon triple bond.

Alkyl, alkenyl and alkynyl groups or compounds sometimes are substituted to the extent that such substitution can be synthesized and can exist. Typical substituents include, but are not limited to, halo, acetyl, $=O$, $=N-CN$, $=N-OR$, $=NR$, $OR$, $NR_2$, $SR$, $SO_2R$, $SO_2NR_2$, $NRSO_2R$, $NRCONR_2$, $NRCOOR$, $NRCOR$, $CN$, $COOR$, $CONR_2$, $OOCR$, $COR$, and $NO_2$, where each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C11 aryl, or C5-C11 heteroaryl, and each R is optionally substituted with halo, =O, =N—CN, =N—OR', =NR', OR', NR'$_2$, SR', SO$_2$R', SO$_2$NR'$_2$, NR'SO$_2$R', NR'CONR'$_2$, NR'COR', NR'COOR', CN, COOR', CONR'$_2$, OOCR', COR', and NO$_2$, where each R' is independently H, C1-C8 alkyl, C2-C8 heteroalkyl, C1-C8 acyl, C2-C8 heteroacyl, C6-C10 aryl or C5-C10 heteroaryl. Alkyl, alkenyl and alkynyl groups can also be substituted by C1-C8 acyl, C2-C8 heteroacyl, C6-C10 aryl or C5-C10 heteroaryl, each of which can be substituted by the substituents that are appropriate for the particular group.

"Acetylene" or "acetyl" substituents are 2-10C alkynyl groups that are optionally substituted, and are of the formula —C≡C—Ri, where Ri is H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and each Ri group is optionally substituted with one or more substituents selected from halo, =O, =N—CN, =N—OR', =NR', OR', NR'2, SR', SO$_2$R', SO$_2$NR'$_2$, NR'SO$_2$R', NR'CONR'$_2$, NR'COOR', NR'COR', CN, COOR', CONR'$_2$, OOCR', COR', and NO$_2$, where each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O; and where two R' can be linked to form a 3-7 membered ring optionally containing up to three heteroatoms selected from N, O and S. In some embodiments, Ri of —C≡C—Ri is H or Me.

A carbon source sometimes comprises a heteroalkyl, heteroalkenyl and/or heteroalkynyl molecule or compound (e.g., comprises heteroalkyl, heteroalkenyl and/or heteroalkynyl moiety (e.g., heteroalkane, heteroalkene or heteroalkyne)). "Heteroalkyl", "heteroalkenyl", and "heteroalkynyl" and the like are defined similarly to the corresponding hydrocarbyl (alkyl, alkenyl and alkynyl) groups, but the 'hetero' terms refer to groups that contain one to three O, S or N heteroatoms or combinations thereof within the backbone; thus at least one carbon atom of a corresponding alkyl, alkenyl, or alkynyl group is replaced by one of the specified heteroatoms to form a heteroalkyl, heteroalkenyl, or heteroalkynyl group. The typical and sizes for heteroforms of alkyl, alkenyl and alkynyl groups are generally the same as for the corresponding hydrocarbyl groups, and the substituents that may be present on the heteroforms are the same as those described above for the hydrocarbyl groups. For reasons of chemical stability, it is also understood that, unless otherwise specified, such groups do not include more than two contiguous heteroatoms except where an oxo group is present on N or S as in a nitro or sulfonyl group.

The term "alkyl" as used herein includes cycloalkyl and cycloalkylalkyl groups and compounds, the term "cycloalkyl" may be used herein to describe a carbocyclic non-aromatic compound or group that is connected via a ring carbon atom, and "cycloalkylalkyl" may be used to describe a carbocyclic non-aromatic compound or group that is connected to a molecule through an alkyl linker. Similarly, "heterocyclyl" may be used to describe a non-aromatic cyclic group that contains at least one heteroatom as a ring member and that is connected to the molecule via a ring atom, which may be C or N; and "heterocyclylalkyl" may be used to describe such a group that is connected to another molecule through a linker. The sizes and substituents that are suitable for the cycloalkyl, cycloalkylalkyl, heterocyclyl, and heterocyclylalkyl groups are the same as those described above for alkyl groups. As used herein, these terms also include rings that contain a double bond or two, as long as the ring is not aromatic.

A carbon source sometimes comprises an acyl compound or moiety (e.g., compound comprising an acyl moiety). As used herein, "acyl" encompasses groups comprising an alkyl, alkenyl, alkynyl, aryl or arylalkyl radical attached at one of the two available valence positions of a carbonyl carbon atom, and heteroacyl refers to the corresponding groups where at least one carbon other than the carbonyl carbon has been replaced by a heteroatom chosen from N, O and S. Thus heteroacyl includes, for example, —C(=O)OR and —C(=O)NR$_2$ as well as —C(=O)-heteroaryl.

Acyl and heteroacyl groups are bonded to any group or molecule to which they are attached through the open valence of the carbonyl carbon atom. Typically, they are C1-C8 acyl groups, which include formyl, acetyl, pivaloyl, and benzoyl, and C2-C8 heteroacyl groups, which include methoxyacetyl, ethoxycarbonyl, and 4-pyridinoyl. The hydrocarbyl groups, aryl groups, and heteroforms of such groups that comprise an acyl or heteroacyl group can be substituted with the substituents described herein as generally suitable substituents for each of the corresponding component of the acyl or heteroacyl group.

A carbon source sometimes comprises one or more aromatic moieties and/or heteroaromatic moieties. "Aromatic" moiety or "aryl" moiety refers to a monocyclic or fused bicyclic moiety having the well-known characteristics of aromaticity; examples include phenyl and naphthyl. Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5 membered rings as well as 6 membered rings. Typical heteroaromatic systems include monocyclic C5-C6 aromatic groups such as pyridyl, pyrimidyl, pyrazinyl, thienyl, furanyl, pyrrolyl, pyrazolyl, thiazolyl, oxazolyl, and imidazolyl and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms. The monocyclic heteroaryls sometimes contain 5-6 ring members, and the bicyclic heteroaryls sometimes contain 8-10 ring members.

Aryl and heteroaryl moieties may be substituted with a variety of substituents including C1-C8 alkyl, C2-C8 alkenyl, C2-C8 alkynyl, C5-C12 aryl, C1-C8 acyl, and heteroforms of these, each of which can itself be further substituted; other substituents for aryl and heteroaryl moieties include halo, OR, NR$_2$, SR, SO$_2$R, SO$_2$NR$_2$, NRSO$_2$R, NRCONR$_2$, NRCOOR, NRCOR, CN, COOR, CONR$_2$, OOCR, COR, and NO$_2$, where each R is independently H, C1-C8 alkyl, C2-C8 heteroalkyl, C2-C8 alkenyl, C2-C8 heteroalkenyl, C2-C8 alkynyl, C2-C8 heteroalkynyl, C6-C10 aryl, C5-C10 heteroaryl, C7-C12 arylalkyl, or C6-C12 heteroarylalkyl, and each R is optionally substituted as described above for alkyl groups. The substituent groups on an aryl or heteroaryl group may be further substituted with the groups described herein as suitable for each type of such substituents or for each component of the substituent. Thus, for example, an arylalkyl substituent may be substituted on the aryl portion with substituents typical for aryl groups, and it may be further substituted on the alkyl portion with substituents as typical or suitable for alkyl groups.

Similarly, "arylalkyl" and "heteroarylalkyl" refer to aromatic and heteroaromatic ring systems, which are stand-alone molecules (e.g., benzene or substituted benzene, pyridine or substituted pyridine), or which are bonded to an attachment point through a linking group such as an alkylene, including substituted or unsubstituted, saturated or unsaturated, cyclic or acyclic linkers. A linker often is C1-C8 alkyl or a hetero form thereof. These linkers also may include a carbonyl group, thus making them able to provide substituents as an acyl or heteroacyl moiety. An aryl or heteroaryl ring in an arylalkyl or heteroarylalkyl group may be substituted with the same substituents described above for aryl groups. An arylalkyl group sometimes includes a phenyl ring optionally substituted with the groups defined above for aryl groups and a C1-C4 alkylene that is unsubstituted or is substituted with one or two C1-C4 alkyl groups or heteroalkyl groups, where the alkyl or heteroalkyl groups can optionally cyclize to form a ring such as cyclopropane, dioxolane, or oxacyclopentane. Similarly, a heteroarylalkyl group often includes a C5-C6 monocyclic heteroaryl group optionally substituted with one or more of the groups described above as substituents typical on aryl groups and a C1-C4 alkylene that is unsubstituted. A heteroarylalkyl group sometimes is substituted with one or two C1-C4 alkyl groups or heteroalkyl groups, or includes an optionally substituted phenyl ring or C5-C6 monocyclic heteroaryl and a C1-C4 heteroalkylene that is unsubstituted or is substituted with one or two C1-C4 alkyl or heteroalkyl groups, where the alkyl or heteroalkyl groups can optionally cyclize to form a ring such as cyclopropane, dioxolane, or oxacyclopentane.

Where an arylalkyl or heteroarylalkyl group is described as optionally substituted, the substituents may be on the alkyl or heteroalkyl portion or on the aryl or heteroaryl portion of the group. The substituents optionally present on the alkyl or heteroalkyl portion sometimes are the same as those described above for alkyl groups, and the substituents optionally present on the aryl or heteroaryl portion often are the same as those described above for aryl groups generally.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl includes pyridylmethyl, phenoxy, and N-pyrrolyl methoxy.

"Alkylene" as used herein refers to a divalent hydrocarbyl group. Because an alkylene is divalent, it can link two other groups together. An alkylene often is referred to as —(CH$_2$)$_n$— where n can be 1-20, 1-10, 1-8, or 1-4, though where specified, an alkylene can also be substituted by other groups, and can be of other lengths, and the open valences need not be at opposite ends of a chain. Thus —CH(Me)— and —C(Me)$_2$— may also be referred to as alkylenes, as can a cyclic group such as cyclopropan-1,1-diyl. Where an alkylene group is substituted, the substituents include those typically present on alkyl groups as described herein.

Nitrogen may be supplied from an inorganic (e.g., (NH$_4$)$_2$SO$_4$) or organic source (e.g., urea or glutamate). In addition to appropriate carbon and nitrogen sources, culture media also can contain suitable minerals, salts, cofactors, buffers, vitamins, metal ions (e.g., Mn$^{+2}$, Co$^{+2}$, Zn$^{+2}$, Mg$^{+2}$) and other components suitable for culture of microorganisms.

Engineered microorganisms sometimes are cultured in complex media (e.g., yeast extract-peptone-dextrose broth (YPD)). In some embodiments, engineered microorganisms are cultured in a defined minimal media that lacks a component necessary for growth and thereby forces selection of a desired expression cassette (e.g., Yeast Nitrogen Base (DIFCO Laboratories, Detroit, Mich.)). Culture media in some embodiments are common commercially prepared media, such as Yeast Nitrogen Base (DIFCO Laboratories, Detroit, Mich.). Other defined or synthetic growth media may also be used and the appropriate medium for growth of the particular microorganism are known. A variety of host organisms can be selected for the production of engineered microorganisms. Non-limiting examples include yeast (e.g., *Candida tropicalis* (e.g., ATCC20336, ATCC20913, ATCC20962), *Yarrowia lipolytica* (e.g., ATCC20228)) and filamentous fungi (e.g., *Aspergillus nidulans* (e.g., ATCC38164) and *Aspergillus parasiticus* (e.g., ATCC 24690)). In specific embodiments, yeast are cultured in YPD media (10 g/L Bacto Yeast Extract, 20 g/L Bacto Peptone, and 20 g/L Dextrose). Filamentous fungi, in particular embodiments, are grown in CM (Complete Medium) containing 10 g/L Dextrose, 2 g/L Bacto Peptone, 1 g/L Bacto Yeast Extract, 1 g/L Casamino acids, 50 mL/L 20× Nitrate Salts (120 g/L NaNO$_3$, 10.4 g/L KCl, 10.4 g/L MgSO$_4$.7H$_2$O), 1 mL/L 1000× Trace Elements (22 g/L ZnSO$_4$.7H$_2$O, 11 g/L H$_3$BO$_3$, 5 g/L MnCl$_2$.7H$_2$O, 5 g/L FeSO$_4$.7H$_2$O, 1.7 g/L CoCl$_2$.6H$_2$O, 1.6 g/L CuSO$_4$.5H$_2$O, 1.5 g/L Na$_2$MoO$_4$.2H$_2$O, and 50 g/L Na$_4$EDTA), and 1 mL/L Vitamin Solution (100 mg each of Biotin, pyridoxine, thiamine, riboflavin, p-aminobenzoic acid, and nicotinic acid in 100 mL water).

A suitable pH range for the fermentation often is between about pH 4.0 to about pH 8.0, where a pH in the range of about pH 5.5 to about pH 7.0 sometimes is utilized for initial culture conditions. Depending on the host organism, culturing may be conducted under aerobic or anaerobic conditions, where microaerobic conditions sometimes are maintained. A two-stage process may be utilized, where one stage promotes microorganism proliferation and another state promotes production of target molecule. In a two-stage process, the first stage may be conducted under aerobic conditions (e.g., introduction of air and/or oxygen) and the second stage may be conducted under anaerobic conditions (e.g., air or oxygen are not introduced to the culture conditions). In some embodiments, the first stage may be conducted under anaerobic conditions and the second stage may be conducted under aerobic conditions. In certain embodiments, a two-stage process may include two more organisms, where one organism generates an intermediate product (e.g., hexanoic acid produced by *Megasphera* spp.) in one stage and another organism processes the intermediate product into a target product (e.g., adipic acid) in another stage, for example.

A variety of fermentation processes may be applied for commercial biological production of a target product. In some embodiments, commercial production of a target product from a recombinant microbial host is conducted using a batch, fed-batch or continuous fermentation process, for example.

A batch fermentation process often is a closed system where the media composition is fixed at the beginning of the process and not subject to further additions beyond those required for maintenance of pH and oxygen level during the process. At the beginning of the culturing process the media is inoculated with the desired organism and growth or metabolic activity is permitted to occur without adding additional sources (i.e., carbon and nitrogen sources) to the medium. In batch processes the metabolite and biomass compositions of the system change constantly up to the time the culture is terminated. In a typical batch process, cells proceed through a static lag phase to a high-growth log phase and finally to a stationary phase, wherein the growth rate is diminished or halted. Left untreated, cells in the stationary phase will eventually die.

A variation of the standard batch process is the fed-batch process, where the carbon source is continually added to the fermentor over the course of the fermentation process. Fed-batch processes are useful when catabolite repression is apt to inhibit the metabolism of the cells or where it is desirable to have limited amounts of carbon source in the media at any one time. Measurement of the carbon source concentration in fed-batch systems may be estimated on the basis of the changes of measurable factors such as pH, dissolved oxygen and the partial pressure of waste gases (e.g., $CO_2$).

Batch and fed-batch culturing methods are known in the art. Examples of such methods may be found in Thomas D. Brock in Biotechnology: A Textbook of Industrial Microbiology, 2.sup.nd ed., (1989) Sinauer Associates Sunderland, Mass. and Deshpande, Mukund V., Appl. Biochem. Biotechnol., 36:227 (1992).

In continuous fermentation process a defined media often is continuously added to a bioreactor while an equal amount of culture volume is removed simultaneously for product recovery. Continuous cultures generally maintain cells in the log phase of growth at a constant cell density. Continuous or semi-continuous culture methods permit the modulation of one factor or any number of factors that affect cell growth or end product concentration. For example, an approach may limit the carbon source and allow all other parameters to moderate metabolism. In some systems, a number of factors affecting growth may be altered continuously while the cell concentration, measured by media turbidity, is kept constant. Continuous systems often maintain steady state growth and thus the cell growth rate often is balanced against cell loss due to media being drawn off the culture. Methods of modulating nutrients and growth factors for continuous culture processes, as well as techniques for maximizing the rate of product formation, are known and a variety of methods are detailed by Brock, supra.

In some embodiments involving fermentation, the fermentation can be carried out using two or more microorganisms (e.g., host microorganism, engineered microorganism, isolated naturally occurring microorganism, the like and combinations thereof), where a feedstock is partially or completely utilized by one or more organisms in the fermentation (e.g., mixed fermentation), and the products of cellular respiration or metabolism of one or more organisms can be further metabolized by one or more other organisms to produce a desired target product (e.g., adipic acid, hexanoic acid). In certain embodiments, each organism can be fermented independently and the products of cellular respiration or metabolism purified and contacted with another organism to produce a desired target product. In some embodiments, one or more organisms are partially or completely blocked in a metabolic pathway (e.g., beta oxidation, omega oxidation, the like or combinations thereof), thereby producing a desired product that can be used as a feedstock for one or more other organisms. Any suitable combination of microorganisms can be utilized to carry out mixed fermentation or sequential fermentation. A non-limiting example of an organism combination and feedstock suitable for use in mixed fermentations or sequential fermentations where the fermented media from a first organism is used as a feedstock for a second organism is the use of long chain dicarboxylic acids as a fermentation media for *Megasphaera elsdenii* to produce hexanoic acid, and *Candida tropicalis* engineered as described herein to produce adipic acid from the hexanoic acid produced by *Megasphaera elsdenii*. *Megasphaera elsdenii* is a facultative anaerobe. Without being limited by theory, it is believe that *Megasphaera elsdenii* naturally accumulates hexanoic acid as a result of anaerobic respiration. *Candida tropicalis* can grow aerobically and anaerobically. In some embodiments, the hexanoic acid produced by *Megasphaera elsdenii* can be utilized as a feedstock for *Candida tropicalis* to produce adipic acid. In certain embodiments, the *Megasphaera* produced hexanoic acid is purified (e.g., partially, completely) prior to being used as a feedstock for *C. tropicalis*.

In various embodiments adipic acid is isolated or purified from the culture media or extracted from the engineered microorganisms. In some embodiments, fermentation of feedstocks by methods described herein can produce a target product (e.g., adipic acid) at a level of about 80% or more of theoretical yield (e.g., 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more of theoretical yield). The term "theoretical yield" as used herein refers to the amount of product that could be made from a starting material if the reaction is 100% complete. Theoretical yield is based on the stoichiometry of a reaction and ideal conditions in which starting material is completely consumed, undesired side reactions do not occur, the reverse reaction does not occur, and there are no losses in the work-up procedure. Culture media may be tested for target product (e.g., adipic acid) concentration and drawn off when the concentration reaches a predetermined level. Detection methods are known in the art, including but not limited to those set forth in B Stieglitz and P J Weimer, Novel microbial screen for detection of 1,4-butanediol, ethylene glycol, and adipic acid, Appl Environ Microbiol. 198. Target product (e.g., adipic acid) may be present at a range of levels as described herein.

A target product sometimes is retained within an engineered microorganism after a culture process is completed, and in certain embodiments, the target product is secreted out of the microorganism into the culture medium. For the latter embodiments, (i) culture media may be drawn from the culture system and fresh medium may be supplemented, and/or (ii) target product may be extracted from the culture media during or after the culture process is completed. Engineered microorganisms may be cultured on or in solid, semi-solid or liquid media. In some embodiments media is drained from cells adhering to a plate. In certain embodiments, a liquid-cell mixture is centrifuged at a speed sufficient to pellet the cells but not disrupt the cells and allow extraction of the media, as known in the art. The cells may then be resuspended in fresh media. Target product may be purified from culture media according to known methods, such as those described in U.S. Pat. No. 6,787,669 and U.S. Pat. No. 5,296,639, for example.

In certain embodiments, target product is extracted from the cultured engineered microorganisms. The micoorganism cells may be concentrated through centrifugation at a speed sufficient to shear the cell membranes. In some embodiments, the cells may be physically disrupted (e.g., shear force, sonication) or chemically disrupted (e.g., contacted with detergent or other lysing agent). The phases may be separated by centrifugation or other method known in the art and target product may be isolated according to known methods.

Commercial grade target product sometimes is provided in substantially pure form (e.g., 90% pure or greater, 95% pure or greater, 99% pure or greater or 99.5% pure or greater). In some embodiments, target product may be modified into any one of a number of downstream products. For example, adipic acid may be polycondensed with hexamethylenediamine to produce nylon. Nylon may be further processed into fibers for applications in carpeting, automobile tire cord and clothing. Adipic acid is also used for manufacturing plasticizers, lubricant components and polyester polyols for polyurethane systems. Food grade adipic acid is used as a gelling aid, acidulant, leavening and buffering agent. Adipic acid has two carboxylic acid (—COOH) groups, which can yield two kinds of salts. Its derivatives, acyl halides, anhydrides, esters, amides and nitriles, are used in making downstream products such as flavoring agents, internal plasticizers, pesticides, dyes, textile treatment agents, fungicides, and pharmaceuticals through further reactions of substitution, catalytic reduction, metal hydride reduction, diborane reduction, keto formation with organometallic reagents, electrophile bonding at oxygen, and condensation.

Target product may be provided within cultured microbes containing target product, and cultured microbes may be supplied fresh or frozen in a liquid media or dried. Fresh or frozen microbes may be contained in appropriate moisture-proof containers that may also be temperature controlled as necessary. Target product sometimes is provided in culture medium that is substantially cell-free. In some embodiments target product or modified target product purified from microbes is provided, and target product sometimes is provided in substantially pure form. In certain embodiments crystallized or powdered target product is provided. Crystalline adipic acid is a white powder with a melting point of 360° F. and may be transported in a variety of containers including one ton cartons, drums, 50 pound bags and the like.

In certain embodiments, a target product (e.g., adipic acid, 6-hydroxyhexanoic acid) is produced with a yield of about 0.30 grams of target product, or greater, per gram of glucose added during a fermentation process (e.g., about 0.31 grams of target product per gram of glucose added, or greater; about 0.32 grams of target product per gram of glucose added, or greater; about 0.33 grams of target product per gram of glucose added, or greater; about 0.34 grams of target product per gram of glucose added, or greater; about 0.35 grams of target product per gram of glucose added, or greater; about 0.36 grams of target product per gram of glucose added, or greater; about 0.37 grams of target product per gram of glucose added, or greater; about 0.38 grams of target product per gram of glucose added, or greater; about 0.39 grams of target product per gram of glucose added, or greater; about 0.40 grams of target product per gram of glucose added, or greater; about 0.41 grams of target product per gram of glucose added, or greater; 0.42 grams of target product per gram of glucose added, or greater; 0.43 grams of target product per gram of glucose added, or greater; 0.44 grams of target product per gram of glucose added, or greater; 0.45 grams of target product per gram of glucose added, or greater; 0.46 grams of target product per gram of glucose added, or greater; 0.47 grams of target product per gram of glucose added, or greater; 0.48 grams of target product per gram of glucose added, or greater; 0.49 grams of target product per gram of glucose added, or greater; 0.50 grams of target product per gram of glucose added, or greater; 0.51 grams of target product per gram of glucose added, or greater; 0.52 grams of target product per gram of glucose added, or greater; 0.53 grams of target product per gram of glucose added, or greater; 0.54 grams of target product per gram of glucose added, or greater; 0.55 grams of target product per gram of glucose added, or greater; 0.56 grams of target product per gram of glucose added, or greater; 0.57 grams of target product per gram of glucose added, or greater; 0.58 grams of target product per gram of glucose added, or greater; 0.59 grams of target product per gram of glucose added, or greater; 0.60 grams of target product per gram of glucose added, or greater; 0.61 grams of target product per gram of glucose added, or greater; 0.62 grams of target product per gram of glucose added, or greater; 0.63 grams of target product per gram of glucose added, or greater; 0.64 grams of target product per gram of glucose added, or greater; 0.65 grams of target product per gram of glucose added, or greater; 0.66 grams of target product per gram of glucose added, or greater; 0.67 grams of target product per gram of glucose added, or greater; 0.68 grams of target product per gram of glucose added, or greater; 0.69 or 0.70 grams of target product per gram of glucose added or greater).

EXAMPLES

The examples set forth below illustrate certain embodiments and do not limit the technology. Certain examples set forth below utilize standard recombinant DNA and other biotechnology protocols known in the art. Many such techniques are described in detail in Maniatis, T., E. F. Fritsch and J. Sambrook (1982) *Molecular Cloning: a Laboratory Manual*; Cold Spring Harbor Laboratory, Cold Spring Harbor, N.Y. DNA mutagenesis can be accomplished using the Stratagene (San Diego, Calif.) "QuickChange" kit according to the manufacturer's instructions.

Example 1

Cloning Hexanoate Synthase ("HexS") Subunit Genes

Total RNA from *Aspergillus parasiticus* was prepared using the RiboPure™ (Ambion, Austin, Tex.) kit for yeast. The genes encoding the two subunits of hexanoate synthase (referred to as "hexA" and "hex B" were isolated from this total RNA using the 2-step RT-PCR method with Superscript III reverse transcriptase (Life Technologies, Carlsbad, Calif.) and the fragments were gel purified. The primers used for each RT-PCR reaction are as follows:

```
HexA Aspergillus parasiticus primers
SP_HexA_Apar_1_1149        ATGGTCATCCAAGGGAAGAGATTGGCCGCCTCCTCTATTCAGC ASP_HexA_Apar_1_1149       GTAGGCGTCACAGGAAAGACTGCGTACCA SP_HexA_Apar_941_2270      TATCACCAATGCTGGATGTAAAGAAGTCGCG ASP_HexA_Apar_941_2270     AATTGGGCTAGGAAACCGGGGATGC SP_HexA_Apar_2067_3016     CGGTCTAATGACGGCGCATGATATCATAGCCGAAACGGTCGAG ASP_HexA_Apar_2067_3016    ACTTGGCTGGAGTCCATCCCTTCGGCA SP_HexA_Apar_2812_4181     CTGCCCGAGTTTGAAGTATCTCAACTTACCGCCGACGCCATG ASP_HexA_Apar_2812_4181    TGAGACGCGCTGCGCAGGGC SP_HexA_Apar_3975_5016     CGAGGTGATCGAGACGCAGATGC ASP_HexA_Apar_3975_5016    TTATGAAGCACCAGACATCAGCCCCAGC HexB Aspergillus parasiticus primers
SP_HexB_Apar_1_1166        ATGGGTTCCGTTAGTAGGGAACATGAGTCAATC ASP_HexB_Apar_1_1166       GTTCCTTGTGTGAGCTCCTGAATAAGACTGCATG SP_HexB_Apar_962_2042      CCATCAAAATCCCCCTCTATCACACGGGCACTGGGAGCAAC ASP_HexB_Apar_962_2042     CCCACGCCTTGCGCATCTATAATCAGG SP_HexB_Apar_1837_3527     TGTCCGAATATTCTCCTCGTTGTAGGTAGTGGATT ASP_HexB_Apar_1837_3527    GCAGTAGTCGATAGGTACACATCCTTGGGGGTTCCATGACTGC SP_HexB_Apar_3322_4460     AGAGGATCAAGGCATTATACATGAGTCTGTGGAACTTGGGCTTTCC ASP_HexB_Apar_3322_4460    TTCCCCGTCCTCCATGGCCTTATGC SP_HexB_Apar_4256_5667     GGCCTTTGCGCGATACGCTGGTCTCTCGGGTCCCAT ASP_HexB_Apar_4256_5667    TCACGCCATTTGTTGAAGCAGGGAATG
```

Each of the fragments was inserted separately into the plasmid pCRBlunt II (Life Technologies, Carlsbad, Calif.) such that there were four hexA plasmids, each with a different hexA gene fragment, and five hex B plasmids each with a different hexB gene fragment. Each hexA and hexB fragment was sequence verified, after which the fragments were PCR cloned from each plasmid. Overlap PCR was then used to create the full length hexA and hexB genes. The hexA gene was inserted into the vector p425GPD which has a LEU2 selectable marker and a glyceraldehyde 3-phosphate dehydrogenase promoter (American Type Culture Collection) and the hexB full length gene was inserted into p426GPD which has a URA3 selectable marker and a glyceraldehyde 3-phosphate dehydrogenase promoter (American Type Culture Collection).

Example 2

Transformation of *Saccharomyces cerevisiae* with HexA and HexB Genes

*Saccharomyces cereviseae* cells (strain BY4742, ATCC Accession Number 201389) were grown in standard YPD (10 g Yeast Extract, 20 g Bacto-Peptone, 20 g Glucose, 1 L total) media at about 30 degrees Celsius for about 3 days. The plasmids containing the hexA and hexB genes were co-transformed into the *Saccharomyces cerevisiae*. Transformation was accomplished using the Zymo kit (Catalog number T2001; Zymo Research Corp., Orange, Calif. 92867) using 1 µg plasmid DNA and cultured on SC drop out media with glucose (minus uracil and minus leucine) (20 g glucose; 2.21 g SC (-URA, -LEU) dry mix, 6.7 g Yeast Nitrogen Base, 1 L total) for 2-3 days at about 30° C.

| SC(-URA) mix contains: | |
|---|---|
| 0.4 g | Adenine hemisulfate |
| 3.5 g | Arginine |
| 1 g | Glutamic Acid |
| 0.433 g | Histidine |
| 0.4 g | Myo-Inositol |
| 5.2 g | Isoleucine |
| 0.9 g | Lysine |
| 1.5 g | Methionine |
| 0.8 g | Phenylalanine |
| 1.1 g | Serine |
| 1.2 g | Threonine |
| 0.8 g | Tryptophan |
| 0.2 g | Tyrosine |
| 1.2 g | Valine |
| When needed: | |
| 0.263 g | Leucine |
| 0.2 g | Uracil |

Co-transformants were selected and established as liquid cultures in YPD media under standard conditions.

Example 3

Production of Synthetic HexA and HexB Genes

Synthetic hexaonoate synthase subunit genes were designed for use in *Candida tropicalis*. This organism uses an alternate genetic code in which the codon "CTG" encodes serine instead of leucine. Therefore, all "CTG" codons were replaced with the codon "TTG" to ensure that these genes, when translated by *C. tropicalis*, would generate polypeptides with amino acid sequences identical to the wild type polypeptides found in *A. parasiticus*. Due to the large size of each subunit, each was synthesized as four fragments, and each fragment was inserted into the vector pUC57. PCR was used to clone each fragment, and overlap extension PCR was then used to generate each full length gene.

The sequence of the synthetic gene for each hexanoate synthase subunit is set forth below. The synthetic gene encoding the hexA subunit is referred to as hexA-AGC ("Alternate Genetic Code") and the synthetic gene encoding the hexB subunit is referred to as hexB-AGC.

```
>hexA-AGC for Candida tropicalis
atggtcatccaagggaagagattggccgcctcctctattcagcttctcgc aagctcgttagacgcgaagaagctttgttatgagtatgacgagaggcaag ccccaggtgtaacccaaatcaccgaggaggcgcctacagagcaaccgcct ctctctacccctccctcgctaccccaaacgcccaatatttcgcctataag tgcttcaaagatcgtgatcgacgatgtggcgctatctcgagtgcaaattg ttcaggctcttgttgccagaaagttgaagacggcaattgctcagcttcct acatcaaagtcaatcaaagagttgtcgggtggtcggtcttctttgcagaa cgagctcgtgggggatatacacaacgagttcagctccatcccggatgcac cagagcagatcttgttgcgggactttggcgacgccaacccaacagtgcaa ttggggaaaacgtcctccgcggcagttgccaaactaatctcgtccaagat gcctagtgacttcaacgccaacgctattcgagcccacctagcaaacaagt ggggtctaggacccttgcgacaaacagcggtgttgctctacgccattgcg tcagaaccccccatcgcgtttagcttcatcgagcgcagcggaagagtactg ggacaacgtgtcatccatgtacgccgaatcgtgtggcatcaccctccgcc cgagacaagacactatgaatgaagatgctatggcatcgtcggcgattgat ccggctgtggtagccgagttttccaaggggcaccgtaggctcggagttca acagttccaagcgctagcagaatacttacaaattgatttgtcggggtctc aagcctctcagtcggatgctttggtggcggaacttcagcagaaagtcgat ctctggacggccgaaatgacccccgagtttctcgccgggatatcaccaat gttggatgtaaagaagtcgcgacgctatggctcgtggtggaacatggcac ggcaggatgtcttggccttctatcgccgtccttcctacagtgaattcgtg gacgacgccttggccttcaaagtttttctcaatcgtctctgtaaccgagc tgatgaggccctcctcaacatggtacgcagtctttcctgtgacgcctact tcaagcaaggttctttgcccggatatcatgccgcctcgcgactccttgag caggccatcacatccacagtggcggattgcccgaaggcacgcctcattct cccggcggtgggcccccacaccaccattacaaaggacggcacgattgaat acgcggaggcaccgcgccagggagtgagtggtcccactgcgtacatccag tctctccgccaaggcgcatctttcattggtctcaagtcagccgacgtcga tactcagagcaacttgaccgacgctttgcttgacgccatgtgcttagcac tccataatggaatctcgtttgttggtaaaaccttttttggtgacgggagcg ggtcaggggtcaataggagcgggagtggtgcgtctattgttagagggagg
```

-continued

```
agcccgagtattggtgacgacgagcagggagccggcgacgacatccagat acttccagcagatgtacgataatcacggtgcgaagttctccgagttgcgg gtagttccttgcaatctagccagcgcccaagattgcgaagggttgatccg gcacgtctacgatccccgtgggctaaattgggatttggatgccatccttc ccttcgctgccgcgtccgactacagcaccgagatgcatgacattcgggga cagagcgagttgggccaccggctaatgttggtcaatgtcttccgcgtgtt ggggcatatcgtccactgtaaacgagatgccggggttgactgccatccga cgcaggtgttgttgccattgtcgccaaatcacggcatcttcggtggcgat gggatgtatccggagtcaaagctagcccttgagagcttgttccatcgcat ccgatcagagtcttggtcagaccagttatctatatgcggcgttcgtatcg gttggacccggtcgaccggtctaatgacggcgcatgatatcatagccgaa acggtcgaggaacacggaatacgcacattttccgtggccgagatggcact caacatagccatgttgttaacccccgactttgtggcccattgtgaagatg gacctttggatgccgatttcaccggcagcttgggaacattgggtagcatc cccggtttcctagcccaattgcaccagaaagtccagttggcagccgaggt gatccgtgccgtgcaggccgaggatgagcatgagagattcttgtctccgg gaacaaaacctaccttgcaagcacccgtggccccaatgcacccccgcagt agccttcgtgtaggctatccccgtctccccgattatgagcaagagattcg cccgttgtccccacggttggaaaggttgcaagatccggccaatgctgtgg tggtggtcgggtactcggagttggggccatggggtagcgcgcgattacgg tgggaaatagagagccagggccagtggacttcagccggttatgtcgaact tgcctggttgatgaacctcatccgccacgtcaacgatgaatcctacgtcg gctgggtggatactcagaccggaaagccagtgcgggatggcgagatccag gcattgtacggggaccacattgacaaccacaccggtatccgtcctatcca gtccacctcgtacaacccagagcgcatggaggtcttgcaggaggtcgctg tcgaggaggatttgcccgagtttgaagtatctcaacttaccgccgacgcc atgcgtctccgccatggagctaacgtttccatccgccccagtggaaatcc cgacgcatgccacgtgaagcttaaacgaggcgctgttatccttgttccca agacagttccctttgtttggggatcgtgtgccggtgagttgccgaaggga tggactccagccaagtacggcatccctgagaacctaattcatcaggtcga ccccgtcacgctctatacaatttgctgcgtggcggaggcattttacagtg ccggtataactcaccctcttgaggtctttcgacacattcacctctcggaa ctaggcaactttatcggatcctccatgggtgggccgacgaagactcgtca gctctaccgagatgtctacttcgaccatgagattccgtcggatgttttgc aagacacttatctcaacacacctgctgcctgggttaatatgctactcctt ggctgcacggggccgatcaaaactcccgtcggcgcatgtgccaccggggt cgagtcgatcgattccggctacgagtcaatcatggcgggcaagacaaaga tgtgtcttgtgggtggctacgacgatttgcaggaggaggcatcgtatgga ttcgcacaacttaaggccacggtcaacgttgaagaggagatcgcctgcgg tcgacagccctcggagatgtcgcgccccatggctgagagtcgtgctggct
```

-continued ttgtcgaggcgcatggctgcggtgtacagttgttgtgtcgaggtgacatc
gccttgcaaatgggtcttcctatctatgcggtcattgccagctcagccat
ggccgccgacaagatcggttcctcggtgccagcaccgggccagggcattc
taagcttctcccgtgagcgcgctcgatccagtatgatatccgtcacgtcg
cgcccgagtagccgtagcagcacatcatctgaagtctcggacaaatcatc
cttgacctcaatcacctcaatcagcaatcccgctcctcgtgcacaacgcg
cccgatccaccactgatatggctccgttgcgagcagcgcttgcgacttgg
gggttgactatcgacgacttggatgtggcctcattgcacggcacctcgac
gcgcggtaacgatctcaatgagcccgaggtgatcgagacgcagatgcgcc
atttaggtcgcactcctggccgcccttgtgggccatctgccaaaagtca
gtgacgggacacccctaaagccccagcggccgcatggatgctcaatggatg
cttgcaagtattggactcggggttggtgccgggcaaccgcaatcttgaca
cgttggacgaggccttgcgcagcgcgtctcatctctgcttccctacgcgc
accgtgcagctacgtgaggtcaaggcattcttgttgacctcatttggctt
cggacagaagggggggccaagtcgtcggcgttgcccccaagtacttctttg
ctacgctcccccgccccgaggttgagggctactatcgcaaggtgagggtt
cgaaccgaggcgggtgatcgcgcctacgccgcggcggtcatgtcgcaggc
ggtggtgaagatccagacgcaaaaccgtacgacgagccggatgcccccc
gcattttctcgatcccttggcacgtatctcccaggatccgtcgacgggc
cagtatcggtttcgttccgatgccactcccgccctcgatgatgatgcttt
gccacctcccggcgaacccaccgagctagtgaagggcatctcctccgcct
ggatcgaggagaaggtgcgaccgcatatgtctcccggcggcacggtgggc
gtggacttggttcctctcgcctccttcgacgcatacaagaatgccatcttt
tgttgagcgcaattatacggtaagggagcgcgattgggctgaaaagagtg
cggatgtgcgcgcggcctatgccagtcggtggtgtgcaaaagaggcggtg
ttcaaatgtctccagacacattcacagggcgcgggggcagccatgaaaga
gattgagatcgagcatggaggtaacgcgcaccgaaagtcaagctccggg
gtgctgcgcaaacagcggcgcggcaacgaggattggaaggagtgcaattg
agcatcagctatggcgacgatgcggtgatagcggtggcgttggggttgat
gtctggtgcttcataa >hexB-AGC for Candida tropicalis
atgggttccgttagtagggaacatgagtcaatccccatccaggccgccca
gagaggcgctgcccggatctgcgctgcttttggaggtcaagggtctaaca
atttggacgtgttaaaaggtctattggagttatacaagcggtatggccca
gatttggatgagctactagacgtggcatccaacacgctttcgcagttggc
atcttcccctgctgcaatagacgtccacgaacccctgggggtttcgacctcc
gacaatggttgaccacaccggaggttgctcctagcaaagaaattcttgcc
ttgccaccacgaagcttttcccttaaatacgttacttagcttggcgctcta
ttgtgcaacttgtcgagagcttgaacttgatcctgggcaatttcgatccc
tccttcatagttccacggggcattcccaaggcatattggcggcggtggcc
atcacccaagccgagagctggccaaccttttatgacgcctgcaggacggt -continued gctccagatctctttctggattggactcgaggccttacctcttcactccat
cctccgccgcctcggatgccatgatccaagattgcatcgaacatggcgag
ggccttcttttcctcaatgctaagtgtctccgggctctcccgctcccaagt
tgagcgagtaattgagcacgtcaataaagggctcggagaatgcaaccgat
gggttcacttggccttggttaactcccacgaaaagttcgtcttagcggga
ccacctcaatcctttatgggccgttttgtcttcatgtccgacggatcagagc
agacaatgacctcgaccagtcgcgtatcttgttccgcaaccgaaagccta
tagtggatatattatttcttcccatatccgcaccatttcacacaccgtac
ttggacggtgttcaagatcgcgttatcgaggctttgagctctgcttcgtt
ggctctccattccatcaaaatcccctctatcacacgggcactgggagca
acctacaagaactacaaccacatcagctaatcccgactcttatccgcgcc
attaccgtggaccaattggactggccgttggtttgccggggcttgaacgc
aacgcacgtgttggactttggacctggacaaacatgcagtcttattcagg
agctcacacaaggaacaggtgtatcagtgatccagttgactactcaatcg
ggaccaaaaccgttggaggccatttggcggcagtgaactgggaggccga
gtttggcttacgacttcatgccaatgtccacggtgcagctaaattgcaca
accgtatgacaacattgcttgggaagcctcctgtgatggtagccggaatg
acacctactacggtgcgctgggactttgtcgctgccgttgctcaagctgg
ataccacgtcgaattgctggtggtggctaccacgcagagcgccagttcg
aggccgagattcggcgcttggcaactgccatcccagcagatcatggcatc
acctgcaatctcctctacgccaagcctacgacttttcctggcagatctc
tgtcatcaaggatttggtgcgccagggagttcccgtggaaggaatcacca
tcggcgccggcatccttctccggaggtcgtccaagaatgtgtacagtcc
atcggactcaagcacatctcattcaagcctgggtctttcgaagccattca
ccaagtcatacagatcgcgcgtacccatcctaacttttttgatcgggttgc
aatggaccgcaggacgagggggaggacatcattcctgggaagacttccat
ggacctattttggcaacctacgctcaaatccgatcatgtccgaatattct
cctcgttgtaggtagtggattcggtggaggcccggacacgtttccctacc
tcacgggccaatgggcccaggcctttggctatccatgcatgcccttcgac
ggagtgttgctcggcagtcgcatgatggtggctcgggaagcccatacgtc
agcccaggcaaaacgcttgattatagatgcgcaaggcgtgggagatgcag
attggcacaagtctttcgatgagcctaccggcggcgtagtgacggtcaac
tcggaattcggtcaacctatccacgttctagctactcgcggagtgatgtt
gtggaaagaactcgacaaccgggtcttttcaatcaaagacacttctaagc
gcttagaatatttgcgcaaccaccggcaagaaattgtgagccgtcttaac
gcagactttgcccgtccctggttggcgttgacggacacggacagaatgt
ggagttggaggacatgacctacctcgaggttctccgccgtttgtgcgatc
tcacgtatgtttcccaccagaagcgatgggtagatccatcatatcgaata
ttattgttggacttcgttcatttgcttcgagaacgattccaatgcgctat
tgacaaccccggcgaatatccactcgacatcatcgtccgggtggaagaga
gcttgaaggataaagcataccgcacgctttatccagaagatgtctctctt -continued

```
ctaatgcatttgttcagccgacgtgacatcaagcccgtaccattcatccc caggttggatgagcgttttgagacctggtttaaaaaagactcattgtggc aatccgaagatgtggaggcggtaattggacaggacgtccagcgaatcttc atcattcaagggcctatggccgttcagtactcaatatccgacgatgagtc tgttaaagacattttacacaatatttgtaatcattacgtggaggctctac aggctgattcaagagaaacttctatcggcgatgtacactcgatcacgcaa aaacctctcagcgcgtttcctgggctcaaagtgacgacaaatagggtcca agggctctataagttcgagaaagtaggagcagtccccgaaatggacgttc tttttgagcatattgtcggattgtcgaagtcatgggctcggacatgtttg atgagtaaatcggtctttagggacggttctcgtttgcataaccccattcg cgccgcactccagctccagcgcggcgacaccatcgaggtgcttttaacag cagactcggaaattcgcaagattcgacttatttcacccacggggatggt ggatccacttctaaggtcgtattagagatagtctctaacgacggacaaag agttttcgccaccttggcccctaacatcccactcagcccgagcccagcg tcgtcttttgcttcaaggtcgaccagaagccgaatgagtggacccttgag gaggatgcgtctggccgggcagagaggatcaaggcattatacatgagttt gtggaacttgggctttccgaacaaggcctctgttttgggtcttaattcgc aattcacggagaagaattgatgatcacaacggacaagattcgtgatttc gaaagggtattgcggcaaaccagtcctcttcagttgcagtcatggaaccc ccaaggatgtgtacctatcgactactgcgtggtcatcgcctggtctgctc ttaccaagcctttgatggtctcctctttgaaatgcgacctcttggatttg ctccacagcgctataagcttccactatgctccatctgtcaaaccattgcg ggtgggcgatattgtcaaaacctcatcccgtatcctagcggtctcggtga gacctagggaactatgttgacggtgtcggcggacattcagcgccaggga caacatgtagtcactgtcaaatcagatttcttctcggaggcccgtttt ggcatgtgaaaccccttcgaactcactgaggagcctgaaatggttgtcc atgtcgactctgaagtgcgccgtgctattttacacagccgcaagtggctc atgcgagaagatcgcgcgctagatttgctagggaggcagctcctcttcag attaaagagcgaaaaattgttcaggccagacggccagctagcattgttac aggtaacaggttccgtgttcagctacagccccgatgggtcaacgacagca ttcggtcgcgtatacttcgaaagcgagtcttgtacagggaacgtggtgat ggacttcttgcaccgctacggtgcacctcgggcgcagttgttggagttgc aacatcccgggtggacgggcacctctactgtggcagtaagaggtcctcga cgcagccaatcctacgcacgcgtctccctcgatcataatcccatccatgt ttgtccggcctttgcgcgatacgctggtctctcgggtcccattgtccatg ggatggaaacctctgccatgatgcgcagaattgccgaatgggccatcgga gatgcagaccggtctcggttccggagctggcatatcaccttgcaagcacc cgtccaccccaacgacccttttgcgggtggagttgcagcataaggccatgg aggacggggaaatggttttgaaagtacaagcatttaacgaaaggacggaa gaacgcgtagcggaggcagatgcccatgttgagcaggaaactacggctta cgtcttctgtggccagggcagtcaacgacaggggatgggaatggacttgt acgtcaactgtccggaggctaaagcgttgtgggctcgcgccgacaagcat ttgtgggagaaatatgggttctccatcttgcacattgtgcaaaacaaccc tccagccctcactgttcactttggcagccagcgagggcgccgtattcgtg ccaactatttgcgcatgatgggacagccaccgatagatggtagacatccg cccatattgaagggattgacgcggaattcgacctcgtacaccttctccta ttcccaggggttgttgatgtccacccagttcgcccagcccgcattggcgt tgatggaaatggctcagttcgaatggctcaaagcccagggagtcgttcag aagggtgcgcggttcgcgggacattcgttgggagaatatgccgcccttgg agcttgtgcttccttcctctcatttgaagatctcatatctctcatcttt atcgggcttgaagatgcagaatgcgttgccgcgcgatgccaacggccac accgactatggaatgttggctgccgatccatcgcggataggaaaaggttt cgaggaagcgagtttgaaatgtcttgtccatatcattcaacaggagaccg gctggttcgtggaagtcgtcaactacaacatcaactcgcagcaatacgtc tgtgcaggccatttccgagcccctttggatgttgggtaagatatgcgatga cctttcatgccaccctcaaccggagactgttgaaggccaagagctacggg ccatggtctggaagcatgtcccgacggtggagcaggtgccccgcgaggat cgcatggaacgaggtcgagcgaccattccgttgccggggatcgatatccc ataccattcgaccatgttacgaggggagattgagccttatcgtgaatatt tgtctgaacgtatcaaggtgggggatgtgaagccgtgcgaattggtggga cgctggatccctaatgttgttggccagcctttctccgtcgataagtctta cgttcagttggtgcacggcatcacaggtagtcctcggcttcattccttgc ttcaacaaatggcgtga
```

Example 4

Transformation of *C. tropicalis* with the Synthetic Hexanoate Synthase Subunit Genes

*Candida tropicalis* cells (ATCC number 20962) and cultured under standard conditions in YPD medium at 30 degrees Celsius. The synthetic genes encoding hexA and hexB are amplified using standard PCR amplification techniques. A linear DNA construct comprising, from 5' to 3', the TEF (transcription elongation factor) promoter, the hexA-AGC gene, the TEF promoter, the hexB-AGC gene, and the URA3 marker. Each end of this construct is designed to contain a mini-URA-Blaster for integration of the construct into *C. tropicalis* genomic DNA (Alani E, Cao L, Kleckner N. A method for gene disruption that allows repeated use of URA3 selection in the construction of multiply disrupted yeast strains. Genetics. 1987 August; 116 (4):541-545).

The construct is amplified using standard techniques. Transformation of *C. tropicalis* cells with this linear construct is accomplished using standard electroporation techniques such as those set forth in U.S. Pat. No. 5,648,247 or 5,204,252. Transformants are selected by plating and growing the transformed cells on SC-URA media as described above in which only transformants will survive. To remove the URA cassette, the confirmed strain is then replated onto SC complete media containing 5-Fluoroorotic Acid (5-FOA) and confirmed for the loss of the URA cassette.

Example 5

Assay of Cytochrome P450 with Activity on Six Carbon Chains in *C. tropicalis*

Cultures of *C. tropicalis* are cultured in YPD media to late log phase and then exposed to hexane exposed to various concentrations of hexane up to about 0.1 percent (v/v) induce the expression of the cytochrome p450 gene having activity specific for six carbon substrates. After about 2 hours exposure to the hexane solution, cells were harvested and RNA isolated using techniques described above. The specifically induced gene may be detected by Northern blotting and/or quantitative RT-PCR.

Cells to be analyzed for cytochrome P450 activity are grown under standard conditions and harvested for the production of microsomes. Microsomes were prepared by lysing cells in Tris-buffered sucrose (10 mM Tris-HCl pH 7.5, 1 mM EDTA, 0.25M sucrose). Differential centrifugation is performed first at 25,000×g then at 100,000×g to pellet cell debris then microsomes, respectively. The microsome pellet is resuspended in 0.1 M phosphate buffer (pH 7.5), 1 mM EDTA to a final concentration of approximately 10 mg protein/mL.

A reaction mixture containing approximately 0.3 mg microsomes, 0.1 mM sodium hexanoate, 0.7 mM NADPH, 50 mM Tris-HCl pH 7.5 in 1 mL is initiated by the addition of NADPH and incubated at 37° C. for 10 minutes. The reaction is terminated by addition of 0.25 mL 5M HCl and 0.25 mL 2.5 ug/mL 10-hydroxydecanoic acid is added as an internal standard (3.3 nmol). The mixture is extracted with 4.5 mL diethyl ether under NaCl-saturated conditions. The organic phase is transferred to a new tube and evaporated to dryness. The residue is dissolved in acetonitrile containing 10 mM 3-bromomethyl-7-methoxy-1,4-benzoxazin-2-one (BrMB) and 0.1 mL of 15 mg/mL 18-crown-6 in acetonitril saturated with $K_2CO_3$. The solution is incubated at 40° C. for 30 minutes before addition of 0.05 mL 2% acetic acid. The fluorescently labeled omega-hydroxy fatty acids are resolved via HPLC with detection at 430 nm and excitation at 355 nm.

Example 6

Examples of Polynucleotide Regulators

Provided in the tables hereafter are non-limiting examples of regulator polynucleotides that can be utilized in embodiments herein. Such polynucleotides may be utilized in native form or may be modified for use herein. Examples of regulatory polynucleotides include those that are regulated by oxygen levels in a system (e.g., upregulated or downregulated by relatively high oxygen levels or relatively low oxygen levels).

| Regulated Yeast Promoters - Up-regulated by oxygen | | | | |
|---|---|---|---|---|
| ORF name | Gene name | Relative mRNA level (Aerobic) | Relative mRNA level (Anaerobic) | Ratio |
| YPL275W | | 4389 | 30 | 219.5 |
| YPL276W | | 2368 | 30 | 118.4 |
| YDR256C | CTA1 | 2076 | 30 | 103.8 |
| YHR096C | HXT5 | 1846 | 30 | 72.4 |
| YDL218W | | 1189 | 30 | 59.4 |
| YCR010C | | 1489 | 30 | 48.8 |
| YOR161C | | 599 | 30 | 29.9 |
| YPL200W | | 589 | 30 | 29.5 |
| YGR110W | | 1497 | 30 | 27 |
| YNL237W | YTP1 | 505 | 30 | 25.2 |
| YBR116C | | 458 | 30 | 22.9 |
| YOR348C | PUT4 | 451 | 30 | 22.6 |
| YBR117C | TKL2 | 418 | 30 | 20.9 |
| YLL052C | | 635 | 30 | 20 |
| YNL195C | | 1578 | 30 | 19.4 |
| YPR193C | | 697 | 30 | 15.7 |
| YDL222C | | 301 | 30 | 15 |
| YNL335W | | 294 | 30 | 14.6 |
| YPL036W | PMA2 | 487 | 30 | 12.8 |
| YML122C | | 206 | 30 | 10.3 |
| YGR067C | | 236 | 30 | 10.2 |
| YPR192W | | 204 | 30 | 10.2 |
| YNL014W | | 828 | 30 | 9.8 |
| YFL061W | | 256 | 30 | 9.1 |
| YNR056C | | 163 | 30 | 8.1 |
| YOR186W | | 153 | 30 | 7.6 |
| YDR222W | | 196 | 30 | 6.5 |
| YOR338W | | 240 | 30 | 6.3 |
| YPR200C | | 113 | 30 | 5.7 |
| YMR018W | | 778 | 30 | 5.2 |
| YOR364W | | 123 | 30 | 5.1 |
| YNL234W | | 93 | 30 | 4.7 |
| YNR064C | | 85 | 30 | 4.2 |
| YGR213C | RTA1 | 104 | 30 | 4 |
| YCL064C | CHA1 | 80 | 30 | 4 |
| YOL154W | | 302 | 30 | 3.9 |
| YPR150W | | 79 | 30 | 3.9 |
| YPR196W | MAL63 | 30 | 30 | 3.6 |
| YDR420W | HKR1 | 221 | 30 | 3.5 |
| YJL216C | | 115 | 30 | 3.5 |
| YNL270C | ALP1 | 67 | 30 | 3.3 |
| YHL016C | DUR3 | 224 | 30 | 3.2 |
| YOL131W | | 230 | 30 | 3 |
| YOR077W | RTS2 | 210 | 30 | 3 |
| YDR536W | STL1 | 55 | 30 | 2.7 |
| YNL150W | | 78 | 30 | 2.6 |
| YHR212C | | 149 | 30 | 2.4 |
| YJL108C | | 106 | 30 | 2.4 |
| YGR069W | | 49 | 30 | 2.4 |
| YDR106W | | 60 | 30 | 2.3 |
| YNR034W | SOL1 | 197 | 30 | 2.2 |
| YEL073C | | 104 | 30 | 2.1 |
| YOL141W | | 81 | 30 | 1.8 |

| Regulated Yeast Promoters - Down-regulated by oxygen | | | | |
|---|---|---|---|---|
| ORF name | Gene name | Relative mRNA level (Aerobic) | Relative mRNA level (Anaerobic) | Ratio |
| YJR047C | ANB1 | 30 | 4901 | 231.1 |
| YMR319C | FET4 | 30 | 1159 | 58 |
| YPR194C | | 30 | 982 | 49.1 |
| YIR019C | STA1 | 30 | 981 | 22.8 |
| YHL042W | | 30 | 608 | 12 |
| YHR210C | | 30 | 552 | 27.6 |
| YHR079B | SAE3 | 30 | 401 | 2.7 |
| YGL162W | STO1 | 30 | 371 | 9.6 |
| YHL044W | | 30 | 334 | 16.7 |
| YOL015W | | 30 | 320 | 6.1 |
| YCLX07W | | 30 | 292 | 4.2 |
| YIL013C | PDR11 | 30 | 266 | 10.6 |
| YDR046C | | 30 | 263 | 13.2 |
| YBR040W | FIG1 | 30 | 257 | 12.8 |
| YLR040C | | 30 | 234 | 2.9 |
| YOR255W | | 30 | 231 | 11.6 |
| YOL014W | | 30 | 229 | 11.4 |

| Regulated Yeast Promoters - Down-regulated by oxygen | | | | |
|---|---|---|---|---|
| ORF name | Gene name | Relative mRNA level (Aerobic) | Relative mRNA level (Anaerobic) | Ratio |
| YAR028W | | 30 | 212 | 7.5 |
| YER089C | | 30 | 201 | 6.2 |
| YFL012W | | 30 | 193 | 9.7 |
| YDR539W | | 30 | 187 | 3.4 |
| YHL043W | | 30 | 179 | 8.9 |
| YJR162C | | 30 | 173 | 6 |
| YMR165C | SMP2 | 30 | 147 | 3.5 |
| YER106W | | 30 | 145 | 7.3 |
| YDR541C | | 30 | 140 | 7 |
| YCRX07W | | 30 | 138 | 3.3 |
| YHR048W | | 30 | 137 | 6.9 |
| YCL021W | | 30 | 136 | 6.8 |
| YOL160W | | 30 | 136 | 6.8 |
| YCRX08W | | 30 | 132 | 6.6 |
| YMR057C | | 30 | 109 | 5.5 |
| YDR540C | | 30 | 83 | 4.2 |
| YOR378W | | 30 | 78 | 3.9 |
| YBR085W | AAC3 | 45 | 1281 | 28.3 |
| YER188W | | 47 | 746 | 15.8 |
| YLL065W | GIN11 | 50 | 175 | 3.5 |
| YDL241W | | 58 | 645 | 11.1 |
| YBR238C | | 59 | 274 | 4.6 |
| YCR048W | ARE1 | 60 | 527 | 8.7 |
| YOL165C | | 60 | 306 | 5.1 |
| YNR075W | | 60 | 251 | 4.2 |
| YJL213W | | 60 | 250 | 4.2 |
| YPL265W | DIP5 | 61 | 772 | 12.7 |
| YDL093W | PMT5 | 62 | 353 | 5.7 |
| YKR034W | DAL80 | 63 | 345 | 5.4 |
| YKR053C | | 66 | 1268 | 19.3 |
| YJR147W | | 68 | 281 | 4.1 |

| Known and putative DNA binding motifs | |
|---|---|
| Regulator | Known Consensus Motif |
| Abf1 | TCRNNNNNNNACG |
| Cbf1 | RTCACRTG |
| Gal4 | CGGNNNNNNNNNNNCCG |
| Gcn4 | TGACTCA |
| Gcr1 | CTTCC |
| Hap2 | CCAATNA |
| Hap3 | CCAATNA |
| Hap4 | CCAATNA |
| Hsf1 | GAANNTTCNNGAA |
| Ino2 | ATGTGAAA |
| Mata(A1) | TGATGTANNT |
| Mcm1 | CCNNNWWRGG |
| Mig1 | WWWWSYGGGG |
| Pho4 | CACGTG |
| Rap1 | RMACCCANNCAYY |
| Reb1 | CGGGTRR |
| Ste12 | TGAAACA |
| Swi4 | CACGAAA |
| Swi6 | CACGAAA |
| Yap1 | TTACTAA |

| Putative DNA Binding Motifs | | |
|---|---|---|
| Regulator | Best Motif (scored by E-value) | Best Motif (scored by Hypergeometric) |
| Abf1 | TYCGT--R-ARTGAYA | TYCGT--R-ARTGAYA |
| Ace2 | RRRAARARAA-A-RARAA | GTGTGTGTGTGTGTG |
| Adr1 | A-AG-GAGAGAG-GGCAG | YTSTYSTT-TTGYTWTT |
| Arg80 | T--CCW-TTTKTTTC | GCATGACCATCCACG |
| Arg81 | AAAAARARAAAARMA | GSGAYARMGGAMAAAA |
| Aro80 | YKYTYTTYTT----KY | TRCCGAGRYW-SSSGCGS |
| Ash1 | CGTCCGGCGC | CGTCCGGCGC |
| Azf1 | GAAAAAGMAAAAAAA | AARWTSGARG-A--CSAA |
| Bas1 | TTTTYYTTYTTKY-TY-T | CS-CCAATGK--CS |
| Cad1 | CATKYTTTTTKYTY | GCT-ACTAAT |
| Cbf1 | CACGTGACYA | CACGTGACYA |
| Cha4 | CA---ACACASA-A | CAYAMRTGY-C |
| Cin5 | none | none |
| Crz1 | GG-A-A--AR-ARGGC- | TSGYGRGASA |
| Cup9 | TTTKYTKTTY-YTTTKTY | K-C-C---SCGCTACKGC |
| Dal81 | WTTKTTTTTYTTTTT-T | SR-GGCMCGGC-SSG |
| Dal82 | TTKTTTTYTTC | TACYACA-CACAWGA |
| Dig1 | AAA--RAA-GARRAA-AR | CCYTG-AYTTCW-CTTC |
| Dot6 | GTGMAK-MGRA-G-G | GTGMAK-MGRA-G-G |
| Fhl1 | -TTWACAYCCRTACAY-Y | -TTWACAYCCRTACAY-Y |
| Fkh1 | TTT-CTTTKYTT-YTTTT | AAW-RTAAAYARG |
| Fkh2 | AAAARA-RAAA-AAAR-AA | GG-AAWA-GTAAACAA |
| Fzf1 | CACACACACACACAC | SASTKCWCTCKTCGT |
| Gal4 | TTGCTTGAACGSATGCCA | TTGCTTGAACGSATGCCA |
| Gal4 (Gal) | YCTTTTTTTYTTYYKG | CGGM---CW-Y--CCCG |
| Gat1 | none | none |
| Gat3 | RRSCCGMCGMGRCGCGCS | RGARGTSACGCAKRTTCT |
| Gcn4 | AAA-ARAR-RAAAARRAR | TGAGTCAY |
| Gcr1 | GGAAGCTGAAACGYMWRR | GGAAGCTGAAACGYMWRR |
| Gcr2 | GGAGAGGCATGATGGGGG | AGGTGATGGAGTGCTCAG |
| Gln3 | CT-CCTTTCT | GKCTRR-RGGAGA-GM |

-continued

| Known and putative DNA binding motifs | | |
|---|---|---|
| Grf10 | GAAARRAAAAAMRMARA | -GGGSG-T-SYGT-CGA |
| Gts1 | G-GCCRS--TM | AG-AWGTTTTGWCAAMA |
| Haa1 | none | none |
| Hal9 | TTTTTYTTTTY-KTTTT | KCKSGCAGGCWTTKYTCT |
| Hap2 | YTTCTTTTYT-Y-C-KT- | G-CCSART-GC |
| Hap3 | T-SYKCTTTTCYTTY | SGCGMGGG--CC-GACCG |
| Hap4 | STT-YTTTY-TTYTYYYY | YCT-ATTSG-C-GS |
| Hap5 | YK-TTTWYYTC | T-TTSMTT-YTTTCCK-C |
| Hir1 | AAAA-A-AARAR-AG | CCACKTKSGSCCT-S |
| Hir2 | WAAAAAGAAAA-AAAAR | CRSGCYWGKGC |
| Hms1 | AAA-GG-ARAM | -AARAAGC-GGGCAC-C |
| Hsf1 | TYTTCYAGAA--TTCY | TYTTCYAGAA--TTCY |
| Ime4 | CACACACACACACACA | CACACACACACACACA |
| Ino2 | TTTYCACATGC | SCKKCGCKSTSSTTYAA |
| Ino4 | G--GCATGTGAAAA | G--GCATGTGAAAA |
| Ixr1 | GAAAA-AAAAAAARA-A | CTTTTTTTYYTSGCC |
| Leu3 | GAAAAARAARAA-AA | GCCGGTMMCGSYC-- |
| Mac1 | YTTKT--TTTTTYTYTTT | A--TTTTTYTTKYGC |
| Mal13 | GCAG-GCAGG | AAAC-TTTATA-ATACA |
| Mal33 | none | none |
| Mata1 | GCCC-C | CAAT-TCT-CK |
| Mbp1 | TTTYTYKTTT-YYTTTTT | G-RR-A-ACGCGT-R |
| Mcm1 | TTTCC-AAW-RGGAAA | TTTCC-AAW-RGGAAA |
| Met31 | YTTYYTTYTTTTYTYTTC | |
| Met4 | MTTTTTYTYTYTTC | |
| Mig1 | TATACA-AGMKRTATATG | |
| Mot3 | TMTTT-TY-CTT-TTTWK | |
| Msn1 | KT--TTWTTATTCC-C | |
| Msn2 | ACCACC | |
| Msn4 | R--AAAA-RA-AARAAAT | |
| Mss11 | TTTTTTTTCWCTTTKYC | |
| Ndd1 | TTTY-YTKTTTY-YTTYT | |
| Nrg1 | TTY--TTYTT-YTTTYYY | |
| Pdr1 | T-YGTGKRYGT-YG | |
| Phd1 | TTYYYTTTTTYTTTTYTT | |
| Pho4 | GAMAAAAAARAAAAR | |
| Put3 | CYCGGGAAGCSAMM-CCG | |
| Rap1 | GRTGYAYGGRTGY | |
| Rcs1 | KMAARAAAAARAAR | |

-continued

| Known and putative DNA binding motifs | |
|---|---|
| Reb1 | RTTACCCGS |
| Rfx1 | AYGRAAAARARAAAARAA |
| Rgm1 | GGAKSCC-TTTY-GMRTA |
| Rgt1 | CCCTCC |
| Rim101 | GCGCCGC |
| Rlm1 | TTTTC-KTTTYTTTTTC |
| Rme1 | ARAAGMAGAAAARRAA |
| Rox1 | YTTTTCTTTTY-TTTTT |
| Rph1 | ARRARAAAGG- |
| Rtg1 | YST-YK-TYTT-CTCCCM |
| Rtg3 | GARA-AAAAR-RAARAAA |
| Sfl1 | CY--GGSSA-C |
| Sfp1 | CACACACACACACAYA |
| Sip4 | CTTYTWTTKTTKTSA |
| Skn7 | YTTYYYTYTTTYTYYTTT |
| Sko1 | none |
| Smp1 | AMAAAAARAARWARA-AA |
| Sok2 | ARAAAARRAAAAG-RAA |
| Stb1 | RAARAAAAARCMRSRAAA |
| Ste12 | TTYTKTYTY-TYYKTTTY |
| Stp1 | GAAAAMAA-AAAAA-AAA |
| Stp2 | YAA-ARAARAAAAA-AAM |
| Sum1 | TY-TTTTTTYTTTTT-TK |
| Swi4 | RAARAARAAA-AA-R-AA |
| Swi5 | CACACACACACACACA |
| Swi6 | RAARRAAAAA-AAAMAA |
| Thi2 | GCCAGACCTAC |
| Uga3 | GG-GGCT |
| Yap1 | TTYTTYTTYTTTY-YTYT |
| Yap3 | none |
| Yap5 | YKSGCGCGYCKCGKCGGS |
| Yap6 | TTTTYTTTTYYYYKTT |
| Yap7 | none |
| Yfl044c | TTCTTKTYYTTTT |
| Yjl206c | TTYTTTTYTYYTTTYTTT |
| Zap1 | TTGCTTGAACGGATGCCA |
| Zms1 | MG-MCAAAAATAAAAS |

Transcriptional repressors

| Associated Gene(s) | Description(s) |
|---|---|
| WHI5 | Repressor of G1 transcription that binds to SCB binding factor (SBF) at SCB target promoters in early G1; phosphorylation of Whi5p by the CDK, Cln3p/Cdc28p relieves repression and promoter binding by Whi5; periodically expressed in G1 |
| TUP1 | General repressor of transcription, forms complex with Cyc8p, involved in the establishment of repressive chromatin structure through interactions with histones H3 and H4, appears to enhance expression of some genes |
| ROX1 | Heme-dependent repressor of hypoxic genes; contains an HMG domain that is responsible for DNA bending activity |
| SFL1 | Transcriptional repressor and activator; involved in repression of flocculation-related genes, and activation of stress responsive genes; negatively regulated by cAMP-dependent protein kinase A subunit Tpk2p |
| RIM101 | Transcriptional repressor involved in response to pH and in cell wall construction; required for alkaline pH-stimulated haploid invasive growth and sporulation; activated by proteolytic processing; similar to *A. nidulans* PacC |
| RDR1 | Transcriptional repressor involved in the control of multidrug resistance; negatively regulates expression of the PDR5 gene; member of the Gal4p family of zinc cluster proteins |
| SUM1 | Transcriptional repressor required for mitotic repression of middle sporulation-specific genes; also acts as general replication initiation factor; involved in telomere maintenance, chromatin silencing; regulated by pachytene checkpoint |
| XBP1 | Transcriptional repressor that binds to promoter sequences of the cyclin genes, CYS3, and SMF2; expression is induced by stress or starvation during mitosis, and late in meiosis; member of the Swi4p/Mbp1p family; potential Cdc28p substrate |
| NRG2 | Transcriptional repressor that mediates glucose repression and negatively regulates filamentous growth; has similarity to Nrg1p |
| NRG1 | Transcriptional repressor that recruits the Cyc8p-Tup1p complex to promoters; mediates glucose repression and negatively regulates a variety of processes including filamentous growth and alkaline pH response |
| CUP9 | Homeodomain-containing transcriptional repressor of PTR2, which encodes a major peptide transporter; imported peptides activate ubiquitin-dependent proteolysis, resulting in degradation of Cup9p and de-repression of PTR2 transcription |
| YOX1 | Homeodomain-containing transcriptional repressor, binds to Mcm1p and to early cell cycle boxes (ECBs) in the promoters of cell cycle-regulated genes expressed in M/G1 phase; expression is cell cycle-regulated; potential Cdc28p substrate |
| RFX1 | Major transcriptional repressor of DNA-damage-regulated genes, recruits repressor Tup1p and Cyc8p to their promoters; involved in DNA damage and replication checkpoint pathway; similar to a family of mammalian DNA binding RFX1-4 proteins |
| MIG3 | Probable transcriptional repressor involved in response to toxic agents such as hydroxyurea that inhibit ribonucleotide reductase; phosphorylation by Snf1p or the Mec1p pathway inactivates Mig3p, allowing induction of damage response genes |
| RGM1 | Putative transcriptional repressor with proline-rich zinc fingers; overproduction impairs cell growth |
| YHP1 | One of two homeobox transcriptional repressors (see also Yox1p), that bind to Mcm1p and to early cell cycle box (ECB) elements of cell cycle regulated genes, thereby restricting ECB-mediated transcription to the M/G1 interval |
| HOS4 | Subunit of the Set3 complex, which is a meiotic-specific repressor of sporulation specific genes that contains deacetylase activity; potential Cdc28p substrate |
| CAF20 | Phosphoprotein of the mRNA cap-binding complex involved in translational control, repressor of cap-dependent translation initiation, competes with eIF4G for binding to eIF4E |
| SAP1 | Putative ATPase of the AAA family, interacts with the Sin1p transcriptional repressor in the two-hybrid system |
| SET3 | Defining member of the SET3 histone deacetylase complex which is a meiosis-specific repressor of sporulation genes; necessary for efficient transcription by RNAPII; one of two yeast proteins that contains both SET and PHD domains |
| RPH1 | JmjC domain-containing histone demethylase which can specifically demethylate H3K36 tri- and dimethyl modification states; transcriptional repressor of PHR1; Rph1p phosphorylation during DNA damage is under control of the MEC1-RAD53 pathway |
| YMR181C | Protein of unknown function; mRNA transcribed as part of a bicistronic transcript with a predicted transcriptional repressor |

Transcriptional repressors

| Associated Gene(s) | Description(s) |
|---|---|
| | RGM1/YMR182C; mRNA is destroyed by nonsense-mediated decay (NMD); YMR181C is not an essential gene |
| YLR345W | Similar to 6-phosphofructo-2-kinase/fructose-2,6-bisphosphatase enzymes responsible for the metabolism of fructoso-2,6-bisphosphate; mRNA expression is repressed by the Rfx1p-Tup1p-Ssn6p repressor complex; YLR345W is not an essential gene |
| MCM1 | Transcription factor involved in cell-type-specific transcription and pheromone response; plays a central role in the formation of both repressor and activator complexes |
| PHR1 | DNA photolyase involved in photoreactivation, repairs pyrimidine dimers in the presence of visible light; induced by DNA damage; regulated by transcriptional repressor Rph1p |
| HOS2 | Histone deacetylase required for gene activation via specific deacetylation of lysines in H3 and H4 histone tails; subunit of the Set3 complex, a meiotic-specific repressor of sporulation specific genes that contains deacetylase activity |
| RGT1 | Glucose-responsive transcription factor that regulates expression of several glucose transporter (HXT) genes in response to glucose; binds to promoters and acts both as a transcriptional activator and repressor |
| SRB7 | Subunit of the RNA polymerase II mediator complex; associates with core polymerase subunits to form the RNA polymerase II holoenzyme; essential for transcriptional regulation; target of the global repressor Tup1p |
| GAL11 | Subunit of the RNA polymerase II mediator complex; associates with core polymerase subunits to form the RNA polymerase II holoenzyme; affects transcription by acting as target of activators and repressors |

Transcriptional activators

| Associated Gene(s) | Description(s) |
|---|---|
| SKT5 | Activator of Chs3p (chitin synthase III), recruits Chs3p to the bud neck via interaction with Bni4p; has similarity to Shc1p, which activates Chs3p during sporulation |
| MSA1 | Activator of G1-specific transcription factors, MBF and SBF, that regulates both the timing of G1-specific gene transcription, and cell cycle initiation; potential Cdc28p substrate |
| AMA1 | Activator of meiotic anaphase promoting complex (APC/C); Cdc20p family member; required for initiation of spore wall assembly; required for Clb1p degradation during meiosis |
| STB5 | Activator of multidrug resistance genes, forms a heterodimer with Pdr1p; contains a Zn(II)2Cys6 zinc finger domain that interacts with a PDRE (pleotropic drug resistance element) in vitro; binds Sin3p in a two-hybrid assay |
| RRD2 | Activator of the phosphotyrosyl phosphatase activity of PP2A, peptidyl-prolyl cis/trans-isomerase; regulates G1 phase progression, the osmoresponse, microtubule dynamics; subunit of the Tap42p-Pph21p-Rrd2p complex |
| BLM10 | Proteasome activator subunit; found in association with core particles, with and without the 19S regulatory particle; required for resistance to bleomycin, may be involved in protecting against oxidative damage; similar to mammalian PA200 |
| SHC1 | Sporulation-specific activator of Chs3p (chitin synthase III), required for the synthesis of the chitosan layer of ascospores; has similarity to Skt5p, which activates Chs3p during vegetative growth; transcriptionally induced at alkaline pH |
| NDD1 | Transcriptional activator essential for nuclear division; localized to the nucleus; essential component of the mechanism that activates the expression of a set of late-S-phase-specific genes |
| IMP2' | Transcriptional activator involved in maintenance of ion homeostasis and protection against DNA damage caused by bleomycin and other oxidants, contains a C-terminal leucine-rich repeat |
| LYS14 | Transcriptional activator involved in regulation of genes of the lysine biosynthesis pathway; requires 2-aminoadipate semialdehyde as co-inducer |
| MSN1 | Transcriptional activator involved in regulation of invertase and glucoamylase expression, invasive growth and pseudohyphal |

Transcriptional activators

| Associated Gene(s) | Description(s) |
|---|---|
| | differentiation, iron uptake, chromium accumulation, and response to osmotic stress; localizes to the nucleus |
| HAA1 | Transcriptional activator involved in the transcription of TPO2, YRO2, and other genes putatively encoding membrane stress proteins; involved in adaptation to weak acid stress |
| UGA3 | Transcriptional activator necessary for gamma-aminobutyrate (GABA)-dependent induction of GABA genes (such as UGA1, UGA2, UGA4); zinc-finger transcription factor of the Zn(2)-Cys(6) binuclear cluster domain type; localized to the nucleus |
| GCR1 | Transcriptional activator of genes involved in glycolysis; DNA-binding protein that interacts and functions with the transcriptional activator Gcr2p |
| GCR2 | Transcriptional activator of genes involved in glycolysis; interacts and functions with the DNA-binding protein Gcr1p |
| GAT1 | Transcriptional activator of genes involved in nitrogen catabolite repression; contains a GATA-1-type zinc finger DNA-binding motif; activity and localization regulated by nitrogen limitation and Ure2p |
| GLN3 | Transcriptional activator of genes regulated by nitrogen catabolite repression (NCR), localization and activity regulated by quality of nitrogen source |
| PUT3 | Transcriptional activator of proline utilization genes, constitutively binds PUT1 and PUT2 promoter sequences and undergoes a conformational change to form the active state; has a Zn(2)-Cys(6) binuclear cluster domain |
| ARR1 | Transcriptional activator of the basic leucine zipper (bZIP) family, required for transcription of genes involved in resistance to arsenic compounds |
| PDR3 | Transcriptional activator of the pleiotropic drug resistance network, regulates expression of ATP-binding cassette (ABC) transporters through binding to cis-acting sites known as PDREs (PDR responsive elements) |
| MSN4 | Transcriptional activator related to Msn2p; activated in stress conditions, which results in translocation from the cytoplasm to the nucleus; binds DNA at stress response elements of responsive genes, inducing gene expression |
| MSN2 | Transcriptional activator related to Msn4p; activated in stress conditions, which results in translocation from the cytoplasm to the nucleus; binds DNA at stress response elements of responsive genes, inducing gene expression |
| PHD1 | Transcriptional activator that enhances pseudohyphal growth; regulates expression of FLO11, an adhesin required for pseudohyphal filament formation; similar to StuA, an A. nidulans developmental regulator; potential Cdc28p substrate |
| FHL1 | Transcriptional activator with similarity to DNA-binding domain of Drosophila forkhead but unable to bind DNA in vitro; required for rRNA processing; isolated as a suppressor of splicing factor prp4 |
| VHR1 | Transcriptional activator, required for the vitamin H-responsive element (VHRE) mediated induction of VHT1 (Vitamin H transporter) and BIO5 (biotin biosynthesis intermediate transporter) in response to low biotin concentrations |
| CDC20 | Cell-cycle regulated activator of anaphase-promoting complex/cyclosome (APC/C), which is required for metaphase/anaphase transition; directs ubiquitination of mitotic cyclins, Pds1p, and other anaphase inhibitors; potential Cdc28p substrate |
| CDH1 | Cell-cycle regulated activator of the anaphase-promoting complex/cyclosome (APC/C), which directs ubiquitination of cyclins resulting in mitotic exit; targets the APC/C to specific substrates including Cdc20p, Ase1p, Cin8p and Fin1p |
| AFT2 | Iron-regulated transcriptional activator; activates genes involved in intracellular iron use and required for iron homeostasis and resistance to oxidative stress; similar to Aft1p |
| MET4 | Leucine-zipper transcriptional activator, responsible for the regulation of the sulfur amino acid pathway, requires different combinations of the auxiliary factors Cbf1p, Met28p, Met31p and Met32p |
| CBS2 | Mitochondrial translational activator of the COB mRNA; interacts with translating ribosomes, acts on the COB mRNA 5'-untranslated leader |
| CBS1 | Mitochondrial translational activator of the COB mRNA; membrane protein that interacts with translating ribosomes, acts on the COB mRNA 5'-untranslated leader |
| CBP6 | Mitochondrial translational activator of the COB mRNA; phosphorylated |
| PET111 | Mitochondrial translational activator specific for the COX2 mRNA; located in the mitochondrial inner membrane |

Transcriptional activators

| Associated Gene(s) | Description(s) |
|---|---|
| PET494 | Mitochondrial translational activator specific for the COX3 mRNA, acts together with Pet54p and Pet122p; located in the mitochondrial inner membrane |
| PET122 | Mitochondrial translational activator specific for the COX3 mRNA, acts together with Pet54p and Pet494p; located in the mitochondrial inner membrane |
| RRD1 | Peptidyl-prolyl cis/trans-isomerase, activator of the phosphotyrosyl phosphatase activity of PP2A; involved in G1 phase progression, microtubule dynamics, bud morphogenesis and DNA repair; subunit of the Tap42p-Sit4p-Rrd1p complex |
| YPR196W | Putative maltose activator |
| POG1 | Putative transcriptional activator that promotes recovery from pheromone induced arrest; inhibits both alpha-factor induced G1 arrest and repression of CLN1 and CLN2 via SCB/MCB promoter elements; potential Cdc28p substrate; SBF regulated |
| MSA2 | Putative transcriptional activator, that interacts with G1-specific transcription factor, MBF and G1-specific promoters; ortholog of Msa2p, an MBF and SBF activator that regulates G1-specific transcription and cell cycle initiation |
| PET309 | Specific translational activator for the COX1 mRNA, also influences stability of intron-containing COX1 primary transcripts; localizes to the mitochondrial inner membrane; contains seven pentatricopeptide repeats (PPRs) |
| TEA1 | Ty1 enhancer activator required for full levels of Ty enhancer-mediated transcription; C6 zinc cluster DNA-binding protein |
| PIP2 | Autoregulatory oleate-specific transcriptional activator of peroxisome proliferation, contains Zn(2)-Cys(6) cluster domain, forms heterodimer with Oaf1p, binds oleate response elements (OREs), activates beta-oxidation genes |
| CHA4 | DNA binding transcriptional activator, mediates serine/threonine activation of the catabolic L-serine (L-threonine) deaminase (CHA1); Zinc-finger protein with Zn[2]-Cys[6] fungal-type binuclear cluster domain |
| SFL1 | Transcriptional repressor and activator; involved in repression of flocculation-related genes, and activation of stress responsive genes; negatively regulated by cAMP-dependent protein kinase A subunit Tpk2p |
| RDS2 | Zinc cluster transcriptional activator involved in conferring resistance to ketoconazole |
| CAT8 | Zinc cluster transcriptional activator necessary for derepression of a variety of genes under non-fermentative growth conditions, active after diauxic shift, binds carbon source responsive elements |
| ARO80 | Zinc finger transcriptional activator of the Zn2Cys6 family; activates transcription of aromatic amino acid catabolic genes in the presence of aromatic amino acids |
| SIP4 | C6 zinc cluster transcriptional activator that binds to the carbon source-responsive element (CSRE) of gluconeogenic genes; involved in the positive regulation of gluconeogenesis; regulated by Snf1p protein kinase; localized to the nucleus |
| SPT10 | Putative histone acetylase, sequence-specific activator of histone genes, binds specifically and highly cooperatively to pairs of UAS elements in core histone promoters, functions at or near the TATA box |
| MET28 | Basic leucine zipper (bZIP) transcriptional activator in the Cbf1p-Met4p-Met28p complex, participates in the regulation of sulfur metabolism |
| GCN4 | Basic leucine zipper (bZIP) transcriptional activator of amino acid biosynthetic genes in response to amino acid starvation; expression is tightly regulated at both the transcriptional and translational levels |
| CAD1 | AP-1-like basic leucine zipper (bZIP) transcriptional activator involved in stress responses, iron metabolism, and pleiotropic drug resistance; controls a set of genes involved in stabilizing proteins; binds consensus sequence TTACTAA |
| INO2 | Component of the heteromeric Ino2p/Ino4p basic helix-loop-helix transcription activator that binds inositol/choline-responsive elements (ICREs), required for derepression of phospholipid biosynthetic genes in response to inositol depletion |
| THI2 | Zinc finger protein of the Zn(II)2Cys6 type, probable transcriptional activator of thiamine biosynthetic genes |
| SWI4 | DNA binding component of the SBF complex (Swi4p-Swi6p), a transcriptional activator that in concert with MBF (Mbp1-Swi6p) regulates late G1-specific transcription of targets including cyclins and genes required for DNA synthesis and repair |
| HAP5 | Subunit of the heme-activated, glucose-repressed Hap2/3/4/5 CCAAT-binding complex, a transcriptional activator and global regulator of |

Transcriptional activators

| Associated Gene(s) | Description(s) |
|---|---|
| | respiratory gene expression; required for assembly and DNA binding activity of the complex |
| HAP3 | Subunit of the heme-activated, glucose-repressed Hap2p/3p/4p/5p CCAAT-binding complex, a transcriptional activator and global regulator of respiratory gene expression; contains sequences contributing to both complex assembly and DNA binding |
| HAP2 | Subunit of the heme-activated, glucose-repressed Hap2p/3p/4p/5p CCAAT-binding complex, a transcriptional activator and global regulator of respiratory gene expression; contains sequences sufficient for both complex assembly and DNA binding |
| HAP4 | Subunit of the heme-activated, glucose-repressed Hap2p/3p/4p/5p CCAAT-binding complex, a transcriptional activator and global regulator of respiratory gene expression; provides the principal activation function of the complex |
| YML037C | Putative protein of unknown function with some characteristics of a transcriptional activator; may be a target of Dbf2p-Mob1p kinase; GFP-fusion protein co-localizes with clathrin-coated vesicles; YML037C is not an essential gene |
| TRA1 | Subunit of SAGA and NuA4 histone acetyltransferase complexes; interacts with acidic activators (e.g., Gal4p) which leads to transcription activation; similar to human TRRAP, which is a cofactor for c-Myc mediated oncogenic transformation |
| YLL054C | Putative protein of unknown function with similarity to Pip2p, an oleate-specific transcriptional activator of peroxisome proliferation; YLL054C is not an essential gene |
| RTG2 | Sensor of mitochondrial dysfunction; regulates the subcellular location of Rtg1p and Rtg3p, transcriptional activators of the retrograde (RTG) and TOR pathways; Rtg2p is inhibited by the phosphorylated form of Mks1p |
| YBR012C | Dubious open reading frame, unlikely to encode a functional protein; expression induced by iron-regulated transcriptional activator Aft2p |
| JEN1 | Lactate transporter, required for uptake of lactate and pyruvate; phosphorylated; expression is derepressed by transcriptional activator Cat8p during respiratory growth, and repressed in the presence of glucose, fructose, and mannose |
| MRP1 | Mitochondrial ribosomal protein of the small subunit; MRP1 exhibits genetic interactions with PET122, encoding a COX3-specific translational activator, and with PET123, encoding a small subunit mitochondrial ribosomal protein |
| MRP17 | Mitochondrial ribosomal protein of the small subunit; MRP17 exhibits genetic interactions with PET122, encoding a COX3-specific translational activator |
| TPI1 | Triose phosphate isomerase, abundant glycolytic enzyme; mRNA half-life is regulated by iron availability; transcription is controlled by activators Reb1p, Gcr1p, and Rap1p through binding sites in the 5' non-coding region |
| PKH3 | Protein kinase with similarity to mammalian phosphoinositide-dependent kinase 1 (PDK1) and yeast Pkh1p and Pkh2p, two redundant upstream activators of Pkc1p; identified as a multicopy suppressor of a pkh1 pkh2 double mutant |
| YGL079W | Putative protein of unknown function; green fluorescent protein (GFP)-fusion protein localizes to the endosome; identified as a transcriptional activator in a high-throughput yeast one-hybrid assay |
| TFB1 | Subunit of TFIIH and nucleotide excision repair factor 3 complexes, required for nucleotide excision repair, target for transcriptional activators |
| PET123 | Mitochondrial ribosomal protein of the small subunit; PET123 exhibits genetic interactions with PET122, which encodes a COX3 mRNA-specific translational activator |
| MHR1 | Protein involved in homologous recombination in mitochondria and in transcription regulation in nucleus; binds to activation domains of acidic activators; required for recombination-dependent mtDNA partitioning |
| MCM1 | Transcription factor involved in cell-type-specific transcription and pheromone response; plays a central role in the formation of both repressor and activator complexes |
| EGD1 | Subunit beta1 of the nascent polypeptide-associated complex (NAC) involved in protein targeting, associated with cytoplasmic ribosomes; enhances DNA binding of the Gal4p activator; homolog of human BTF3b |
| STE5 | Pheromone-response scaffold protein; binds Ste11p, Ste7p, and Fus3p kinases, forming a MAPK cascade complex that interacts with the plasma membrane and Ste4p-Ste18p; allosteric activator of Fus3p that facilitates Ste7p-mediated activation |

Transcriptional activators

Figure 4:
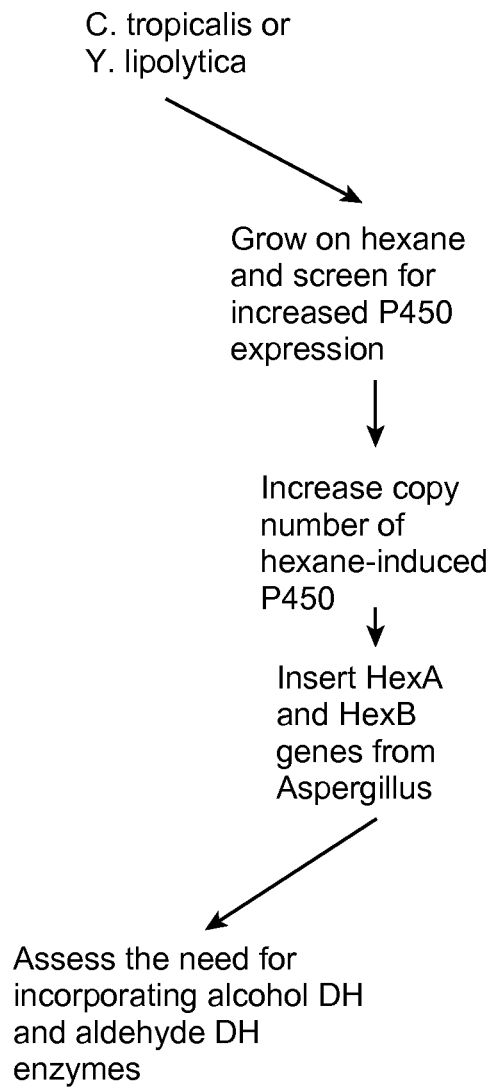
FIG. 4 depicts an embodiment of a method for generating an adipic acid producing organism. The method comprises expressing one or more genes encoding hexanoate synthase in a host microorganism that produces dicarboxylic acids via an omega-oxidation pathway. The microorganisms can include, without limitation, *C. tropicalis* and *C. maltosa*. In some embodiments, the method comprises growing a host microorganism on hexane and screening for increased P450 expression. In certain embodiments, copy number of hexane-induced P450 may be increased. HEXA and HEXB genes may be inserted into the host microorganism. In certain embodiments, the host microorganism may be altered to increase the flux of a six-carbon substrate through the final two oxidation steps.
Figure 5:
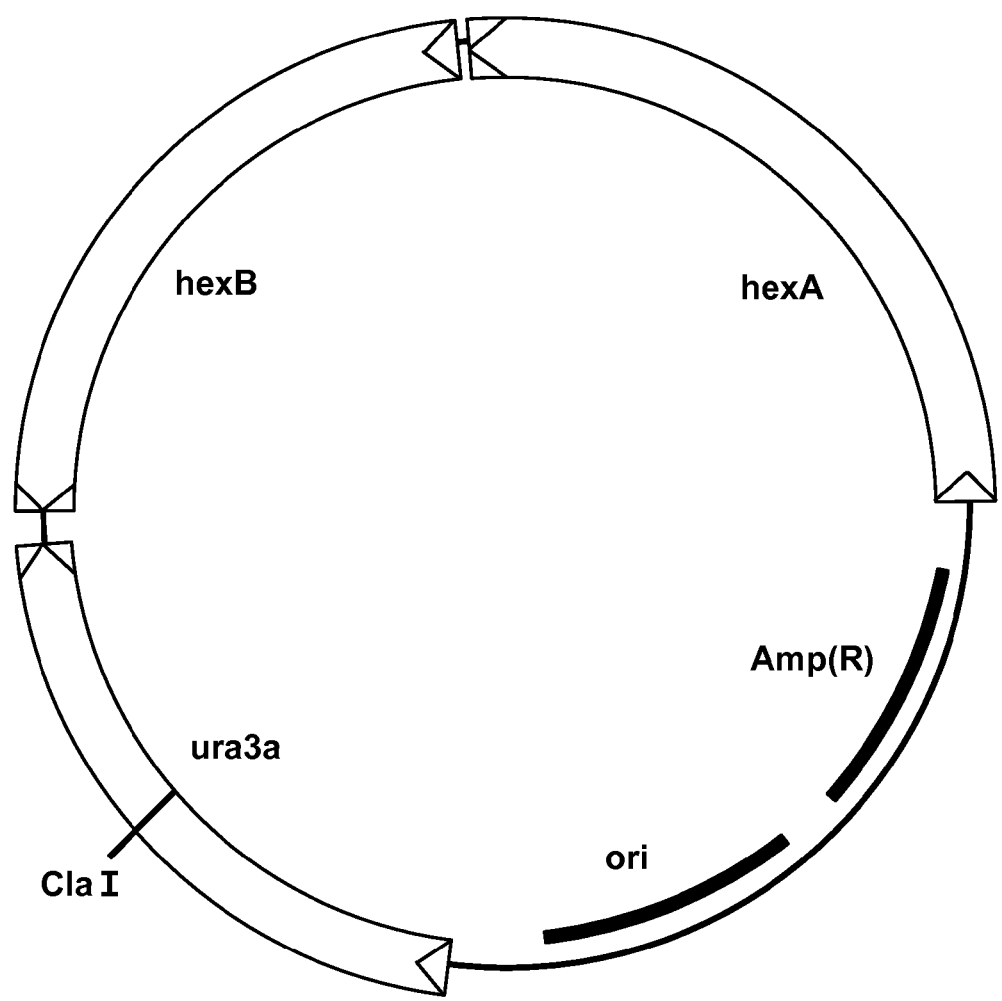
FIG. 5 depicts a plasmid diagram for inserting *Aspergillus* hexanoate synthase genes HEXA and HEXB into *C. tropicalis* or *Y. lipolytica*.
Figure 6:
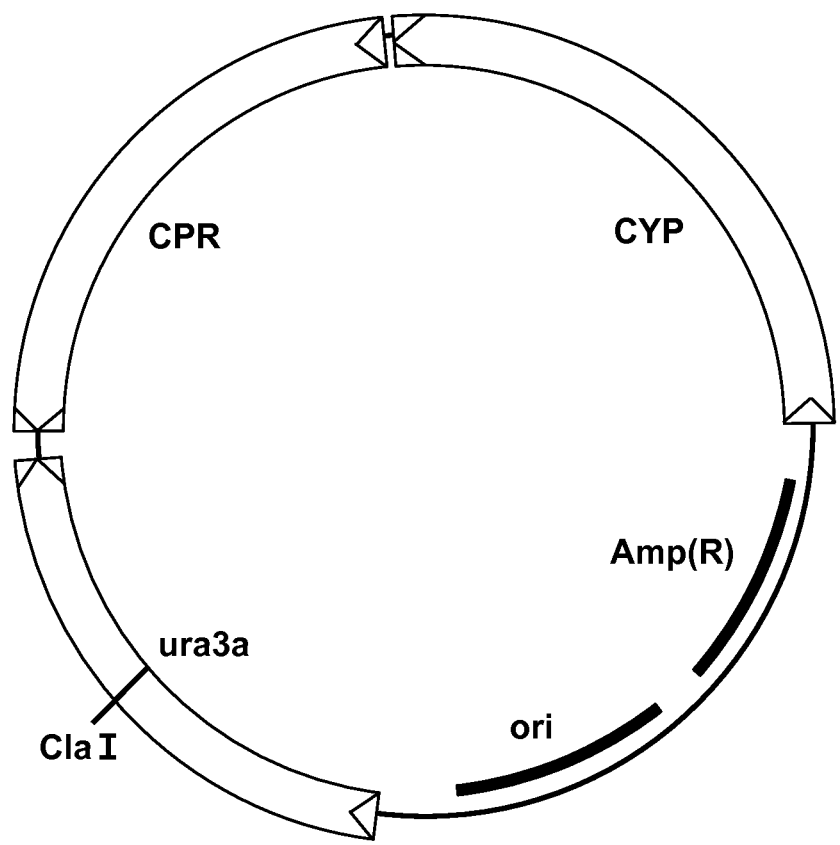
FIG. 6 depicts a plasmid diagram for inserting a heterologous cytochrome P450 monooxygenase gene and cytochrome P450 reductase gene into *C. tropicalis* or *Y. lipolytica*.
Figure 7:
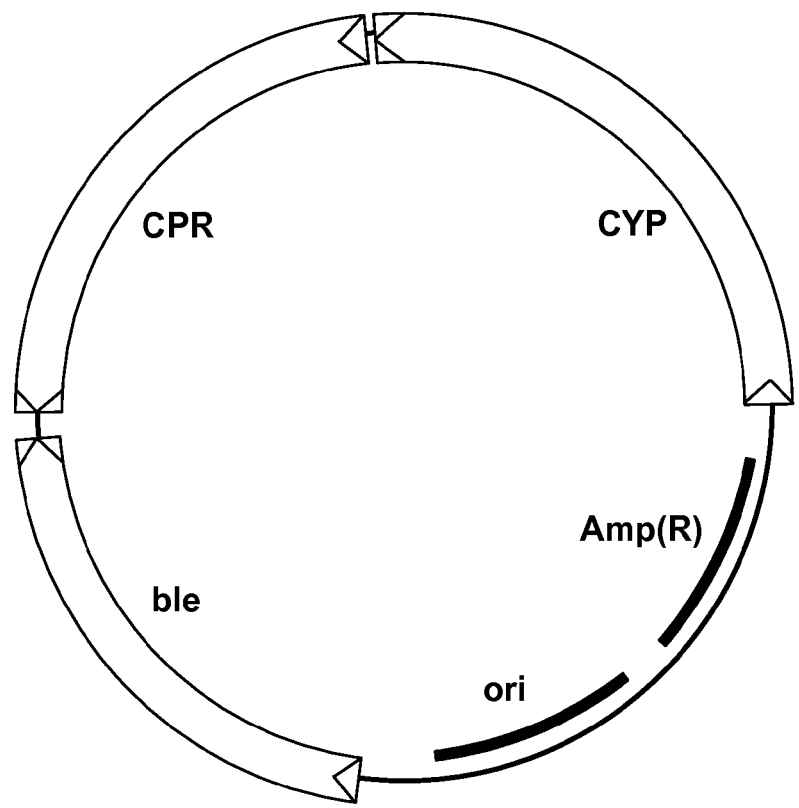
FIG. 7 depicts a plasmid diagram for inserting a heterologous cytochrome P450 monooxygenase gene and cytochrome P450 reductase gene into *A. parasiticus* or *A. nidulans*.
Figure 8:
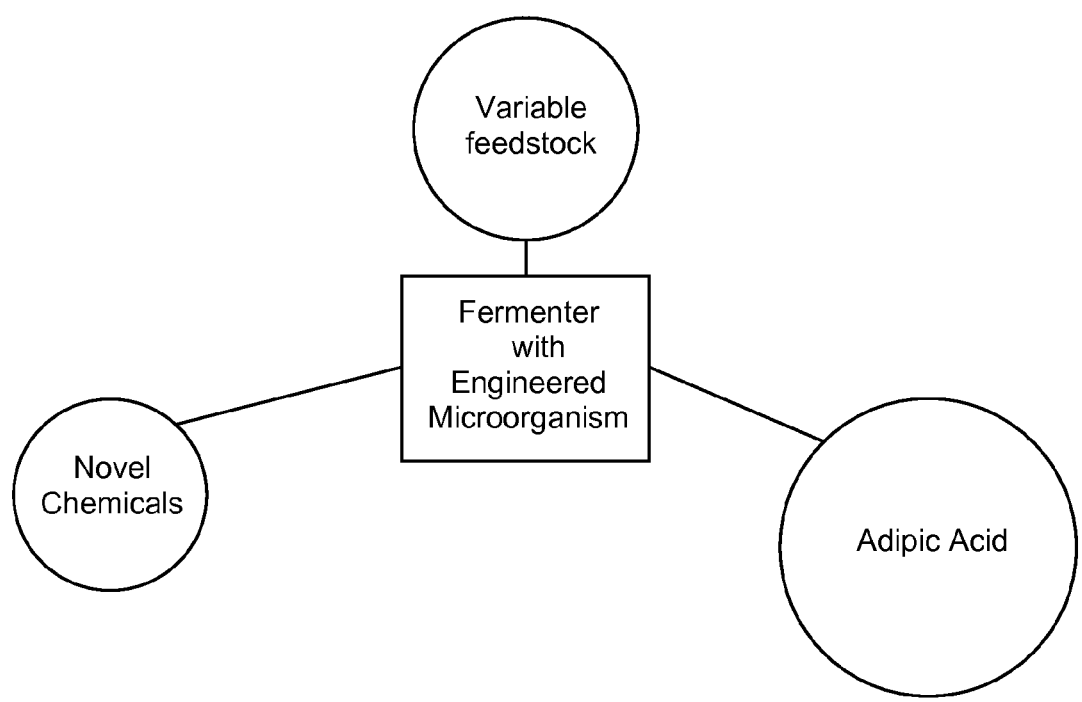
FIG. 8 depicts a system for biological production of a target product. As depicted, a fermenter is populated with microorganisms engineered for target product production. A flexible feedstock supplies the fermenter with an energy and nutrition source for the microorganisms. In some embodiments the feedstock comprises a sugar. In certain embodiments the feedstock comprises fatty acids. The feedstock may also include biomass, industrial waste products and other sources of carbon. Vitamins, minerals, enzymes and other growth or production enhancers may be added to the feedstock. In certain embodiments the fermentation produces adipic acid. The fermentation process may produce other novel chemicals.

| Associated Gene(s) | Description(s) |
|---|---|
| RGT1 | Glucose-responsive transcription factor that regulates expression of several glucose transporter (HXT) genes in response to glucose; binds to promoters and acts both as a transcriptional activator and repressor |
| TYE7 | Serine-rich protein that contains a basic-helix-loop-helix (bHLH) DNA binding motif; binds E-boxes of glycolytic genes and contributes to their activation; may function as a transcriptional activator in Ty1-mediated gene expression |
| VMA13 | Subunit H of the eight-subunit V1 peripheral membrane domain of the vacuolar H+-ATPase (V-ATPase), an electrogenic proton pump found throughout the endomembrane system; serves as an activator or a structural stabilizer of the V-ATPase |
| GAL11 | Subunit of the RNA polymerase II mediator complex; associates with core polymerase subunits to form the RNA polymerase II holoenzyme; affects transcription by acting as target of activators and repressors |
| VAC14 | Protein involved in regulated synthesis of PtdIns(3, 5)P(2), in control of trafficking of some proteins to the vacuole lumen via the MVB, and in maintenance of vacuole size and acidity; interacts with Fig4p; activator of Fab1p |

Example 7

Cloning of HEXA and HEXB genes

*Aspergillus parasiticus* (ATCC 24690) cultures were grown in malt extract broth media (15 g/L malt extract broth, Difco) with shaking at 25° C. for 3 days. *A. parasiticus* pellets were transferred to a 1.5 mL tube to provide a volume of pellets equal to approximately 500 uL. The mycelia were frozen in a dry ice ethanol bath, transferred to a mortar and pestle, and ground into a fine powder. The powder was placed in a 1.5 mL tube with approximately 500 uL 0.7 mm Zirconia beads, and total RNA was prepared using a Ribopure Plant Kit (Ambion), according to manufacturer's recommendations.

First strand synthesis of cDNA was performed with gene-specific primers oAA0031 (for HEXA) and oAA0041 (for HEXB) in a reaction containing 0.2 uL of gene-specific primer (10 uM), 300 ng total RNA, 1.0 uL dNTP (10 mM), and sterile water to bring the volume to 13 uL. The total RNA/primer mixtures were heated at 65° C. for 5 minutes then cooled on ice for 5 minutes before the addition of 4 uL 5× First strand buffer, 1 uL 0.1M DTT, 1 uL H20, and 1 uL Superscript III RT (Invitrogen). First strand synthesis reactions were incubated at 55° C. for 1 hour, followed by inactivation of the enzyme at 70° C. for 15 minutes and cooling of the reactions to 4° C. The primers utilized for isolation of HEXA and HEXB genes were configured to independently amplify the HEXA and HEXB genes in fragments, having fragment lengths in the range of between about 1.0 kilobases (kb) to about 1.6 kb, with approximately 200 bp of overlapping sequence between the fragments. The sequences are shown in the tables below.

| Oligos | Sequence | HEXA sequence | PCR product (bp) |
|---|---|---|---|
| oAA0022 | ATGGTCATCCAAGGGAAGAGATTGGCCGCCTCCTCTATTCAGC | 1-1149 | 1149 |
| oAA0023 | GTAGGCGTCACAGGAAAGACTGCGTACCA | | |
| oAA0024 | TATCACCAATGCTGGATGTAAAGAAGTCGCG | 941-2270 | 1330 |
| oAA0025 | AATTGGGCTAGGAAACCGGGGATGC | | |
| oAA0026 | CGGTCTAATGACGGCGCATGATATCATAGCCGAAACGGTCGAG | 2067-3016 | 950 |
| oAA0027 | ACTTGGCTGGAGTCCATCCCTTCGGCA | | |
| oAA0028 | CTGCCCGAGTTTGAAGTATCTCAACTTACCGCCGACGCCATG | 2812-4181 | 1370 |
| oAA0029 | TGAGACGCGCTGCGCAGGGC | | |
| oAA0030 | CGAGGTGATCGAGACGCAGATGC | 3975-5016 | 1042 |
| oAA0031 | TTATGAAGCACCAGACATCAGCCCCAGC | | |
| oAA0046 | gtactagtaaaaaaATGGTCATCCAAGGGAAGAGATTGGCCGCCTCCTCTATTCAGC | 1-5016 | 5041 |
| oAA0047 | gtcccgggctaTTATGAAGCACCAGACATCAGCCCCAGC | | |
| oAA0051 | tacccgggctattagtgatggtggtgatggtgTGAAGCACCAGACATCAGCCCCAGC | 1-5016 | 5062 |

| Oligonucleotides for cloning of HEXB DNA fragments | | | |
|---|---|---|---|
| Oligos | Sequence | HEXB sequence | PCR product (bp) |
| oAA0032 | ATGGGTTCCGTTAGTAGGGAACATGAGTCAATC | 1-1166 | 1166 |
| oAA0033 | GTTCCTTGTGTGAGCTCCTGAATAAGACTGCATG | | |
| oAA0034 | CCATCAAAATCCCCCTCTATCACACGGGCACTGGGAGCAAC | 962-2042 | 1081 |
| oAA0035 | CCCACGCCTTGCGCATCTATAATCAGG | | |
| oAA0036 | TGTCCGAATATTCTCCTCGTTGTAGGTAGTGGATT | 1837-3527 | 1691 |
| oAA0037 | GCAGTAGTCGATAGGTACACATCCTTGGGGGTTCCATGACTGC | | |
| oAA0038 | AGAGGATCAAGGCATTATACATGAGTCTGTGGAACTTGGGCTTTC | 3323-4461 | 1139 |
| oAA0039 | TTCCCCGTCCTCCATGGCCTTATGC | | |
| oAA0040 | GGCCTTTGCGCGATACGCTGGTCTCTCGGGTCCCAT | 4256-5667 | 1412 |
| oAA0041 | TCACGCCATTTGTTGAAGCAGGGAATG | | |
| oAA0048 | gtactagtaaaaaaATGGGTTCCGTTAGTAGGGAACATGAGTCAATC | 1-5667 | 5694 |
| oAA0049 | gtgtttaaacctaTCACGCCATTTGTTGAAGCAGGGAATG | | |
| oAA0111 | ggtttaaacctatcagtgatggtggtgatggtgCGCCATTTGTTGAAGCAGGGAATGAA | 1-5667 | 5714 |

HEXA and HEXB gene fragments were PCR amplified using the cDNA generated above by the addition of 5 uL 10×Pfu reaction buffer, 1.0 uL dNTPs (10 mM), 1.0 uL Sense and Antisense Primer Mix (10 uM), 1.0 uL Pfu Ultra Fusion HS (Agilent), 2.0 uL cDNA, 40 uL sterile H20. Thermocycling parameters used to amplify the HEXA and HEXB genes were 94° C. for 5 minutes, 40 cycles of 94° C. 30 seconds, 62° C. 40 seconds, 72° C. 4 minutes, followed by 72° C. 10 minutes and a 4° C. hold. PCR products of the correct size were gel purified and ligated into pCR-Blunt II-TOPO (Invitrogen), transformed into competent TOP10 E. coli cells (Invitrogen) and clones containing PCR inserts were sequenced to confirm correct DNA sequence.

Figure 11B:
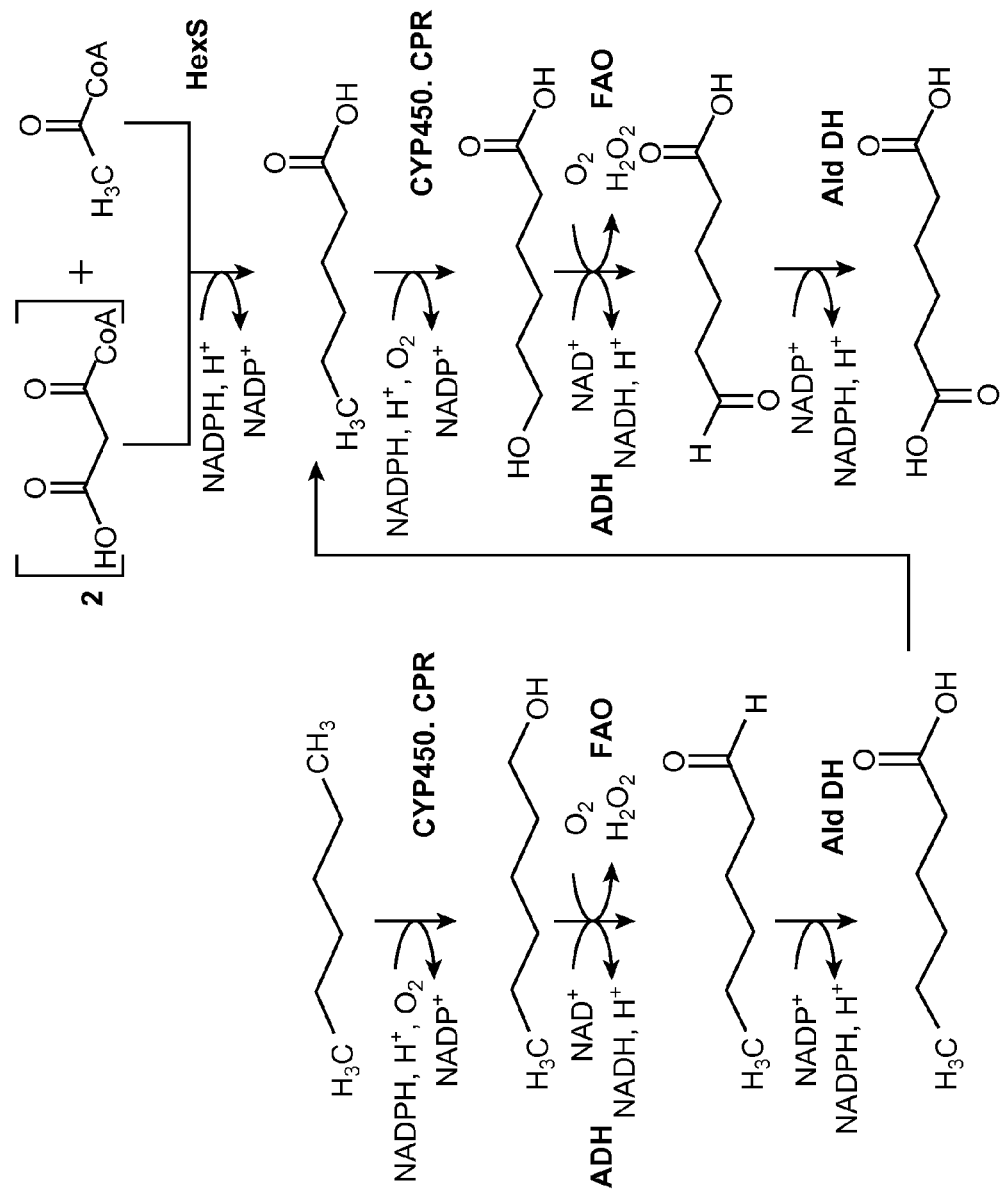
Figure 12:
FIG. 12 shows results of immunodetection of 6×His-tagged proteins expressed in S. cerevisiae BY4742. Strains sAA061, sAA140, sAA141, sAA142 contain 6×His-tagged HEXA and HEXB proteins. Strain sAA144 contains 6×His-tagged STCJ and STCK proteins. Strain sAA048 contains only vectors p425GPD and p426GPD.

DNA fragments of HEXA and HEXB were PCR amplified using the sequence-confirmed fragments in pCR-BluntII as template in order to produce overlapping DNA fragments covering the entire sequence of both HEXA and HEXB. The overlapping DNA fragments for each gene were combined in a 50 uL overlap extension PCR reaction containing each DNA fragment at 0.2 nM, sense and antisense primers at 0.2 uM each, 1×Pfu reaction buffer, 1.0 uL Pfu Ultra Fusion HS polymerase, and 0.2 mM dNTPs. Unique restriction sites were incorporated into the sense and antisense primers to allow for cloning the HEXA and HEXB genes into p425GPD and p426GPD respectively. For HEXA the restriction sites were SpeI/SmaI and for HEXB the restriction sites were SpeI/PmeI. Ligation of the HEXA and HEXB genes into p425GPD and p426GPD resulted in plasmids pAA020 and pAA021 respectively. Variants of the HEXA and HEXB genes that incorporated C-terminal 6xHis tags were constructed by using an antisense primer encoding a 6xHis sequence. Ligation of the HEXA-6xHis and HEXB-6xHis genes into p425GPD and p426GPD resulted in plasmids pAA031 and pAA032, respectively. Vectors pAA020, pAA021, pAA031 and pAA032 were used to demonstrate protein expression in S. cerevisiae, as shown in FIGS. 11 and 12.

Example 8

Cloning of STCJ and STCK Genes

Total RNA was prepared from Aspergillus nidulans (ATCC 38163), as described in Example 1. First strand synthesis of cDNA was performed with gene-specific primers oAA0008 (for STCJ) and oAA0021 (for STCK) in a reaction containing 0.2 uL of gene-specific primer (10 uM), 300 ng total RNA, 1.0 uL dNTP (10 mM), and sterile water to bring the volume to 13 uL. The total RNA/primer mixtures were heated at 65° C. for 5 minutes then cooled on ice for 5 minutes before the addition of 4 uL 5× First strand buffer, 1 uL 0.1M DTT, 1 uL H$_2$O, and 1 uL Superscript III RT (Invitrogen). First strand synthesis reactions were incubated at 55° C. for 1 hour, followed by inactivation of the enzyme at 70° C. for 15 minutes and cooling of the reactions to 4° C. Primers design strategies substantially similar to those described herein were used to amplify the STCJ and STCK genes in fragments in the range of between about 1.1 kb to about 1.6 kb, with approximately 200 bp of overlapping sequence between the fragments. The primers used to amplify the STCJ and STCK genes are shown in the tables below.

| Oligonucleotides for cloning of STCJ DNA fragments | | | |
|---|---|---|---|
| Oligos | Sequence | STCJ sequence | PCR product (bp) |
| oAA0001 | ATGACCCAAAAGACTATACAGCAGGTCCCAAGA | 1-1290 | 1290 |
| oAA0002 | TATGGTGCATCGAATGTTGTTTGCCTGG | | |
| oAA0009 | AAAATGCGTGAGCACTTTGTCCAGCGC | 1021-2506 | 1486 |
| oAA0004 | CGACGTAATTGACGTTGTCAACATGCCG | | |

| | | | |
|---|---|---|---|
| oAA0005 | CATCTCGGGTTCCCATCACTCCCTGAGTATGAC | 2284-3424 | 1141 |
| oAA0006 | GACAAAGAAGCTGGACACCGCAGCCTTGGGATTCCACGAAC | | |
| oAA0007 | GATCTGCCTTGTCGGTGGCTATGACGACCTTCAGCCTGAGGAGTCA | 3234-4680 | 1447 |
| oAA0008 | TTAACGGATGATAGAGGCCAACGGCCAAAGACACCACTTGCGTACAC | | |
| oAA0126 | cacacaactagtaaaaaaATGACCCAAAAGACTATACAGCAGGTCCCAAGA | 1-4680 | 4710 |
| 0AA0127 | tgtgtgcccgggTTAACGGATGATAGAGGCCAACGGCCAAAGACACCACTTGCGTACAC | | |
| oAA0154 | tacccgggctattagtgatggtggtgatggtgACGGATGATAGAGGCCAAC | 1-4680 | 4730 |

| Oligonucleotides for cloning of STCK DNA fragments | | | |
|---|---|---|---|
| Oligos | Sequence | STCK sequence | PCR product (bp) |
| oAA0012 | ATGACTCCATCACCGTTTCTCGATGCTGT | 1-1110 | 1110 |
| oAA0013 | CACATGGGTAGCATCGTTCATTGCCCAACACAAAGCGGGCCAGTTAACTC | | |
| oAA0014 | GTCGAGCTAAGAGTGACTGATGCCATTGGC | 901-2510 | 1610 |
| oAA0015 | CGTAATTCAGCTTCTGAACCTGAGCCCAGG | | |
| oAA0016 | CTTTGCCCGGCCGTGGTTCGC | 2301-3555 | 1255 |
| oAA0017 | CCCCCAAGCTCGACAACGGGC | | |
| oAA0018 | TTCTCAAAATGCACCGGACTGATTACTTGGA | 3350-4682 | 1333 |
| oAA0019 | CCCATTCCTCTCTCCTGCGTGCCCTGGCCGGTAAAGACGTAT | | |
| oAA0020 | CCCTCCTTCGATGGACTTGTCCGGGCAAACGACCGGTTGCGAATGGAGAT | 4477-5745 | 1268 |
| oAA0021 | CTACCTATTCTCTTCAACCCGCCGTAACAGC | | |
| oAA0128 | cacacaactagtaaaaaaATGACTCCATCACCGTTTCTCGATGCTGT | 1-5745 | 5775 |
| oAA0129 | tgtgtgcccgggCTACCTATTCTCTTCAACCCGCCGTAACAGC | | |
| oAA0170 | tgtgtgcccgggctatcagtgatggtggtgatggtgCCTATTCTCTTCAAC | 1-5745 | 5796 |

STCJ and STCK fragments were amplified using the cDNA prepared above in PCR reactions containing 5 uL 10×Pfu reaction buffer, 1.0 uL dNTPs (10 mM), 1.0 uL Sense and Antisense Primer Mix (10 uM), 1.0 uL Pfu Ultra Fusion HS (Agilent), 2.0 uL cDNA, 40 uL sterile H20. Thermocycling parameters used were 94° C. for 5 minutes, 40 cycles of 94° C. 30 seconds, 62° C. 40 seconds, 72° C. 4 minutes, followed by 72° C. 10 minutes and a 4° C. hold. PCR products of the correct size were gel purified and ligated into pCR-Blunt II-TOPO (Invitrogen), transformed into competent TOP10 *E. coli* cells (Invitrogen). PCR inserts were sequenced to confirm the correct DNA sequence. DNA fragments of STCJ and STCK were PCR amplified using the sequence-confirmed fragments in pCR-BluntII as template in order to produce overlapping DNA fragments covering the entire sequence of both STCJ and STCK. The overlapping DNA fragments for each gene were combined in a 50 uL overlap extension PCR reaction containing each DNA fragment at 0.2 nM, sense and antisense primers at 0.2 uM each, 1×Pfu reaction buffer, 1.0 uL Pfu Ultra Fusion HS polymerase, and 0.2 mM dNTPs.

Sense and antisense primers were designed to incorporate unique restriction sites for cloning the STCJ and STCK genes into p425GPD and p426GPD respectively. For STCJ the restriction sites were SpeI/XmaI and for STCK the restriction sites were SpeI/SmaI. Ligation of the STCJ and STCK genes into p425GPD and p426GPD resulted in plasmids pAA040 and pAA042 respectively. Variants of the STCJ and STCK genes that incorporated C-terminal 6×His tags were constructed by using an antisense primer encoding a 6×His sequence. Ligation of the STCJ-6×His and STCK-6×His genes into p425GPD and p426GPD resulted in plasmids pAA041 and pAA043. Vectors pAA040, pAA0421 pAA042 and pAA043 were used to demonstrate protein expression in *S. cerevisiae*, as shown in FIGS. 11 and 12.

Example 9

Design and Cloning of HEXA and HEXB Genes for *C. tropicalis* Alternate Genetic Code The HEXA and HEXB genes contain multiple CTG codons, which normally code for leucine. However, certain organisms, *Candida tropicalis* for example, translate CTG as serine. DNA sequences for HEXA and HEXB were prepared that replaced all CTG codons with TTG codons, which is translated as leucine in *C. tropicalis*. The TTG codon was chosen due to it being the most frequently used leucine codon in *C. tropicalis*. The alternate genetic code (AGC) HEXA and HEXB genes were synthesized as equal size fragments with 200 bp overlaps and ligated into pUC57 vector (Integrated DNA Technologies). DNA fragments of AGC-HEXA and AGC-HEXB were PCR amplified using the fragments in pUC57 as template in order to produce overlapping DNA fragments covering the entire sequence of both AGC-HEXA and AGC-HEXB.

The overlapping DNA fragments for each gene were combined in a 50 uL overlap extension PCR reaction containing each DNA fragment at 0.2 nM, sense and antisense primers at 0.2 uM each, 1×Pfu reaction buffer, 1.0 uL Pfu Ultra Fusion HS polymerase, and 0.2 mM dNTPs. Sense and antisense primers incorporated unique SapI restriction sites for cloning the AGC-HEXA and AGC-HEXB genes into pAA105 resulting in plasmids pAA127 and pAA129 respectively. Gene variants of AGC-HEXA and AGC-HEXB that contained C-terminal 6×His tags were ligated into pAA105 resulting in plasmids pAA128 and pAA130 respectively. The alternate genetic code primers used to alter leucine codons for *C. tropicalis* expression of HEXA and HEXB are shown in the tables below.

media; SC-URA (for p426-based vectors) or SC-LEU (for p425-based vectors).

Example 11

Transformation of *C. tropicalis* Procedure 5 mL YPD start cultures were inoculated with a single colony of *C. tropicalis* and incubated overnight at 30° C., with shaking at about 200 rpm. The following day, fresh 25 mL YPD cultures, containing 0.05% Antifoam B, were inoculated to an initial $OD_{600\,nm}$ of 0.4 and the culture incubated at 30° C., with shaking at about 200 rpm until an $OD_{600\,nm}$ of 1.0-2.0 was reached. Cells were pelleted by centrifugation at 1,000×g, 4° C. for 10 minutes. Cells were washed by resuspending in 10 mL sterile water, pelleted, resuspended in 1 mL

| Oligonucleotides for cloning of AGC-HEXA DNA fragments | | | |
|---|---|---|---|
| Oligos | Sequence | AGC-HEXA sequence | PCR product (bp) |
| oAA0383 | cacacagctcttctagaATGGTCATCCAAGGGAAGAG | 1-1404 | 1421 |
| oAA0055 | AGTATCGACGTCGGCTGACTTGAGACCA | | |
| oAA0056 | CCATCACATCCACAGTGGCGG | 1205-2609 | 1405 |
| oAA0057 | AACCAGGCAAGTTCGACATAACCGGC | | |
| oAA0058 | GTAGGCTATCCCCGTCTCCCCGATTATG | 2410-3814 | 1405 |
| oAA0059 | TGATTGAGGTCAAGGATGATTTGTCCGAGA | | |
| oAA0060 | TCTTCCTATCTATGCGGTCATTGCCAGCT | 3615-5016 | 1419 |
| oAA0384 | cacacagctcttcctttTTATGAAGCACCAGACATCAAC | | |
| oAA0385 | cacacagctcttcctttttagtgatggtggtgatggtgTGAAGCACCAGACATCAACCCCAACG | 1-5016 | 5071 |

| Oligonucleotides for cloning of AGC-HEXB DNA fragments | | | |
|---|---|---|---|
| Oligos | Sequence | AGC-HEXB sequence | PCR product (bp) |
| oAA0386 | cacacagctcttctagaATGGGTTCCGTTAGTAGGGA | 1-1566 | 1583 |
| oAA0064 | CAAATCCTTGATGACAGAGATCTGCCAGGA | | |
| oAA0065 | GCTGGGACTTTGTCGCTGCCGTTGCTCAAGCTGGAT | 1367-2933 | 1567 |
| oAA0066 | ACTGCTCCTACTTTCTCGAACTTATAGAGCCCTTG | | |
| oAA0067 | ATATCCGACGATGAGTCTGT | 2734-4299 | 1566 |
| oAA0068 | ATGGACAATGGGACCCGAGA | | |
| oAA0069 | GGACTTCTTGCACCGCTACG | 4101-5667 | 1584 |
| oAA0387 | cacacagctcttcctttTCACGCCATTTGTTGAAGCAAAG | | |
| oAA0388 | cacacagctcttccttttcagtgatggtggtgatggtgCGCCATTTGTTGAAGCA | 1-5667 | 5692 |

Example 10

Transformation of *S. cerevisiae* Procedure

Competent cells of *S. cerevisiae* strain BY4742 were prepared using the Frozen-EZ Yeast Transformation II Kit (Zymo Research) following manufacturer's instructions. 50 uL aliquots of competent cells were stored at −80° C. until use. Competent cells were transformed by the addition of 0.5-1.0 ug of intact plasmid DNA as instructed by the Frozen-EZ Yeast Transformation II Kit (Zymo Research). Selection for transformants was performed by plating on selective sterile water and transferred to a 1.5 mL microcentrifuge tube. The cells were then washed in 1 mL sterile TE/LiOAC solution, pH 7.5, pelleted, resuspended in 0.25 mL TE/LiOAC solution and incubated with shaking at 30° C. for 30 minutes.

The cell solution was divided into 50 uL aliquots in 1.5 mL tubes to which was added 5-8 ug of linearized DNA and 5 uL of carrier DNA (boiled and cooled salmon sperm DNA, 10 mg/mL). 300 uL of sterile PEG solution (40% PEG 3500, 1×TE, 1×LiOAC) was added, mixed thoroughly and incubated at 30° C. for 60 minutes with gentle mixing every 15 minutes. 40 uL of DMSO was added, mixed thoroughly and the cell solution was incubated at 42° C. for 15 minutes. Cells were then pelleted by centrifugation at 1,000×g 30 seconds, resuspended in 500 uL of YPD media and incubated at 30° C. with shaking at about 200 rpm for 2 hours. Cells were then pelleted by centrifugation and resuspended in 1 mL 1×TE, cells were pelleted again, resuspended in 0.2 mL 1×TE and plated on selective media. Plates were incubated at 30° C. for growth of transformants.

Example 12

HEXA and HEXB Expression in *S. cerevisiae*

Plasmids pAA031 and pAA032 were transformed into competent BY4742 *S. cerevisiae* cells independently and in combination. Selection for transformants containing pAA031 was performed on SC-LEU plates. Selection for transformants containing pAA032 was performed on SC-URA plates. Selection for transformants containing both pAA031 and pAA032 was performed on SC-URA-LEU plates. Single colonies were used to inoculate 5 mL of SC drop out media and grown overnight at 30° C., with shaking as described herein. Cells from 3 mL of overnight culture were harvested by centrifugation at 12,000 rpm for 2 minutes. Cell pellets were incubated at –80° C. until frozen.

Approximately 500 uL of cold 0.7 mm zirconia beads (Ambion) were added on top of the frozen cell pellets. Yeast lysis buffer (50 mM Tris pH 8.0, 0.1% Triton X100, 0.5 mM EDTA, 1× ProCEASE protease inhibitors [G Biosciences]) was added to fill the tube leaving as little air in the tube as possible, the tubes were placed on ice during manipulations. Cells were broken using three, 2 minute cycles in a Bead Beater (BioSpec) with 1 minute rests on ice between cycles. 200 uL of whole cell extract (WCE) was removed to a new tube and the remainder of the whole cell extract was centrifuged at 16,000×g, 4° C. for 15 minutes to pellet insoluble debris. The supernatant was removed to a new tube as the soluble cell extract (SCE). The protein content in the soluble cell extract was determined by Bradford assay (Pierce). A volume of SCE containing 50 ug of protein (and the same volume WCE) was precipitated by the addition of 4 volumes of cold 100% acetone. After centrifugation at 16,000×g, and 4° C. for 15 minutes, the supernatant was carefully removed and the pellet washed with 200 uL of cold 80% acetone and centrifuged again. The supernatant again was carefully removed and the cell pellets air dried for 5 minutes.

Protein pellets were then resuspended in 1×LDS sample buffer containing 50 mM DTT (Invitrogen) by incubating at 70° C., with shaking at about 1200 rpm. After brief centrifugation and cooling to room temperature, samples (20 ug) were separated by SDS PAGE and transferred to nitrocellulose for immunodetection with mouse anti-6×His antibodies (Abcam). Incubation in 1:5,000 primary antibody was performed overnight at room temperature, incubation in 1:5,000 donkey anti-mouse HRP conjugate secondary antibody was performed for 3 hours at room temperature, and detection was performed with SuperSignal West Pico chemiluminescent substrate (Pierce). Multiple clones displayed soluble expression of both HEXA and HEXB subunits of hexanoate synthase. As shown in FIG. 11, a substantial portion of the expressed protein fractionated with the insoluble pellet. Strains sAA061, sAA140, sAA141, sAA142 contained 6×His-tagged HEXA and HEXB proteins. Strain sAA048 contained only vectors p425GPD and p426GPD.

Example 13

STCJ and STCK Expression in *S. cerevisiae*

Plasmids pAA041 and pAA043 were cotransformed into competent BY4742 *S. cerevisiae*. Selection for transformants containing both pAA041 and pAA043 was performed on SC-URA-LEU plates. Culture growth, cell extract preparation, SDS PAGE, and immunodetection were performed as described herein. One clone displayed soluble expression of both STCJ and STCK subunits. As shown in FIG. 11, a substantial portion of the expressed protein fractionated with the insoluble pellet. Strain sAA144 contained 6×His-tagged STCJ and STCK proteins. Strain sAA048 contained only vectors p425GPD and p426GPD.

Example 14

HEXA and HEXB Expression in *C. tropicalis*

Plasmids pAA128 and pAA130 were linearized using ClaI, and cotransformed into competent sAA103 cells (ura3/ura3, pox4::ura3/pox4::ura3, pox5::ura3/pox5::ura3). The ClaI recognition sites in the HEXA and HEXB ORF's are blocked due to overlapping dam methylation. Selection for transformants containing integrated vector DNA was performed on SC-URA plates. Confirmation of vector integration was performed by PCR using HEXA and HEXB specific primers. Transformants that were PCR positive for both HEXA and HEXB were selected for analysis of target protein expression. Overnight culture growth was performed as described herein. Fresh 5 mL YPD cultures were inoculated from the overnight cultures to an initial $OD_{600\,nm}$ of 0.4 and incubated until the $OD_{600\,nm}$ reached ~5-8, at which point the culture was harvested. Cell extract preparation, SDS PAGE, and immunodetection were performed as described herein. Strains sAA269 and sAA270 contained plasmids pAA128 and pAA130 integrated into the genome for expression of 6×His-tagged HEXA and HEXB proteins. Both strains displayed soluble expression of 6×His-tagged HEXA and HEXB subunits as shown in FIG. 12. 6×His tagged HEXA and HEXB expressed in strains sAA269 and sAA270 are indicated with arrows. 6×His tagged STCJ and STCK from strain sAA144 were included as a positive control. Strain sAA103 is the parent strain for sAA269 and sAA270 and does not contain integrated vectors for the expression of 6×His-tagged HEXA and HEXB.

Example 15

Procedure for Recycling of the URA3 Marker

*C. tropicalis* has a limited number of selectable marker, as compared to *S. cerevisiae*, therefore, the URA3 marker is "recycled" to allow multiple rounds of selection using URA3. To reutilize the URA3 marker for subsequent engineering of *C. tropicalis*, a single colony having the Ura$^+$ phenotype was inoculated into 3 mL YPD and grown overnight at 30° C. with shaking. The overnight culture was then harvested by centrifugation and resuspended in 1 mL YNB+YE (6.7 g/L Yeast Nitrogen Broth, 3 g/L Yeast Extract). The resuspended cells were then serially diluted in YNB+YE and 100 uL aliquots plated on YPD plates (incubation overnight at 30° C.) to determine titer of the original suspension. Additionally, triplicate 100 uL aliquots of the undiluted suspension were plated on SC Dextrose (Bacto Agar 20 g/L, Uracil 0.3 g/L, Dextrose 20 g/L, Yeast Nitrogen Broth 6.7 g/L, Amino Acid Dropout Mix 2.14 g/L) and 5-FOA. at 3 different concentrations (0.5, 0.75, 1 mg/mL).

Plates were incubated for at least 5 days at 30° C. Colonies arising on the SC Dextrose+5-FOA plates were resuspended in 50 uL sterile, distilled water and 5 uL utilized to streak on to YPD and SC-URA (SC Dextrose medium without Uracil)

plates. Colonies growing only on YPD and not on SC-URA plates were then inoculated into 3 mL YPD and grown overnight at 30° C. with shaking. Overnight cultures were harvested by centrifugation and resuspended in 1.5 mL YNB (6.7 g/L Yeast Nitrogen Broth). The resuspended cells were serially diluted in YNB and 100 uL aliquots plated on YPD plates and incubation overnight at 30° C. to determine initial titer. 1 mL of each undiluted cell suspension also was plated on SC-URA and incubated for up to 7 days at 30° C. Colonies on the SC-URA plates are revertants and the isolate with the lowest reversion frequency ($<10^{-7}$) was used for subsequent strain engineering.

Example 16

Omega Oxidation of Hexane and Hexanoic Acid to Adipic Acid

Starter cultures of strain sAA003 were grown in $YPD_{2.0}$ (1% yeast extract, 2% peptone, 2% dextrose) overnight as described. Starter cultures were used to inoculate 100 mL of fresh $YPD_{2.0}$ to an initial $OD_{600\ nm}$ of 0.4 and incubated overnight at 30° C., with shaking at about 200 rpm. The 100 mL culture was pelleted by centrifugation at 4,000×g, 23° C. for 10 minutes and resuspended in 100 mL fresh $YPD_{0.1}$ media (1% yeast extract, 1% peptone, 0.1% dextrose). The culture was divided into 4×25 mL cultures to which were added either 1% hexane, 0.05% hexanoic acid, 1.0% hexanoic acid, or no other carbon source. Strain sAA003 is completely blocked in β-oxidation, therefore fermentation tested the ability of the β-oxidation pathway to oxidize C6 substrates. Samples were taken at 24, 48, and 72 hours and analyzed by LC-MS (Scripps Center for Mass Spectrometry) using published methods for the detection of adipic acid (Cheng et al., 2000). The data for the 72 hour time-point, shown in the table below demonstrates that strain sAA003 was able to oxidize both hexanoic acid and hexane to adipic acid. The results also indicate that the 1% hexanoic acid level was toxic to the cells leading to no production of adipic acid over background levels.

Oxidation of hexane and hexanoic acid to adipic acid

| Time (h) | MEDIA | Adipic acid (mg/L) |
|---|---|---|
| 0 | $YPD_{0.1}$ | 0.000 |
| 72 | $YPD_{0.1}$ | 0.005 |
| 72 | $YPD_{0.1}$ + 0.05% Hexanoic Acid | 0.406 |
| 72 | $YPD_{0.1}$ + 1% Hexanoic Acid | 0.003 |
| 72 | $YPD_{0.1}$ + 1% Hexane | 0.091 |

Example 17

Identification of P450 Alleles Induced by Exposure to Hexane or Hexanoic Acid 350 mL cultures grown overnight in YNB-Salts+2.0% Glucose (6.7 g/L Yeast Nitrogen Broth, 3.0 g/L Yeast Extract, 3.0 g/L ammonium sulfate, 3.0 g/L monopotassium phosphate, 0.5 g/L sodium chloride, and 20 g/L dextrose) were inoculated from a 3 mL overnight culture of YPD (1% Yeast Extract, 2% Peptone, 2% Dextrose), and used for RNA preparation. Cultures were harvested by centrifugation. Each pellet was resuspended in 100 mL of YNB-Salts medium with no glucose. A 1 mL aliquot was taken for RNA isolation as a time=0 control. To each 100 mL suspension, a different inducer was added, 1% glucose, 1% hexane or 0.05% hexanoic acid and aliquoted as two 50 mL portions into 250 mL baffled flasks and incubated for 2 or 4 hours at 30° C. with shaking. At 2 hours and 4 hours, one flask for each inducer was harvested by centrifugation and resuspended in its own spent media in order to collapse culture foam. 1 mL samples were isolated by centrifugation of 1 mL of each culture and RNA prepared using the RiboPure-Yeast Kit, according to the manufacturer's directions, with an additional extraction of the initial RNA preparations with 1 volume of Chloroform:Isoamyl Alcohol (24:1) to the aqueous phase after lysis and extraction with Phenol:Chloroform:Isoamyl Alcohol (25:24:1).

Each RNA preparation was further purified by precipitation with ethanol and treatment with DNase I, again according to manufacturers' recommendations. All RNA preparations were shown to be free of contaminating genomic DNA by electrophoresis and by failure to prime a PCR product of the URA3 gene. First strand synthesis reactions were completed for each RNA preparation using Superscript III Reverse Transcriptase (Invitrogen), as described herein. Reactions for each sample consisted of 1 uL oAA0542 (polyT 10 uM), 1 uL dNTP mix (10 mM each), 1 mg RNA in 13 uL sterile, distilled water. The RNA/primer mix was heated to 65° C. for 5 minutes, and on ice for 1 minute. Primers were generated that amplified a substantially unique area of each cytochrome P450 and are shown in the table below.

Figure 13:
FIG. 13 shows results of immunodetection of 6×His-tagged proteins expressed in either S. cerevisiae (sAA144) or in C. tropicalis (sAA103, sAA270, sAA269). 6×His tagged HEXA and HEXB expressed in strains sAA269 and sAA270 are indicated with arrows. 6×His tagged STCJ and STCK from strain sAA144 were included as a positive control. Strain sAA103 is the parent strain for sAA269 and sAA270 and does not contain integrated vectors for the expression of 6×His-tagged HEXA and HEXB.
Figure 14:
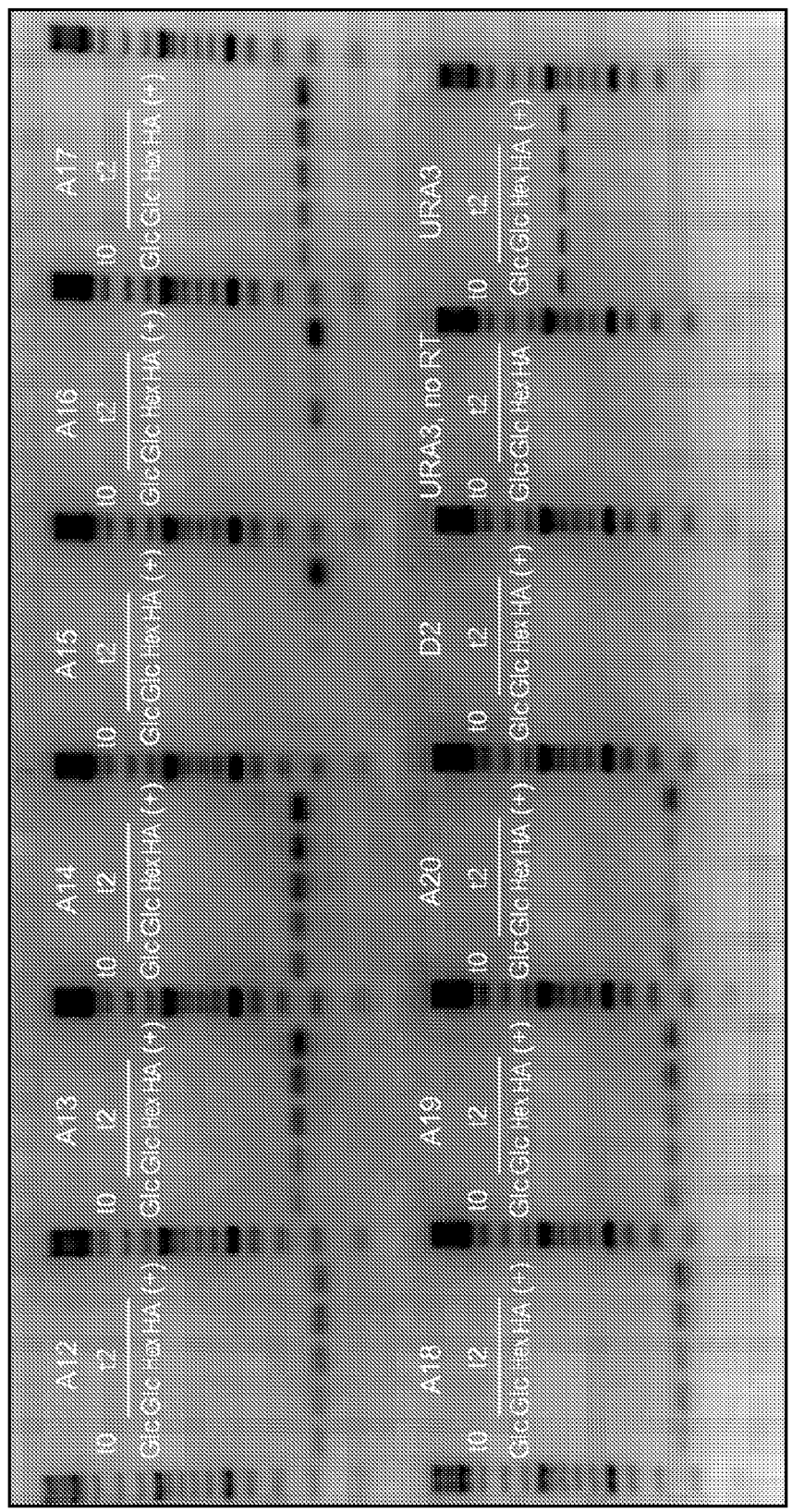
FIG. 14 shows results of RT-PCR from cultures of C. tropicalis strain sAA003 exposed to glucose only (Glc), hexane only (Hex), or hexanoic acid only (HA). PCR products of A15 and A16 alleles show hexane and hexanoic acid specific induction.

PCR reactions were performed on the 2 hour induced cDNA samples and compared to the Time=0 and genomic DNA controls. PCR reactions for each cDNA and primer pair combination consisted of 0.5 uL template, sense and antisense primers at 0.4 uM each, 1×Taq DNA polymerase Buffer (New England Biolabs), 0.1 uL Taq DNA polymerase, and 0.2 mM dNTPs and sterile, distilled water to 25 uL. Cycling parameters used were 95° C. for 5 minutes, 30 cycles of 95° C. 30 seconds, 50° C. 40 seconds, 72° C. 2 minutes, followed by 72° C. 5 minutes and a 4° C. hold. PCR reactions were electrophoresed on 1.2% agarose gels to identify differential expression due to the inducer used. Several P450s displayed increased induction in the presence of hexane or hexanoic acid, however the results were not quantitative. Two Cytochrome P450's, CYP52A15 and CYP52A16, showed induction only in the presence of hexane and hexanoic acid and not in the presence of glucose, as shown in FIG. 13. The primers used for PCR analysis of induced expression are shown in the table below.

Oligonucleotides for identification of P450 DNA fragments

| Oligos | Sequence | P450 | P450 sequence | PCR product (bp) |
|---|---|---|---|---|
| oAA0082 | gattactgcagcagtattagtcttc | CYP52A12 | 60-249 | 190 |
| oAA0083 | gtcgaaaacttcatcggcaaag | | | |
| oAA0084 | cacgatattatcgccacatacttc | CYP52A13 | 10-256 | 247 |
| oAA0085 | cgggacgatcgagatcgtggatacg | | | |

Oligonucleotides for identification of P450 DNA fragments

| Oligos | Sequence | P450 | P450 sequence | PCR product (bp) |
|---|---|---|---|---|
| oAA0086 | caggatattatcgccacatacatc | CYP52A14 | 10-256 | 247 |
| oAA0087 | ctggacgattgagcgcttggatacg | | | |
| oAA0088 | cgtcttctccatcgtttgcccaagag | CYP52A15 | 5-199 | 195 |
| oAA0089 | ggtccctgacaaagttaccgagtg | | | |
| oAA0090 | cgtcttctccatcgtttgctcaggag | CYP52A16 | 5-199 | 195 |
| oAA0091 | gatccaacacgacgttaccgagcg | | | |
| oAA0092 | ggtatgtcgttgtgccagtgttg | CYP52A17 | 26-248 | 223 |
| oAA0093 | cccacgctttgggttcttggagtggtc | | | |
| oAA0094 | ggtatattgttgtgcctgtgttg | CYP52A18 | 26-248 | 223 |
| oAA0095 | ccgacgctttgggttcttggagctgtc | | | |
| oAA0096 | ggaaggatgaggtggtgcagtac | CYP52A19 | 1217-1458 | 242 |
| oAA0097 | gtcttgtgacaagtttggaaactc | | | |
| oAA0098 | gaaagaatgaggtggtgcaatac | CYP52A20 | 1217-1458 | 242 |
| oAA0099 | gtcctgtgacaagctagggaattc | | | |
| oAA0104 | ctatcgtgggatgtgatctgtgtcg | CYP52D2 | 19-231 | 213 |
| oAA0105 | ctcgaatctcttgacactgaactcg | | | |

Example 18

Cloning and Analysis of *C. tropicalis* Fatty Alcohol Oxidase (FAO) Alleles

Isolation of Fatty Alcohol Oxidase Genes from *C. tropicalis*

*C. tropicalis* (ATCC20336) fatty alcohol oxidase genes were isolated by PCR amplification using primers generated to amplify the sequence region covering promoter, fatty alcohol oxidase gene (FAO) and terminator of the FAO1 sequence (GenBank accession number of FAO1 AY538780). The primers used to amplify the fatty alcohol oxidase nucleotide sequences from *C. tropicalis* strain ATCC20336, are showing in the table below.

PCR reactions contained 25 uL 2× master mix, 1.5 uL of oAA0144 and oAA0145 (10 uM), 3.0 uL genomic DNA, and 19 uL sterile H$_2$0. Thermocycling parameters used were 98° C. for 2 minutes, 35 cycles of 98° C. 20 seconds, 52° C. 20 seconds, 72° C. 1 minute, followed by 72° C. 5 minutes and a 4° C. hold. PCR products of the correct size were gel purified, ligated into pCR-Blunt II-TOPO (Invitrogen) and transformed into competent TOP10 *E. coli* cells (Invitrogen). Clones containing PCR inserts were sequenced to confirm correct DNA sequence. Four FAO alleles were identified from sequence analysis and designated as FAO-13, FAO-17, FAO-18 and FAO-20. The sequence of the clone designated FAO-18 had a sequence that was substantially identical to the sequence of FAO1 from Gen Bank. The resulting plasmids of the four alleles were designated pAA083, pAA084, pAA059

Oligonucleotides for cloning FAO alleles

| Oligo | Sequence |
|---|---|
| oAA0144 | AACGACAAGATTAGATTGGTTGAGA |
| oAA0145 | GTCGAGTTTGAAGTGTGTGTCTAAG |
| oAA0268 | AGATCTCATATGGCTCCATTTTTGCCCGACCAGGTCGACTACAAACACGTC |
| oAA0269 | ATCTGGATCCTCATTACTACAACTTGGCTTTGGTCTTCAAGGAGTCTGCCAAACCTAAC |
| oAA0282 | ACATCTGGATCCTCATTACTACAACTTGGCCTTGGTCT |
| oAA0421 | CACACAGCTCTTCTAGAATGGCTCCATTTTTGCCCGACCAGGTCGAC |
| oAA0422 | CACACAGCTCTTCCTTTCTACAACTTGGCTTTGGTCTTCAAGGAGTCTGC |
| oAA0429 | GTCTACTGATTCCCCTTTGTC |
| oAA0281 | TTCTCGTTGTACCCGTCGCA | and pAA085, respectively. Sequence identity comparisons of FAO genes isolated as described herein are shown in the tables below.

DNA sequence identity

|  | FAO1 | FAO-18 | FAO-17 | FAO-13 | FAO-20 | FAO2a | FAO2b |
|---|---|---|---|---|---|---|---|
| FAO1 | 100 | 100 | 98 | 96 | 95 | 83 | 82 |
| FAO-18 |  | 100 | 98 | 96 | 95 | 83 | 82 |
| FAO-17 |  |  | 100 | 98 | 98 | 83 | 82 |
| FAO-13 |  |  |  | 100 | 99 | 83 | 83 |
| FAO-20 |  |  |  |  | 100 | 83 | 83 |
| FAO2a |  |  |  |  |  | 100 | 96 |
| FAO2b |  |  |  |  |  |  | 100 |

Protein sequence identity

|  | FAO1 | FAO-18 | FAO-17 | FAO-13 | FAO-20 | FAO2a | FAO2b |
|---|---|---|---|---|---|---|---|
| FAO1 | 100 | 100 | 99 | 98 | 98 | 81 | 80 |
| FAO-18 |  | 100 | 99 | 98 | 98 | 81 | 80 |
| FAO-17 |  |  | 100 | 99 | 99 | 82 | 81 |
| FAO-13 |  |  |  | 100 | 99 | 82 | 81 |
| FAO-20 |  |  |  |  | 100 | 82 | 81 |
| FAO2a |  |  |  |  |  | 100 | 97 |
| FAO2b |  |  |  |  |  |  | 100 |

Amino acid differences in FAO alleles

|  | 32 | 75 | 89 | 179 | 185 | 213 | 226 | 352 | 544 | 590 |
|---|---|---|---|---|---|---|---|---|---|---|
| FAO1 | E | M | G | L | Y | T | R | H | S | P |
| FAO-13 | Q | T | A | L | Y | A | K | Q | A | A |
| FAO-20 | Q | T | A | M | D | A | K | Q | A | A |

Expression of FAO Alleles in E. Coli

To determine the levels of FAO enzyme activity with respect to various carbon sources, the four isolated FAO alleles were further cloned and over-expressed in E. coli. The FAOs were amplified using the plasmids mentioned above as DNA template by PCR with primers oAA0268 and oAA0269 for FAO-13 and FAO-20 and oAA0268 and oAA0282 for FAO-17 and FAO-18, using conditions as described herein. PCR products of the correct size were gel purified and ligated into pET11a vector between NdeI and BamHI sites and transformed into BL21 (DE3) E. coli cells. The colonies containing corresponding FAOs were confirmed by DNA sequencing. Unmodified pET11a vector also was transformed into BL21 (DE3) cells, as a control. The resulting strains and plasmids were designated sAA153 (pET11a), sAA154 (pAA079 containing FAO-13), sAA155 (pAA080 containing FAO-17), sAA156 (pAA081 containing FAO-18) and sAA157 (pAA082 containing FAO-20), respectively. The strains and plasmids were used for FAO over-expression in E. coli. One colony of each strain was transferred into 5 mL of LB medium containing 100 mg/mL ampicillin and grown overnight at 37° C., 200 rpm. The overnight culture was used to inoculate a new culture to $OD_{600\,nm}$ 0.2 in 25 ml LB containing 100 mg/ml ampicillin. Cells were induced at $OD_{600\,nm}$ 0.8 with 0.3 mM IPTG for 3 hours and harvested by centrifugation at 4° C. 1,050×g for 10 minutes. The cell pellet was stored at −20° C.

Expression of FAOs in C. tropicalis

Two alleles, FAO-13 and FAO-20, were chosen for amplification in C. tropicalis based on their substrate specificity profile, as determined from enzyme assays of soluble cell extracts of E. coli with over expressed FAOs. DNA fragments containing FAO-13 and FAO-20 were amplified using plasmids pAA079 and pAA082 as DNA templates, respectively, by PCR with primers oAA0421 and oAA0422. PCR products of the correct sizes were gel purified and ligated into pCR-Blunt II-TOPO (Invitrogen), transformed into competent TOP10 E. coli cells (Invitrogen) and clones containing FAO inserts were sequenced to confirm correct DNA sequence. Plasmids containing FAO-13 and FAO-20 were digested with SapI and ligated into vector pAA105, which includes the C. tropicalis PGK promoter and terminator. The resulting plasmids were confirmed by restriction digestion and DNA sequencing and designated as pAA115 (FAO-13) and pAA116 (FAO-20), respectively. Plasmids pAA115 and pAA116 were linearized with SpeI, transformed into competent C. tropicalis Ura− strains sAA002 (SU-2, ATCC20913) and sAA103. The integration of FAO-13 and FAO-20 was confirmed by colony PCR using primers oAA0429 and oAA0281. The resulting strains were designated as sAA278 (pAA115 integrated in sAA002), sAA280 (pAA116 integrated in sAA002), sAA282 (pAA115 integrated in sAA103), and sAA284 (pAA116 integrated in sAA103), and were used for fatty alcohol oxidase over-expression in C. tropicalis.

One colony of each strain was inoculated into 5 ml YPD and grown overnight as described herein.

The overnight culture was used to inoculate a new 25 mL YPD culture to about $OD_{600\,nm}$ 0.5. FAO over-expression was regulated by the PGK promoter/terminator, induced with glucose in the medium and expressed constitutively. Strains sAA002 and sAA103 (e.g., untransformed starting strains) were included as negative controls for FAO over-expression. Cells were harvested at early log phase ($OD_{600\,nm}$=in the range of between about 3 to about 5) by centrifugation at 4° C. for 10 minutes at 1,050×g. Cell pellets were stored at −20° C.

Cell Extract Preparation from E. Coli

Cell pellets from 25 mL of FAO expressing E. coli cultures were resuspended in 10 mL phosphate-glycerol buffer containing 50 mM potassium phosphate buffer (pH7.6), 20% glycerol, 1 mM Phenylmethylsulfonyl fluoride (PMSF), 2 uL Benzonase 25 U/uL, 20 uL 10 mg/mL lysozyme. The cells were then lysed by incubation at room temperature for 50 minutes on a rotating shaker, and the cell suspension centrifuged for 30 minutes at 4° C. using 15,000×g for. The supernatant was aliquoted in 1.5 ml microcentrifuge tubes and stored at −20° C. for FAO enzyme activity assays.

Cell Extract Preparation from C. Tropicalis

Frozen C. tropicalis cell pellets were resuspended in 1.2 ml of phosphate-glycerol buffer containing 50 mM potassium phosphate buffer (pH7.6), 20% glycerol, 1 mM Phenylmethylsulfonyl fluoride (PMSF). Resuspended cells were transferred to 1.5 mL screw-cap tubes containing about 500 uL of zirconia beads on ice. The cells were lysed with a Bead Beater (Biospec) using 2 minute pulses and 1 minute rest intervals on ice. The process was repeated 3 times. The whole cell extract was then transferred to a new 1.5 ml tube and centrifuged at 16,000×g for 15 minutes at 4° C. The supernatant was transferred into a new tube and used for FAO enzyme activity assays.

Protein Concentration Determination

Protein concentration of the cell extracts was determined using the Bradford Reagent following manufacturers' recommendations (Cat#23238, Thermo scientific).

FAO Enzyme Activity Assay

FAO enzyme activity assays were performed using a modification of Eirich et al., 2004). The assay utilizes a two-enzyme coupled reaction (e.g., FAO and horse radish peroxidase (HRP)) and can be monitored by spectrophotometry. 1-Dodecanol was used as a standard substrate for fatty alcohol oxidase enzymatic activity assays. FAO oxidizes the dodecanol to dodecanal while reducing molecular oxygen to hydrogen peroxide simultaneously. HRP reduces (2,2'-azino-bis 3-ethylbenzthiazoline-6-sulfonic acid; ABTS) in the two-enzyme coupled reaction, where the electron obtained from oxidizing hydrogen peroxide to ABTS, which can be measured by spectrometry at 405 nm. The assay was modified using aminotriazole (AT) to prevent the destruction of $H_2O_2$ by endogenous catalase, thus eliminating the need for microsomal fractionation. The final reaction mixture (1.0 mL) for FAO enzyme assay consisted of 500 μL of 200 mM HEPES buffer, pH 7.6; 50 μL of a 10 mg/mL ABTS solution in deionized water; 10 μL of 5 mM solution of dodecanol in acetone; 40 μL of 1M AT and 5 μL of a 2 mg/mL horseradish peroxidase solution in 50 mM potassium phosphate buffer, pH 7.6. Reaction activity was measured by measuring light absorbance at 405 nm for 10 minutes at room temperature after adding the extract. The amount of extract added to the reaction mixture was varied so that the activity fell within the range of 0.2 to 1.0 $\Delta A_{405\ nm}$/min. The actual amounts of extract used were about 1.69 U/mg for *E. coli* expressed FAO-13, 0.018 U/mg for *E. coli* expressed FAO-17, 0.35 U/mg for *E. coli* expressed FAO-18 (e.g., FAO1), 0.47 U/mg *E. coli* expressed FAO-20, 0.036 U/mg *C. tropicalis* (strain sAA278) expressed FAO-13, 0.016 U/mg *C. tropicalis* (strain sAA282) expressed FAO-13, 0.032 U/mg *C. tropicalis* (strain sAA280) expressed FAO-20 and 0.029 U/mg *C. tropicalis* (strain sAA284) expressed FAO-20. FAO activity was reported as activity units/mg of total protein (1 unit=1 mmole substrate oxidized/min). An extinction coefficient at 405 nm of 18.4 was used for ABTS and was equivalent to 0.5 mM oxidized substrate. The results of the activity assays are shown in the tables below.

FAO activity (units/mg total protein) on primary alcohols

| | 1-Buta-nol | 1-Pen-ta-nol | 1-Hex-a-nol | 1-Octa-nol | 1-Deca-nol | 1-Do-deca-nol | 1-Tet-radec-anol | Hexa-decanol |
|---|---|---|---|---|---|---|---|---|
| FAO-13 | 0.01 | 0.09 | 1.17 | 82.67 | 70.94 | 100 | 79.35 | 58.88 |
| FAO-17 | 0.72 | 0.26 | 1.06 | 66.23 | 22.00 | 100 | 47.86 | 60.98 |
| FAO-18 | 0.07 | 0.11 | 0.26 | 60.56 | 54.56 | 100 | 114.47 | 50.65 |
| FAO-20 | 0.07 | 0.11 | 0.91 | 55.96 | 74.57 | 100 | 89.52 | 42.59 |

FAO activity (units/mg total protein) on omega hydroxy fatty acids

| | 1-Dodecanol | 6-OH-HA | 10-OH-DA | 12-OH-DDA | 16-OH-HDA |
|---|---|---|---|---|---|
| FAO-13 | 100 | 4.18 | 4.14 | 6.87 | 8.57 |
| FAO-17 | 100 | 1.18 | 0.00 | 0.59 | 0.94 |
| FAO-18 | 100 | 0.00 | 0.00 | 4.87 | 2.94 |
| FAO-20 | 100 | 0.03 | 0.04 | 2.25 | 7.46 |

Example 19

Construction of *C. Tropicalis* Shuttle Vector pAA061

Figure 30:
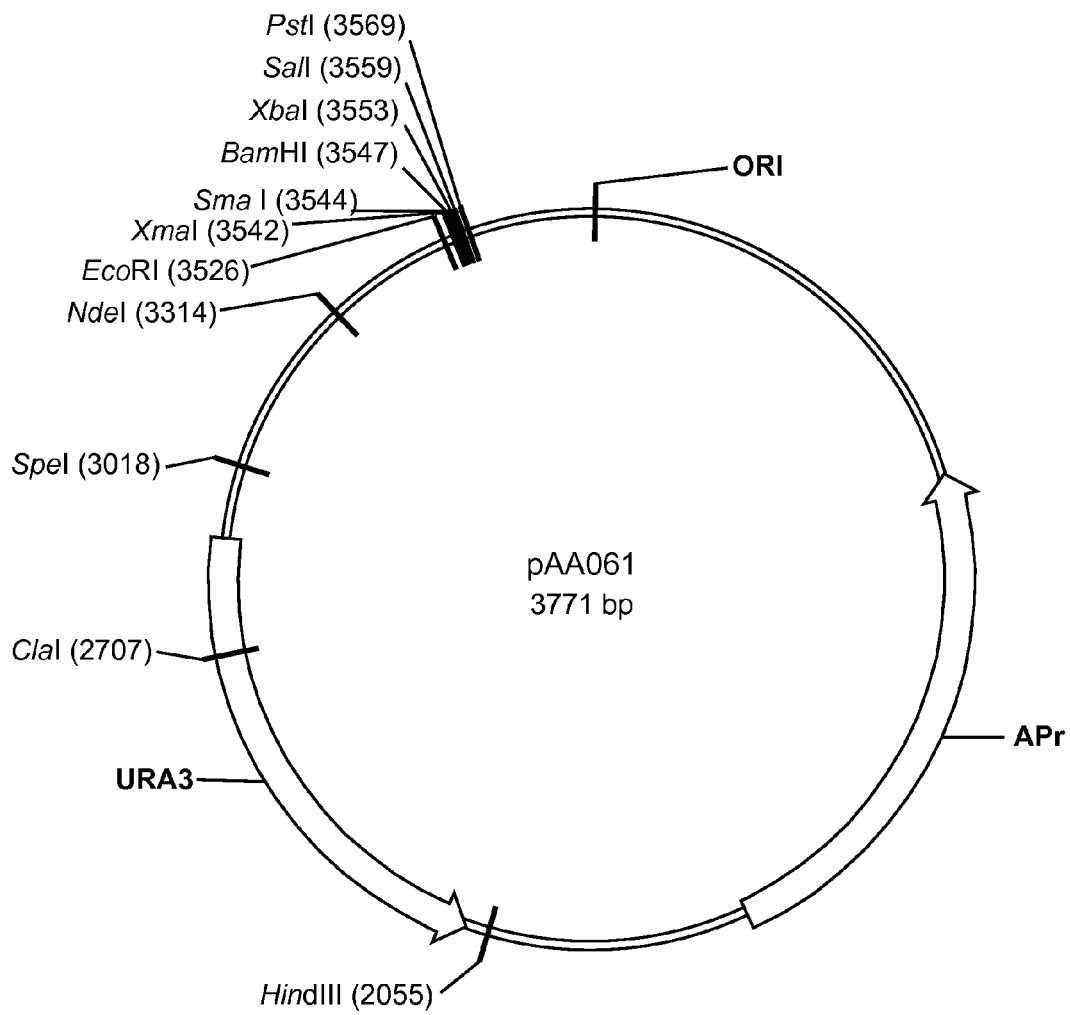
Figure 31:
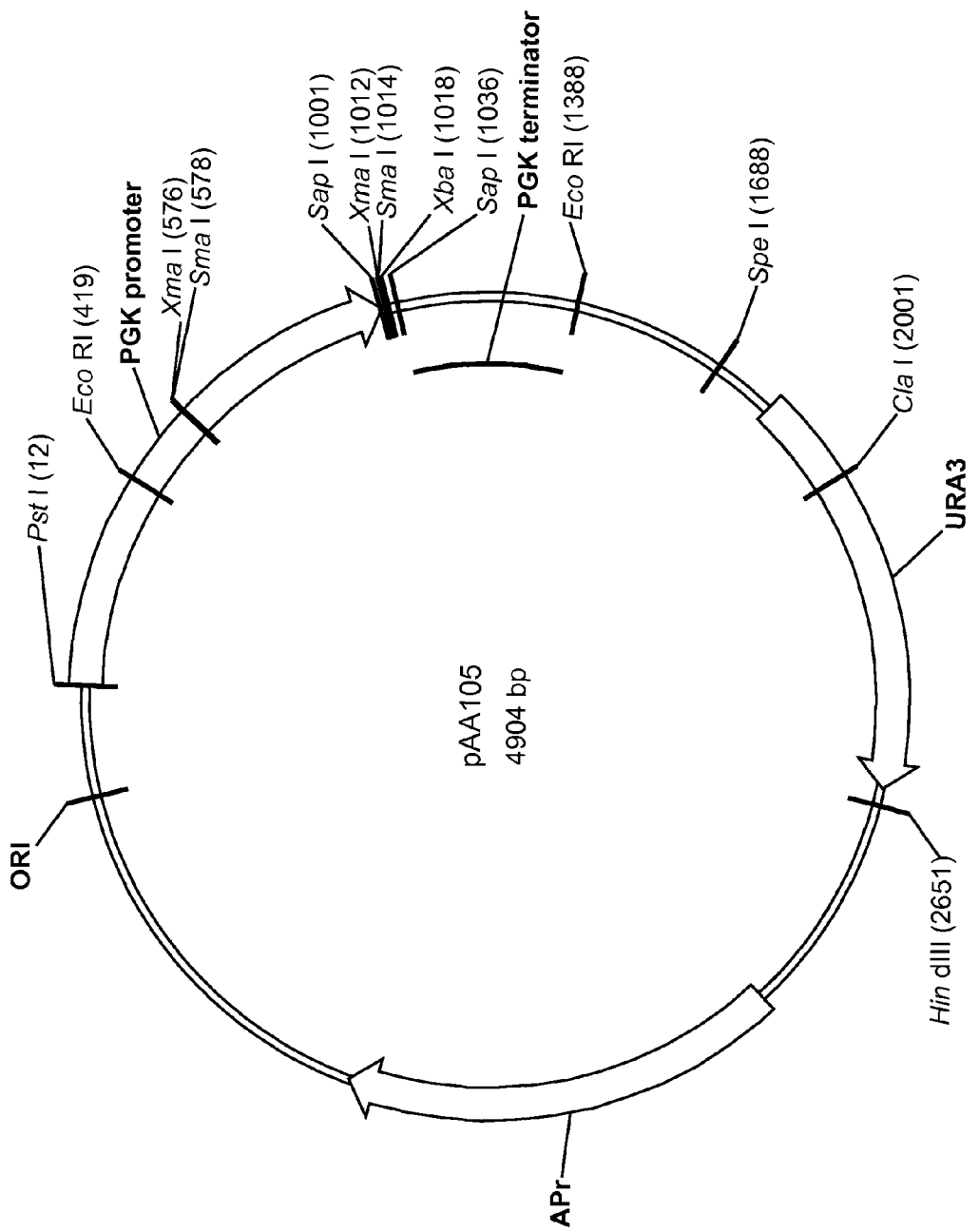

Vector pAA061 was constructed from a pUC19 backbone to harbor the selectable marker URA3 from *C. tropicalis* strain ATCC20336 as well as modifications to allow insertion of *C. tropicalis* promoters and terminators. A 1,507 bp DNA fragment containing the promoter, ORF, and terminator of URA3 from *C. tropicalis* ATCC20336 was amplified using primers oAA0124 and oAA0125, shown in the table below. The URA3 PCR product was digested with NdeI/MluI and ligated into the 2,505 bp fragment of pUC19 digested with NdeI/BsmBI (an MluI compatible overhang was produced by BsmBI). In order to replace the lac promoter with a short 21 bp linker sequence, the resulting plasmid was digested with SphI/SapI and filled in with a linker produced by annealing oligos oAA0173 and oAA0174. The resulting plasmid was named pAA061, and is shown in FIG. 30.

Oligonucleotides for construction of pAA061

| Oligos | Sequence | PCR product (bp) |
|---|---|---|
| oAA0124 | cacacacatatgCGACGGGTACAACGAGAATT | 1507 |
| oAA0125 | cacacaacgcgtAGACGAAGCCGTTCTTCAAG | |
| oAA0173 | ATGATCTGCCATGCCGAACTC | 21 (linker) |
| oAA0174 | AGCGAGTTCGGCATGGCAGATCATCATG | |

Example 20

Cloning of *C. tropicalis* PGK Promoter and Terminator

Vector pAA105 was constructed from base vector pAA061 to include the phosphoglycerate kinase (PGK) promoter and terminator regions from *C. tropicalis* ATCC20336 with an intervening multiple cloning site (MCS) for insertion of open reading frames (ORF's). The PGK promoter region was amplified by PCR using primers oAA0347 and oAA0348, shown in the table below. The 1,029 bp DNA fragment containing the PGK promoter was digested with restriction enzymes PstI/XmaI. The PGK terminator region was amplified by PCR using primers oAA0351 and oAA0352, also shown in the table below. The 396 bp DNA fragment containing the PGK terminator was digested with restriction enzymes XmaI/EcoRI. The 3,728 bp PstI/EcoRI DNA fragment from pAA061 was used in a three piece ligation reaction with the PGK promoter and terminator regions to produce pAA105. The sequence between the PGK promoter and terminator contains restriction sites for incorporating ORF's to be controlled by the functionally linked constitutive PGK promoter.

| Oligonucleotides for cloning C. tropicalis PGK promoter and terminator | | |
|---|---|---|
| Oligos | Sequence | PCR product (bp) |
| oAA0347 | CACACACTGCAGTTGTCCAATGTAATAATTTT | 1028 |
| oAA0348 | CACACATCTAGACCCGGGCTCTTCTTCTGAATAGGCAATTGATAAACTTACTTATC | |
| oAA0351 | GAGCCCGGGTCTAGATGTGTGCTCTTCCAAAGTACGGTGTTGTTGACA | 396 |
| oAA0352 | CACACACATATGAATTCTGTACTGGTAGAGCTAAATT | |

Example 21

Cloning of the POX4 Locus

Figure 29:
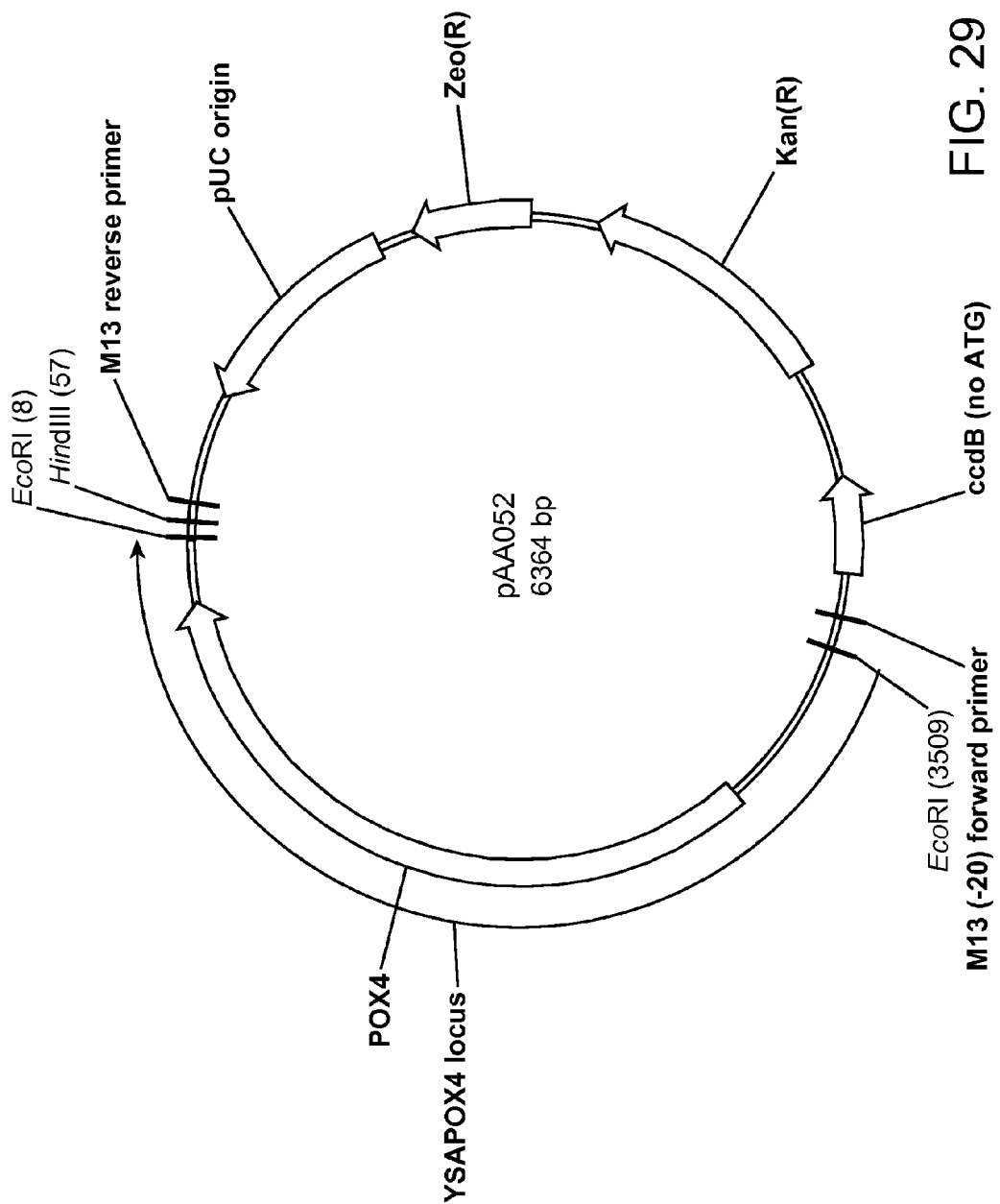

Primers oAA0138 and oAA0141 (shown in the table below) were generated to amplify the entire sequence of NCBI accession number M12160 for the YSAPOX4 locus from genomic DNA prepared from C. tropicalis strain ATCC20336. The 2,845 bp PCR product was cloned into the vector, pCR-BluntII-TOPO (Invitrogen), sequenced and designated pAA052, and is shown in FIG. 29.

| Oligonucleotides for cloning of POX4 | | |
|---|---|---|
| Oligos | Sequence | PCR product (bp) |
| oAA0138 | GAGCTCCAATTGTAATATTTCGGG | 2845 |
| oAA0141 | GTCGACCTAAATTCGCAACTATCAA | |

Example 22

Cloning of the POX5 Locus

Figure 28:
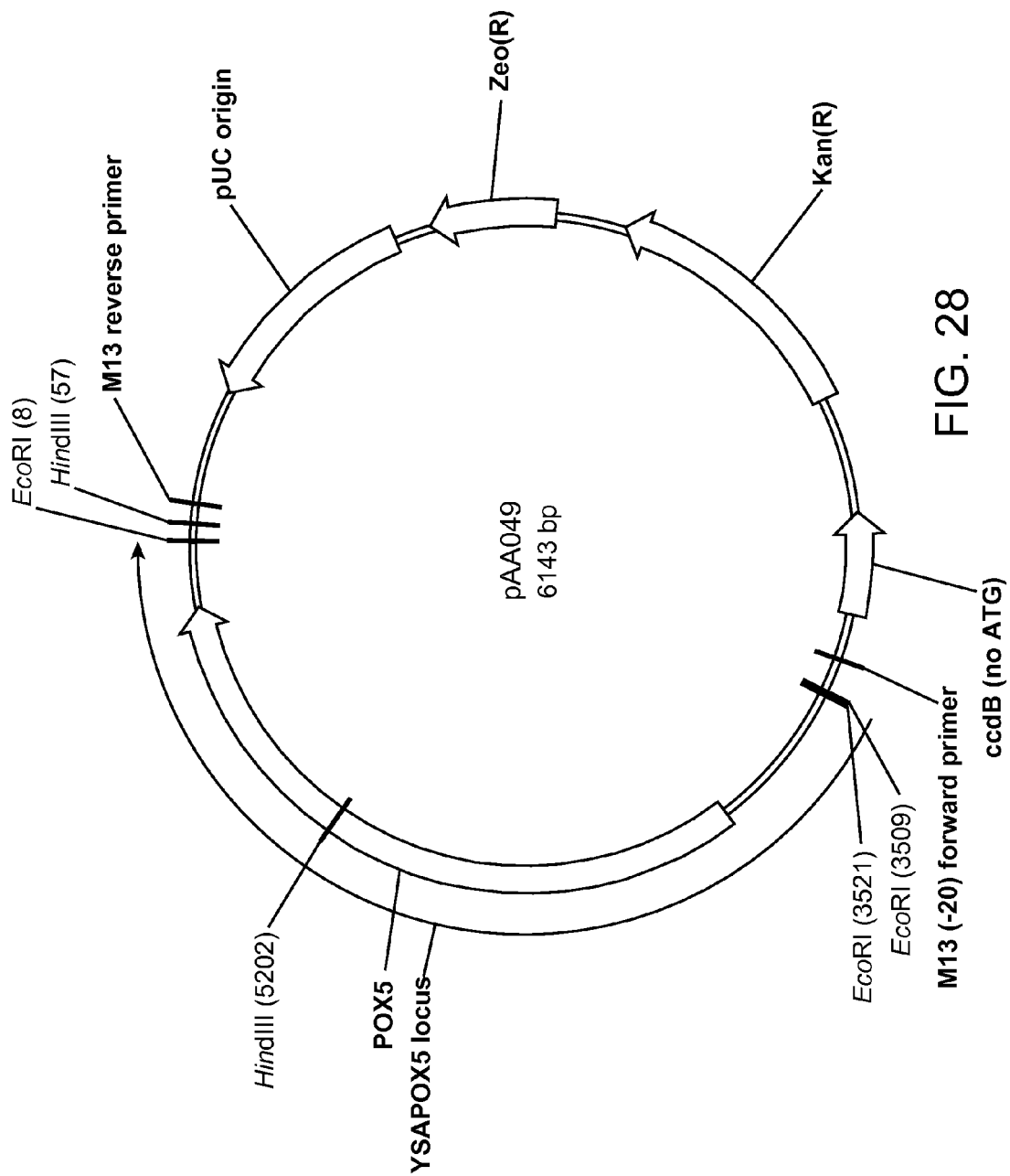

Primers oAA0179 and oAA0182 (shown in the table below) were generated to amplify the entire sequence of NCBI accession number M12161 for the YSAPOX5 locus from genomic DNA prepared from C. tropicalis strain ATCC20336. The 2,624 bp PCR product was cloned into the vector, pCR-BluntII-TOPO (Invitrogen), sequenced and designated pAA049, and is shown in FIG. 28.

| Oligonucleotides for cloning of POX5 | | |
|---|---|---|
| Oligos | Sequence | PCR product (bp) |
| oAA0179 | GAATTCACATGGCTAATTTGGCCTCGGTTCCACAACGCACTCAGCATTAAAAA | 2624 |
| oAA0182 | GAGCTCCCCTGCAAACAGGGAAACACTTGTCATCTGATTT | |

Example 23

Construction of Strain sAA105 and sAA106

Functional POX4 alleles were restored in C. tropicalis strain sAA003 (ATCC20962; ura3/ura3, pox4::ura3/pox4::ura3, pox5::ura3/pox5::URA3) by transformation of sAA003 with POX4 linear DNA to replace the ura3-disrupted loci with functional alleles. A 2,845 bp DNA fragment was amplified by PCR using primers oAA0138 and oAA0141 (described in Example 21) that contained the POX4 ORF as well as 531 bp upstream and 184 bp downstream of the ORF, using plasmid pAA052 as template. The purified PCR product was used to transform competent sAA003 cells which were plated on YNB-agar plates supplemented with hexadecane vapor as the carbon source (e.g., by placing a filter paper soaked with hexadecane in the lid of the inverted petri dish) and incubated at 30° C. for 4-5 days. Colonies growing on hexadecane as the sole carbon source were restreaked onto YPD-agar and incubated at 30° C. Single colonies were grown in YPD cultures and used for the preparation of genomic DNA.

PCR analysis of the genomic DNA prepared from the transformants was performed with oligos oAA0138 and oAA0141. An URA3-disrupted POX4 would produce a PCR product of 5,045 bp, while a functional POX4 would produce a PCR product of 2,845 bp. In strain sAA105 only one PCR product was amplified with a size of 2,845 bp indicating that both POX4 alleles had been functionally restored. In strain sAA106 PCR products of both 2,845 bp and 5,045 bp were amplified indicating that one POX4 allele had been functionally restored while the other POX4 allele remained disrupted by URA3. The resultant strain genotypes were: sAA105 (ura3/ura3, POX4/POX4, pox5::ura3/pox5::URA3) and sAA106 (ura3/ura3, POX4/pox4::ura3, pox5::ura3/pox5::URA3).

Example 24

Construction of Strain sAA 152

Functional POX5 alleles were restored in C. tropicalis strain sAA103 (ura3/ura3, pox4::ura3/pox4::ura3, pox5::ura3/pox5::ura3) by transformation of sAA103 with PmlI-linearized plasmid pAA086 (containing the POX5 promoter, gene, terminator and a URA3 marker). Selection of transformants was performed by plating on SC-URA agar plates. Verification of plasmid integration was performed by PCR with primers oAA179 and oAA182 (described in Example 22). Integration of the plasmid was shown by a PCR product of 2,584 bp indicating the presence of a functional POX5 allele. Other POX5 alleles in sAA152 were disrupted with an ura3 gene increasing the PCR product size for nonfunctional alleles to 4,734 bp. Genotype for strain sAA152 is ura3/ura3, pox4::ura3/pox4::ura3, pox5::ura3/pox5::ura3, ura3::POX5, URA3).

Example 25

Construction of Strain sAA232

Functional POX5 alleles were restored in *C. tropicalis* strain sAA003 by transformation of sAA003 with POX5 linear DNA to replace the URA3-disrupted loci with a functional allele. A 2,584 bp DNA fragment was amplified by PCR using primers oAA0179 and oAA0182 (described in Example 22) that contained the POX5 ORF as well as 456 bp upstream and 179 bp downstream of the ORF using plasmid pAA049 as template. The purified PCR product was used to transform competent sAA003 cells which were plated on SC+URA+5FOA plates and incubated at 30° C. for 3-4 days. Colonies were restreaked onto YPD-agar and incubated at 30° C. Single colonies were grown in YPD cultures and used for the preparation of genomic DNA. PCR analysis of the genomic DNA prepared from the transformants was performed with oligos oAA0179 and oAA0182. An ura3-disrupted POX5 would produce a PCR product of 4,784 bp while a functional POX5 would produce a PCR product of 2,584 bp. In strain sAA232 PCR products of both 2,584 bp and 4,784 bp were amplified indicating that one POX5 allele had been functionally restored while the other POX5 allele remained disrupted by ura3. The resultant genotype of strain sAA232 is ura3/ura3, pox4::ura3/pox4::ura3, pox5::ura3/POX5. 5-FOA selection restored the POX5 allele that had been disrupted with the functional URA3 leaving the sAA232 strain Ura⁻.

Example 26

Construction of Strain sAA235

Functional POX5 alleles were restored in *C. tropicalis* strain sAA003 by transformation of sAA003 with POX5 linear DNA to replace the URA3-disrupted loci with a functional allele. A 2,584 bp DNA fragment was amplified by PCR using primers oAA0179 and oAA0182 (described in Example 22) that contained the POX5 ORF as well as 456 bp upstream and 179 bp downstream of the ORF using plasmid pAA049 as template. The purified PCR product was used to transform competent sAA003 cells which were plated on YNB-agar plates supplemented with dodecane vapor as the carbon source (e.g., by placing a filter paper soaked with dodecane in the lid of the inverted petri dish) and incubated at 30° C. for 4-5 days. Colonies growing on dodecane as the sole carbon source were restreaked onto YPD-agar and incubated at 30° C. Single colonies were grown in YPD cultures and used for the preparation of genomic DNA. PCR analysis of the genomic DNA prepared from the transformants was performed with oligos oAA0179 and oAA0182. An ura3-disrupted POX5 would produce a PCR product of 4,784 bp while a functional POX5 would produce a PCR product of 2,584 bp. In strain sAA235 a PCR product of 2,584 bp was amplified indicating that both POX5 alleles had been functionally restored. An unintended consequence of the selection strategy (YNB-agar with dodecane) was that the cells reverted back to an Ura phenotype. Without being limited by any theory, it is believed the absence of uracil in the solid media and the replacement of the only functional URA3 forced the cells to mutate one of the other ura3 loci back to a functional allele. Therefore the genotype of the strain sAA235 is believed to be URA3/ura3, pox4::ura3/pox4::ura3, POX5/POX5. Verification of which of the loci is the functional URA3 is underway.

Example 27

Construction of Strains with Amplified CPR and CYP52 Genes

Strains having an increased number of copies of cytochrome P450 reductase (CPR) and/or for cytochrome P450 monooxygenase (CYP52) genes were constructed to determine how over expression of CPR and CYP52 affected diacid production.

Cloning and Integration of the CPR Gene.

Figure 32:
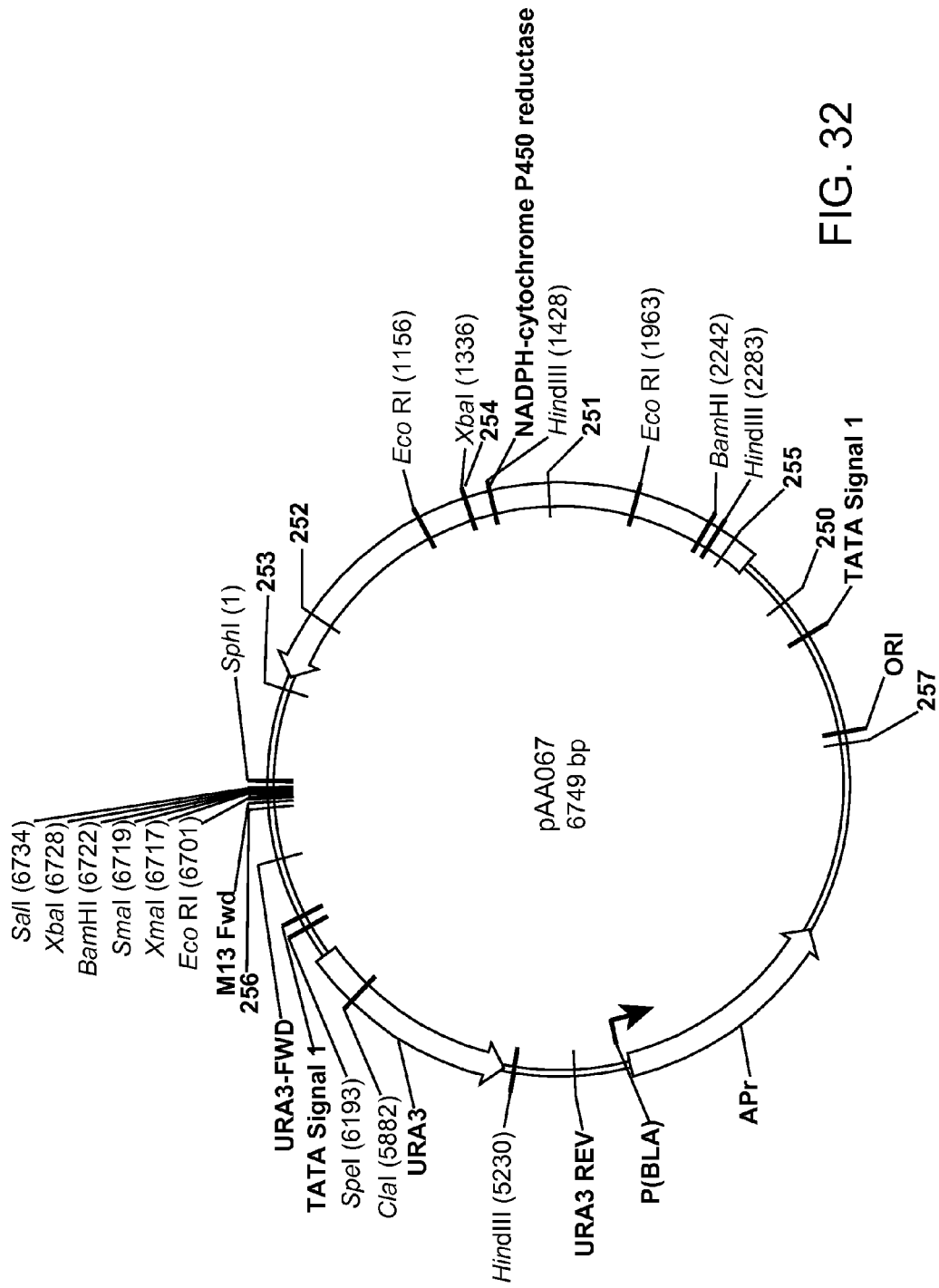

A 3,019 bp DNA fragment encoding the CPR promoter, ORF, and terminator from *C. tropicalis* ATCC750 was amplified by PCR using primers oAA0171 and oAA0172 (see table below) incorporating unique SapI and SphI sites. The amplified DNA fragment was cut with the indicated restriction enzymes and ligated into plasmid pAA061, shown in FIG. 30, to produce plasmid pAA067, shown in FIG. 32. Plasmid pAA067 was linearized with ClaI and transformed into *C. tropicalis* Ura⁻ strain sAA103 (ura3/ura3, pox4::ura3/pox4::ura3, pox5::ura3/pox5::ura3). Transformations were performed with plasmid pAA067 alone and in combination with plasmids harboring the CYP52A15 or CYP52A16 genes, described below.

Cloning and Integration of CYP52A15 Gene.

Figure 33:
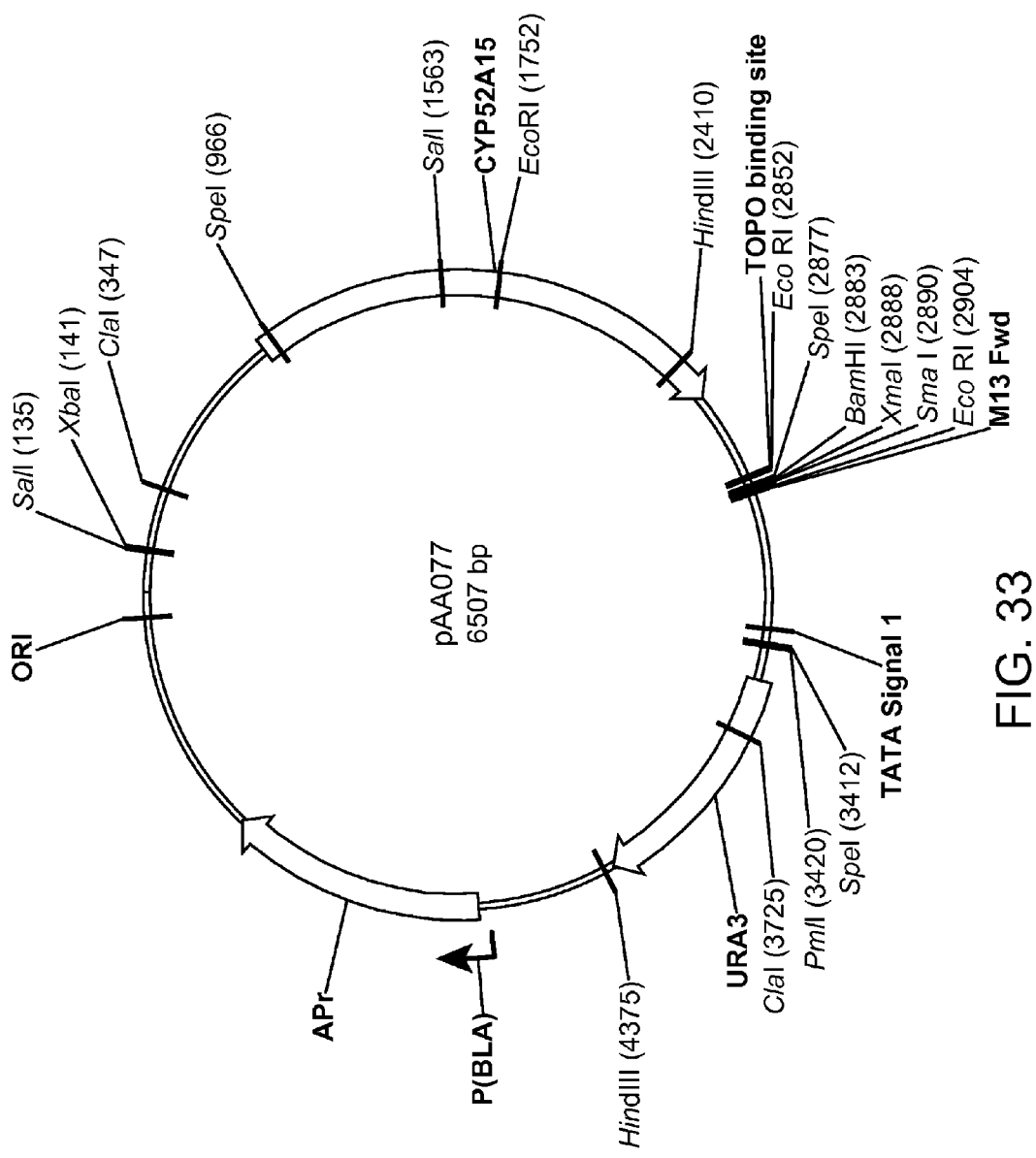

A 2,842 bp DNA fragment encoding the CYP52A15 promoter, ORF, and terminator from *C. tropicalis* ATCC20336 was amplified by PCR using primers oAA0175 and oAA0178 (see table below) and cloned into pCR-BluntII-TOPO for DNA sequence verification. The cloned CYP52A15 DNA fragment was isolated by restriction digest with XbaI/BamHI (2,742 bp) and ligated into plasmid pAA061, shown in FIG. 30, to produce plasmid pAA077, shown in FIG. 33. Plasmid pAA077 was linearized with PmlI and transformed into *C. tropicalis* Ura⁻ strain sAA103 (ura3/ura3, pox4::ura3/pox4::ura3, pox5::ura3/pox5::ura3). pAA077 was cotransformed with plasmid pAA067 harboring the CPR gene.

Cloning and Integration of CYP52A16 Gene.

Figure 34:
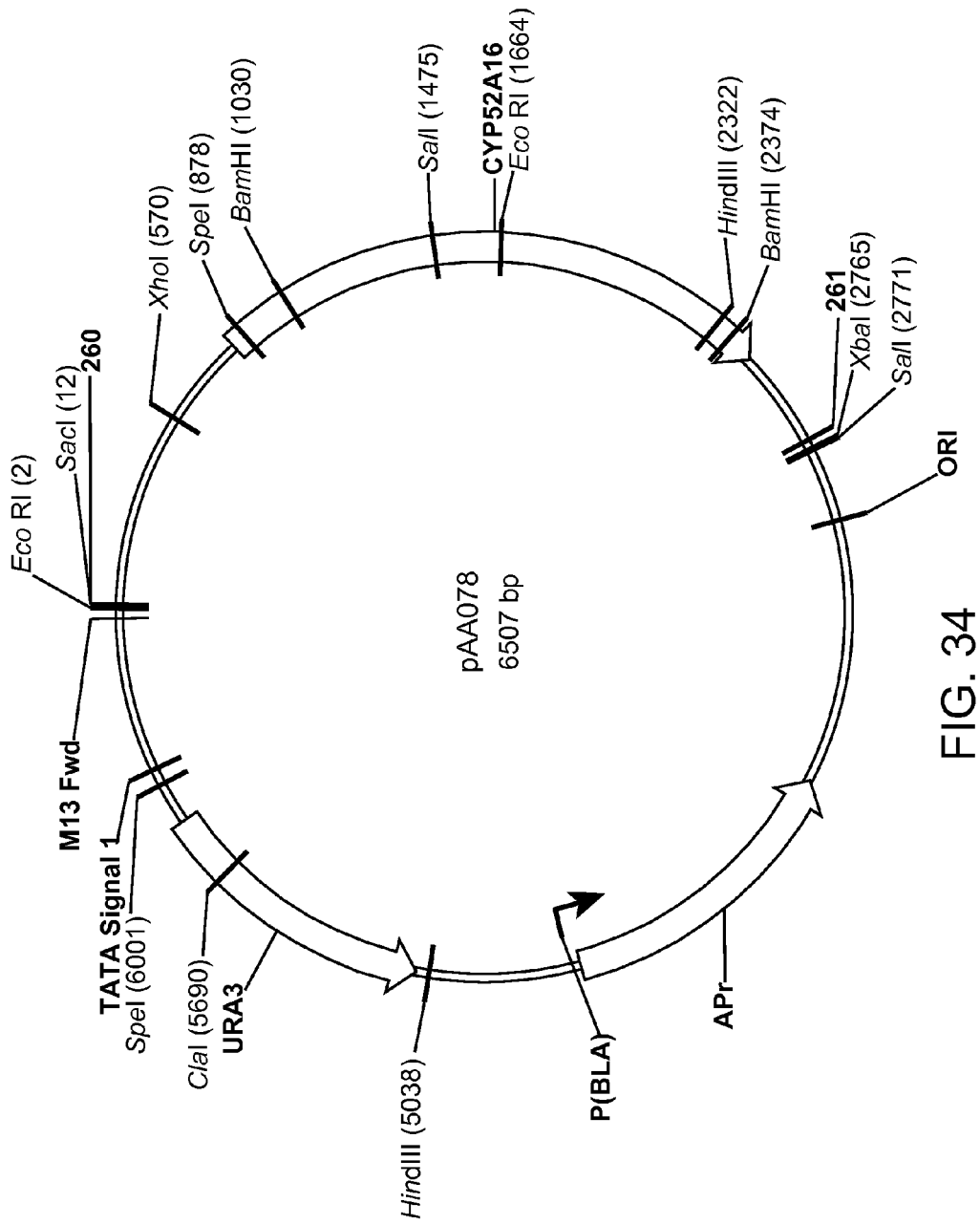

A 2,728 bp DNA fragment encoding the CYP52A16 promoter, ORF, and terminator from *C. tropicalis* ATCC20336 was amplified by PCR using primers oAA0177 and oAA0178 (see table below) and cloned into pCR-BluntII-TOPO for DNA sequence verification. The cloned CYP52A16 DNA fragment was amplified with primers oAA0260 and oAA0261 (see table below) which incorporated unique SacI/XbaI restriction sites. The amplified DNA fragment was digested with SacI and XbaI restriction enzymes and ligated into plasmid pAA061 to produce plasmid pAA078, shown in FIG. 34. Plasmid pAA078 was linearized with ClaI and transformed into *C. tropicalis* Ura⁻ strain sAA103 (ura3/ura3, pox4::ura3/pox4::ura3, pox5::ura3/pox5::ura3). pAA078 was cotransformed with plasmid pAA067 harboring the CPR gene.

Oligonucleotides for cloning of CPR, CYP52A15 and CYP52A16

| Oligos | Sequence | PCR product (bp) |
|---|---|---|
| oAA0171 | cacctcgctcttccAGCTGTCATGTCTATTCAATGCTTCGA | 3019 |
| oAA0172 | cacacagcatgcTAATGTTTATATCGTTGACGGTGAAA | |
| oAA0175 | cacaaagcggaagagcAAATTTTGTATTCTCAGTAGGATTTCATC | 2842 |
| oAA0178 | cacacagcatgCAAACTTAAGGGTGTTGTAGATATCCC | |
| oAA0177 | cacacacccgggATCGACAGTCGATTACGTAATCCATATTATTT | 2772 |
| oAA0178 | cacacagcatgCAAACTTAAGGGTGTTGTAGATATCCC | |
| oAA0260 | cacacagagctcACAGTCGATTACGTAATCCAT | 2772 |
| oAA0261 | cacatctagaGCATGCAAACTTAAGGGTGTTGTA | |

Preparation of Genomic DNA.

Genomic DNA was prepared from transformants for PCR verification and for Southern blot analysis. Isolated colonies were inoculated into 3 mL YPD and grown overnight at 30° C. with shaking. Cells were pelleted by centrifugation. To each pellet, 200 uL Breaking Buffer (2% Triton X-100, 1% SDS, 100 mM NaCl, 10 mM Tris pH 8 and, 1 mM EDTA) was added, and the pellet resuspended and transferred to a fresh tube containing 200 uL 0.5 mm Zirconia/Silica Beads. 200 uL Phenol:Chloroform:Isoamyl Alcohol (25:24:1) was added to each tube, followed by vortexing for 1 minute. Sterile distilled water was added (200 uL) to each tube and the tubes were centrifuged at 13000 rpm for 10 minutes. The aqueous layer was ethanol precipitated and washed with 70% ethanol. The pellet was resuspended in 100-200 μl 10 mM Tris, after drying. Genomic DNA preparation for southern blot analysis was performed using the same procedure on 25 mL cultures for each colony tested.

Characterization of Strains with Amplified CPR and CYP52 Genes.

Verification of integrants was performed by PCR using primers oAA0252 and oAA0256 (CPR), oAA0231 and oAA0281 (CYP52A15), and oAA242 and oAA0257 (CYP52A16). The primers used for verification are shown in the table below.

Oligonucleotides for PCR verification of CPR, CYP52A15 and CYP52A16

| Oligos | Sequence | PCR product (bp) |
|---|---|---|
| oAA0252 | TTAATGCCTTCTCAAGACAA | 743 |
| oAA0256 | GGTTTTCCCAGTCACGACGT | |
| oAA0231 | CCTTGCTAATTTTCTTCTGTATAGC | 584 |
| oAA0281 | TTCTCGTTGTACCCGTCGCA | |

Oligonucleotides for PCR verification of CPR, CYP52A15 and CYP52A16

| Oligos | Sequence | PCR product (bp) |
|---|---|---|
| oAA0242 | CACACAACTTCAGAGTTGCC | 974 |
| oAA0257 | TCGCCACCTCTGACTTGAGC | |

Southern blot analysis was used to determine the copy number of the CPR, CYP52A15 and CYP52A15 genes. Biotinylated DNA probes were prepared with gene specific oligonucleotides using the NEBlot Phototope Kit from New England BioLabs (Catalog #N7550S) on PCR products generated from each gene target as specified in the table below. Southern Hybridizations were performed using standard methods (e.g., Sambrook, J. and Russell, D. W. (2001) Molecular Cloning: A Laboratory Manual, (3$^{rd}$ ed.), pp. 6.33-6.64. Cold Spring Harbor Laboratory Press). Detection of hybridized probe was performed using the Phototope-Star Detection Kit from New England BioLabs (Catalog #N7020S). Copy number was determined by densitometry of the resulting bands.

Oligonucleotides for Probe Template PCR of CPR, CYP52A15 and CYP52A16

| Oligos | Sequence | Gene | Template | PCR product (bp) |
|---|---|---|---|---|
| oAA0250 | AATTGAACATCAGAAGAGGA | CPR | pAA067 | 1313 |
| oAA0254 | CCTGAAATTTCCAAATGGTGTCTAA | | | |
| oAA0227 | TTTTTTGTGCGCAAGTACAC | CYP52A15 | pAA077 | 905 |
| oAA0235 | CAACTTGACGTGAGAAACCT | | | |
| oAA0239 | AGATGCTCGTTTTACACCCT | CYP52A16 | pAA078 | 672 |
| oAA0247 | ACACAGCTTTGATGTTCTCT | | | |

Example 28

Strain Evaluation of Partially β-Oxidation Blocked Strains

Fermentation of Methyl Laurate Feedstock.

5 mL starter cultures, in SP92 media (6.7 g/L Difco yeast nitrogen base, 3.0 g/L Difco yeast extract, 3.0 g/L ammonium sulfate, 1.0 g/L potassium phosphate monobasic, 1.0 g/L potassium phosphate dibasic, 75 g/L dextrose) were incubated overnight at 30° C., with shaking and used to inoculate flasks containing 25 mL of SP92 media to an initial OD$_{600\,nm}$ of about 0.4. Cultures were incubated approximately 18 hours at 30° C., with shaking at about 200 rpm. Cells were pelleted by centrifugation at 4° C. for 10 minutes at 4,000×g, then resuspended in SP92-D media (6.7 g/L Difco yeast nitrogen base, 3.0 g/L Difco yeast extract, 3.0 g/L ammonium sulfate, 1.0 g/L potassium phosphate monobasic, 1.0 g/L potassium phosphate dibasic) supplemented with 0.1% dextrose and 2% methyl laurate. Incubation of the cultures continued at 30° C., with shaking and samples were taken for analysis of fatty acids and diacids by gas chromatography (GC).

Sample for GC were prepared by adding 0.8 mL of 6.0M HCl to 1 mL of whole culture samples and the samples were stored at 4° C. to await processing. Samples were processed by incubating in a 60° C. water bath for 5 minutes, after which 4.0 mL of MTBE was added to the 1.8 mL acidified whole culture samples and vortexed for 20 seconds. The phases were allowed to separate for 10 min at room temperature. 1 mL of the MTBE phase was drawn and dried with sodium sulfate. Aliquots of the MTBE phase were derivatized with BSTFA reagent (Regis Technologies Inc.) and analyzed by GC equipped with a Flame Ionization Detector. The results of the gas chromatography are shown in the table below.

Fatty acid and Diacid profile (g/L) in Methyl Laurate fermentation

| Strain | Time (h) | C12 Acid | C12 Diacid | C10 Diacid | C8 Diacid | C6 Diacid |
|---|---|---|---|---|---|---|
| sAA105 | 0 | 0.00 | 0.00 | 0.00 | 0.00 | 0.00 |
|  | 24 | 0.05 | 0.00 | 0.00 | 0.07 | 0.42 |
|  | 48 | 0.00 | 0.00 | 0.00 | 0.00 | 0.00 |
| sAA106 | 0 | 0.00 | 0.00 | 0.00 | 0.00 | 0.00 |
|  | 24 | 2.92 | 1.29 | 0.15 | 0.58 | 0.37 |
|  | 48 | 0.04 | 0.02 | 0.00 | 0.00 | 0.01 |
| sAA152 | 0 | 0.02 | 0.00 | 0.00 | 0.00 | 0.00 |
|  | 24 | 0.58 | 0.55 | 0.07 | 0.43 | 0.03 |
|  | 48 | 0.00 | 0.03 | 0.00 | 0.05 | 0.58 |
| sAA003 | 0 | 0.00 | 0.00 | 0.00 | 0.00 | 0.00 |
|  | 24 | 1.96 | 0.41 | 0.00 | 0.00 | 0.00 |
|  | 48 | 1.43 | 0.47 | 0.00 | 0.00 | 0.00 |

Fermentation of Methyl Myristate and Oleic Acid Feedstocks.

Fermentations were performed essentially as described for methyl laurate feedstock except that 2% methyl myristate or 2% oleic acid was substituted for the 2% methyl laurate. The results of the gas chromatography are shown in the tables below.

Fatty acid and Diacid profile (g/L) in Methyl Myristate fermentation

| Strain | Time (h) | C14 Acid | C14 Diacid | C12 Diacid | C10 Diacid | C8 Diacid | C6 Diacid |
|---|---|---|---|---|---|---|---|
| sAA105 | 0 | 0.02 | 0.00 | 0.00 | 0.00 | 0.00 | 0.00 |
|  | 24 | 0.02 | 0.00 | 0.00 | 0.00 | 0.00 | 0.29 |
|  | 48 | 0.01 | 0.00 | 0.00 | 0.00 | 0.00 | 0.03 |
| sAA106 | 0 | 0.01 | 0.00 | 0.00 | 0.00 | 0.00 | 0.00 |
|  | 24 | 0.02 | 0.00 | 0.00 | 0.00 | 0.08 | 1.71 |
|  | 48 | 0.01 | 0.00 | 0.00 | 0.00 | 0.00 | 0.04 |
| sAA232 | 0 | 0.01 | 0.00 | 0.00 | 0.00 | 0.00 | 0.00 |
|  | 24 | 0.01 | 0.00 | 0.00 | 0.00 | 0.59 | 0.26 |
|  | 48 | 0.01 | 0.00 | 0.00 | 0.00 | 0.35 | 0.47 |
| sAA235 | 0 | 0.01 | 0.00 | 0.00 | 0.00 | 0.00 | 0.00 |
|  | 24 | 0.02 | 0.00 | 0.00 | 0.00 | 0.25 | 0.38 |
|  | 48 | 0.01 | 0.00 | 0.00 | 0.00 | 0.04 | 0.66 |
| sAA003 | 0 | 0.02 | 0.01 | 0.01 | 0.00 | 0.00 | 0.00 |
|  | 24 | 0.55 | 0.25 | 0.00 | 0.00 | 0.00 | 0.00 |
|  | 48 | 0.49 | 0.38 | 0.00 | 0.00 | 0.00 | 0.00 |

Diacid profile (g/L) in Oleic acid fermentation

| Strain | Time (h) | C14 Diacid | C12 Diacid | C10 Diacid | C8 Diacid | C6 Diacid |
|---|---|---|---|---|---|---|
| sAA105 | 0 | 0.00 | 0.00 | 0.00 | 0.00 | 0.00 |
|  | 24 | 0.00 | 0.00 | 0.00 | 0.00 | 0.03 |
|  | 48 | 0.00 | 0.00 | 0.00 | 0.00 | 0.01 |
| sAA106 | 0 | 0.00 | 0.00 | 0.00 | 0.00 | 0.00 |
|  | 24 | 0.00 | 0.00 | 0.00 | 0.00 | 1.48 |
|  | 48 | 0.00 | 0.00 | 0.00 | 0.00 | 0.42 |
| sAA232 | 0 | 0.00 | 0.00 | 0.00 | 0.00 | 0.00 |
|  | 24 | 0.00 | 0.00 | 0.00 | 0.00 | 0.09 |
|  | 48 | 0.00 | 0.00 | 0.00 | 0.00 | 0.10 |
| sAA235 | 0 | 0.00 | 0.00 | 0.00 | 0.00 | 0.00 |
|  | 24 | 0.00 | 0.00 | 0.00 | 0.00 | 0.10 |
|  | 48 | 0.00 | 0.00 | 0.00 | 0.00 | 0.11 |

Fermentations also were performed using coconut oil as a feed stock. Coconut oil contains a mixture of fatty acids of different carbon chain lengths. The percent composition of fatty acids, by weight, is about 6% capric acid (C10:0, where 0 refers to the number of double or unsaturated bonds), about 47% lauric acid (C12:0), about 18% myristic acid (C14:0), about 9% palmitic acid (C16:0). About 3% stearic acid (C18:0), about 6% oleic acid (C18:1, where 1 refers to the number of double bonds), and about 2% linoleic acid (omega-6 fatty acid, C18:2). In some embodiments, palm kernel oil can be substituted for coconut oil. Palm kernel oil has a distribution of fatty acids similar to that of coconut oil. Fermentations and GC were carried out essentially as described herein with the exception of feedstock used. The result of fermentations performed using coconut oil as a feedstock are presented below.

Diacid profile (g/L) in Coconut Oil fermentation

| Strain | Time (h) | C14 Diacid | C12 Diacid | C10 Diacid | C8 Diacid | C6 Diacid |
|---|---|---|---|---|---|---|
| sAA105 | 0 | 0.00 | 0.00 | 0.00 | 0.00 | 0.00 |
|  | 24 | 0.00 | 0.00 | 0.00 | 0.00 | 0.00 |
|  | 48 | 0.00 | 0.00 | 0.00 | 0.00 | 0.00 |
| sAA106 | 0 | 0.00 | 0.00 | 0.00 | 0.00 | 0.00 |
|  | 24 | 0.00 | 0.00 | 0.00 | 0.00 | 0.01 |
|  | 48 | 0.00 | 0.00 | 0.00 | 0.00 | 0.00 |
| sAA152 | 0 | 0.00 | 0.00 | 0.00 | 0.00 | 0.00 |
|  | 24 | 0.00 | 0.00 | 0.00 | 0.00 | 0.43 |
|  | 48 | 0.00 | 0.00 | 0.00 | 0.00 | 0.45 |
| sAA232 | 0 | 0.00 | 0.00 | 0.00 | 0.00 | 0.00 |
|  | 24 | 0.00 | 0.00 | 0.00 | 0.00 | 0.41 |
|  | 48 | 0.00 | 0.00 | 0.00 | 0.00 | 0.58 |
| sAA235 | 0 | 0.00 | 0.00 | 0.00 | 0.00 | 0.00 |
|  | 24 | 0.00 | 0.00 | 0.00 | 0.00 | 0.43 |
|  | 48 | 0.00 | 0.00 | 0.00 | 0.00 | 0.76 |

Example 29

Strain Evaluation of Completely β-Oxidation Blocked Strains

Fermentations also were performed using methyl myristate as a feed stock. Fermentations and GC were carried out essentially as described herein with the exception of feedstock used. The result of fermentations performed using coconut oil as a feedstock are presented below.

| C14 Diacid production in strains with amplified CPR, CYP52A15, and/or CYP52A16 | | | | |
|---|---|---|---|---|
| Strain | C14 diacid, 72 h (g/L) | CPR | A15 | A16 |
| sAA003 | 0.98 | 2 | 1 | 1 |
| sAA318 | 1.19 | 3 | 1 | 1 |
| sAA239 | 2.75 | 3 | 1 | 3 |
| sAA319 | 1.37 | 7 | 1 | 1 |
| sAA238 | 1.93 | 7 | 2 | 1 |

Example 30

Nucleic Acid and Amino Acid Sequences of Novel Fatty Alcohol Oxidase Genes

As noted above, novel fatty alcohol oxidase genes were identified and cloned. The nucleotide and amino acid sequences of the novel sequences are presented herein. Nucleotide and amino acid sequence identity comparison are shown in Example 18.

Nucleotide Sequences

```
FAO-13 (SEQ ID NO: 1)
atggctccattttttgcccgaccaggtcgactacaaacacgtcgacacccttatgttattatgtgacgggatcatccacga
aaccaccgtcgaccaaatcaaagacgttattgctcctgacttccctgctgacaagtacgaagagtacgtcaggacattca
ccaaaccctccgaaaccccaggggttcagggaaaccgtctacaacacagtcaacgcaaacaccacggacgcaatccaccag
ttcattatcttgaccaatgtttttggcatccagggtcttggctccagctttgaccaactcgttgacgcctatcaaggacat
gagcttggaagaccgtgaaaaattgttggcctcgtggcgcgactccccaatcgctgccaaaaggaagttgttcaggttgg
tttctacgcttaccttggtcacgttcacgagattggccaatgagttgcatttgaaagccattcattatccaggaagagaa
gaccgtgaaaaggcttatgaaacccaggagattgacccttttaagtaccagttttttggaaaaaaccgaagttttacggcgc
tgagttgtacttgccagatattgatgtgatcattattggatctggtgccggtgctggtgttgtgggcccacactttggcca
acgatggcttcaagagtttggttttggaaaagggcaaatactttagcaactccgagttgaactttgatgacaaggacggc
gttcaagaattataccaaagtggaggtactttgactacagtcaaccaacagttgtttgttcttgctggttccacttttgg
tggcggtaccactgtcaattggtcagcctgtcttaagacgccattcaaggtgcgtaaggaatggtatgatgagtttggtg
ttgacttggctgctgatgaagcatacgataaagcgcaggattatgtttggcagcaaatgggagcttctaccgaaggcatc
acccactctttggctaacgagattattattgaaggtggtaagaaattaggttacaaggccaaggtattagaccaaaacag
cggtggtcatcctcagcacagatgcggtttctgttattttgggttgtaagcacggtatcaagcaggggcctgttaataact
ggtttagagacgcagctgcccacggttcccagttcatgcaacaggttagagttttgcaaatacttaacaagaagggaggatc
gcttacggtatcttgtgtgaggatgttgtaaccggcgccaagttcaccattactggccccaaaaagtttgttgttgctgc
cggtgctttgaacactccatctgtgttggtcaactccggcttcaagaacaagaacatcggtaagaacttaactttgcacc
cagtttctgtcgtgtttggtgattttggcaaagacgttcaagcagaccacttccacaactccatcatgactgcccttgtt
tcagaagccgctgatttagacggcaagggccatggatgcagaattgaaaccatcttgaacgctccattcatccaggcttc
attcttaccatggagaggtagtaacgaggctagacgagacttgttgcgttacaacaacatggtggcgatgttgctccta
gtcgtgacaccaccagtggttccgtttctgctcatccaaccaaacctgaagctttggttgtcgagtacgacgtgaacaag
tttgacagaaactcgatcttgcaggcattgttggtcactgctgacttgttgtatatccaaggtgccaagagaatccttag
tccacaggcatgggtgccaattttttgaatccgacaagccaaaggataaagagatcaatcaaggacgaggactatgtcgaat
ggagagccaaggttgccaagattccttttcgacacctacggctcacccttatggttcggcacatcaaatgtcttcttgccgt
atgtcaggtaagggtcctaaatacggtgctgttgacaccgatggtagattgtttgaatgttcgaatgtttatgttgccga
tgcaagtctttttgccaactgcaagcggtgccaaccctatggtcaccaccatgactcttgccagacatgttgcgttaggtt
tggcagactccttgaagaccaaagccaagttgtag FAO-17 (SEQ ID NO: 2)
atggctccattttttgcccgaccaggtcgactacaaacacgtcgacacccttatgttattatgtgacgggatcatccacga
aaccaccgtggacgaaatcaaagacgtcattgcccctgacttccccgccgacaaatacgaggagtacgtcaggacattca
ccaaaccctccgaaaccccaggggttcagggaaaccgtctacaacaccgtcaacgcaaacaccatggatgcaatccaccag
ttcattatcttgaccaatgtttttgggatcaagggtcttggcaccagctttgaccaactcgttgactcctatcaaggacat
gagcttggaagaccgtgaaaagttgttagcctcgtggcgtgactcccctattgctgctaaaaggaagttgttcaggttgg
tttctacgcttaccttggtcacgttcacgagattggccaatgagttgcatttgaaagccattcattatccaggaagagaa
gaccgtgaaaaggcttatgaaacccaggagattgacccttttaagtaccagttttttggaaaaaaccgaagttttacggcgc
tgagttgtacttgccagatattgatgtgatcattattggatctggtgccggtgctggtgttgtgggcccacactttggcca
acgatggcttcaagagtttggttttggaaaagggcaaatactttagcaactccgagttgaactttgatgacaaggacggc
gttcaagaattataccaaagtggaggtactttgactacagtcaaccaacagttgtttgttcttgctggttccacttttgg
tggcggtaccactgtcaattggtcagcctgtcttaagacgccattcaaggtgcgtaaggaatggtatgatgagtttggtg
ttgacttggctgctgatgaagcatacgataaagcgcaggattatgtttggcagcaaatgggagcttctaccgaaggcatc
acccactctttggctaacgagattattattgaaggtggtaagaaattaggttacaaggccaaggtattagaccaaaacag
cggtggtcatcctcagcacagatgcggtttctgttattttgggttgtaagcacggtatcaagcaggggcctgttaataact
ggtttagagacgcagctgcccacggttctcagttcatgcaacaggttagagttttgcaaatacttaacaagaagggaggatc
gcttatggtatcttgtgtgaggatgttgtaaccggtgccaagttcaccattactggccccaaaaagtttgttgttgccgc
cggcgccttaaacactccatctgtgttggtcaactccggattcaagaacaagaacatcggtaagaacttaactttgcatc
cagtttctgtcgtgtttggtgattttggcaaagacgttcaagcagaccacttccacaactccatcatgactgcccttgtt
tcagaagccgctgatttagacggcaagggccatggatgcagaattgaaaccatcttgaacgctccattcatccaggcttc
attcttaccatggagaggtagtaacgaggctagacgagacttgttgcgttacaacaacatggtcgcgatgttgctccta
gtcgtgacaccaccagtggttccgtttctgctcatccaaccaaacctgaagctttggttgtcgagtacgacgtgaacaag
tttgacagaaactcgatcttgcaggcattgttggtcactgctgacttgttgtatatccaaggtgccaagagaatccttag
tccacaggcatgggtgccaattttttgaatccgacaagccaaaggataaagagatcaatcaaggacgaggactatgtcgaat
ggagagccaaggttgccaagattccttttcgacacctacggctcacccttatggttcggcacatcaaatgtcttcttgccgt
atgtcaggtaagggtcctaaatacggtgctgttgacaccgatggtagattgtttgaatgttcgaatgtttatgttgccga
tgcaagtctttttgccaactgcaagcggtgccaaccctatggtcaccaccatgactcttgcaagacatgttgcgttaggtt
tggcagactccttgaagaccaaggccaagttgtag FAO-20 (SEQ ID NO: 3)
atggctccattttttgcccgaccaggtcgactacaaacacgtcgacacccttatgttattatgtgacgggatcatccacga
aaccaccgtcgaccaaatcaaagacgttattgctcctgacttccctgctgacaagtacgaagagtacgtcaggacattca
ccaaaccctccgaaaccccaggggttcagggaaaccgtctacaacacagtcaacgcaaacaccacggacgcaatccaccag
ttcattatcttgaccaatgtttttggcatccagggtcttggctccagctttgaccaactcgttgacgcctatcaaggacat
gagcttggaagaccgtgaaaaattgttggcctcgtggcgcgactccccaatcgctgccaaaaggaaattgttcaggttgg
```

| Nucleotide Sequences |
|---|
| tttccacgcttaccttggttactttcacgagattggccaatgagttgcatttgaaagccattcactatccaggaagagaa<br>gaccgtgaaaaggcttatgaaacccaggagattgaccctttcaagtaccagtttatggaaaagccaaagtttgacggcgc<br>tgagttgtacttgccagatattgatgttatcattattggatctggtgccggtgctggtgttgtggcccacactttggcca<br>acgatggcттcaagagтттggттттggaaaagggcaaaтacттагсаасгссgagттgaacтттgатgасааggасggc<br>gттcaagaaттатассaagтggaggтасттгgастасаgтсаассаасаgттgттгgттсттgстggттссастттгgg<br>tggcggтассасгgтсааттggтсаgссгgтсттаagасgссаттсаaggтgсгааggaaтggтатgатgагттggтg<br>ттgacтттgcтgстgатgаagсатасgатаааgсgсаggатттатgтттggсаgсаaатgggагсттстассgаaggсат<br>accсастсттгggстаасgаgаттатттатгgааgтggгааgааатгаggттасааggссаaggтаттаgассааааcag<br>cggтggтсатссгсаgсасаgатgсgгттсгgттаттгgggстgтaagсасggтатсаagсаgggтстgттаатаасг<br>ggтттаgаgасgсаgстgссасggттсссagттсатgсаасаggттаgagтттгсаaатасттааcaagaagggатс<br>gcttacggtatcttgtgtgaggatgttgtaaccggcgccaagттсассаттастggcccaaaagtttgttgttgctgc<br>cggtgcttgаасастссатстgtgttggtcaactccggcttcaagaacaagacatcggtaagаасттаасстттgcacc<br>cagтттстgтсgтgтттggтgаттттggсaaаgасgттсаagсаgассастгссасаастссатсатgастgсссттгgт<br>тсаgаagссgстgатттаgасggсааgggссатggатgсаgаатгgааасcатсттgаасgстссаттсатссаggсттс<br>атгстгтассатggаgаggтаgтаасgаggстаgасgаgасттgттgсgттасааcaaсатggтggсgатgттgстсста<br>gтсgтgасассаccagтggттссgтттстgстсатссаассааассгgaagстттggттgтcgагтасgасgтgаасаag<br>тттgасаgаaастсgатстгgсаggсаттgттggтсастgстgасттgттgтатассаaggтgссаagаgаатссттаg<br>ccacaggcatgggtgccaattttttgaatccgacaagccaaaggataagaatcaatcaaggacgaggactatgtcgaat<br>ggagagссаaggттgссааgaтtсcттсgасассгасggстсасстгтатggттcggсасатсaaатgтсттсттgссgт<br>atgtcaggtaagggtcctaaatacggtgctgttgacaccgatggtagattgtttgaatgttcgaatgtttatgttgccga<br>тgсаagтсттттgссаастgсаagсggтgссаасссатggтсассассатгасттgссаgасатgттgсgттаggтт<br>tggcagactccttgaagaccaaagccaagttgtag |

FAO2a (SEQ ID NO: 4)
atgaataccттcттgccagacgтgcтcgaatacaaacacgтcgacaccтттгgттattgтgтgacgggaтcатccacga
aaccacagтcgaтcagatcaaggacgccатgcтcccgacттcссгgаggассаgтасgаggагтатстсаagасстса
ccaagccatctgagacccctgggttcaaagaagccgtctacgacacgatcaacgccaccccaaccgatgccgtgcacatg
тgтатгgтстгgасcассgсатгgастссаgаатcттggссcссасgттgсссаастстгgасgссгатсааggатат
gacсттgаaggagcgтgаасаатгgттggссгстгggctgтgatтссccgатгgсggсааgaagaagattgттcagатга
ттгссгсgстгассттgасgасgтттасgаgатгggссаgсgаatтgсасттgаaаgссатссастасссгggсаgаgас
тгgсgтgаааggсgтатgаааcссаggтggттgассссттcаggтасстgтттатggаgаааccaаagтттgасggcgс
cgаatтgтасттgссаgататсgасgтcaтсатсатгggатсаggсgссggгgсгggтgтcатgсссcacасctcogcca
acgаcgggгtсааgассгтggтcтттggаааaгggаааатасгтcагсаастссgаgттgааcтттаatgасgстgатgс
gтgаааgаgттgтаccaaggтaаaggтgсттгggссасcассаатcаgcаgатgтттаттcттgссggттссастттggg
cggтggтассасгgтсаастggтстgсттgcстгааааасассатттаaагтgсgтааggаgтggтacgacgагтттggтс
ттgaатттgстgссgатgаagссгасgаcaаagсgсаggатгтатgттгgааасаaатgggгgсттсаасаgатggaатс
астcастсcттggccаасgаagттgтggттgааggаggтааgаagттgggсгасаagасаaаgаaатгgасgттgсас
cggгggccасccтgaсcаccаcтгсаtgгgттстgттаcттgggсгgтаagтасggгaттaааcaсagggттстgтgаатааст
ggтттаgаgасgcаgстgсссасgggтccaagттcатgсаасаagтсаgagттgтgсaaатссгсaacaаgатggcgтc
gсттатggтатсттgтgтgаggатgтcgaaaccggagтcаggттcасгатгagтggсcсааааagттгgттgттгстgc
тggтгсттгgaасасgсcaaстgттgгgассасгссggaтссgааааcатtggтааgасттgасgттgсacc
cagтттссасcgтgтттggтgасттгggсаgаgасgтgсaagссgассатттссасаaатсгатгатgасттcgстстgт
тасgаgтгgсгтgасттggасggсааgggссасggатgсаgаатcgаааccатcттgааcgсгссaттсатcсаagсттc
тгтgтгgссатggаgаggаagтgасgаggсаgаagаgасттgттgсgттасаасаасатggтggссатgттgсттатса
cgсgтgатассассagтggттсаgтттстgстgасссаааgааgсccgасgстттgаттгтcgастатgасатсаасааg
тттgасааgаатgссатcттgсаagсттгcттgатсасттссgасатgттgтасатгgааggтgссаagagатсстcаg
ccacaggcатgggтgссaатcттгgаgтcgаасааgссааaggаgсааgааcaатcаaggасаaggасгатgттgагт
ggagagccaaggctgccaagataccctttcgacacctacggttctgcatatgggtccgcacatcaaatgtccacctgtcgt
атgтccggaaagggтccтaaатасggтgсгgттgаtасгgаtggтagаттgтттgаатgтccgaатgтстатgттgстgа
тgстаgтgтттгтgссгастgссаgсggтgссаасccaaтgататccассатgacстттgстagасagатгgsgстаggтт
тggcagaстссттgaagассаааcccaагттgтаg FAO2b (SEQ ID NO: 5)
atgaataccттcттgccagacgтgcтcgaatacaaacacgтcgатасcтттгgттатгgтgасgggатcатccacga
aaccacagтcgaccagатсаgggacgссатgcтcccgacттcссгgаggассаgтасgаggагтатстcаagассттса
ccaagcсатcтgagaссссгgggттcаgaagaagccgтстасgасасgатсаacagccacсссаaccgaggcтgтgcасатg
тgтатгgтаттgассассgсатггgастccgаgаатсттggссcсcacgттgсссааcтсgттgасgссгатсaaggатат
gacсттgаaggаgcgтgааcаатгgттggсгccттgggстgатгccсcgатсgcggсcaagaagaттgттcagатга
ттгссгсасттассттgаcgасстттасgагатгggссаgсgасттgсасттgаgаgссатссастасссгggсаgаgас
тгgсgтgаааggсататgаааcссаggтggттgасссттcаggтасстgтттатggаgаааccaаagтттgасggcасс
cgаgттgтасттgссаgататсgасgтcатсатсатгggатccggтgссggтgстggтgтcатgсссcaсасттаgсса
acgacgggттcааgассгтggтcтттggaaaaгggaaaататгтcagсаастccgаgттgаaстттaatgасgссgатgс
atgaaagagttgtaccaaggtaaatgtgcgttgaccaccacgaaccagcagatgtttattcttgccggttccactttggg
cggтggтассасгgттааcтggтcтgсттgтсттaааасасссатттaaагтgсgтaaggаgтggтасgacgагтттggтс
ттgaатттgстgссgасgааgссгасgаcaaаgcасaаgастатgтттggаaacaaатgggсgсттстасcgаaggaатс
actcactccttggccaacgcggttgtggttgaaggaggtaaaagttgggttacaagacaagaaatcgagcagaacaa
тggтgссатсстgаccасcссгgтgтттсгgттастгggсгgтaagтагgсgтаттаagсagggттстgтgаатaаcт
ggтттаgаgасgсаgстgсссacgggтcсaagттcатgсаасаagтсаgagттgтgсааатссгссасaaтаaaggсgтc
gсттатggсатсттgтgтgаggатgтcgаgаccggagтсаaаттсастатcagтggсссcaaaaагттгgттgттгстgс
аggттcттгgаасасgссаасggттgтгассасгссggатссаagаасaааcасатcggтaagаасттgасgттgсасc
cagтттсgассgтgтттggтgасттгggсаgаgасgтgсaagссgасcатттссасaaатсгатгатgасттcgстстgт
тасgаagтсgсгтgасттggасggсааgggссacggатgсаgаатcgаааccатcттgааcgсгссаттсатсcaagсттc
тгтgтгgссатggаgаggаagтgасgаggсаgаagаgасттgттgсgттасаасаасатggтggссатgттgсттатса
cccgтgасасcассagтggттсаgтттсгgстgасссаaaagaaгсccgасgстттgaтгgтcgастатgасатcaасааg
тттgасааgаатgссатcттgсаagсттcттгgатсасстссgасатgттgтасатcgааggтgссаagaгаатccтcаg
ccacaggcатgggтgссaатсттгgаgтcgаacaagсcaaaggаgcаagааcaатcаaggаcaaggасгатgттgаgт
ggagagccaaggcтgссaagаtасссттcgасасстасggттсгgссататgggтccgсасатсaaатgтccасстgтcgт

| Nucleotide Sequences |
|---|
| atgtccggaaagggtcctaaatacggcgccgttgataccgatggtagattgtttgaatgttcgaatgtctatgttgctga<br>tgctagtgttttgcctactgccagcggtgccaacccaatgatctccaccatgacgtttgctagacagattgcgttaggtt<br>tggctgactcttgaagaccaaacccaagttgtag |

In addition to the novel FAO genes isolated, a sequence substantially identical to the sequence used for primer design, described above, also was isolated. The nucleotide sequence of the gene is presented below.

FAO-18 (SEQ ID NO: 6)
atggctccattttgcccgaccaggtcgactacaaacacgtcgacacccttatgttattatgtgacgggatcatccacga
aaccaccgtggacgaaatcaaagacgtcattgcccctgacttccccgccgacaaatacgaggagtacgtcaggacattca
ccaaaccctccgaaaccccagggttcagggaaaccgtctacaacaccgtcaacgcaaacaccatggatgcaatccaccag
ttcattatcttgaccaatgttttgggatcaagggtcttggcaccagctttgaccaactcgttgactcctatcaaggacat
gagcttggaagaccgtgaaaagttgttagcctcgtggcgtgactcccctattgctgctaaaaggaagttgttcaggttgg
tttctacgcttaccttggtcacgttcacgagattggccaatgagttgcatttgaaagccattcattatccaggaagagaa
gaccgtgaaaaggcttatgaaaaccaggagattgaccctttaagtaccagtttttggaaaaaccgaagttttacggcgc
tgagttgtacttgccagatattgatgtgatcattattggatctggggccggtgctggtgtcgtggcccacactttgacca
acgacggcttcaagagtttggttttggaaaagggcagatactttagcaactccgagttgaactttgatgacaaggacggg
gttcaagaattataccaaagtggaggtactttgaccaccgtcaaccagcagttgtttgttcttgctggttccactttgg
tggtggtaccactgtcaattggtcggcctgtcttaaaacgccattcaaggtgcgtaaggaatggtatgatgagttggcg
ttgactttgctgccgatgaagcctacgacaaagcacaggatatgtttggcagcaaatgggagcttctaccgaaggcatc
acccactctttggctaacgagattattattgaaggtggcaagaaattaggttacaaggccaaggtattagaccaaaacag
cggtggtcatcctcatcacagatgcgtttctgttatttgggttgtaagcacggtatcaagcagggctctgttaataact
ggtttagagacgcagctgcccacggttcactcagttcatgcaacaggttagagttttgcaaatccttaacaagaagggcatc
gcttatggtatcttgtgtgaggatgttgtaaccggtgccaagttcaccattactggcccaaaaagtttgttgttgccgc
cggcgccttaaacactccatctgtgttggtcaactccggattcaagaacaagaacatcggtaagaacttaactttgcatc
cagtttctgtcgtgtttggtgattttggcaaagacgttcaagcagatcacttccacaactccatcatgactgctctttgt
tcagaagccgctgatttagacggcaagggtcatggatgcagaattgaaaccatcttgaacgctccattcatccaggcttc
attcttaccatggagaggtagtaacgaggctagacgagacttgttgcgttacaacaacatggtggccatgttacttctta
gtcgtgataccaccagtggttccgtttcgtcccatccaactaaacctgaagcattagttgtcgagtacgacgtgaacaag
tttgacagaaactccatcttgcaggcattgttggtcactgctgacttgttgtacattcaaggtgccaagagaatccttag
tccccaaccatgggtgccaattttgaatccgacaagccaaggataagagatcaatcaaggacgaggactatgtcgaat
ggagagccaaggttgccaagattccttttgacacctacggctcgccttatggttcggcgcatcaaatgtcttcttgtcgt
atgtcaggtaagggtcctaaatacggtgctgttgataccgatggtagattgtttgaatgttcgaatgtttatgttgctga
cgctagtcttttgccaactgctagcggtgctaatcctatggtcaccaccatgactcttgcaagacatgttgcgttaggtt
tggcagactccttgaagaccaaggccaagttgtag

| Clustal nucleotide sequence alignments |
|---|

CLUSTAL 2.0.12 multiple sequence alignment
```
FAO-13    ATGGCTCCATTTTTGCCCGACCAGGTCGACTACAAACACGTCGACACCCTTATGTTATTA    60
FAO-20    ATGGCTCCATTTTTGCCCGACCAGGTCGACTACAAACACGTCGACACCCTTATGTTATTA    60
FAO-17    ATGGCTCCATTTTTGCCCGACCAGGTCGACTACAAACACGTCGACACCCTTATGTTATTA    60
FAO-18    ATGGCTCCATTTTTGCCCGACCAGGTCGACTACAAACACGTCGACACCCTTATGTTATTA    60
FAO2a     ATGAATACCTTCTTGCCAGACGTGCTCGAATACAAACACGTCGACACCCTTTTGTTATTG    60
FAO2b     ATGAATACCTTCTTGCCAGACGTGCTCGAATACAAACACGTCGATACCCTTTTGTTATTA    60
          ***  *  * *  ***** ***  *  *** *************   ******  *******

FAO-13    TGTGACGGGATCATCCACGAAACCACCGTCGACCAAATCAAAGACGTTATTGCTCCTGAC   120
FAO-20    TGTGACGGGATCATCCACGAAACCACCGTCGACCAAATCAAAGACGTTATTGCTCCTGAC   120
FAO-17    TGTGACGGGATCATCCACGAAACCACCGTGGACGAAATCAAAGACGTCATTGCCCCTGAC   120
FAO-18    TGTGACGGGATCATCCACGAAACCACCGTGGACGAAATCAAAGACGTCATTGCCCCTGAC   120
FAO2a     TGTGACGGGATCATCCACGAAACCACAGTCGATCAGATCAAGGACGCCATTGCTCCCGAC   120
FAO2b     TGTGACGGGATCATCCACGAAACCACAGTCGACCAGATCAGGGACGCCATTGCTCCCGAC   120
          *************************  ** **   * ****   ****  ***** ** ***

FAO-13    TTCCCTGCTGACAAGTACGAAGAGTACGTCAGGACATTCACCAAACCCTCCGAAACCCCA   180
FAO-20    TTCCCTGCTGACAAGTACGAAGAGTACGTCAGGACATTCACCAAACCCTCCGAAACCCCA   180
FAO-17    TTCCCCGCCGACAAATACGAGGAGTACGTCAGGACATTCACCAAACCCTCCGAAACCCCA   180
FAO-18    TTCCCCGCCGACAAATACGAGGAGTACGTCAGGACATTCACCAAACCCTCCGAAACCCCA   180
FAO2a     TTCCCTGAGGACCAGTACGAGGAGTATCTCAAGACCTTCACCAAGCCATCTGAGACCCCT   180
FAO2b     TTCCCTGAAGACCAGTACGAGGAGTATCTCAAGACCTTCACCAAGCCATCTGAGACCCCT   180
          ***** *   *** * *****  *****  *** *** ********  ** ** ** *****

FAO-13    GGGTTCAGGGAAACCGTCTACAACACAGTCAACGCAAACACCACGGACGCAATCCACCAG   240
FAO-20    GGGTTCAGGGAAACCGTCTACAACACAGTCAACGCAAACACCACGGACGCAATCCACCAG   240
FAO-17    GGGTTCAGGGAAACCGTCTACAACACCGTCAACGCAAACACCATGGATGCAATCCACCAG   240
FAO-18    GGGTTCAGGGAAACCGTCTACAACACCGTCAACGCAAACACCATGGATGCAATCCACCAG   240
FAO2a     GGGTTCAGAGAAGCCGTCTACGACACAGAACGCCACCCCAACCGATGCCGTGCACATG   240
FAO2b     GGGTTCAGAGAAGCCGTCTACGACACGATCAACAGCACCCCCAACCGAGGCGTGCACATG   240
          ********  ***  ********* ****   *****  * * * ** **   *** *

FAO-13    TTCATTATCTTGACCAATGTTTTGGCATCCAGGGTCTTGGCTCCAGCTTTGACCAACTCG   300
FAO-20    TTCATTATCTTGACCAATGTTTTGGCATCCAGGGTCTTGGCTCCAGCTTTGACCAACTCG   300
```

Clustal nucleotide sequence alignments

```
FAO-17   TTCATTATCTTGACCAATGTTTTGGGATCAAGGGTCTTGGCACCAGCTTTGACCAACTCG   300
FAO-18   TTCATTATCTTGACCAATGTTTTGGGATCAAGGGTCTTGGCACCAGCTTTGACCAACTCG   300
FAO2a    TGTATTGTCTTGACCACCGCATTGGACTCCAGAATCTTGGCCCCCACGTTGACCAACTCG   300
FAO2b    TGTATTGTATTGACCACCGCATTGGACTCGAGAATCTTGGCCCCCACGTTGACCAACTCG   300
          *  ***  ******* *   ****  ** **  ******* **  *  ************

FAO-13   TTGACGCCTATCAAGGACATGAGCTTGGAAGACCGTGAAAAATTGTTGGCCTCGTGGCGC   360
FAO-20   TTGACGCCTATCAAGGACATGAGCTTGGAAGACCGTGAAAAATTGTTGGCCTCGTGGCGC   360
FAO-17   TTGACTCCTATCAAGGACATGAGCTTGGAAGACCGTGAAAAGTTGTTAGCCTCGTGGCGT   360
FAO-18   TTGACTCCTATCAAGGACATGAGCTTGGAAGACCGTGAAAAGTTGTTAGCCTCGTGGCGT   360
FAO2a    TTGACGCCTATCAAGGATATGACCTTGAAGGAGCGTGAACAATTGTTGGCCTCTTGGCGT   360
FAO2b    TTGACGCCTATCAAGGATATGACCTTGAAAGAGCGTGAACAATTGTTGGCTGCCTGGCGT   360
         ***** ***********  ****  *** * ** ****** * ****** **  * *****

FAO-13   GACTCCCCAATCGCTGCCAAAAGGAAGTTGTTCAGGTTGGTTTCTACGCTTACCTTGGTC   420
FAO-20   GACTCCCCAATCGCTGCCAAAAGGAAATTGTTCAGGTTGGTTTCCACGCTTACCTTGGTT   420
FAO-17   GACTCCCCTATTGCTGCTAAAAGGAAGTTGTTCAGGTTGGTTTCTACGCTTACCTTGGTC   420
FAO-18   GACTCCCCTATTGCTGCTAAAAGGAAGTTGTTCAGGTTGGTTTCTACGCTTACCTTGGTC   420
FAO2a    GATTCCCCGATTGCGGCAAAGAGAAGATTGTTCAGATTGATTTCCTCGCTTACCTTGACG   420
FAO2b    GATTCCCCGATCGCGGCCAAGAGAAGATTGTTCAGATTGATTTCCTCACTTACCTTGACG   420
         ** *****  ** ** ** **  * **  ******** *** ****  * *********

FAO-13   ACGTTCACGAGATTGGCCAATGAGTTGCATTTGAAAGCCATTCATTATCCAGGAAGAGAA   480
FAO-20   ACTTTCACGAGATTGGCCAATGAGTTGCATTTGAAAGCCATTCACTATCCAGGAAGAGAA   480
FAO-17   ACGTTCACGAGATTGGCCAATGAGTTGCATTTGAAAGCCATTCATTATCCAGGAAGAGAA   480
FAO-18   ACGTTCACGAGATTGGCCAATGAGTTGCATTTGAAAGCCATTCATTATCCAGGAAGAGAA   480
FAO2a    ACGTTTACGAGATTGGCCAGCGAATTGCACTTGAAAGCCATCCACTACCCTGGCAGAGAC   480
FAO2b    ACCTTTACGAGATTGGCCAGCGACTTGCACTTGAGAGCCATCCACTACCCTGGCAGAGAC   480
         **  ** ************   **  ***** ****** ** ** ** ** ** *****

FAO-13   GACCGTGAAAAGGCTTATGAAACCCAGGAGATTGACCCTTTTAAGTACCAGTTTTTGGAA   540
FAO-20   GACCGTGAAAAGGCTTATGAAACCCAGGAGATTGACCCTTTTCAAGTACCAGTTTATGGAA   540
FAO-17   GACCGTGAAAAGGCTTATGAAACCCAGGAGATTGACCCTTTTAAGTACCAGTTTTTGGAA   540
FAO-18   GACCGTGAAAAGGCTTATGAAACCCAGGAGATTGACCCTTTTAAGTACCAGTTTTTGGAA   540
FAO2a    TTGCGTGAAAAGGCGTATGAAACCCAGGTGGTTGACCCTTTCAGGTACCTGTTTATGGAG   540
FAO2b    TTGCGTGAAAAGGCATATGAAACCCAGGTGGTTGACCCTTTCAGGTACCTGTTTATGGAA   540
            *********  ************* *  ********* *  ** ** * **** ****

FAO-13   AAACCGAAGTTTTACGGCGCTGAGTTGTACTTGCCAGATATTGATGTGATCATTATTGGA   600
FAO-20   AAGCCAAAGTTTGACGGCGCTGAGTTGTACTTGCCAGATATTGATGTTATCATTATTGGA   600
FAO-17   AAACCGAAGTTTTACGGCGCTGAGTTGTACTTGCCAGATATTGATGTGATCATTATTGGA   600
FAO-18   AAACCGAAGTTTTACGGCGCTGAGTTGTACTTGCCAGATATTGATGTGATCATTATTGGA   600
FAO2a    AAACCAAAGTTTGACGGCGCCGAATTGTACTTGCCAGATATCGACGTCATCATCATTGGA   600
FAO2b    AAACCAAAGTTTGACGGCACCGAGTTGTACTTGCCAGATATCGACGTCATCATCATTGGA   600
         ** **  *****  * ** *  **  ******************  ** ** *** ******

FAO-13   TCTGGTGCCGGTGCTGGTGTTGTGGCCCACACTTTGGCCAACGATGGCTTCAAGAGTTTG   660
FAO-20   TCTGGTGCCGGTGCTGGTGTTGTGGCCCACACTTTGGCCAACGATGGCTTCAAGAGTTTG   660
FAO-17   TCTGGTGCCGGTGCTGGTGTTGTGGCCCACACTTTGGCCAACGATGGCTTCAAGAGTTTG   660
FAO-18   TCTGGGGCCGGTGCTGGTGTCGTGGCCCACACTTTGACCAACGACGGCTTCAAGAGTTTG   660
FAO2a    TCAGGCGCCGGTGCTGGTGTCATGGCCCACACTCTCGCCAACGACGGGTTCAAGACCTTG   660
FAO2b    TCCGGTGCCGGTGCTGGTGTCATGGCCCACACTTTAGCCAACGACGGGTACAAGACCTTG   660
         ** **  ************    **********  *  ****** **  * ***** ***

FAO-13   GTTTTGGAAAAGGGCAAATACTTTAGCAACTCCGAGTTGAACTTTGATGACAAGGACGGC   720
FAO-20   GTTTTGGAAAAGGGCAAATACTTTAGCAACTCCGAGTTGAACTTTGATGACAAGGACGGC   720
FAO-17   GTTTTGGAAAAGGGCAAATACTTTAGCAACTCCGAGTTGAACTTTGATGACAAGGACGGC   720
FAO-18   GTTTTGGAAAAGGGCAGATACTTTAGCAACTCCGAGTTGAACTTTGATGACAAGGACGGG   720
FAO2a    GTTTTGGAAAAGGGAAAGTATTTCAGCAACTCCGAGTTGAACTTTAATGACGCTGATGGC   720
FAO2b    GTTTTGGAAAAGGGAAAGTATTTCAGCAACTCCGAGTTGAACTTTAATGATGCCGATGGT   720
         **************  * ** ** *******************  ****    ** **

FAO-13   GTTCAAGAATTATACCAAAGTGGAGGTACTTTGACTACAGTCAACCAACAGTTGTTTGTT   780
FAO-20   GTTCAAGAATTATACCAAAGTGGAGGTACTTTGACTACAGTCAACCAACAGTTGTTTGTT   780
FAO-17   GTTCAAGAATTATACCAAAGTGGAGGTACTTTGACTACAGTCAACCAACAGTTGTTTGTT   780
FAO-18   GTTCAAGAATTATACCAAAGTGGAGGTACTTTGACCACCGTCAACCAGCAGTTGTTTGTT   780
FAO2a    GTGAAAGAGTTGTACCAAGGTAAAGGTGCTTTGGCCACCACCAATCAGCAGATGTTTATT   780
FAO2b    ATGAAAGAGTTGTACCAAGGTAAATGTGCGTTGACCACCACGAACCAGCAGATGTTTATT   780
            *  **** *  ***** **  *  **  ***       **  ** ***  ****  **

FAO-13   CTTGCTGGTTCCACTTTTGGTGGCGGTACCACTGTCAATTGGTCAGCCTGTCTTAAGACG   840
FAO-20   CTTGCTGGTTCCACTTTTGGTGGCGGTACCACTGTCAATTGGTCAGCCTGTCTTAAGACG   840
FAO-17   CTTGCTGGTTCCACTTTTGGTGGCGGTACCACTGTCAATTGGTCAGCCTGTCTTAAGACG   840
FAO-18   CTTGCTGGTTCCACTTTTGGTGGTGGTACCACTGTCAATTGGTCAGCCTGTCTTAAAACG   840
FAO2a    CTTGCCGGTTCCACTTTGGGCGGTGGTACCACTGTCAACTGGTCTGCTTGCCTTAAAACA   840
FAO2b    CTTGCCGGTTCCACTTTGGGCGGTGGTACCACTGTTAACTGGTCTGCTTGTCTTAAAACA   840
         ***** *********** ** ** ***********  **  ***** ** **** **
```

| Clustal nucleotide sequence alignments |
|---|

```
FAO-13    CCATTCAAGGTGCGTAAGGAATGGTATGATGAGTTTGGTGTTGACTTTGCTGCTGATGAA   900
FAO-20    CCATTCAAGGTGCGTAAGGAATGGTATGATGAGTTTGGTGTTGACTTTGCTGCTGATGAA   900
FAO-17    CCATTCAAGGTGCGTAAGGAATGGTATGATGAGTTTGGTGTTGACTTTGCTGCTGATGAA   900
FAO-18    CCATTCAAGGTGCGTAAGGAATGGTATGATGAGTTTGGCGTTGACTTTGCTGCCGATGAA   900
FAO2a     CCATTTAAAGTGCGTAAGGAGTGGTACGACGAGTTTGGTCTTGAATTTGCTGCCGATGAA   900
FAO2b     CCATTTAAAGTGCGTAAGGAGTGGTACGACGAGTTTGGTCTTGAATTTGCTGCCGACGAA   900
          ***** ** *********** ***** ** ******* **** ******** **  ***

FAO-13    GCATACGATAAAGCGCAGGATTATGTTTGGCAGCAAATGGGAGCTTCTACCGAAGGCATC   960
FAO-20    GCATACGATAAAGCGCAGGATTATGTTTGGCAGCAAATGGGAGCTTCTACCGAAGGCATC   960
FAO-17    GCATACGATAAAGCGCAGGATTATGTTTGGCAGCAAATGGGAGCTTCTACCGAAGGCATC   960
FAO-18    GCCTACGACAAAGCACAGGATTATGTTTGGCAGCAAATGGGAGCTTCTACCGAAGGCATC   960
FAO2a     GCCTACGACAAAGCGCAGGATTATGTTTGGAAACAAATGGGTGCTTCAACAGATGGAATC   960
FAO2b     GCCTACGACAAAGCACAAGACTATGTTTGGAAACAAATGGGCGCTTCTACCGAAGGAATC   960
          ** ***** ***** ** ** ********  * ******** ***** ** ** ** ***

FAO-13    ACCCACTCTTTGGCTAACGAGATTATTATTGAAGGTGGTAAGAAATTAGGTTACAAGGCC  1020
FAO-20    ACCCACTCTTTGGCTAACGAGATTATTATTGAAGGTGGTAAGAAATTAGGTTACAAGGCC  1020
FAO-17    ACCCACTCTTTGGCTAACGAGATTATTATTGAAGGTGGTAAGAAATTAGGTTACAAGGCC  1020
FAO-18    ACCCACTCTTTGGCTAACGAGATTATTATTGAAGGTGGCAAGAAATTAGGTTACAAGGCC  1020
FAO2a     ACTCACTCCTTGGCCAACGAAGTTGTGGTTGAAGGAGGTAAGAAGTTGGGCTACAAGAGC  1020
FAO2b     ACTCACTCTTTGGCGAACGCGGTTGTGGTTGAAGGAGGTAAGAAGTTGGGTTACAAGAGC  1020
          ** ***** **** ****       ** * ******* ** ***** ** ******  *

FAO-13    AAGGTATTAGACCAAAACAGCGGTGGTCATCCTCAGCACAGATGCGGTTTCTGTTATTTG  1080
FAO-20    AAGGTATTAGACCAAAACAGCGGTGGTCATCCTCAGCACAGATGCGGTTTCTGTTATTTG  1080
FAO-17    AAGGTATTAGACCAAAACAGCGGTGGTCATCCTCAGCACAGATGCGGTTTCTGTTATTTG  1080
FAO-18    AAGGTATTAGACCAAAACAGCGGTGGTCATCCTCATCACAGATGCGGTTTCTGTTATTTG  1080
FAO2a     AAGGAAATTGAGCAGAACAACGGTGGCCACCCTGACCACCCATGTGGTTTCTGTTACTTG  1080
FAO2b     AAGGAAATCGAGCAGAACAATGGTGGCCATCCTGACCACCCCTGTGGTTTCTGTTACTTG  1080
          ****  *  ** ** ****  ***** ***  *** ***    ** ************ ***

FAO-13    GGCTGTAAGCACGGTATCAAGCAGGGTTCTGTTAATAACTGGTTTAGAGACGCAGCTGCC  1140
FAO-20    GGCTGTAAGCACGGTATCAAGCAGGGTTCTGTTAATAACTGGTTTAGAGACGCAGCTGCC  1140
FAO-17    GGTTGTAAGCACGGTATCAAGCAGGGTTCTGTTAATAACTGGTTTAGAGACGCAGCTGCC  1140
FAO-18    GGTTGTAAGCACGGTATCAAGCAGGGCTCTGTTAATAACTGGTTTAGAGACGCAGCTGCC  1140
FAO2a     GGCTGTAAGTACGGTATTAAACAGGGTTCTGTGAATAACTGGTTTAGAGACGCAGCTGCC  1140
FAO2b     GGCTGTAAGTACGGTATTAAGCAGGGTTCTGTGAATAACTGGTTTAGAGACGCAGCTGCC  1140
          ** ****** ******* ** ***** ***** ***************************

FAO-13    CACGGTTCCCAGTTCATGCAACAGGTTAGAGTTTTGCAAATACTTAACAAGAAGGGGATC  1200
FAO-20    CACGGTTCCCAGTTCATGCAACAGGTTAGAGTTTTGCAAATACTTAACAAGAAGGGGATC  1200
FAO-17    CACGGTTCTCAGTTCATGCAACAGGTTAGAGTTTTGCAAATCCTTAACAAGAAGGGCATC  1200
FAO-18    CACGGTTCTCAGTTCATGCAACAGGTTAGAGTTTTGCAAATCCTTAACAAGAAGGGCATC  1200
FAO2a     CACGGGTCCAAGTTCATGCAACAAGTCAGAGTTGTGCAAATCCTCAACAAGAATGGCGTC  1200
FAO2b     CACGGGTCCAAGTTCATGCAACAAGTCAGAGTTGTGCAAATCCTCCACAATAAAGGCGTC  1200
          ***** ** ************* ** ****** ******* **  ** ** ** **  **

FAO-13    GCTTACGGTATCTTGTGTGAGGATGTTGTAACCGGCGCCAAGTTCACCATTACTGGCCCC  1260
FAO-20    GCTTACGGTATCTTGTGTGAGGATGTTGTAACCGGCGCCAAGTTCACCATTACTGGCCCC  1260
FAO-17    GCTTATGGTATCTTGTGTGAGGATGTTGTAACCGGTGCCAAGTTCACCATTACTGGCCCC  1260
FAO-18    GCTTATGGTATCTTGTGTGAGGATGTTGTAACCGGTGCCAAGTTCACCATTACTGGCCCC  1260
FAO2a     GCTTATGGTATCTTGTGTGAGGATGTCGAAACCGGAGTCAGGTTCACTATTAGTGGCCCC  1260
FAO2b     GCTTATGGCATCTTGTGTGAGGATGTCGAGACCGGAGTCAAATTCACTATCAGTGGCCCC  1260
          ***** ** ***************  *  *****    *  ***** **  * *******

FAO-13    AAAAAGTTTGTTGTTGCTGCCGGTGCTTTGAACACTCCATCTGTGTTGGTCAACTCCGGC  1320
FAO-20    AAAAAGTTTGTTGTTGCTGCCGGTGCTTTGAACACTCCATCTGTGTTGGTCAACTCCGGC  1320
FAO-17    AAAAAGTTTGTTGTTGCCGCCGGCGCCTTAAACACTCCATCTGTGTTGGTCAACTCCGGA  1320
FAO-18    AAAAAGTTTGTTGTTGCCGCCGGCGCCTTAAACACTCCATCTGTGTTGGTCAACTCCGGA  1320
FAO2a     AAAAAGTTTGTTGTTTCTGCTGGTTCTTTGAACACGCCAACTGTGTGACCAACTCCGGA  1320
FAO2b     AAAAAGTTTGTTGTTTCTGCAGGTTCTTTGAACACGCCAACGGTGTTGACCAACTCCGGA  1320
          *************** * ** **   * ** ***** ***    ****** *********

FAO-13    TTCAAGAACAAGAACATCGGTAAGAACTTAACTTTGCACCCAGTTTCTGTCGTGTTTGGT  1380
FAO-20    TTCAAGAACAAGAACATCGGTAAGAACTTAACTTTGCACCCAGTTTCTGTCGTGTTTGGT  1380
FAO-17    TTCAAGAACAAGAACATCGGTAAGAACTTAACTTTGCATCCAGTTTCTGTCGTGTTTGGT  1380
FAO-18    TTCAAGAACAAGAACATCGGTAAGAACTTAACTTTGCATCCAGTTTCTGTCGTGTTTGGT  1380
FAO2a     TTCAAGAACAAGCACATTGGTAAGAACTTGACGTTGCACCCAGTTTCCACCGTGTTTGGT  1380
FAO2b     TTCAAGAACAAACACATCGGTAAGAACTTGACGTTGCACCCAGTTTCGACCGTGTTTGGT  1380
          ***********  *** ** ********* ** ***** *********     **********

FAO-13    GATTTTGGCAAAGACGTTCAAGCAGACCACTTCCACAACTCCATCATGACTGCCCTTTGT  1440
FAO-20    GATTTTGGCAAAGACGTTCAAGCAGACCACTTCCACAACTCCATCATGACTGCCCTTTGT  1440
FAO-17    GATTTTGGCAAAGACGTTCAAGCAGACCACTTCCACAACTCCATCATGACTGCCCTTTGT  1440
FAO-18    GATTTTGGCAAAGACGTTCAAGCAGATCACTTCCACAACTCCATCATGACTGCTCTTTGT  1440
```

Clustal nucleotide sequence alignments

```
FAO2a    GACTTTGGCAGAGACGTGCAAGCCGACCATTTCCACAAATCTATTATGACTTCGCTTTGT  1440
FAO2b    GACTTTGGCAGAGACGTGCAAGCCGACCATTTCCACAAATCTATTATGACTTCGCTCTGT  1440
         ** ******* ***** ***** ** ******** ** ** ****** * ** ***

FAO-13   TCAGAAGCCGCTGATTTAGACGGCAAGGGCCATGGATGCAGAATTGAAACCATCTTGAAC  1500
FAO-20   TCAGAAGCCGCTGATTTAGACGGCAAGGGCCATGGATGCAGAATTGAAACCATCTTGAAC  1500
FAO-17   TCAGAAGCCGCTGATTTAGACGGCAAGGGCCATGGATGCAGAATTGAAACCATCTTGAAC  1500
FAO-18   TCAGAAGCCGCTGATTTAGACGGCAAGGGTCATGGATGCAGAATTGAAACCATCTTGAAC  1500
FAO2a    TACGAGGTTGCTGACTTGGACGGCAAGGGCCACGGATGCAGAATCGAAACCATCTTGAAC  1500
FAO2b    TACGAAGTCGCTGACTTGGACGGCAAGGGCCACGGATGCAGAATCGAGACCATCTTGAAC  1500
         *  **  *  ***** ** ********** ** ***********  ** ***********

FAO-13   GCTCCATTCATCCAGGCTTCATTCTTACCATGGAGAGGTAGTAACGAGGCTAGACGAGAC  1560
FAO-20   GCTCCATTCATCCAGGCTTCATTCTTACCATGGAGAGGTAGTAACGAGGCTAGACGAGAC  1560
FAO-17   GCTCCATTCATCCAGGCTTCATTCTTACCATGGAGAGGTAGTAACGAGGCTAGACGAGAC  1560
FAO-18   GCTCCATTCATCCAGGCTTCATTCTTACCATGGAGAGGTAGTAACGAGGCTAGACGAGAC  1560
FAO2a    GCTCCATTCATCCAAGCTTCTTTGTTGCCATGGAGAGGAAGTGACGAGGTCAGAAGAGAC  1560
FAO2b    GCTCCATTCATCCAAGCTTCTTTGTTGCCATGGAGAGGAAGCGACGAGGTCAGAAGAGAC  1560
         ************** ***** **  ** ********** **  ******   *** *****

FAO-13   TTGTTGCGTTACAACAACATGGTGGCGATGTTGCTCCTTAGTCGTGACACCACCAGTGGT  1620
FAO-20   TTGTTGCGTTACAACAACATGGTGGCGATGTTGCTCCTTAGTCGTGACACCACCAGTGGT  1620
FAO-17   TTGTTGCGTTACAACAACATGGTGGCGATGTTGCTCCTTAGTCGTGACACCACCAGTGGT  1620
FAO-18   TTGTTGCGTTACAACAACATGGTGGCCATGTTACTTCTTAGTCGTGATACCACCAGTGGT  1620
FAO2a    TTGTTGCGTTACAACAACATGGTGGCCATGTTGCTTATACGCGTGATACCACCAGTGGT  1620
FAO2b    TTGTTGCGTTACAACAACATGGTGGCCATGTTGCTTATCACCCGTGACACCACCAGTGGT  1620
         **************************  *****  *   *   ***** ***********

FAO-13   TCCGTTTCTGCTCATCCAACCAAACCTGAAGCTTTGGTTGTCGAGTACGACGTGAACAAG  1680
FAO-20   TCCGTTTCTGCTCATCCAACCAAACCTGAAGCTTTGGTTGTCGAGTACGACGTGAACAAG  1680
FAO-17   TCCGTTTCTGCTCATCCAACCAAACCTGAAGCTTTGGTTGTCGAGTACGACGTGAACAAG  1680
FAO-18   TCCGTTTCGTCCCATCCAACTAAACCTGAAGCATTAGTTGTCGAGTACGACGTGAACAAG  1680
FAO2a    TCAGTTTCTGCTGACCCAAAGAAGCCCGACGCTTTGATTGTCGACTATGAGATTAACAAG  1680
FAO2b    TCAGTTTCTGCTGACCCAAAGAAGCCCGACGCTTTGATTGTCGACTATGACATCAACAAG  1680
         ** *****   *  * * ****  ** ** ** ** ******* ** **  * ******

FAO-13   TTTGACAGAAACTCGATCTTGCAGGCATTGTTGGTCACTGCTGACTTGTTGTATATCCAA  1740
FAO-20   TTTGACAGAAACTCGATCTTGCAGGCATTGTTGGTCACTGCTGACTTGTTGTATATCCAA  1740
FAO-17   TTTGACAGAAACTCGATCTTGCAGGCATTGTTGGTCACTGCTGACTTGTTGTATATCCAA  1740
FAO-18   TTTGACAGAAACTCCATCTTGCAGGCATTGTTGGTCACTGCTGACTTGTTGTACATTCAA  1740
FAO2a    TTTGACAAGAATGCCATCTTGCAAGCTTTCTTGATCACTTCCGACATGTTGTACATTGAA  1740
FAO2b    TTTGACAAGAATGCCATCTTGCAAGCTTTCTTGATCACCTCCGACATGTTGTACATCGAA  1740
         *******  **  * ********  **  * **** *  * ****** *******  **  **

FAO-13   GGTGCCAAGAGAATCCTTAGTCCACAGGCATGGGTGCCAATTTTTGAATCCGACAAGCCA  1800
FAO-20   GGTGCCAAGAGAATCCTTAGTCCACAGGCATGGGTGCCAATTTTTGAATCCGACAAGCCA  1800
FAO-17   GGTGCCAAGAGAATCCTTAGTCCACAGGCATGGGTGCCAATTTTTGAATCCGACAAGCCA  1800
FAO-18   GGTGCCAAGAGAATCCTTAGTCCCCAACCTGGGTGCCAATTTTTGAATCCGACAAGCCA  1800
FAO2a    GGTGCCAAGAGAATCCTCAGTCCACAGCCATGGGTGCCAATCTTTGAGTCGAACAAGCCA  1800
FAO2b    GGTGCCAAGAGAATCCTCAGTCCACAGGCATGGGTGCCAATCTTTGAGTCGAACAAGCCA  1800
         ***************** ***** **  *************  ***** **  ********

FAO-13   AAGGATAAGAGATCAATCAAGGACGAGGACTATGTCGAATGGAGAGCCAAGGTTGCCAAG  1860
FAO-20   AAGGATAAGAGATCAATCAAGGACGAGGACTATGTCGAATGGAGAGCCAAGGTTGCCAAG  1860
FAO-17   AAGGATAAGAGATCAATCAAGGACGAGGACTATGTCGAATGGAGAGCCAAGGTTGCCAAG  1860
FAO-18   AAGGATAAGAGATCAATCAAGGACGAGGACTATGTCGAATGGAGAGCCAAGGTTGCCAAG  1860
FAO2a    AAGGAGCAAAGAACGATCAAGGACAAGGACTATGTTGAGTGGAGAGCCAAGGCTGCTAAG  1860
FAO2b    AAGGAGCAAAGAACAATCAAGGACAAGGACTATGTCGAATGGAGAGCCAAGGCTGCCAAG  1860
         *****  * *** * ********* ********** ** ************* *** ***

FAO-13   ATTCCTTTCGACACCTACGGCTCACCTTATGGTTCGGCACATCAAATGTCTTCTTGCCGT  1920
FAO-20   ATTCCTTTCGACACCTACGGCTCACCTTATGGTTCGGCACATCAAATGTCTTCTTGCCGT  1920
FAO-17   ATTCCTTTCGACACCTACGGCTCACCTTATGGTTCGGCACATCAAATGTCTTCTTGCCGT  1920
FAO-18   ATTCCTTTTGACACCTACGGCTCGCCTTATGGTTCGGCGCATCAAATGTCTTCTTGTCGT  1920
FAO2a    ATACCTTTCGACACCTACGGTTCTGCATATGGGTCCGCACATCAAATGTCCACCTGTCGT  1920
FAO2b    ATACCTTTCGACACCTACGGTTCTGCCTATGGGTCCGCACATCAAATGTCCACCTGTCGT  1920
         ** ***** ***********  **   * ****** ** *********** *  ** ***

FAO-13   ATGTCAGGTAAGGGTCCTAAAATACGGTGCTGTTGACACCGATGGTAGATTGTTTGAATGT  1980
FAO-20   ATGTCAGGTAAGGGTCCTAAAATACGGTGCTGTTGACACCGATGGTAGATTGTTTGAATGT  1980
FAO-17   ATGTCAGGTAAGGGTCCTAAAATACGGTGCTGTTGACACCGATGGTAGATTGTTTGAATGT  1980
FAO-18   ATGTCAGGTAAGGGTCCTAAAATACGGTGCTGTTGATACCGATGGTAGATTGTTTGAATGT  1980
FAO2a    ATGTCCGGAAAGGGTCCTAAATACGGTGCTGTTGATACTGATGGTAGATTGTTTGAATGT  1980
FAO2b    ATGTCCGGAAAGGGTCCTAAATACGGCGCCGTTGATACCGATGGTAGATTGTTTGAATGT  1980
         ***** ** ***************** ** ****** ** ********************
```

Clustal nucleotide sequence alignments

```
FAO-13   TCGAATGTTTATGTTGCCGATGCAAGTCTTTTGCCAACTGCAAGCGGTGCCAACCCTATG  2040
FAO-20   TCGAATGTTTATGTTGCCGATGCAAGTCTTTTGCCAACTGCAAGCGGTGCCAACCCTATG  2040
FAO-17   TCGAATGTTTATGTTGCCGATGCAAGTCTTTTGCCAACTGCAAGCGGTGCCAACCCTATG  2040
FAO-18   TCGAATGTTTATGTTGCTGACGCTAGTCTTTTGCCAACTGCTAGCGGTGCTAATCCTATG  2040
FAO2a    TCGAATGTCTATGTTGCTGATGCTAGTGTTTTGCCTACTGCCAGCGGTGCCAACCCAATG  2040
FAO2b    TCGAATGTCTATGTTGCTGATGCTAGTGTTTTGCCTACTGCCAGCGGTGCCAACCCAATG  2040
         ******** ******** ** ** *** ******* ***** ******** ** ** ***

FAO-13   GTCACCACCATGACTCTTGCCAGACATGTTGCGTTAGGTTTGGCAGACTCCTTGAAGACC  2100
FAO-20   GTCACCACCATGACTCTTGCCAGACATGTTGCGTTAGGTTTGGCAGACTCCTTGAAGACC  2100
FAO-17   GTCACCACCATGACTCTTGCAAGACATGTTGCGTTAGGTTTGGCAGACTCCTTGAAGACC  2100
FAO-18   GTCACCACCATGACTCTTGCAAGACATGTTGCGTTAGGTTTGGCAGACTCCTTGAAGACC  2100
FAO2a    ATATCCACCATGACCTTTGCTAGACAGATTGCGTTAGGTTTGGCTGACTCCTTGAAGACC  2100
FAO2b    ATCTCCACCATGACGTTTGCTAGACAGATTGCGTTAGGTTTGGCTGACTCTTTGAAGACC  2100
           * ********** **** ***** ***** ***************** *** *********

FAO-13   AAAGCCAAGTTGTAG                                               2115
FAO-20   AAAGCCAAGTTGTAG                                               2115
FAO-17   AAGGCCAAGTTGTAG                                               2115
FAO-18   AAGGCCAAGTTGTAG                                               2115
FAO2a    AAACCCAAGTTGTAG                                               2115
FAO2b    AAACCCAAGTTGTAG                                               2115
         **   **********
```

Amino acid sequences

FAO-1 - SEQ ID NO: 7
MAPFLPDQVDYKHVDTLMLLCDGIIHETTVDEIKDVIAPDFPADKYEEYVRTFTKPSETPGFRETVYNTVNANTMDAIHQ
FIILTNVLGSRVLAPALTNSLTPIKDMSLEDREKLLASWRDSPIAAKRKLFRLVSTLTLVTFTRLANELHLKAIHYPGRE
DREKAYETQEIDPFKYQFLEKPKFYGAELYLPDIDVIIGSGAGAGVVAHTLTNDGFKSLVLEKGRYFSNSELNFDDKDG
VQELYQSGGTLTTVNQQLFVLAGSTFGGGTTVNWSACLKTPFKVRKEWYDEFGVDFAADEAYDKAQDYVWQQMGASTEGI
THSLANEIIIEGGKKLGYKAKVLDQNSGGHPHHRCGFCYLGCKHGIKQGSVNNWFRDAAAHGSQFMQQVRVLQILNKKGI
AYGILCEDVVTGAKFTITGPKKFVVAAGALNTPSVLVNSGFKNKNIGKNLTLHPVSVVFGDFGKDVQADHFHNSIMTALC
SEAADLDGKGHGCRIETILNAPFIQASFLPWRGSNEARRDLLRYNNMVAMLLLSRDTTSGSVSSHPTKPEALVVEYDVNK
FDRNSILQALLVTADLLYIQGAKRILSPQPWVPIFESDKPKDKRSIKDEDYVEWRAKVAKIPFDTYGSPYGSAHQMSSCR
MSGKGPKYGAVDTDGRLFECSNVYVADASLLPTASGANPMVTTMTLARHVALGLADSLKTKAKL

FAO-13 - SEQ ID NO: 8
MAPFLPDQVDYKHVDTLMLLCDGIIHETTVDQIKDVIAPDFPADKYEEYVRTFTKPSETPGFRETVYNTVNANTTDAIHQ
FIILTNVLASRVLAPALTNSLTPIKDMSLEDREKLLASWRDSPIAAKRKLFRLVSTLTLVTFTRLANELHLKAIHYPGRE
DREKAYETQEIDPFKYQFLEKPKFYGAELYLPDIDVIIGSGAGAGVVAHTLANDGFKSLVLEKGKYFSNSELNFDDKDG
VQELYQSGGTLTTVNQQLFVLAGSTFGGGTTVNWSACLKTPFKVRKEWYDEFGVDFAADEAYDKAQDYVWQQMGASTEGI
THSLANEIIIEGGKKLGYKAKVLDQNSGGHPQHRCGFCYLGCKHGIKQGSVNNWFRDAAAHGSQFMQQVRVLQILNKKGI
AYGILCEDVVTGAKFTITGPKKFVVAAGALNTPSVLVNSGFKNKNIGKNLTLHPVSVVFGDFGKDVQADHFHNSIMTALC
SEAADLDGKGHGCRIETILNAPFIQASFLPWRGSNEARRDLLRYNNMVAMLLLSRDTTSGSVSAHPTKPEALVVEYDVNK
FDRNSILQALLVTADLLYIQGAKRILSPQAWVPIFESDKPKDKRSIKDEDYVEWRAKVAKIPFDTYGSPYGSAHQMSSCR
MSGKGPKYGAVDTDGRLFECSNVYVADASLLPTASGANPMVTTMTLARHVALGLADSLKTKAKL

FAO-20 - SEQ ID NO: 9
MAPFLPDQVDYKHVDTLMLLCDGIIHETTVDQIKDVIAPDFPADKYEEYVRTFTKPSETPGFRETVYNTVNANTTDAIHQ
FIILTNVLASRVLAPALTNSLTPIKDMSLEDREKLLASWRDSPIAAKRKLFRLVSTLTLVTFTRLANELHLKAIHYPGRE
DREKAYETQEIDPFKYQFMEKPKFDGAELYLPDIDVIIGSGAGAGVVAHTLANDGFKSLVLEKGKYFSNSELNFDDKDG
VQELYQSGGTLTTVNQQLFVLAGSTFGGGTTVNWSACLKTPFKVRKEWYDEFGVDFAADEAYDKAQDYVWQQMGASTEGI
THSLANEIIIEGGKKLGYKAKVLDQNSGGHPQHRCGFCYLGCKHGIKQGSVNNWFRDAAAHGSQFMQQVRVLQILNKKGI
AYGILCEDVVTGAKFTITGPKKFVVAAGALNTPSVLVNSGFKNKNIGKNLTLHPVSVVFGDFGKDVQADHFHNSIMTALC
SEAADLDGKGHGCRIETILNAPFIQASFLPWRGSNEARRDLLRYNNMVAMLLLSRDTTSGSVSAHPTKPEALVVEYDVNK
FDRNSILQALLVTADLLYIQGAKRILSPQAWVPIFESDKPKDKRSIKDEDYVEWRAKVAKIPFDTYGSPYGSAHQMSSCR
MSGKGPKYGAVDTDGRLFECSNVYVADASLLPTASGANPMVTTMTLARHVALGLADSLKTKAKL

FAO-17 - SEQ ID NO: 10
MAPFLPDQVDYKHVDTLMLLCDGIIHETTVDEIKDVIAPDFPADKYEEYVRTFTKPSETPGFRETVYNTVNANTMDAIHQ
FIILTNVLGSRVLAPALTNSLTPIKDMSLEDREKLLASWRDSPIAAKRKLFRLVSTLTLVTFTRLANELHLKAIHYPGRE
DREKAYETQEIDPFKYQFLEKPKFYGAELYLPDIDVIIGSGAGAGVVAHTLANDGFKSLVLEKGKYFSNSELNFDDKDG
VQELYQSGGTLTTVNQQLFVLAGSTFGGGTTVNWSACLKTPFKVRKEWYDEFGVDFAADEAYDKAQDYVWQQMGASTEGI
THSLANEIIIEGGKKLGYKAKVLDQNSGGHPQHRCGFCYLGCKHGIKQGSVNNWFRDAAAHGSQFMQQVRVLQILNKKGI
AYGILCEDVVTGAKFTITGPKKFVVAAGALNTPSVLVNSGFKNKNIGKNLTLHPVSVVFGDFGKDVQADHFHNSIMTALC
SEAADLDGKGHGCRIETILNAPFIQASFLPWRGSNEARRDLLRYNNMVAMLLLSRDTTSGSVSAHPTKPEALVVEYDVNK
FDRNSILQALLVTADLLYIQGAKRILSPQAWVPIFESDKPKDKRSIKDEDYVEWRAKVAKIPFDTYGSPYGSAHQMSSCR
MSGKGPKYGAVDTDGRLFECSNVYVADASLLPTASGANPMVTTMTLARHVALGLADSLKTKAKl

FAO-2a - SEQ ID NO: 11
MNTFLPDVLEYKHVDTLLLLCDGIIHETTVDQIKDAIAPDFPEDQYEEYLKTFTKPSETPGFREAVYDTINATPTDAVHM
CIVLTTALDSRILAPTLTNSLTPIKDMTLKEREQLLASWRDSPIAAKRRLFRLISSLTLTTFTRLASELHLKAIHYPGRD

| Amino acid sequences |
|---|
| LREKAYETQVVDPFRYSFMEKPKFDGAELYLPDIDVIIIGSGAGAGVMAHTLANDGFKTLVLEKGKYFSNSELNFNDADG<br>VKELYQGKGALATTNQQMFILAGSTLGGGTTVNWSACLKTPFKVRKEWYDEFGLEFAADEAYDKAQDYVWKQMGASTDGI<br>THSLANEVVVEGGKKLGYKSKEIEQNNGGHPDHPCGFCYLGCKYGIKQGSVNNWFRDAAAHGSKFMQQVRVVQILNKNGV<br>AYGILCEDVETGVRFTISGPKKFVVSAGSLNTPTVLTNSGFKNKHIGKNLTLHPVSTVFGDFGRDVQADHFHKSIMTSLC<br>YEVADLDGKGHGCRIETILNAPFIQASLLPWRGSDEVRRDLLRYNNMVAMLLITRDTTSGSVSADPKKPDALIVDYEINK<br>FDKNAILQAFLITSDMLYIEGAKRILSPQPWVPIFESNKPKEQRTIKDKDYVEWRAKAAKIPFDTYGSAYGSAHQMSTCR<br>MSGKGPKYGAVDTDGRLFECSNVYVADASVLPTASGANPMISTMTFARQIALGLADSLKTKPKL<br><br>FAO-2b - SEQ ID NO:12<br>MNTFLPDVLEYKHVDTLLLLCDGIIHETTVDQIRDAIAPDFPEDQYEEYLKTFTKPSETPGFREAVYDTINSTPTEAVHM<br>CIVLTTALDSRILAPTLTNSLTPIKDMTLKEREQLLAAWRDSPIAAKRRLFRLISSLTLTTFTRLASDLHLRAIHYPGRD<br>LREKAYETQVVDPFRYSFMEKPKFDGTELYLPDIDVIIIGSGAGAGVMAHTLANDGYKTLVLEKGKYFSNSELNFNDADG<br>MKELYQGKCALTTTNQQMFILAGSTLGGGTTVNWSACLKTPFKVRKEWYDEFGLEFAADEAYDKAQDYVWKQMGASTEGI<br>THSLANAVVVEGGKKLGYKSKEIEQNNGGHPDHPCGFCYLGCKYGIKQGSVNNWFRDAAAHGSKFMQQVRVVQILHNKGV<br>AYGILCEDVETGVKFTISGPKKFVVSAGSLNTPTVLTNSGFKNKHIGKNLTLHPVSTVFGDFGRDVQADHFHKSIMTSLC<br>YEVADLDGKGHGCRIETILNAPFIQASLLPWRGSDEVRRDLLRYNNMVAMLLITRDTTSGSVSADPKKPDALIVDYDINK<br>FDKNAILQAFLITSDMLYIEGAKRILSPQAWVPIFESNKPKEQRTIKDKDYVEWRAKAAKIPFDTYGSAYGSAHQMSTCR<br>MSGKGPKYGAVDTDGRLFECSNVYVADASVLPTASGANPMISTMTFARQIALGLADSLKTKPKL |

| Clustal amino acid sequence alignments |
|---|
| FAO-13    MAPFLPDQVDYKHVDTLMLLCDGIIHETTVDQIKDVIAPDFPADKYEEYVRTFTKPSETP     60<br>FAO-20    MAPFLPDQVDYKHVDTLMLLCDGIIHETTVDQIKDVIAPDFPADKYEEYVRTFTKPSETP     60<br>FAO-1     MAPFLPDQVDYKHVDTLMLLCDGIIHETTVDEIKDVIAPDFPADKYEEYVRTFTKPSETP     60<br>          ****************************:************************<br><br>FAO-13    GFRETVYNTVNANTTDAIHQFIILTNVLASRVLAPALTNSLTPIKDMSLEDREKLLASWR    120<br>FAO-20    GFRETVYNTVNANTTDAIHQFIILTNVLASRVLAPALTNSLTPIKDMSLEDREKLLASWR    120<br>FAO-1     GFRETVYNTVNANTMDAIHQFIILTNVLGSRVLAPALTNSLTPIKDMSLEDREKLLASWR    120<br>          **********.**********.**************************<br><br>FAO-13    DSPIAAKRKLFRLVSTLTLVTFTRLANELHLKAIHYPGREDREKAYETQEIDPFKYQFLE    180<br>FAO-20    DSPIAAKRKLFRLVSTLTLVTFTRLANELHLKAIHYPGREDREKAYETQEIDPFKYQFME    180<br>FAO-1     DSPIAAKRKLFRLVSTLTLVTFTRLANELHLKAIHYPGREDREKAYETQEIDPFKYQFLE    180<br>          ******************************************************:*<br><br>FAO-13    KPKFYGAELYLPDIDVIIIGSGAGAGVVAHTLANDGFKSLVLEKGKYFSNSELNFDDKDG    240<br>FAO-20    KPKFDGAELYLPDIDVIIIGSGAGAGVVAHTLANDGFKSLVLEKGKYFSNSELNFDDKDG    240<br>FAO-1     KPKFYGAELYLPDIDVIIIGSGAGAGVVAHTLTNDGFKSLVLEKGRYFSNSELNFDDKDG    240<br>          ** ***********************:*******:**********<br><br>FAO-13    VQELYQSGGTLTTVNQQLFVLAGSTFGGGTTVNWSACLKTPFKVRKEWYDEFGVDFAADE    300<br>FAO-20    VQELYQSGGTLTTVNQQLFVLAGSTFGGGTTVNWSACLKTPFKVRKEWYDEFGVDFAADE    300<br>FAO-1     VQELYQSGGTLTTVNQQLFVLAGSTFGGGTTVNWSACLKTPFKVRKEWYDEFGVDFAADE    300<br>          ********************************************************<br><br>FAO-13    AYDKAQDYVWQQMGASTEGITHSLANEIIIEGGKKLGYKAKVLDQNSGGHPQHRCGFCYL    360<br>FAO-20    AYDKAQDYVWQQMGASTEGITHSLANEIIIEGGKKLGYKAKVLDQNSGGHPQHRCGFCYL    360<br>FAO-1     AYDKAQDYVWQQMGASTEGITHSLANEIIIEGGKKLGYKAKVLDQNSGGHPHHRCGFCYL    360<br>          **********************************************:****<br><br>FAO-13    GCKHGIKQGSVNNWFRDAAAHGSQFMQQVRVLQILNKKGIAYGILCEDVVTGAKFTITGP    420<br>FAO-20    GCKHGIKQGSVNNWFRDAAAHGSQFMQQVRVLQILNKKGIAYGILCEDVVTGAKFTITGP    420<br>FAO-1     GCKHGIKQGSVNNWFRDAAAHGSQFMQQVRVLQILNKKGIAYGILCEDVVTGAKFTITGP    420<br>          ********************************************************<br><br>FAO-13    KKFVVAAGALNTPSVLVNSGFKNKNIGKNLTLHPVSVVFGDFGKDVQADHFHNSIMTALC    480<br>FAO-20    KKFVVAAGALNTPSVLVNSGFKNKNIGKNLTLHPVSVVFGDFGKDVQADHFHNSIMTALC    480<br>FAO-1     KKFVVAAGALNTPSVLVNSGFKNKNIGKNLTLHPVSVVFGDFGKDVQADHFHNSIMTALC    480<br>          ********************************************************<br><br>FAO-13    SEAADLDGKGHGCRIETILNAPFIQASFLPWRGSNEARRDLLRYNNMVAMLLLSRDTTSG    540<br>FAO-20    SEAADLDGKGHGCRIETILNAPFIQASFLPWRGSNEARRDLLRYNNMVAMLLLSRDTTSG    540<br>FAO-1     SEAADLDGKGHGCRIETILNAPFIQASFLPWRGSNEARRDLLRYNNMVAMLLLSRDTTSG    540<br>          ********************************************************<br><br>FAO-13    SVSAHPTKPEALVVEYDVNKFDRNSILQALLVTADLLYIQGAKRILSPQAWVPIFESDKP    600<br>FAO-20    SVSAHPTKPEALVVEYDVNKFDRNSILQALLVTADLLYIQGAKRILSPQAWVPIFESDKP    600<br>FAO-1     SVSSHPTKPEALVVEYDVNKFDRNSILQALLVTADLLYIQGAKRILSPQPWVPIFESDKP    600<br>          *:******************************************.******** |

```
Clustal amino acid sequence alignments

FAO-13    KDKRSIKDEDYVEWRAKVAKIPFDTYGSPYGSAHQMSSCRMSGKGPKYGAVDTDGRLFEC    660
FAO-20    KDKRSIKDEDYVEWRAKVAKIPFDTYGSPYGSAHQMSSCRMSGKGPKYGAVDTDGRLFEC    660
FAO-1     KDKRSIKDEDYVEWRAKVAKIPFDTYGSPYGSAHQMSSCRMSGKGPKYGAVDTDGRLFEC    660
          ************************************************************

FAO-13    SNVYVADASLLPTASGANPMVTTMTLARHVALGLADSLKTKAKL                    704
FAO-20    SNVYVADASLLPTASGANPMVTTMTLARHVALGLADSLKTKAKL                    704
FAO-1     SNVYVADASLLPTASGANPMVTTMTLARHVALGLADSLKTKAKL                    704
          *******************************************
```

Example 31

Examples of Embodiments

Provided hereafter are non-limiting examples of certain embodiments.

A1. An engineered microorganism capable of producing adipic acid, which microorganism comprises one or more altered activities selected from the group consisting of 6-oxohexanoic acid dehydrogenase activity, omega oxo fatty acid dehydrogenase activity, 6-hydroxyhexanoic acid dehydrogenase activity, omega hydroxyl fatty acid dehydrogenase activity, hexanoate synthase activity, monooxygenase activity, monooxygenase reductase activity, fatty alcohol oxidase activity, acyl-CoA ligase activity, acyl-CoA oxidase activity, enoyl-CoA hydratase activity, 3-L-hydroxyacyl-CoA dehydrogenase activity and acetyl-CoA C-acyltransferase activity.

A1.1. The engineered microorganism of embodiment A1, which comprises a genetic modification that adds or increases the 6-oxohexanoic acid dehydrogenase activity, omega oxo fatty acid dehydrogenase activity, 6-hydroxyhexanoic acid dehydrogenase activity, omega hydroxyl fatty acid dehydrogenase activity, hexanoate synthase activity, monooxygenase activity, monooxygenase reductase activity, fatty alcohol oxidase activity, acyl-CoA ligase activity, acyl-CoA oxidase activity, enoyl-CoA hydratase activity, 3-L-hydroxyacyl-CoA dehydrogenase activity and/or acetyl-CoA C-acyltransferase activity.

A1.2. The engineered microorganism of embodiment A1, which comprises a genetic modification that reduces the acyl-CoA oxidase activity.

A1.3. The engineered microorganism of embodiment A1.1, wherein the genetic modification comprises increased copies of a polynucleotide that encodes a polypeptide having 6-oxohexanoic acid dehydrogenase activity, omega oxo fatty acid dehydrogenase activity, 6-hydroxyhexanoic acid dehydrogenase activity, omega hydroxyl fatty acid dehydrogenase activity, hexanoate synthase activity, monooxygenase activity, monooxygenase reductase activity, fatty alcohol oxidase activity, acyl-CoA ligase activity, acyl-CoA oxidase activity, enoyl-CoA hydratase activity, 3-L-hydroxyacyl-CoA dehydrogenase activity or acetyl-CoA C-acyltransferase activity.

A1.4. The engineered microorganism of embodiment A1.1, wherein the genetic modification comprises insertion of a heterologous promoter and/or 5' UTR, into genomic DNA of the microorganism in functional connection with a polynucleotide that encodes a polypeptide having 6-oxohexanoic acid dehydrogenase activity, 6-hydroxyhexanoic acid dehydrogenase activity, hexanoate synthase activity, monooxygenase activity, monooxygenase reductase activity, fatty alcohol oxidase activity, acyl-CoA ligase activity, acyl-CoA oxidase activity, enoyl-CoA hydratase activity, 3-L-hydroxyacyl-CoA dehydrogenase activity or acetyl-CoA C-acyltransferase activity.

A2. The engineered microorganism of any one of embodiments A1 to A1.4, which comprises an altered thioesterase activity.

A2.1. The engineered microorganism of embodiment A2, which comprises a genetic alteration that adds or increases a thioesterase activity.

A2.2. The engineered microorganism of embodiment A2.1, which comprises a heterologous polynucleotide encoding a polypeptide having thioesterase activity.

A3. The engineered microorganism of any one of embodiments A1 to A2.2, which comprises a heterologous polynucleotide encoding a polypeptide having 6-oxohexanoic acid dehydrogenase activity.

A3.1 The engineered microorganism of any one of embodiments A1 to A3, which comprises a heterologous polynucleotide encoding a polypeptide having omega oxo fatty acid dehydrogenase activity.

A4. The engineered microorganism of embodiment A3 and A3.1, wherein the heterologous polynucleotide is from a bacterium.

A5. The engineered microorganism of embodiment A4, wherein the bacterium is an *Acinetobacter, Nocardia, Pseudomonas* or *Xanthobacter* bacterium.

A6. The engineered microorganism of embodiment A1 or A2, which comprises a heterologous polynucleotide encoding a polypeptide having 6-hydroxyhexanoic acid dehydrogenase activity.

A6.1 The engineered microorganism of embodiment A1 or A2, which comprises a heterologous polynucleotide encoding a polypeptide having omega hydroxyl fatty acid dehydrogenase activity A7. The engineered microorganism of embodiment A6 or A6.1, wherein the heterologous polynucleotide is from a bacterium.

A8. The engineered microorganism of embodiment A7, wherein the bacterium is an *Acinetobacter, Nocardia, Pseudomonas* or *Xanthobacter* bacterium.

A9. The engineered microorganism of embodiment A1 or A2, which comprises a heterologous polynucleotide encoding a polypeptide having hexanoate synthase subunit A activity.

A10. The engineered microorganism of embodiment A1 or A2, which comprises a heterologous polynucleotide encoding a polypeptide having hexanoate synthase subunit B activity.

A11. The engineered microorganism of embodiment A9 or A10, wherein the heterologous polynucleotide independently is selected from a bacterium.

A12. The engineered microorganism of embodiment A11, wherein the bacterium is a *Bacillus* bacterium.

A13. The engineered microorganism of embodiment A12, wherein the *Bacillus* bacterium is *B. megaterium*.

A14. The engineered microorganism of embodiment A1 or A2, which comprises a heterologous polynucleotide encoding a polypeptide having monooxygenase activity.

A15. The engineered microorganism of embodiment A14, wherein the heterologous polynucleotide is from a fungus.

A16. The engineered microorganism of embodiment A15, wherein the fungus is an *Aspergillus* fungus.

A17. The engineered microorganism of embodiment A16, wherein the *Aspergillus* fungus is *A. parasiticus*.

A18. The engineered microorganism of embodiment A1 or A2, which comprises a genetic modification that results in primary hexanoate usage by monooxygenase activity.

A19. The engineered microorganism of embodiment A18, wherein the genetic modification reduces a polyketide synthase activity.

A20. The engineered microorganism of any one of embodiments A1-A19, which is a eukaryote.

A21. The engineered microorganism of embodiment A20, which is a yeast.

A22. The engineered microorganism of embodiment A21, wherein the yeast is a *Candida* yeast.

A23. The engineered microorganism of embodiment A22, wherein the *Candida* yeast is a *C. tropicalis* strain.

A24. The engineered microorganism of embodiment A20, which is a fungus.

A25. The engineered microorganism of embodiment A24, wherein the fungus is a *Yarrowia* fungus.

A26. The engineered microorganism of embodiment A25, wherein the *Yarrowia* fungus is *Y. lipolytica*.

A27. The engineered microorganism of embodiment A24, wherein the fungus is an *Aspergillus* fungus.

A28. The engineered microorganism of embodiment A27, wherein the *Aspergillus* fungus is a *A. parasiticus* strain or a *A. nidulans* strain.

A29. The engineered microorganism of any one of embodiments A1-A28, which comprises a genetic modification that reduces 6-hydroxyhexanoic acid conversion.

A30. The engineered microorganism of embodiment A29, wherein the genetic modification reduces 6-hydroxyhexanoic acid dehydrogenase activity.

A31. The engineered microorganism of any one of embodiments A1-A30, which comprises a genetic modification that reduces beta-oxidation activity.

A32. The engineered microorganism of embodiment A31, wherein the genetic modification renders beta-oxidation activity undetectable.

A33. The engineered microorganism of embodiment A31, wherein the genetic modification partially reduces beta-oxidation activity.

A34. The engineered microorganism of any one of embodiments A31 to A33, wherein the genetic modification comprises disrupting a polynucleotide that encodes a polypeptide having an acyl-CoA oxidase activity.

A35. The engineered microorganism of any one of embodiments A31 to A33, wherein the genetic modification comprises disrupting a promoter in functional connection with a polynucleotide that encodes a polypeptide having the acyl-CoA oxidase activity.

A36. The engineered microorganism of embodiment A34 or A35, wherein the polypeptide having the acyl-CoA oxidase activity is a POX polypeptide.

A37. The engineered microorganism of embodiment A36, wherein the POX polypeptide is a POX4 polypeptide, POX5 polypeptide or POX4 polypeptide and POX5 polypeptide.

A38. The engineered microorganism of any one of embodiments A1 to A37, which is in contact with a feedstock.

A39. The engineered microorganism of embodiment A38, wherein the feedstock comprises a saccharide.

A40. The engineered microorganism of embodiment A39, wherein the saccharide is a monosaccharide, polysaccharide or a mixture or a monosaccharide and polysaccharide.

A41. The engineered microorganism of embodiment A38, wherein the feedstock comprises a paraffin.

A42. The engineered microorganism of embodiment A41, wherein the paraffin is a saturated paraffin, unsaturated paraffin, substituted paraffin, branched paraffin, linear paraffin or combination thereof.

A43. The engineered microorganism of embodiment A41 or A42, wherein the paraffin includes about 1 to about 60 carbon atoms.

A44. The engineered microorganism of embodiments A41 to A43, wherein the paraffin is in a mixture of paraffins.

A45. The engineered microorganism of embodiment A44, wherein the paraffins in the mixture of paraffins have a mean number of carbon atoms of about 8 to about 18 carbon atoms.

A46. The engineered microorganism of embodiment A45, wherein the mean number of carbon atoms is about 10 to about 16 carbon atoms.

A46.1. The engineered microorganism of embodiment A46, wherein the mean number of carbon atoms is about 12 atoms.

A47. The engineered microorganism of any one of embodiments A41 to A46.1, wherein the paraffin is in a wax.

A48. The engineered microorganism of any one of embodiments A41 to A46.1, wherein the paraffin is in an oil.

A49. The engineered microorganism of any one of embodiments A41 to A48, wherein the paraffin is from a petroleum product.

A50. The engineered microorganism of embodiment A49, wherein the petroleum product is a petroleum distillate.

A51. The engineered microorganism of any one of embodiments A41 to A48, wherein the paraffin is from a plant or plant product.

B1. An engineered microorganism that produces adipic acid, which microorganism comprises an altered monooxygenase activity.

B1.1. The engineered microorganism of embodiment B1, which comprises a genetic modification that alters the monooxygenase activity.

B1.2. The engineered microorganism of embodiment B1 or B1.1, which comprises a genetic modification that alters a monooxygenase activity selected from the group consisting of.

B2. The engineered microorganism of embodiment B1.1, which comprises a heterologous polynucleotide encoding a polypeptide having monooxygenase activity.

B3. The engineered microorganism of embodiment B2, wherein the heterologous polynucleotide is from a fungus.

B4. The engineered microorganism of embodiment B3, wherein the fungus is an *Aspergillus* fungus.

B5. The engineered microorganism of embodiment B4, wherein the *Aspergillus* fungus is *A. parasiticus*.

B6. The engineered microorganism of any one of embodiments B1-B5, which comprises a genetic modification that results in substantial hexanoate usage by the monooxygenase activity.

B7. The engineered microorganism of embodiment B6, wherein the genetic modification reduces a polyketide synthase activity.

B8. The engineered microorganism of any one of embodiments B1-B5, which comprises an altered hexanoate synthase activity.

B9. The engineered microorganism of embodiment B8, wherein the altered hexanoate synthase activity is an altered hexanoate synthase subunit A activity, altered hexanoate synthase subunit B activity, or altered hexanoate synthase subunit A activity and altered hexanoate synthase subunit B activity.

B9.1. The engineered microorganism of embodiment B9, which comprises a genetic alteration that adds or increases hexanoate synthase activity.

B10. The engineered microorganism of any one of embodiments B8, B9 or B9.1, which comprises a heterologous polynucleotide encoding a polypeptide having hexanoate synthase activity.

B11. The engineered microorganism of embodiment B10, wherein the heterologous polynucleotide is from a fungus.

B12. The engineered microorganism of embodiment B11, wherein the fungus is an *Aspergillus* fungus.

B13. The engineered microorganism of embodiment B11, wherein the *Aspergillus* fungus is *A. parasiticus*.

B14. The engineered microorganism of any one of embodiments B1-B13, which comprises an altered thioesterase activity.

B14.1. The engineered microorganism of embodiment B14, which comprises a genetic modification that adds or increases the thioesterase activity.

B14.2. The engineered microorganism of embodiment B14 or B14.1, which comprises a heterologous polynucleotide encoding a polypeptide having thioesterase activity.

B15. The engineered microorganism of any one of embodiments B1-B14.2, which comprises an altered 6-oxohexanoic acid dehydrogenase activity.

B15.1. The engineered microorganism of embodiment B15, which comprises a genetic modification that adds or increases the 6-oxohexanoic acid dehydrogenase activity.

B15.2 The engineered microorganism of any one of embodiments B1 to B15.1, which comprises an altered omega oxo fatty acid dehydrogenase activity.

B15.3 The engineered microorganism of embodiment B15.2, which comprises a genetic modification that adds or increases the omega oxo fatty acid dehydrogenase activity B16. The engineered microorganism of any one of embodiments B15 to B15.3, which comprises a heterologous polynucleotide encoding a polypeptide having 6-oxohexanoic acid dehydrogenase activity.

B16.1 The engineered microorganism of any one of embodiments B15 to B16, which comprises a heterologous polynucleotide encoding a polypeptide having omega oxo fatty acid dehydrogenase activity.

B17. The engineered microorganism of embodiment B16 or B16.1, wherein the heterologous polynucleotide is from a bacterium.

B18. The engineered microorganism of embodiment B17, wherein the bacterium is a *Acinetobacter, Nocardia, Pseudomonas* or *Xanthobacter* bacterium.

B19. The engineered microorganism of any one of embodiments B1-B18, which comprises an altered 6-hydroxyhexanoic acid dehydrogenase activity.

B19.1. The engineered microorganism of embodiment B19, which comprises a genetic modification that adds or increases the 6-hydroxyhexanoic acid dehydrogenase activity.

B19.2 The engineered microorganism of any one of embodiments B1-B19.1, which comprises an altered omega hydroxyl fatty acid dehydrogenase activity.

B19.3 The engineered microorganism of embodiment B19.2, which comprises a genetic modification that adds or increases the omega hydroxyl fatty acid dehydrogenase activity.

B20. The engineered microorganism of any one of embodiments B19 to B19.3, which comprises a heterologous polynucleotide encoding a polypeptide having 6-hydroxyhexanoic acid dehydrogenase activity.

B20.1 The engineered microorganism of any one of embodiments B19 to B20, which comprises a heterologous polynucleotide encoding a polypeptide having omega hydroxyl fatty acid dehydrogenase activity.

B21. The engineered microorganism of embodiment B20 or B20.1, wherein the heterologous polynucleotide is from a bacterium.

B22. The engineered microorganism of embodiment B21, wherein the bacterium is a *Acinetobacter, Nocardia, Pseudomonas* or *Xanthobacter* bacterium.

B23. The engineered microorganism of any one of embodiments B1-B22, which is a eukaryote.

B24. The engineered microorganism of embodiment B23, which is a yeast.

B25. The engineered microorganism of embodiment B24, wherein the yeast is a *Candida* yeast.

B26. The engineered microorganism of embodiment B25, wherein the *Candida* yeast is *C. tropicalis*.

B27. The engineered microorganism of embodiment B23, which is a fungus.

B28. The engineered microorganism of embodiment B27, wherein the fungus is a *Yarrowia* fungus.

B29. The engineered microorganism of embodiment B28, wherein the *Yarrowia* fungus is *Y. lipolytica*.

B30. The engineered microorganism of embodiment B27, wherein the fungus is *Aspergillus*.

B31. The engineered microorganism of embodiment B30, wherein the *Aspergillus* fungus is *A. parasiticus* or *A. nidulans*.

B32. The engineered microorganism of any one of embodiments B1-B31, which comprises a genetic modification that reduces 6-hydroxyhexanoic acid conversion.

B33. The engineered microorganism of embodiment B32, wherein the genetic modification reduces 6-hydroxyhexanoic acid dehydrogenase activity.

B34. The engineered microorganism of any one of embodiments B1-B33, which comprises a genetic modification that reduces beta-oxidation activity.

B35. The engineered microorganism of embodiment B34, wherein the genetic modification renders beta-oxidation activity undetectable.

C1. A method for manufacturing adipic acid, which comprises culturing an engineered microorganism of any one of embodiments A1-B35 under culture conditions in which the cultured microorganism produces adipic acid.

C1.1. The method of embodiment C1, wherein the host microorganism from which the engineered microorganism is produced does not produce a detectable amount of adipic acid.

C2. The method of embodiment C1 of C1.1, wherein the culture conditions comprise fermentation conditions.

C3. The method of any one of embodiments C1-C2, wherein the culture conditions comprise introduction of biomass.

C4. The method of C1 or C2, wherein the culture conditions comprise introduction of glucose.

C5. The method of C1 or C2, wherein the culture conditions comprise introduction of hexane.

C6. The method of any one of embodiments C1-C5, wherein the adipic acid is produced with a yield of greater than about 0.3 grams per gram of glucose added.

C7. The method of any one of embodiments C1-C6, which comprises purifying the adipic acid from the cultured microorganisms.

C8. The method of embodiment C7, which comprises modifying the adipic acid, thereby producing modified adipic acid.

C9. The method of any one of embodiments C1-C8, which comprises placing the cultured microorganisms, the adipic acid or the modified adipic acid in a container.

C10. The method of embodiment C9, which comprises shipping the container.

D1. A method for manufacturing 6-hydroxyhexanoic acid, which comprises culturing an engineered microorganism of any one of embodiments A29, A30, B32 or B33 under culture conditions in which the cultured microorganism produces 6-hydroxyhexanoic acid.

D1.1. The method of embodiment D1, wherein the host microorganism from which the engineered microorganism is produced does not produce a detectable amount of 6-hydroxyhexanoic acid.

D2. The method of embodiment D1 or D1.1, wherein the culture conditions comprise fermentation conditions.

D3. The method of any one of embodiments D1-D2, wherein the culture conditions comprise introduction of biomass.

D4. The method of D1 or D2, wherein the culture conditions comprise introduction of glucose.

D5. The method of D1 or D2, wherein the culture conditions comprise introduction of hexane.

D6. The method of any one of embodiments D1-D5, wherein the 6-hydroxyhexanoic acid is produced with a yield of greater than about 0.3 grams per gram of glucose added.

D7. The method of any one of embodiments D1-D6, which comprises purifying the 6-hydroxyhexanoic acid from the cultured microorganisms.

D8. The method of embodiment D7, which comprises modifying the 6-hydroxyhexanoic acid, thereby producing modified 6-hydroxyhexanoic acid.

D9. The method of any one of embodiments D1-D8, which comprises placing the cultured microorganisms, the 6-hydroxyhexanoic acid or the modified 6-hydroxyhexanoic acid in a container.

D10. The method of embodiment D9, which comprises shipping the container.

E1. A method for preparing an engineered microorganism that produces adipic acid, which comprises:
(a) introducing a genetic modification to a host organism that adds or increases monooxygenase activity, thereby producing engineered microorganisms having detectable and/or increased monooxygenase activity; and
(b) selecting for engineered microorganisms that produce adipic acid.

E1.1. The method of embodiment E1, wherein the monooxygenase activity is incorporation of a hydroxyl moiety into a six-carbon molecule.

E1.2. The method of embodiment E1 or E1.1, wherein the six-carbon molecule is hexanoate.

E2. A method for preparing an engineered microorganism that produces adipic acid, which comprises:
(a) culturing a host organism with hexane as a nutrient source, thereby producing engineered microorganisms having detectable monooxygenase activity; and
(b) selecting for engineered microorganisms that produce adipic acid.

E2.1. The method of embodiment E2, wherein the monooxygenase activity is incorporation of a hydroxyl moiety into a six-carbon molecule.

E2.2. The method of embodiment E2 or E2.1, wherein the six-carbon molecule is hexanoate.

E3. The method of any one of embodiments E1-E2.2, which comprises selecting the engineered microorganisms that have a detectable amount of the monooxygenase activity.

E4. The method of any one of embodiments E1-E3, which comprises introducing a genetic modification that adds or increases a hexanoate synthase activity, thereby producing engineered microorganisms, and selecting for engineered microorganisms having detectable and/or increased hexanoate synthase activity.

E5. The method of embodiment E4, wherein the genetic modification encodes a polypeptide having a hexanoate synthase subunit A activity, a hexanoate synthase subunit B activity, or a hexanoate synthase subunit A activity and a hexanoate synthase subunit B activity.

E6. The method of any one of embodiments E1-E5, which comprises introducing a genetic modification that adds or increases 6-oxohexanoic acid dehydrogenase activity, thereby producing engineered microorganisms, and selecting for engineered microorganisms having detectable and/or increased 6-oxohexanoic acid dehydrogenase activity relative to the host microorgansim.

E7. The method of any one of embodiments E1-E6, which comprises introducing a genetic modification that adds or increases a 6-hydroxyhexanoic acid dehydrogenase activity, thereby producing engineered microorganisms, and selecting for engineered microorganisms having a detectable and/or increased 6-hydroxyhexanoic acid dehydrogenase activity relative to the host microorganism.

E7.1 The method of any one of embodiments E1-E7, which comprises introducing a genetic modification that adds or increases a 6-hydroxyhexanoic acid dehydrogenase activity, thereby producing engineered microorganisms, and selecting for engineered microorganisms having a detectable and/or increased omega hydroxyl fatty acid dehydrogenase activity relative to the host microorganism.

E8. The method of any one of embodiments E1-E7.1, which comprises introducing a genetic modification that adds or increases a thioesterase activity, thereby producing engineered microorganisms, and selecting for engineered microorganisms having a detectable and/or increased thioesterase activity relative to the host microorganism.

E9. The method of any one of embodiments E1-E8, which comprises introducing a genetic modification that reduces 6-hydroxyhexanoic acid conversion, thereby producing engineered microorganisms, and selecting for engineered microorganisms having reduced 6-hydroxyhexanoic acid conversion relative to the host microorganism.

E10. The method of any one of embodiments E1-E9, which comprises introducing a genetic modification that reduces beta-oxidation activity, thereby producing engineered microorganisms, and selecting for engineered microorganisms having reduced beta-oxidation activity relative to the host microorganism.

E11. The method of any one of embodiments E1-E11, which comprises introducing a genetic modification that results in substantial hexanoate usage by the monooxygenase activity, thereby producing engineered microorganisms, and selecting for engineered microorganisms in which substantial hexanoate usage is by the monooxygenase activity relative to the host microorganism.

F1. A method for preparing a microorganism that produces adipic acid, which comprises: (a) introducing one or more genetic modifications to a host organism that add or increase one or more activities selected from the group consisting of 6-oxohexanoic acid dehydrogenase activity, omega oxo fatty acid dehydrogenase activity, 6-hydroxyhexanoic acid dehydrogenase activity, omega hydroxyl fatty acid dehydrogenase activity, hexanoate synthase activity and monooxygenase activity, thereby producing engineered microorganisms, and (b) selecting for engineered microorganisms that produce adipic acid.

F2. The method of embodiment F1, which comprises selecting for engineered microorganisms having one or more detectable and/or increased activities selected from the group consisting of 6-oxohexanoic acid dehydrogenase activity, omega oxo fatty acid dehydrogenase activity, 6-hydroxyhexanoic acid dehydrogenase activity, omega hydroxyl fatty acid dehydrogenase activity, hexanoate synthase activity and monooxygenase activity, relative to the host microorganism.

F3. The method of embodiment F1 or F2, which comprises introducing a genetic modification that reduces 6-hydroxyhexanoic acid conversion, thereby producing engineered microorganisms, and selecting for engineered microorganisms having reduced 6-hydroxyhexanoic acid conversion relative to the host microorganism.

F4. The method of any one of embodiments F1-F3, which comprises introducing a genetic modification that reduces beta-oxidation activity, thereby producing engineered microorganisms, and selecting for engineered microorganisms having reduced beta-oxidation activity relative to the host microorganism.

F5. The method of any one of embodiments F1-F4, which comprises introducing a genetic modification that results in substantial hexanoate usage by the monooxygenase activity, thereby producing engineered microorganisms, and selecting for engineered microorganisms in which substantial hexanoate usage is by the monooxygenase activity relative to the host microorganism.

G1. A method for preparing a microorganism that produces 6-hydroxyhexanoic acid, which comprises: (a) introducing one or more genetic modifications to a host organism that add or increase one or more activities selected from the group consisting of 6-oxohexanoic acid dehydrogenase activity, hexanoate synthase activity and monooxygenase activity, thereby producing engineered microorganisms, (b) introducing a genetic modification to the host organism that reduces 6-hydroxyhexanoic acid conversion, and (c) selecting for engineered microorganisms that produce 6-hydroxyhexanoic acid.

G2. The method of embodiment G1, which comprises selecting for engineered microorganisms having reduced 6-hydroxyhexanoic acid conversion relative to the host microorganism.

G3. The method of embodiment G1 or G2, which comprises selecting for engineered microorganisms having one or more detectable and/or increased activities selected from the group consisting of 6-oxohexanoic acid dehydrogenase activity, omega oxo fatty acid dehydrogenase activity, 6-hydroxyhexanoic acid dehydrogenase activity, omega hydroxyl fatty acid dehydrogenase activity, hexanoate synthase activity and monooxygenase activity, relative to the host microorganism.

G4. The method of any one of embodiments G1-G3, which comprises introducing a genetic modification that reduces beta-oxidation activity, thereby producing engineered microorganisms, and selecting for engineered microorganisms having reduced beta-oxidation activity relative to the host microorganism.

G5. The method of any one of embodiments G1-G4, which comprises introducing a genetic modification that results in substantial hexanoate usage by the monooxygenase activity, thereby producing engineered microorganisms, and selecting for engineered microorganisms in which substantial hexanoate usage is by the monooxygenase activity relative to the host microorganism.

H1. A method, comprising:
  contacting an engineered microorganism with an feedstock comprising one or more polysaccharides, wherein the engineered microorganism comprises:
  a. a genetic alteration that blocks beta oxidation activity, and
  b. a genetic alteration that adds or increases a monooxygenase activity or a genetic alteration that adds or increases hexanoate synthetase activity; and
  culturing the engineered microorganism under conditions in which adipic acid is produced.

H1.1. The method of embodiment H1, wherein the engineered microorganism comprises a genetic alteration that adds or increases hexanoate synthetase activity.

H1.2. The method of embodiment H1.1, wherein the engineered microorganism comprises a heterologous polynucleotide encoding a polypeptide having hexanoate synthase subunit A activity.

H1.3. The method of embodiment H1.1, wherein the engineered microorganism comprises a heterologous polynucleotide encoding a polypeptide having hexanoate synthase subunit B activity.

H1.4. The method of embodiment H1.2 or H1.3, wherein the heterologous polynucleotide independently is selected from a bacterium.

H1.5. The method of embodiment H1.4, wherein the bacterium is a *Bacillus* bacterium.

H1.6. The method of embodiment H1.5, wherein the *Bacillus* bacterium is *B. megaterium*.

H2. The method of any one of embodiment H1 or H1.6, wherein the microorganism is a *Candida* yeast.

H3. The method of embodiment H2, wherein the microorganism is a *C. tropicalis* strain.

H4. The method of any one of embodiments H1 to H3, wherein the genetic alteration that increases monooxygenase activity comprises a genetic alteration that increases cytochrome P450 reductase activity.

H5. The method of embodiment H4, wherein the genetic alteration increases the number of copies of a polynucleotide that encodes a polypeptide having the cytochrome P450 reductase activity.

H6. The method of embodiment H4, wherein the genetic alteration places a promoter in functional connection with a polynucleotide that encodes a polypeptide having the cytochrome P450 reductase activity.

H7. The method of any one of embodiments H1 to H6, wherein the monooxygenase activity is a CYP52A15 activity, CYP52A16 activity, or a CYP52A15 activity and CYP52A16 activity.

H8. The method of any one of embodiments H1 to H7, wherein the genetic alteration increases the number of copies of a polynucleotide that encodes a polypeptide having the monooxygenase activity.

H9. The method of any one of embodiments H1 to H7, wherein the genetic alteration places a promoter in functional connection with a polynucleotide that encodes a polypeptide having the monooxygenase activity.

H10. The method of any one of embodiments H1 to H7, wherein the genetic alteration that blocks beta oxidation activity disrupts acyl-CoA oxidase activity.

H11. The method of embodiment H10, wherein the genetic alteration disrupts POX4 and POX5 activity.

H12. The method of embodiment H10 or H11, wherein the genetic alteration disrupts a polynucleotide that encodes a polypeptide having the acyl-CoA oxidase activity.

H13. The method of embodiment H10 or H11, wherein the genetic alteration disrupts a promoter in functional connection with a polynucleotide that encodes a polypeptide having the acyl-CoA oxidase activity.

H14. The method of any one of embodiments H1 to H13, wherein the feedstock comprises a 6-carbon sugar.

H15. The method of any one of embodiments H1 to H13, wherein the feedstock comprises a 5-carbon sugar.

H16. The method of any one of embodiments H1 to H15, wherein the adipic acid is produced at a level of about 80% or more of theoretical yield.

H17. The method of any one of embodiments H1 to H16, comprising detecting the amount of adipic acid produced.

H18. The method of any one of embodiments H1 to H17, comprising isolating the adipic acid produced.

H19. The method of any one of embodiments H1 to H18, wherein the culture conditions comprise fermenting the engineered microorganism.

I1. A method, comprising:
  contacting an engineered microorganism with a feedstock comprising one or more paraffins, wherein the engineered microorganism comprises a genetic alteration that partially blocks beta oxidation activity; and
  culturing the engineered microorganism under conditions in which adipic acid is produced.

I1.1. The method of embodiment I1, wherein the microorganism comprises a genetic alteration that increases a monooxygenase activity.

I2. The method of embodiment I1 or I1.1, wherein the microorganism is a *Candida* yeast.

I3. The method of embodiment I2, wherein the microorganism is a *C. tropicalis* strain.

I4. The method of any one of embodiments I1 to I3, wherein the genetic alteration that increases monooxygenase activity comprises a genetic alteration that increases cytochrome P450 reductase activity.

I5. The method of embodiment I4, wherein the genetic alteration increases the number of copies of a polynucleotide that encodes a polypeptide having the cytochrome P450 reductase activity.

I6. The method of embodiment I4, wherein the genetic alteration places a promoter in functional connection with a polynucleotide that encodes a polypeptide having the cytochrome P450 reductase activity.

I7. The method of any one of embodiments I1 to I6, wherein the monooxygenase activity is a CYP52A15 activity, CYP52A16 activity, or a CYP52A15 activity and CYP52A16 activity.

I8. The method of any one of embodiments I1 to I7, wherein the genetic alteration increases the number of copies of a polynucleotide that encodes a polypeptide having the monooxygenase activity.

I9. The method of any one of embodiments I1 to I7, wherein the genetic alteration places a promoter in functional connection with a polynucleotide that encodes a polypeptide having the monooxygenase activity.

I10. The method of any one of embodiments I1 to I7, wherein the genetic alteration that blocks beta oxidation activity disrupts acyl-CoA oxidase activity.

I11. The method of embodiment I10, wherein the genetic alteration disrupts POX4 or POX5 activity.

I12. The method of embodiment I10 or I11, wherein the genetic alteration disrupts a polynucleotide that encodes a polypeptide having the acyl-CoA oxidase activity.

I13. The method of embodiment I10 or I11, wherein the genetic alteration disrupts a promoter in functional connection with a polynucleotide that encodes a polypeptide having the acyl-CoA oxidase activity.

I114. The method of any one of embodiments I1 to I13, wherein the adipic acid is produced at a level of about 80% or more of theoretical yield.

I15. The method of any one of embodiments I1 to I14, comprising detecting the amount of adipic acid produced.

I16. The method of any one of embodiments I1 to I15, comprising isolating the adipic acid produced.

I17. The method of any one of embodiments I1 to I16, wherein the culture conditions comprise fermenting the engineered microorganism.

I18. The method of any one of embodiments I1 to I17, wherein the paraffin is a saturated paraffin, unsaturated paraffin, substituted paraffin, branched paraffin, linear paraffin or combination thereof.

I19. The method of any one of embodiments I1 to I18, wherein the paraffin includes about 1 to about 60 carbon atoms.

I20. The method of any one of embodiments I1 to I19, wherein the paraffin is in a mixture of paraffins.

I21. The method of embodiment I20, wherein the paraffins in the mixture of paraffins have a mean number of carbon atoms of about 8 to about 18 carbon atoms.

I22. The method of embodiment I21, wherein the mean number of carbon atoms is about 10 to about 16 carbon atoms.

I23. The method of embodiment I22, wherein the mean number of carbon atoms is about 12 atoms.

I24. The method of any one of embodiments I1 to I23, wherein the paraffin is in a wax.

I25. The method of any one of embodiments I1 to I23, wherein the paraffin is in an oil.

I26. The method of any one of embodiments I1 to I25, wherein the paraffin is from a petroleum product.

I27. The method of embodiment I26, wherein the petroleum product is a petroleum distillate.

I28. The method of any one of embodiments I1 to I27, wherein the paraffin is from a plant or plant product.

J1. An isolated polynucleotide selected from the group consisting of:
  a polynucleotide having a nucleotide sequence 96% or more identical to the nucleotide sequence of SEQ ID NO: 1;
  a polynucleotide having a nucleotide sequence that encodes a polypeptide of SEQ ID NO: 8; and
  a polynucleotide having a portion of a nucleotide sequence 96% or more identical to the nucleotide sequence of SEQ ID NO: 1 and encodes a polypeptide having fatty alcohol oxidase activity.

J2. An isolated polynucleotide selected from the group consisting of:
  a polynucleotide having a nucleotide sequence 98% or more identical to the nucleotide sequence of SEQ ID NO: 2;
  a polynucleotide having a nucleotide sequence that encodes a polypeptide of SEQ ID NO: 10; and
  a polynucleotide having a portion of a nucleotide sequence 98% or more identical to the nucleotide sequence of SEQ ID NO: 2 and encodes a polypeptide having fatty alcohol oxidase activity.

J3. An isolated polynucleotide selected from the group consisting of:
  a polynucleotide having a nucleotide sequence 95% or more identical to the nucleotide sequence of SEQ ID NO: 3;

a polynucleotide having a nucleotide sequence that encodes a polypeptide of SEQ ID NO: 9; and a polynucleotide having a portion of a nucleotide sequence 95% or more identical to the nucleotide sequence of SEQ ID NO: 3 and encodes a polypeptide having fatty alcohol oxidase activity.

J3.1. An isolated polynucleotide selected from the group consisting of:

a polynucleotide having a nucleotide sequence 83% or more identical to the nucleotide sequence of SEQ ID NO: 4;

a polynucleotide having a nucleotide sequence that encodes a polypeptide of SEQ ID NO: 11; and a polynucleotide having a portion of a nucleotide sequence 83% or more identical to the nucleotide sequence of SEQ ID NO: 4 and encodes a polypeptide having fatty alcohol oxidase activity.

J3.2. An isolated polynucleotide selected from the group consisting of:

a polynucleotide having a nucleotide sequence 82% or more identical to the nucleotide sequence of SEQ ID NO: 5;

a polynucleotide having a nucleotide sequence that encodes a polypeptide of SEQ ID NO: 12; and a polynucleotide having a portion of a nucleotide sequence 82% or more identical to the nucleotide sequence of SEQ ID NO: 5 and encodes a polypeptide having fatty alcohol oxidase activity.

J4. An expression vector comprising a polynucleotide of any one of embodiments J1 to J3.2.

J5. An integration vector comprising a polynucleotide of any one of embodiments J1 to J3.2.

J6. A microorganism comprising an expression vector of embodiment J4 or an integration vector of embodiment J5.

J7. A culture comprising a microorganism of embodiment J6.

J8. A fermentation device comprising a microorganism of embodiment J7.

J10. A polypeptide encoded by a polynucleotide of any one of embodiments J1 to J3 or produced by an expression vector of embodiment J4 or microorganism of embodiment J6.

J11. An antibody that specifically binds to a polypeptide of embodiment J10.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the claimed technology. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A genetically modified *Candida* yeast, comprising:
   a genetic modification that reduces or eliminates a PDX4 activity, thereby partially blocking beta oxidation activity;
   a genetic modification that adds or increases a CYP52A15, CYP52A16 or CYP52A19 monooxygenase activity; and
   a genetic modification that adds or increases a monooxygenase reductase activity;
   wherein said yeast is capable of producing adipic acid, at a level of at least 0.4 grams per liter of culture medium, from a feedstock comprising a mixture of fatty acids from a vegetable oil.

2. The genetically modified *Candida* yeast of claim 1, wherein the *Candida* yeast is a genetically modified ATCC20336 yeast.

3. The genetically modified *Candida* yeast of claim 1, wherein the genetic modification that adds or increases the CYP52A15, CYP52A16 or CYP52A19 monooxygenase activity comprises (i) an increased copy number of a CYP52A15 monooxygenase coding sequence, or (ii) a modified or added promoter in operable linkage with a CYP52A15 monooxygenase coding sequence.

4. The genetically modified *Candida* yeast of claim 1, wherein the genetic modification that adds or increases the CYP52A15, CYP52A16 or CYP52A19 monooxygenase activity comprises: (i) an increased copy number of a CYP52A16 monooxygenase coding sequence, or (ii) a modified or added promoter in operable linkage with a CYP52A16 monooxygenase coding sequence.

5. The genetically modified *Candida* yeast of claim 1, wherein the genetic modification that adds or increases the CYP52A15, CYP52A16 or CYP52A19 monooxygenase activity comprises (i) an increased copy number of a CYP52A19 monooxygenase coding sequence, or (ii) a modified or added promoter in operable linkage with a CYP52A19 monooxygenase coding sequence.

6. The genetically modified *Candida* yeast of claim 1, wherein the genetic modification that adds or increases the monooxygenase reductase activity comprises (i) an increased copy number of a CPRA monooxygenase reductase coding sequence, or (ii) a modified or added promoter in operable linkage with a CPRA monooxygenase reductase coding sequence.

7. The genetically modified *Candida* yeast of claim 1, wherein the genetic modification that adds or increases the monooxygenase reductase activity comprises (i) an increased copy number of a CPRB monooxygenase reductase coding sequence, or (ii) a modified or added promoter in operable linkage with a CPRB monooxygenase reductase coding sequence.

8. The genetically modified *Candida* yeast of claim 1, wherein the genetic modification that reduces or eliminates the PDX4 activity comprises (i) a disrupted, deleted or knocked out polynucleotide that encodes a PDX4 polypeptide, or (ii) a disrupted promoter and/or 5'UTR in functional connection with a polynucleotide that encodes a PDX4 polypeptide.

9. The genetically modified *Candida* yeast of claim 1, wherein the vegetable oil is a palm oil, soybean oil or fatty acid soap stock.

* * * * *